United States Patent
Hong et al.

(10) Patent No.: US 11,261,437 B2
(45) Date of Patent: Mar. 1, 2022

(54) PROCOAGULANT COMPOUNDS

(71) Applicant: Bioverativ Therapeutics Inc., Waltham, MA (US)

(72) Inventors: Vu Phong Hong, Cambridge, MA (US); Adam R. Mezo, Carmel, IN (US); Joe Salas, Wayland, MA (US); Robert Peters, West Roxbury, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 67 days.

(21) Appl. No.: 16/357,153

(22) Filed: Mar. 18, 2019

(65) Prior Publication Data

US 2019/0309280 A1 Oct. 10, 2019

Related U.S. Application Data

(62) Division of application No. 14/406,163, filed as application No. PCT/US2013/044841 on Jun. 7, 2013, now Pat. No. 10,287,564.

(60) Provisional application No. 61/800,626, filed on Mar. 15, 2013, provisional application No. 61/657,688, filed on Jun. 8, 2012.

(51) Int. Cl.
| | |
|---|---|
| *C12N 9/64* | (2006.01) |
| *A61K 47/62* | (2017.01) |
| *A61K 38/36* | (2006.01) |
| *A61K 38/48* | (2006.01) |
| *A61K 38/02* | (2006.01) |

(52) U.S. Cl.
CPC ............ *C12N 9/6437* (2013.01); *A61K 38/02* (2013.01); *A61K 38/36* (2013.01); *A61K 38/4846* (2013.01); *C12N 9/6432* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,868,112 A | 9/1989 | Toole, Jr. |
| 5,112,950 A | 5/1992 | Meulien et al. |
| 5,171,844 A | 12/1992 | Van Ooyen et al. |
| 5,439,686 A | 8/1995 | Desai et al. |
| 5,460,950 A | 10/1995 | Barr et al. |
| 5,498,421 A | 3/1996 | Grinstaff et al. |
| 5,543,502 A | 8/1996 | Nordfang et al. |
| 5,595,886 A | 1/1997 | Chapman et al. |
| 5,610,278 A | 3/1997 | Nordfang et al. |
| 5,643,575 A | 7/1997 | Martinez et al. |
| 5,648,260 A | 7/1997 | Winter et al. |
| 5,712,122 A | 1/1998 | Boime et al. |
| 5,739,277 A | 4/1998 | Presta et al. |
| 5,789,203 A | 8/1998 | Chapman et al. |
| 5,834,250 A | 11/1998 | Wells et al. |
| 5,840,529 A | 11/1998 | Seidah et al. |
| 5,846,951 A | 12/1998 | Gregoriadis |
| 5,869,046 A | 2/1999 | Presta et al. |
| 5,892,019 A | 4/1999 | Schlom et al. |
| 5,935,815 A | 8/1999 | Van De Ven et al. |
| 5,972,885 A | 10/1999 | Spira et al. |
| 6,030,613 A | 2/2000 | Blumberg et al. |
| 6,048,720 A | 4/2000 | Dalborg et al. |
| 6,060,447 A | 5/2000 | Chapman et al. |
| 6,086,875 A | 7/2000 | Blumberg et al. |
| 6,096,871 A | 8/2000 | Presta et al. |
| 6,121,022 A | 9/2000 | Presta et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,277,375 B1 | 8/2001 | Ward |
| 6,316,226 B1 | 11/2001 | Van Ooyen et al. |

(Continued)

FOREIGN PATENT DOCUMENTS

| | | |
|---|---|---|
| EP | 0 120 694 A2 | 10/1984 |
| EP | 0 125 023 A1 | 11/1984 |

(Continued)

OTHER PUBLICATIONS

Andersen, et al. (2012) "Antibody-Induced Enhancement of Factor VIIa Activity Through Distinct Allosteric Pathways", The Journal of Biological Chemistry, vol. 287, No. 12, pp. 8994-9001.

(Continued)

*Primary Examiner* — Marsha Tsay
(74) *Attorney, Agent, or Firm* — Lathrop GPM; James H. Velema, Esq.

(57) ABSTRACT

The present disclosure provides protease-activatable procoagulant compounds comprising a procoagulant polypeptide, e.g., a procoagulant peptide and/or clotting factor, and a linker comprising a protease-cleavable substrate (e.g., a synthetic thrombin substrate) and a self-immolative spacer (e.g., p-amino benzyl carbamate). Upon cleavage of the protease-cleavable substrate by a protease (e.g., thrombin), the self-immolative spacer cleaves itself from the procoagulant polypeptide such that the polypeptide is in an underivatized and active form. Also provided are pharmaceutical compositions, methods for treating bleeding disorders using the disclosed compounds, methods of enhancing in vivo efficacy of procoagulant polypeptides, methods of increasing the efficacy of proteolytic cleavage of compounds comprising procoagulant polypeptides, methods of activating procoagulant polypeptides, and methods of releasing a procoagulant polypeptide from a heterologous moiety such as PEG.

12 Claims, 22 Drawing Sheets
Specification includes a Sequence Listing.

(56) References Cited

U.S. PATENT DOCUMENTS

| | | |
|---|---|---|
| 6,346,513 B1 | 2/2002 | Van Ooyen et al. |
| 6,380,171 B1 | 4/2002 | Day et al. |
| 6,458,563 B1 | 10/2002 | Lollar |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,696,245 B2 | 2/2004 | Winter et al. |
| 6,737,056 B1 | 5/2004 | Presta |
| 6,821,505 B2 | 11/2004 | Ward |
| 6,998,253 B1 | 2/2006 | Presta et al. |
| 7,041,635 B2 | 5/2006 | Kim et al. |
| 7,083,784 B2 | 8/2006 | Dall'acqua et al. |
| 7,091,186 B2 | 8/2006 | Senter et al. |
| 7,199,223 B2 | 4/2007 | Bossard et al. |
| 7,317,091 B2 | 1/2008 | Lazar et al. |
| 7,348,004 B2 | 3/2008 | Peters et al. |
| 7,375,078 B2 | 5/2008 | Feng |
| 7,381,408 B2 | 6/2008 | Mezo et al. |
| 7,404,956 B2 | 7/2008 | Peters et al. |
| 7,589,178 B2 | 9/2009 | Le Bonniec et al. |
| 7,659,241 B2 | 2/2010 | Senter et al. |
| 7,691,962 B2 | 4/2010 | Boyd et al. |
| 7,709,224 B2 | 5/2010 | Fang et al. |
| 7,754,681 B2 | 7/2010 | Feng |
| 7,807,644 B2 | 10/2010 | Lind et al. |
| 7,846,445 B2 | 12/2010 | Schellenberger et al. |
| 7,855,279 B2 | 12/2010 | Schellenberger et al. |
| 7,862,820 B2 | 1/2011 | Peters et al. |
| 8,449,884 B2 | 5/2013 | Rivera et al. |
| 8,716,448 B2 | 5/2014 | Schellenberger et al. |
| 9,486,507 B2 | 11/2016 | Thorn et al. |
| 9,856,468 B2 | 1/2018 | Salas et al. |
| 1,028,756 A1 | 5/2019 | Hong et al. |
| 2003/0069395 A1 | 4/2003 | Sato et al. |
| 2003/0130189 A1 | 7/2003 | Senter et al. |
| 2003/0235536 A1 | 12/2003 | Blumberg et al. |
| 2005/0147618 A1 | 7/2005 | Rivera et al. |
| 2005/0256030 A1 | 11/2005 | Feng |
| 2006/0115876 A1 | 6/2006 | Pan et al. |
| 2006/0269480 A1 | 11/2006 | Amir et al. |
| 2007/0191597 A1 | 8/2007 | Jain et al. |
| 2007/0218067 A1 | 9/2007 | Buttner et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0057056 A1 | 3/2008 | Lazar et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0241102 A1 | 10/2008 | Hersel et al. |
| 2008/0260738 A1 | 10/2008 | Moore et al. |
| 2008/0261877 A1 | 10/2008 | Ballance et al. |
| 2009/0087411 A1 | 4/2009 | Fares et al. |
| 2009/0092582 A1 | 4/2009 | Bogin et al. |
| 2010/0092496 A1 | 4/2010 | Boyd et al. |
| 2010/0145036 A1 | 6/2010 | Sufi et al. |
| 2010/0239554 A1 | 9/2010 | Schellenberger et al. |
| 2010/0292130 A1 | 11/2010 | Skerra et al. |
| 2010/0323956 A1 | 12/2010 | Schellenberger et al. |
| 2010/0330059 A1 | 12/2010 | Stafford et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0172146 A1 | 7/2011 | Schellenberger et al. |
| 2011/0189162 A1 | 8/2011 | Ghanshani et al. |
| 2011/0189182 A1 | 8/2011 | Metzner et al. |
| 2012/0121613 A1 | 5/2012 | Tang et al. |
| 2012/0263701 A1 | 10/2012 | Schellenberger et al. |
| 2013/0017997 A1 | 1/2013 | Schellenberger et al. |
| 2013/0202596 A1 | 8/2013 | Salas et al. |
| 2013/0216513 A1 | 8/2013 | Salas et al. |
| 2015/0184142 A1 | 7/2015 | Hong et al. |
| 2015/0353911 A1 | 12/2015 | Salas et al. |

FOREIGN PATENT DOCUMENTS

| | | |
|---|---|---|
| EP | 0 295 597 A2 | 12/1988 |
| EP | 2 858 659 A1 | 4/2015 |
| WO | WO 1981/001145 A1 | 4/1981 |
| WO | WO 1987/004187 A1 | 7/1987 |
| WO | WO 1988/000831 A1 | 2/1988 |
| WO | WO 1988/007089 A1 | 9/1988 |
| WO | WO 1991/009122 A1 | 12/1990 |
| WO | WO 1992/007869 A1 | 5/1992 |
| WO | WO 1996/014339 A1 | 5/1996 |
| WO | WO 1998/005787 A1 | 2/1998 |
| WO | WO 1998/023289 A1 | 6/1998 |
| WO | WO 1999/051642 A1 | 10/1999 |
| WO | WO 1999/058572 A1 | 11/1999 |
| WO | WO 2000/009560 A2 | 2/2000 |
| WO | WO 2000/032767 A1 | 6/2000 |
| WO | WO 2000/042072 A2 | 7/2000 |
| WO | WO 2001/087922 A2 | 11/2001 |
| WO | WO 2002/044215 A2 | 6/2002 |
| WO | WO 2002/060919 A2 | 8/2002 |
| WO | WO 2003/074569 A2 | 9/2003 |
| WO | WO 2003/077834 A2 | 9/2003 |
| WO | WO 2003/100053 A1 | 12/2003 |
| WO | WO 2004/005347 A1 | 1/2004 |
| WO | WO 2004/016750 A2 | 2/2004 |
| WO | WO 2004/029207 A2 | 4/2004 |
| WO | WO 2004/035752 A2 | 4/2004 |
| WO | WO 2004/044859 A1 | 5/2004 |
| WO | WO 2004/063351 A2 | 7/2004 |
| WO | WO 2004/074455 A2 | 9/2004 |
| WO | WO 2004/099249 A2 | 11/2004 |
| WO | WO 2004/101740 A2 | 11/2004 |
| WO | WO 2004/113493 A2 | 12/2004 |
| WO | WO 2005/040217 A2 | 5/2005 |
| WO | WO 2005/047327 A2 | 5/2005 |
| WO | WO 2005/070963 A1 | 8/2005 |
| WO | WO 2005/077981 A2 | 8/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/085967 A2 | 8/2006 |
| WO | WO 2007/021494 A2 | 2/2007 |
| WO | WO 2007/077561 A2 | 7/2007 |
| WO | WO 2007/104529 A2 | 9/2007 |
| WO | WO 2007/112005 A2 | 10/2007 |
| WO | WO 2007/115953 A1 | 10/2007 |
| WO | WO 2008/012543 A1 | 1/2008 |
| WO | WO 2008/033413 A2 | 3/2008 |
| WO | WO 2008/143954 A2 | 11/2008 |
| WO | WO 2008/155134 A1 | 12/2008 |
| WO | WO 2009/058322 A1 | 5/2009 |
| WO | WO 2010/091122 A1 | 8/2010 |
| WO | WO 2010/115866 A1 | 10/2010 |
| WO | WO 2010/140148 A1 | 12/2010 |
| WO | WO 2010/144502 A2 | 12/2010 |
| WO | WO 2010/144508 A1 | 12/2010 |
| WO | WO 2011/028228 A1 | 3/2011 |
| WO | WO 2011/028229 A1 | 3/2011 |
| WO | WO 2011/028344 A2 | 3/2011 |
| WO | WO 2011/069164 A2 | 6/2011 |
| WO | WO 2012/006623 A1 | 1/2012 |
| WO | WO 2012/006624 A2 | 1/2012 |
| WO | WO 2012/006633 A1 | 1/2012 |
| WO | WO 2012/006635 A1 | 1/2012 |
| WO | WO 2012/170969 A2 | 12/2012 |
| WO | WO 2013/009627 A2 | 1/2013 |
| WO | WO 2013/106787 A1 | 7/2013 |
| WO | WO 2013/123457 A1 | 8/2013 |

(56) References Cited

FOREIGN PATENT DOCUMENTS

| WO | WO 2013/185113 A1 | 12/2013 |
|---|---|---|
| WO | WO 2013/185114 A2 | 12/2013 |

OTHER PUBLICATIONS

Andrianomenjanahary, et al. (1992) "Synthesis of Novel Targeted Pro-Prodrugs of Anthracyclines Potentially Activated by a Monoclonal Antibody Galactosidase (Part 1)", Bioorganic & Medicinal Chemistry Letters vol. 2, Issue 9, pp. 1093-1096.
Armour, et al. (Aug. 1999) "Recombinant Human IgG Molecules Lacking Fcgamma Receptor I Binding and Monocyte Triggering Activities", European Journal of Immunology, vol. 29, No. 8, pp. 2613-2624.
Bajaj, et al. (Aug. 1, 1983) "Redetermination of the Rate-Limiting Step in the Activation of Factor IX by Factor XIa and by Factor VIIa/tissue Factor. Explanation for Different Electrophoretic Radioactivity Profiles Obtained on Activation of 3H—and 125I-Labeled Factor IX", Biochemistry, vol. 22, No. 17, pp. 4047-4053.
Bertrand, et al. (2007) "Click Chemistry with O-Dimethylpropargylcarbamate for Preparation of pH-Sensitive Functional Groups. A Case Study", The Journal of Organic Chemistry, vol. 72, No. 9, pp. 3596-3599.
Biogen Idec (Feb. 24, 2016) "Hemophilia R&D Roundtable", phx.corporate-ir.net, accessed at http://www.google.de/url?sa=t&rct=j&q=&esrc=s&source=web&cd=9&ved=0ahUKEwi9rODXvpDLAhXkbZoKHbeJDXIQFghfMAg&url=http%3A%2F%2Fphx.corporate-ir.net%2FExternal.File%3Fitem%3DUGFyZW50SUQ9NDQwMDk1fENoaWxkSUQ9NDYxNzcxfFR5cGU9MQ%3D%3D%26t%3D1&usg=AFQjCNHEQPyuN7AIPzPikX2uAUL5fv5JoQ&sig2=8Ur9s6EFYDdNUXKKaqwzQ, accessed on Feb. 24, 2016, 52 Pages (2011).
Bird, et al. (Oct. 21, 1988) "Single-Chain Antigen-Binding Proteins", Science, vol. 242, No. 4877, pp. 423-426.
Blencowe (2011) "Self-Immolative Linkers in Polymeric Delivery Systems", Polymer Chemistry, vol. 2, No. 4, pp. 773-790.
Bovenschen, et al. (2005) "LDL receptor cooperates with LDL receptor-related protein in regulating plasma levels of coagulation factor VIII in vivo", Blood, vol. 106, pp. 906-912.
Bovenschen (2010) "LDL Receptor Polymorphisms Revisited", Blood, vol. 116, No. 25, pp. 5439-5440.
Brady, et al. (Oct. 10, 2002) "Design and synthesis of a pro-drug of vinblastine targeted at treatment of prostate cancer with enhanced efficacy and reduced systemic toxicity", Journal of medical chemistry, vol. 45, No. 21, pp. 4706-4715.
Brandstetter, et al. (Oct. 10, 1995) "X-ray Structure of Clotting Factor IXa: Active Site and Module Structure Related to Xase Activity and Hemophilia B", Proceedings of the National Academy of Sciences of the United States of America, vol. 92, No. 21, pp. 9796-9800.
Brunetti-Pierri, et al. (2009) "Bioengineered Factor IX Molecules with Increased Catalytic Activity Improve the Therapeutic Index of Gene Therapy Vectors for Hemophilia B", Human Gene Therapy, vol. 20, pp. 479-485.
Bunce, et al. (Jan. 6, 2011) "Zymogen-like factor Xa variants restore thrombin generation and effectively bypass the intrinsic pathway in vitro", Blood, vol. 117, No. 1, pp. 290-298.
Burmeister, et al. (Nov. 24, 1994) "Crystal Structure of The Complex of Rat Neonatal Fc Receptor with Fc", Nature, vol. 372, No. 6504, pp. 379-383.
Caliceti, et al. (1999) "Biopharmaceutical Properties of Uricase Conjugated to Neutral and Amphiphilic Polymers", Bioconjugate Chemistry, vol. 10, No. 4, pp. 638-646.
Capon, et al. (Feb. 9, 1989) "Designing CD4 Immunoadhesins For AIDS Therapy", Nature, vol. 337, No. 6207, pp. 525-531.
Carl, et al. (May 1981) "A novel connector linkage applicable in prodrug design", Journal of medicinal chemistry, vol. 24, No. 5, pp. 479-480.

Chang, et al. (May 15, 1998) "Changing Residue 338 in Human Factor IX from Arginine to Alanine Causes an Increase in Catalytic Activity", Journal of biological chemistry, vol. 273, p. 12089-12094.
Cho, et al. (Nov. 22, 1994) "Polysialic Acid Engineering: Synthesis of Polysialylated Neoglycosphingolipids By Using the Polysialyltransferase From Neuroinvasive *Escherichia coli* K1", Proceedings of the National Academy of Sciences of the United States of America, vol. 91, No. 24, pp. 11427-11431.
Claeson et al. (Jun. 1981) "Small Synthetic Peptides with Affinity for Proteases in Coagulation and Fibrinolysis: An Overview", Annals of the New York Academy of Sciences, vol. 370, Issue 1, pp. 798-811.
Cripe, et al. (1992) "Structure of the gene for human coagulation factor V", Biochemistry, vol. 31, No. 15, pp. 3777-3785.
Dawson, et al. (2000) "Synthesis of Native Proteins by Chemical Ligation", Annual Review of biochemistry, vol. 69, pp. 923-960.
Delgado, et al. (1992) "The Uses and Properties Of PEG-Linked Proteins", Critical Reviews in Therapeutic Drug Carrier Systems, vol. 9, No. 3-4, pp. 249-304.
Dennis, et al. (Sep. 20, 2002) "Albumin Binding as a General Strategy for Improving the Pharmacokinetics of Proteins", Journal of Biological Chemistry, vol. 277, No. 38, pp. 35035-35043.
De Groot, et al. (2001) "Elongated Multiple Electronic Cascade and Cyclization Spacer Systems in Activatible Anticancer Prodrugs for Enhanced Drug Release", The Journal of Organic Chemistry, vol. 66, No. 26, pp. 8815-8830.
Doronina (Jul. 2003) "Development of Potent Monoclonal Antibody Auristatin Conjugates for Cancer Therapy", Nature Biotechnology, vol. 21, No. 7, pp. 778-784.
Dumont, et al. (Mar. 29, 2012) "Prolonged Activity of a Recombinant Factor VIII-Fc Fusion Protein in Hemophilia A Mice and Dogs", Blood, vol. 119, No. 13, pp. 3024-3030.
Eaton, et al. (Dec. 1986) "Construction and Characterization of an Active Factor VIII Variant Lacking the Central One-Third of the Molecule", Biochemistry, vol. 25, No. 26, pp. 8343-8347.
Eaton, et al. (1986.) "Proteolytic Processing of Human Factor VIII. Correlation of Specific Cleavages by Thrombin, Factor Xa, and Activated Protein C with Activation and Inactivation of Factor VIII Coagulant Activity", Biochemistry, vol. 25, No. 2, pp. 505-512.
Elsadek et al. (May 26, 2010) "Optimization of an Albumin-Binding Prodrug of Doxorubicin That is Cleaved by Prostate-Specific Antigen", ACS Medicinal Chemistry Letters, vol. 5, No. 5, pp. 234-238.
Everett, et al. (May 3, 1999) "Bioreductively-Activated Prodrugs for Targeting Hypoxic Tissues: Elimination of Aspirin From 2-Nitroimidazole Derivatives", Bioorganic Medicinal Chemistry Letters, vol. 9, No. 9, pp. 1267-1272.
Extended European Search Report received for European Patent Application No. 13799824.1, dated Jul. 7, 2016, 14 Pages.
Extended European Search Report received for European Patent Application No. 13799785.4, dated Aug. 25, 2016, 15 Pages.
Fay, et al. (1991) "Human Factor VIIIa Subunit Structure. Reconstruction of Factor VIIIa from the Isolated A1/A3-C1-C2 Dimer and A2 Subunit", The Journal of Biological Chemistry, vol. 266, No. 14, pp. 8957-8962.
Frank, et al. (1992) "Spot-Synthesis: An Easy Technique for the Positionally Addressable, Parallel Chemical Synthesis on a Membrane Support", Tetrahedron, vol. 48, No. 42, pp. 9217-9232.
Friend, et al. (Dec. 15, 1999) "Phase I Study of an Engineered Aglycosylated Humanized Cd3 Antibody in Renal Transplant Rejection1", Transplantation, vol. 68, Issue 11, pp. 1632-1637.
Gallwitz, et al. (2012) "The Extended Cleavage Specificity of Human Thrombin", PloS One, Public Library of Science, vol. 7, No. 2, e31756.
Genbank Database (Jan. 14, 1995) "Human Transferrin mRNA, Complete cds", GenBank Accession No. M12530.1, accessed at http://www.ncbi.nlm.nih.gov/nuccore/M1253014, 2 Pages.
Genbank Database (May 7, 1993) "Transferrin [human, liver, mRNA, 2347 nt]", Accession No. S95936.1, accessed at http://www.ncbi.nlm.nih.gov/nuccore/S95936, 2 Pages.
Genbank Database (May 13, 2002) "*Homo sapiens* Transferrin (TF), mRNA", GenBank accession No. XM002793, accessed at

(56) References Cited

OTHER PUBLICATIONS https://www.ncbi.nlm.nih.gov/nuccore/XM_002793.7?report=genbank, accessed on Sep. 24, 2014, 2 Pages.

Genbank Database (Jul. 16, 2001) "*Homo sapiens* Transferrin (TF), mRNA", GenBank accession No. XM039845, accessed at https://www.ncbi.nlm.nih.gov/nuccore/XM_039845.1 ?report=genbank, 2 Pages.

Genbank Database (Jul. 16, 2001) "*Homo sapiens* Transferrin (TF), mRNA", GenBank accession No. XM039847, accessed at https://www.ncbi.nlm.nih.gov/nuccore/XM_039847.1 ?report=genbank, accessed on Sep. 24, 2014, 2 Pages.

Genbank Database (May 25, 2014) "*Homo sapiens* Transferrin (TF), Transcript Variant 1, mRNA", Accession No. NM001063.3, accessed at http://www.ncbi.nlm.nih.gov/nuccore/NM_001063, 5 Pages.

Genbank Database (Jan. 14, 1995) "Transferrin Precursor [*Homo sapiens*]", Accession No. AAA61140.1, accessed at http://www.ncbi.nlm.nih.gov/protein/AAA61140.1, 1 Page.

Geys, et al. (2008) "Acute Toxicity and Prothrombotic Effects of Quantum Dots: Impact of Surface Charge", Environmental Health Perspectives, vol. 116, No. 12, pp. 1607-1613.

Gitschier, et al. (Nov. 22-28, 1984) "Characterization of the Human Factor VIII Gene", Nature, vol. 312, No. 5992, pp. 326-330.

Greenwald, et al. (Feb. 10, 2000) "Drug Delivery Systems Based on Trimethyl Lock Lactonization: Poly (Ethylene Glycol) Prodrugs of Amino-Containing Compounds", Journal of medicinal chemistry, vol. 43, No. 3, pp. 475-487.

Hay, et al. (Dec. 1997) "A New Synthesis of Carmethizole and Related Nitrogen Analogues", Tetrahedron Letters, vol. 38, No. 48, pp. 8425-8428.

Hay, et al. (1999) "Substituent Effects on the Kinetics of Reductively-Initiated Fragmentation of Nitrobenzyl Carbamates Designed as Triggers for Bioreductive Prodrugs", Journal of chemical Society, Issue 19, pp. 2759-2770.

Hay, et al. (2003) "Synthesis and Evaluation of Nitroheterocyclic Carbamate Prodrugs for Use with Nitroreductase-Mediated Gene-Directed Enzyme Prodrug Therapy", Journal of medicinal chemistry, vol. 46, No. 25, pp. 5533-5545.

Ho, et al. (Apr. 15, 1989) "Site-Directed Mutagenesis by Overlap Extension Using the Polymerase Chain Reaction", Gene, vol. 77, No. 1, pp. 51-59.

Hoeben, et al. (1990) "Expression of Functional Factor VIII in Primary Human Skin Fibroblasts After Retrovirus-Mediated Gene Transfer", Journal of Biological Chemistry, vol. 265, No. 13, pp. 7318-7323.

Holt, et al. (May 2008) "Anti-Serum Albumin Domain Antibodies for Extending the Half-Lives of Short Lived Drugs", Protein Engineering, Design and Selection, vol. 21, No. 5, pp. 283-288.

International Search Report and Written Opinion received for PCT Patent Application No. PCT/US2013/044841, dated Nov. 20, 2013, 18 Pages.

International Search Report and Written Opinion received for PCT Patent Application No. PCT/US2013/44842, dated Nov. 25, 2013, 11 Pages.

International Search Report and Written Opinion received for PCT Patent Application No. PCT/US2011/48517, dated Mar. 14, 2012.

Israel, et al. (Sep. 1997) "Expression of the Neonatal Fc Receptor, FcRn, on Human Intestinal Epithelial Cells", Immunology, vol. 92, No. 1, pp. 69-74.

Izquierdo, et al. (1989) "Synthetic Substrates for Thrombin", International Journal of Biochemistry, vol. 21, Issue 6, pp. 579-592.

Jaffer, et al. (2002) "In Vivo Imaging of Thrombin Activity in Experimental Thrombi with Thrombin-Sensitive Near-Infrared Molecular Probe", Arteriosclerosis Thrombosis and Vascular Biology, vol. 22, No. 11, pp. 1929-1935.

Janeway, et al. (2001) "Immunobiology: the immune system in health and disease.", 5th edition, p. 235.

Jenny, et al. (1987) "Complete cDNA and Derived Amino Acid Sequence of Human Factor V", Proceedings of the National Academy of Sciences USA, vol. 84, No. 14, pp. 4846-4850.

Kane, et al. (1986) "Cloning of a cDNA Coding for Human Factor V, A Blood Coagulation Factor Homologous to Factor VIII and Ceruloplasmin", Proceedings of the National Academy of Sciences USA, vol. 83, No. 18, pp. 6800-6804.

Kobayashi, et al. (Feb. 2002) "FcRn-Mediated Transcytosis of Immunoglobulin G in Human Renal Proximal Tubular Epithelial Cells", American Journal of Physiology-Renal Physiology, vol. 282, No. 2, pp. F358-F365.

Kohchi, et al. (2007) "Design and Synthesis of Novel Prodrugs of 2'-Deoxy-2'—Methylidenecytidine Activated by Membrane Dipeptidase Overexpressed in Tumor Tissues", Bioorganic & Medicinal Chemistry Letters, vol. 17, No. 8, pp. 2241-2245.

Konig, et al. (Sep. 1, 1998) "Use of an Albumin-Binding Domain for the Selective Immobilisation of Recombinant Capture Antibody Fragments on ELISA Plates", Journal of Immunological Methods, vol. 218, No. 1-2, pp. 73-83.

Kraulis, et al. (Jan. 8, 1996) "The Serum Albumin-Binding Domain of Streptococcal Protein G is a Three-Helical Bundle: A Heteronuclear NMR Study", FEBS Letters, vol. 378, Issue 2, pp. 190-194.

Langner, et al. (Apr. 1988) "Synthesis of Biologically Active Deletion Mutants of Human Factor VIII:C", Behring Institute Mitteilungen, No. 82, pp. 16-25.

Lenting, et al. (2010) "The Disappearing Act of Factor VIII", Haemopbilia, vol. 16, No. 102, pp. 6-15.

Lin, et al. (Aug. 2010) "Generation of a Novel Factor IX with Augmented Clotting Activities in Vitro and in Vivo", Journal of Thrombosis and Haemostasis, vol. 8, No. 8, pp. 1773-1783.

Linhult, et al. (Feb. 2002) "Mutational Analysis of the Interaction Between Albumin-Binding Domain from Streptococcal Protein G and Human Serum Albumin", Protein Science, vol. 11, No. 2, pp. 206-213.

Lollar, et al. (Jul. 5, 1991) "Structural Basis for the Deceased Procoagulant Activity of Human Factor VIII Compared to the Porcine Homolog", Journal of biological chemistry, vol. 266, Number, pp. 12481-12486.

Louvain-Quintard, et al. (2005) "Thrombin-Activable Factor X Re-Establishes an Intrinsic Amplification in Tenase-Deficient Plasmas", The Journal of Biological Chemistry, vol. 280, No. 50, pp. 41352-41359.

Lusson, et al. (Jul. 15, 1993) "cDNA Structure of the Mouse and Rat Subtilisin/Kexin-Like Pc5: A Candidate Proprotein Convertase Expressed in Endocrine and Nonendocrine Cells", Proceedings of the National Academy of Sciences of the United States of America, vol. 90, No. 14, pp. 6991-6995.

Martinelli, et al. (2010) "Polymorphisms at LDLR Locus May Be Associated with Coronary Artery Disease Through Modulation of Coagulation Factor VIII Activity and Independently from Lipid Profile", Blood, vol. 116, pp. 5688-5697.

McKnight, et al. (Sep. 1983) "Expression of the Chicken Transferrin Gene in Transgenic Mice", Cell, vol. 34, Issue 2, pp. 335-341.

Mei, et al. (Jul. 15, 2010) "Rational Design of a Fully Active, Long-Acting PEGylated Factor VIII for Hemophilia A Treatment", Blood, vol. 116, No. 2, pp. 270-279.

Meulien, et al. (1988) "A New Recombinant Procoagulant Protein Derived from the cDNA Encoding Human Factor VIII", Protein Engineering, Design and Selection, vol. 2, No. 4, pp. 301-306.

Meyer (2010) "A Comparative Study of the Self-Immolation of Para-Aminobenzylalcohol and Hemithioaminal-Based Linkers in the Context of Protease-Sensitive Fluorogenic Probes", Organic & Biomolecular Chemistry, vol. 8, No. 8, pp. 1777-1780.

Milenic, et al. (Dec. 1991) "Construction, Binding Properties, Metabolism, and Tumor Targeting of a Single-Chain Fv Derived from the Pancarcinoma Monoclonal Antibody CC49", Cancer research, vol. 51, No. 23 part 1, pp. 6363-6371.

Morpurgo, et al. (Jan. 1996) "Covalent Modification of Mushroom Tyrosinase With Different Amphiphic Polymers for Pharmaceutical and Biocatalysis Applications", Applied Biochemistry and Biotechnology, vol. 56, No. 1, pp. 59-72.

Mount, et al. (Apr. 15, 2002) "Sustained Phenotypic Correction of Hemophilia B Dogs with A Factor IX Null Mutation by Liver-Directed Gene Therapy", Blood, vol. 99, No. 8, pp. 2670-2676.

(56) References Cited

OTHER PUBLICATIONS

Muller, et al. (Aug. 2007) "Recombinant Bispecific Antibodies for Cellular Cancer Immunotherapy", Current opinion in molecular therapeutics, vol. 9, No. 4, pp. 319-326.
Nakagawa, et al. (Feb. 1993) "Identification and Functional Expression of a New Member of the Mammalian Kex2-Like Processing Endoprotease Family: Its Striking Structural Similarity to PACE4", The journal of biochemistry, vol. 113, No. 2, pp. 132-135.
Nakayama, Kazuhisa (1997) "Furin: A Mammalian Subtilisin/Kex2p-Like Endoprotease Involved in Processing of a Wide Variety of Precursor Proteins", Biochemical Journal, vol. 327, pp. 625-635.
Narita, et al. (1998) "The Low-Density Lipoprotein Receptor-Related Protein (LRP) Mediates Clearance of Coagulation Factor Xa In Vivo", Blood, vol. 91, No. 2, pp. 555-560.
Neumann, et al. (1982) "Gene Transfer into Mouse Lyoma Cells by Electroporation in High Electric Fields", The EMBO Journal, vol. 1, No. 7, pp. 841-845.
Noel, et al. (Mar. 11, 1990) "Nucleotide sequence of the coat protein gene and flanking regions of cucumber virus (CMV) strain 117F", Nucleic Acids Research, vol. 18, No. 5, pp. 1332.
Osterlund, et al. (Dec. 2,) "Sequential coagulation factor VIIa domain binding to tissue factor", Biochemical and biophysical research communication, vol. 337, No. 4, pp. 1276-1282.
Pan, et al. (Sep. 24, 2009) "Enhanced efficacy of recombinant FVIII in noncovalent complex with PEGylated liposome in hemophilia A mice", Blood Journal, vol. 114, No. 13, pp. 2802-2811.
Pantoliano, et al. (Oct. 22, 1991) "Conformational Stability, Folding, and Ligand-Binding Affinity of Single-Chain Fv Immunoglobulin Fragments Expressed in *Escherichia Coli*", Biochemistry, vol. 30, No. 42, p. 10117-10125.
Partial European Search Report received for European Patent Application No. 13799785.4, dated May 3, 2016, 7 Pages.
Perry-Feigenbaum (Dec. 7, 2009) "The Pyridinone-Methide Elimination", Organic & Biomolecular Chemistry, vol. 7, No. 23, pp. 4825-4828.
Persson, et al. (Nov. 2001) "Rational Design of Coagulation Factor VIIa Variants with Substantially Increased Intrinsic Activity", Proceedings of the National Academy of Sciences USA, vol. 98, No. 2, p. 13583-13588.
Persson, et al. (Jun. 1, 2001) "Substitution of Valine for Leucine 305 in Factor VIIa Increases the Intrinsic Enzymatic Activity", Journal of Biological Chemistry, vol. 276, No. 31, pp. 29195-29199.
Peters, et al. (Mar. 1, 2010) "Prolonged Activity of Factor IX as a Monomeric Fc Fusion Protein", Blood, vol. 115, No. 10, pp. 2057-2064.
Peterson (2003) "A Site Involving the "Hybrid" and PSI Homology Do (Beta 3-lntegrin Subunit) is a Common Target for Antibodies Associated with Mains of GPIIIA Quinine-Induced Immune Thrombocytopenia", Blood, vol. 101, No. 3, pp. 937-942.
Petrovan, et al. (Nov. 14, 2000) "Residue Met156 Contributes to the Labile Enzyme Conformation of Coagulation Factor VIIa", The Journal of Biological Chemistry, vol. 276, No. 9, pp. 6616-6620.
Peyvandi, et al. (Jul. 2006) "Genetic Diagnosis of Haemophilia and Other Inherited Bleeding Disorders", Haemophilia, vol. 12, Supplement 3, pp. 82-89.
Rautio, et al. (Mar. 2008) "Prodrugs: Design and Clinical Applications", Nature Reviews, vol. 7, No. 3, pp. 255-270.
Rehemtulla, et al. (1993) "PACE4 is a Member of the Mammalian Propeptidase Family That Has Overlapping but Not Identical Substrate Specificity to PACE", Biochemistry, vol. 32, No. 43, p. 11586-11590.
Rijkers, et al. (1995) "Design and Synthesis of Thrombin Substrates with Modified Kinetic Parameters", Thrombosis Research, vol. 79, No. 5-6, pp. 491-499.
Ritchie, et al. (Dec. 6, 1984) "Allelic Exclusion and Control of Endogenous Immunoglobulin Gene Rearrangement in K Transgenic Mice", Nature, vol. 312, No. 5994, pp. 517-520.
Roovers, et al. (Mar. 2007) "Efficient Inhibition of EGFR Signaling and of Tumour Growth by Antagonistic anti-EFGR Nanobodies", Cancer Immunology, Immunotherapy, vol. 56, No. 3, pp. 303-317.
Rostin, et al. (May 15, 2000) "B-Domain Deleted Recombinant Coagulation Factor VIII Modified with Monomethoxy Polyethylene Glycol", Bioconjugate Chemistry, vol. 11, No. 3, pp. 387-396.
Roth, et al. (1993) "Expression of Polysialic Acid in Human Tumors and Its Significance for Tumor Growth", Polysialic Acid: From microbes to man, Edited by Roth et al., pp. 335-348.
Routledge, et al. (Oct. 1, 1995) "The Effect of Aglycosylation on the Immunogenicity of a Humanized Therapeutic CD3 Monoclonal Antibody", Transplantation, vol. 60, No. 8, pp. 847-853.
Salas, J, et al. (Jul. 26, 2011) "Enhanced Pharmacokinetics of factor VIIA as a monomeric FC Fusion", Journal of Thrombosis and Haemostasis, vol. 9, Supplement 2, Abstract O-TU-026, p. 268.
Salas, et al. (2011) "Targeting factor VIIa to platelet receptors results in enhanced activity", Journal of Thrombosis and Haemostasis, Supplement 2, Abstract O-TU-078, p. 285.
Sarver, et al. (Dec. 1987) "Stable Expression of Recombinant Factor Viii Molecules Using a Bovine Papillomavirus Vector", DNA, vol. 6, No. 6, pp. 553-564.
Schulte, Stefan (Dec. 2008) "Use of Albumin Fusion Technology to Prolong the Half-Life of Recombinant Factor", Thrombosis Research, vol. 122, Supplement 4, pp. S14-S19.
Schwarz, et al. (2006) "Conformation-Specific Blockade of the Integrin GPIIb/IIIa: A Novel Antiplatelet Strategy that Selectively Targets Activated Platelets", Circulation Research, vol. 99, No. 1, pp. 25-33.
Senter, et al. (Apr. 1, 1990) "Development of a drug-release strategy based on the reductive fragmentation of benzyl carbamate disulfides", The journal of organic chemistry, vol. 55, No. 9, pp. 2975-2978.
Shields, et al. (Mar. 2, 2001) "High Resolution Mapping of the Binding Site on Human lgG1 for Fc Gamma RI, Fc Gamma RII, Fc Gamma RIII, and FcRn and Design of lgG1 Variants with Improved Binding to The Fc Gamma R", Journal of Biological Chemistry, vol. 276, No. 9, pp. 6591-6604.
Sichler, et al. (Feb. 7, 2003) "Physiological FIXA Activation Involves a Cooperative Conformational Rearrangement of the 99-Loop", The Journal of Biological Chemistry, vol. 278, No. 6, pp. 4121-4126.
Simioni, et al. (Oct. 22, 2009) "X-Linked Thrombophilia with a Mutant Factor Ix (Factor Ix Padua)", The New England Journal of Medicine, vol. 361, No. 17, pp. 1671-1675.
Simplicio, et al. (Mar. 3, 2008) "Prodrugs for Amines", Molecules, vol. 13, No. 3, pp. 519-547.
Singh, et al. (2008) "Recent Trends in Targeted Anticancer Prodrug and Conjugate Design", Current Medicinal Chemistry, vol. 15, No. 18, pp. 1802-1826.
Soejima, et al. (Feb. 2, 2001) "Factor VIIa Modified in the 170 Loop Shows Enhanced Catalytic Activity but does not Change the Zymogen-like Property", The Journal of Biological Chemistry, vol. 276, No. 20, pp. 17229-17235.
Soejima, et al. (Oct. 2, 2002) "The 99 and 170 Loop-Modified Factor VIIa Mutants Show Enhanced Catalytic Activity Without Tissue Factor", The Journal of Biological Chemistry, vol. 277, No. 50, pp. 49027-49035.
Sommermeyer, et al. (1987) "Klinisch verwendete Hydroxyethylstärke: physikalischchemische Charakterisierung", Krankenhauspharmazie, vol. 8, No. 8, Deutscher Apotheker Verlag, Birkenwaldstr, Germany, pp. 271-278.
Spicer, et al. (1987) "Isolation of cDNA clones coding for human tissue factor: primary structure of the protein and cDNA", Proceedings of the National Academy of Sciences USA, vol. 84, No. 15, pp. 5148-5152.
Spira, et al. (2006) "Prolonged Bleeding-Free Period Following Prophylactic Infusion of Recombinant Factor VIII Reconstituted with Pegylated Liposomes", Blood, vol. 108, No. 12, pp. 3668-3673.
Spitzer, et al. (Jan. 1, 1990) "Replacement of lsoleucine-397 by Threonine in the Clotting Proteinase Factor IXa (Los Angeles and Long Beach Variants) Affects Macromolecular Catalysis but not L-tosylarginine Methyl Ester Hydrolysis", Biochemical Journal, vol. 265, No. 1, pp. 219-225.
Stennicke, et al. (2008) "Generation and Biochemical Characterization of Glycopegylated Factor Vila Derivatives", Thrombosis and Haemostasis, vol. 100, No. 5, pp. 920-928.

(56) References Cited

OTHER PUBLICATIONS

Story, et al. (Dec. 1, 1994) "A Major Histocompatibility Complex Class I-like Fc Receptor Cloned from Human Placenta: Possible Role in Transfer of Immunoglobulin G from Mother to Fetus", Journal of Experimental Medicine, vol. 180, No. 6, pp. 2377-2381.

Strickland, et al. (Jul. 2006) "Low-Density Lipoprotein Receptor-Related Protein (LRP)-Mediated Clearance of Activated Blood Coagulation Co-Factors and Proteases: Clearance Mechanism or Regulation?", Journal of Thrombosis and Haemostasis, vol. 4, No. 7, pp. 1484-1486.

Stubbs, et al. (1990) "CDNA Cloning of a Mouse Mammary Epithelial Cell Surface Protein Reveals the Existence of Epidermal Growth Factor-Like Domains Linked to Factor VIII-Like Sequences", Proceedings of the National Academy of Sciences, vol. 87, No. 21, pp. 8417-8421.

Sturzebecher, et al. (Jul. 28, 1997) "Dramatic enhancement of the catalytic activity of coagulation factor IXa by alcohols", The Federation of the European Biochemical Societies Letters, vol. 412, No. 2, pp. 295-300.

Supplementary European Search Report received for European Patent Application No. 13799824.1, dated Mar. 10, 2016, 10 Pages.

Sykes, et al. (2000) "Leaving group effects in reductively triggered fragmentation of 4-nitrobenzyl carbamates", Journal of chemical Society, Perkin transaction 1, pp. 1601-1608.

Takahashi, et al. (1984) "Single-Chain Structure of Human Ceruloplasmin: The Complete Amino Acid Sequence of the Whole Molecule", Proceedings of the National Academy of Sciences, vol. 81, No. 2, pp. 390-394.

Takkinen, et al. (Oct. 1, 1991) "An Active Single-Chain Antibody Containing a Cellulase Linker Domain is Secreted by *Escherichia coli*", Protein Engineering design and selection, vol. 4, Issue 7, pp. 837-841.

Tan, et al. (Dec. 2014) "Paper: Enhancing the Acute Hemostatic Efficacy in Cynomolgus Monkeys by Targeting Activated Coagulation Factor VII to Platelets", Blood journal, vol. 124, No. 21, Abstract, p. 1488.

Tanihara, et al. (1998) "Thrombin-Sensitive Peptide Linkers for Biological Signal-Responsive Drug Release Systems", Peptides, vol. 19, No. 3, pp. 421-425.

Taylor, et al. (1978) "Use of o—and p. hydroxybenzyl functions as blocking groups which are removable with base", Journal of organic chemistry, vol. 43, No. 6, pp. 1197-1200.

Toole, et al. (Aug. 1986) "A Large Region (Approximately Equal To 95 kDa) of Human Factor VIII is Dispensable For In Vitro Procoagulant Activity", Proceedings of the National Academy of Sciences, vol. 83, No. 16, pp. 5939-5942.

Toole, et al. (Nov. 22-28, 1984) "Molecular Cloning Of a cDNA Encoding Human Antihaemophilic Factor", Nature, vol. 312, No. 5992, pp. 342-347.

Trussel, et al. (Dec. 2009) "New Strategy for the Extension of the Serum Half-Life of Antibody Fragments", Bioconjugate Chemistry, vol. 20, No. 12, pp. 2286-2292.

Tung, et al. (2002) "A Novel Near-Infrared Fluorescence Sensor for Detection of Thrombin Activation in Blood", European Journal of Chemical Biology, vol. 3, No. (2-3), pp. 207-211.

UNIPROTKB (May 15, 2015) "Coagulation factor V, *Homo sapiens* (Human)", Accession No. P12259, Retrieve From http://www.uniprot.org/uniprot/PI2259, 26 Pages.

UNIPROTKB (May 15, 2015) "Tissue Factor, *Homo sapiens* (human)", Accession No. P13726-1, accessed at http://www.uniprot.org/uniprot/P13726, accessed on May 15, 2015, 18 Pages.

Van Den Ouweland, et al. (Jan. 1990) "Structural Homology Between the Human Fur Gene Product and the Subtilisin-Like Protease Encoded by Yeast KEX2", Nucleic Acids Research, vol. 18, No. 3, pp. 664.

Vehar, et al. (Nov. 1984) "Structure of Human Factor VIII", Nature, vol. 312, No. 5992, pp. 337-342.

Vorobjev, et al. (Nov.-Dec. 1999) "Oligonucleotide Conjugated to Linear and Branched High Molecular Weight Polyethylene Glycol as Substrates for RNase H", Nucleosides and Nucleotides, vol. 18, No. 11-12, pp. 2745-2750.

Vysotchin, et al. (Apr. 25, 1993) "Domain Structure and Domain-Domain Interactions in Human Coagulation Factor IX*", Journal of Biological Chemistry, vol. 268, No. 12, pp. 8436-8446.

Ward, et al. (Apr. 1995) "The Effector Functions of Immunoglobulins: Implications for Therapy", Therapeutic immunology, vol. 2, No. 2, pp. 77-94.

Wasley, et al. (Apr. 25, 1993) "PACE/Furin can Process the Vitamin K-Dependent Pro-Factor IX Precursor within the Secretory Pathway", The Journal of Biological Chemistry, vol. 268, No. 12, pp. 8458-8465.

Weidler, et al. (May 1991) "Pharmacokinetic Parameters as Criteria for Clinical Use of Hydroxyethyl Starch Preparations", Arzneimittelforschung/Drug Research, vol. 41, No. 5, pp. 494-498.

Weinstain, et al. (2010) "Real-Time Monitoring of Drug Release", Chemical Communications, vol. 46, No. 4, pp. 553-555.

Wigler, et al. (Jul. 1978) "Biochemical Transfer of Single-Copy Eucaryotic Genes Using Total Cellular DNA as Donor", Cell, vol. 14, No. 3, pp. 725-731.

Wolberg, et al. (May 2012) "Tissue Factor 1-15 and Factor Vila—Hemostasis and Beyond", Thrombosis Research, vol. 129, Supplement 2, pp. S1-S4.

Wolf, et al. (1995) "Procoagulant Activity of Reversibly Acylated Human Factor Xa", Blood, vol. 86, No. 11, pp. 4153-4157.

Zogg, et al. (Dec. 9, 2009) "Structural Basis of The Cofactor—and Substrate-Assisted Activation of Human Coagulation Factor IXa", Structure, vol. 17, No. 12, pp. 1669-1678.

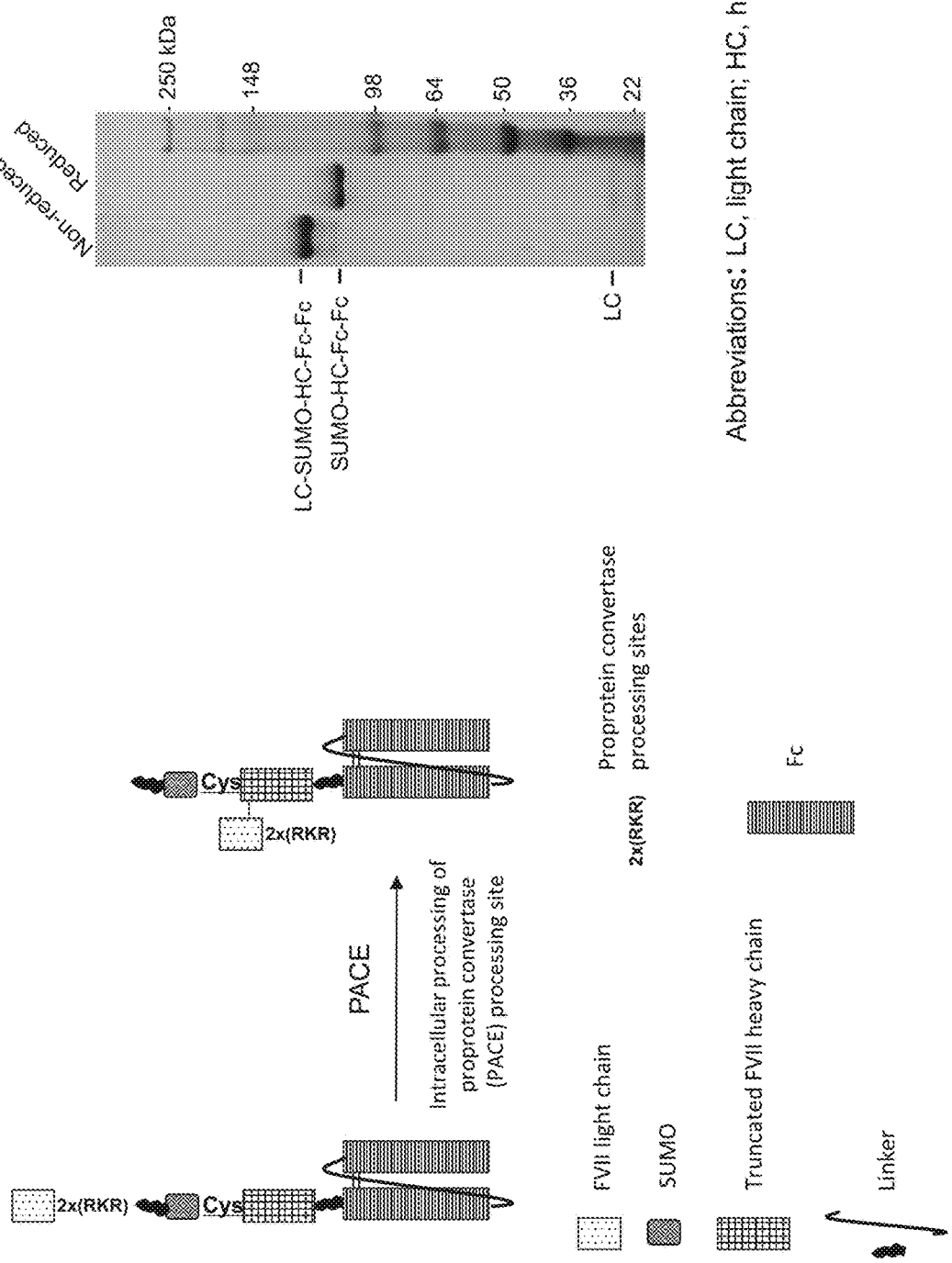

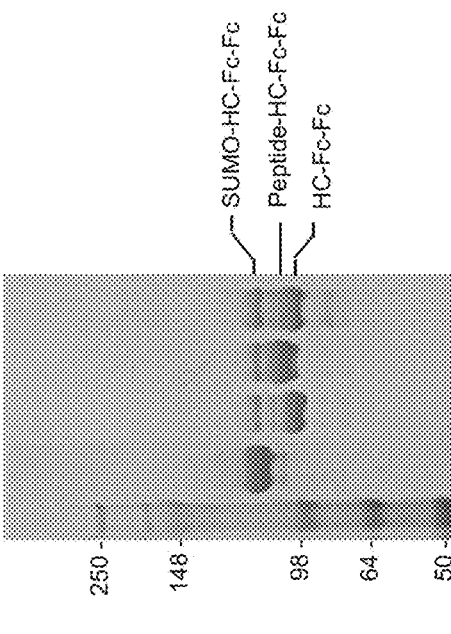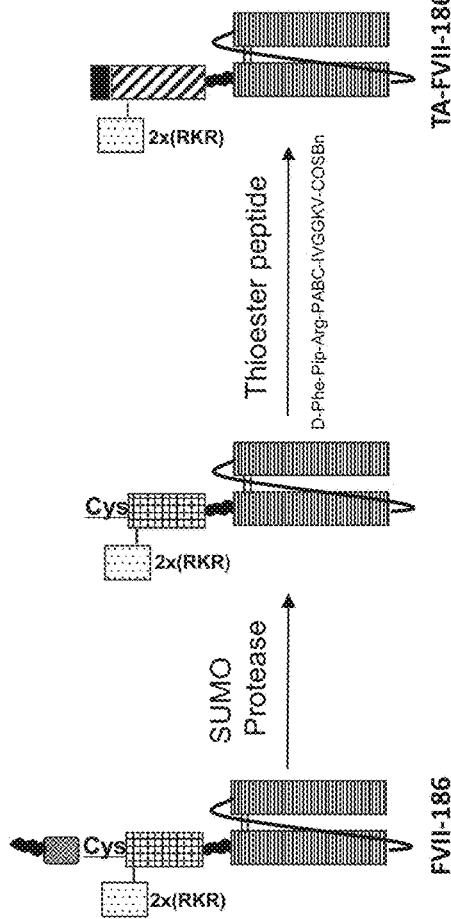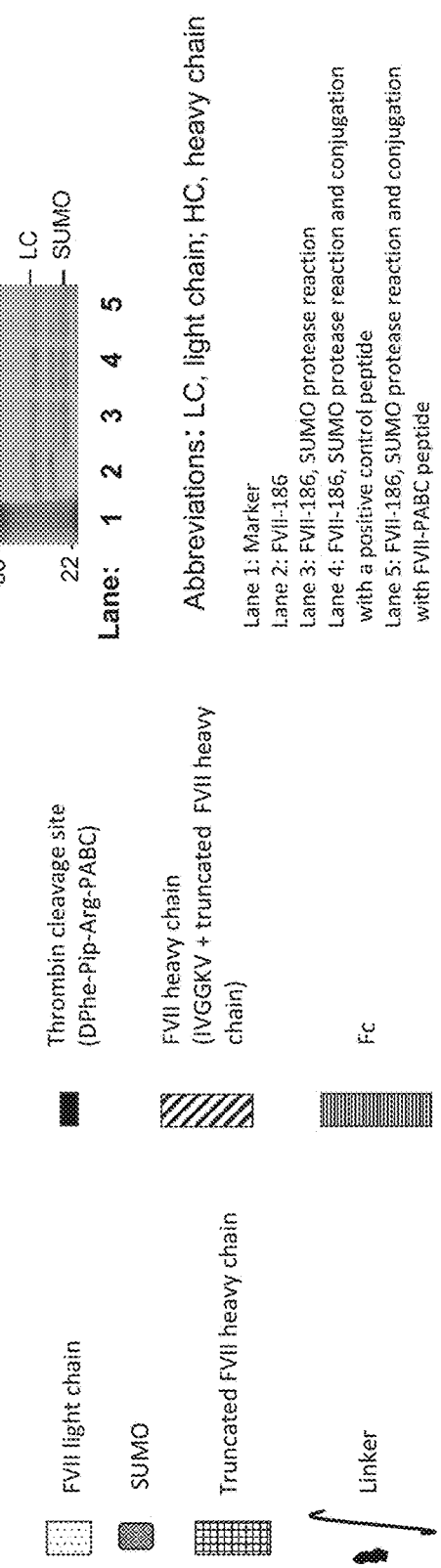

FX-011 Expression

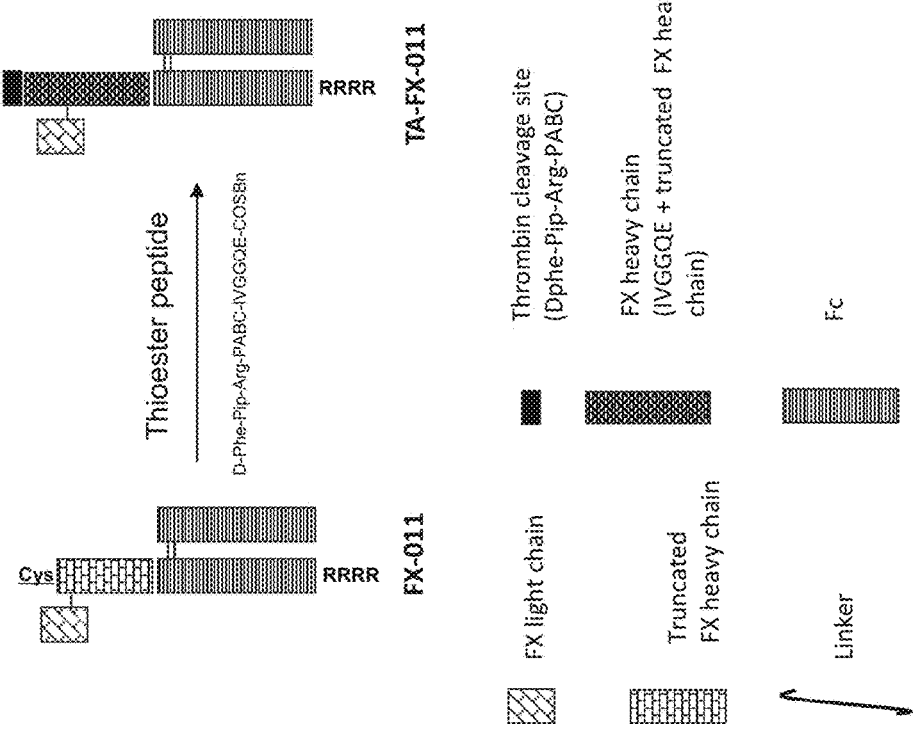

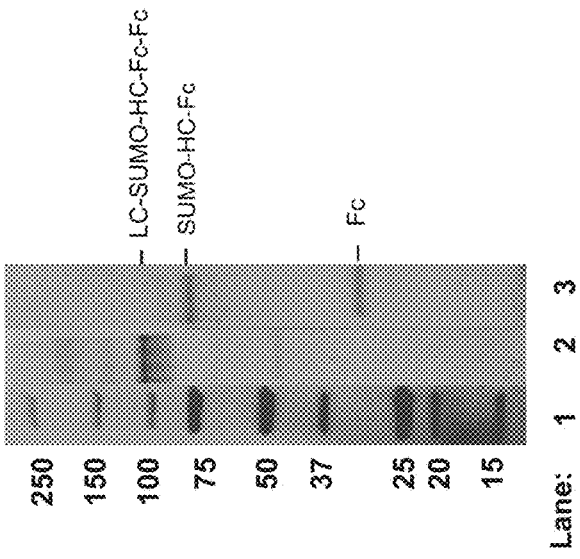
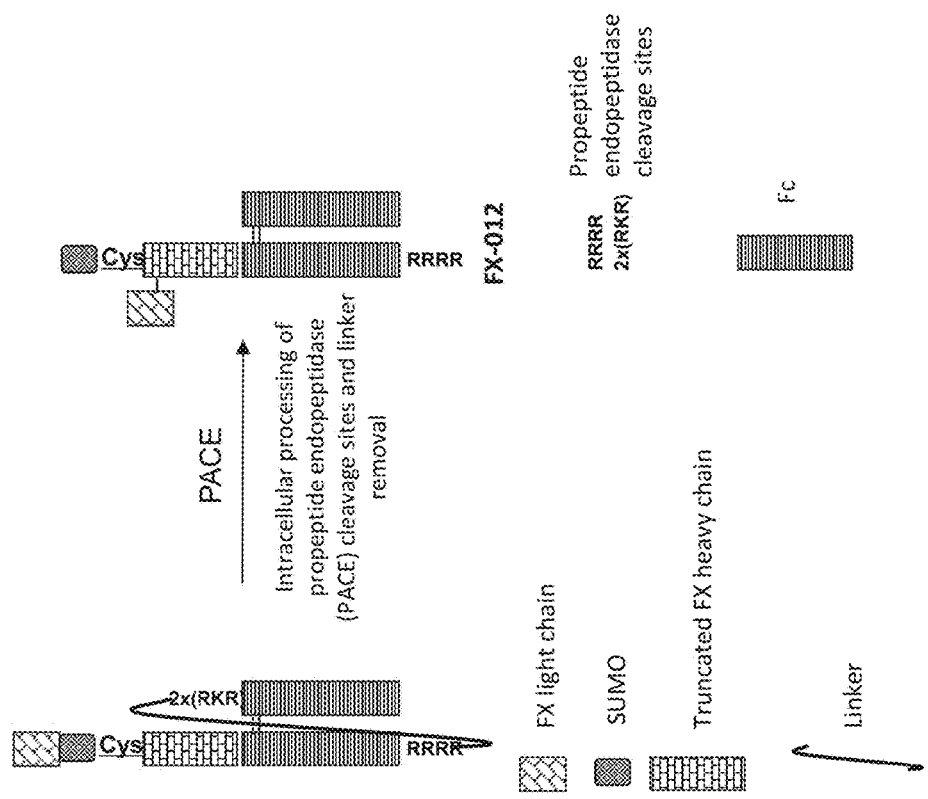

FX-012 SUMO Cleavage and TA-FX-012 Semisynthesis by Native Chemical Ligation

PROCOAGULANT COMPOUNDS

RELATED APPLICATIONS

This application is a division of U.S. patent application Ser. No. 14/406,163, filed Dec. 5, 2014, now U.S. Pat. No. 10,287,564, which is a 35 U.S.C. § 371 filing of International Patent Application No. PCT/US2013/044841, filed Jun. 7, 2013, which claims priority to U.S. Provisional Patent Application Ser. No. 61/800,626, filed Mar. 15, 2013, and 61/657,688, filed Jun. 8, 2012, the entire disclosures of which are hereby incorporated herein by reference.

BACKGROUND

Field of the Disclosure

The present invention relates to procoagulant compounds useful for the treatment of bleeding diseases or disorders.

Background

The blood coagulation pathway, in part, involves the formation of an enzymatic complex of Factor VIIIa (FVIIIa) and Factor IXa (FIXa) (Xase complex) on the surface of platelets. FIXa is a serine protease with relatively weak catalytic activity without its cofactor FVIIIa. The Xase complex cleaves Factor X (FX) into Factor Xa (FXa), which in turn interacts with Factor Va (FVa) to cleave prothrombin and generate thrombin. Hemophilia A is a bleeding disorder caused by mutations and/or deletions in the factor VIII (FVIII) gene resulting in a deficiency of FVIII activity (Peyvandi et al. 2006). Hemophilia B (also known as Christmas disease) is one of the most common inherited bleeding disorders in the world. It results in decreased in vivo and in vitro blood clotting activity and requires extensive medical monitoring throughout the life of the affected individual.

Treatment of hemophilia is by replacement therapy targeting restoration of clotting activity. There are plasma-derived and recombinant clotting factor products available to treat bleeding episodes on-demand or to prevent bleeding episodes from occurring by treating prophylactically. Based on the half-life of these products, treatment regimens require frequent intravenous administration. Such frequent administration is painful and inconvenient. Strategies to extend the half-life of clotting factors include pegylation (Rostin J, et al., *Bioconj. Chem.* 2000; 11:387-96), glycopegylation (Stennicke H R, et al., *Thromb. Haemost.* 2008; 100:920-8), formulation with pegylated liposomes (Spira J, et al., *Blood* 2006; 108:3668-3673, Pan J, et al., *Blood* 2009; 114:2802-2811) and conjugation with albumin (Schulte S., *Thromb. Res.* 2008; 122 Suppl 4:S14-9). However, modification of coagulation factors and procoagulant peptides with half-life extending moieties (e.g., PEG) and other similar strategies to extend their half-lives can lead to compromised activity. In order to rescue their activity, a cleavable linker can be inserted between the protein or peptide of interest and its modifier. The chosen cleavable linker must be cleaved efficiently and rapidly by a protease, for example, a protease involved in the coagulation cascade. Thrombin being the activator of many clotting factors is the most popular choice. However, all known substrate sequences composed of natural amino acids (e.g., LVPR, ALRPR (SEQ ID NO: 7), etc.) are not optimal substrates. Furthermore, covalent binding of the cleavable linker to a coagulation factors or procoagulant peptide can result in steric hindrances (e.g., due to the presence of amino acids such as such as proline, isoleucine or arginine C-terminal to the cleavage site) that can prevent an efficient enzymatic cleavage reaction.

BRIEF SUMMARY

The present disclosure provides procoagulant compounds comprising a protease-cleavable substrate (e.g., a synthetic thrombin substrate) and a self-immolative spacer (e.g., PABC) linked to a procoagulant polypeptide, e.g., a clotting factor or a procoagulant peptide. Accordingly, in some embodiments, the present disclosure provides A procoagulant compound having a formula:

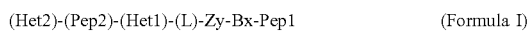
(Het2)-(Pep2)-(Het1)-(L)-Zy-Bx-Pep1           (Formula I)

wherein,

Het1 is a first heterologous molecule, which is either absent or present;

Het2 is a second heterologous molecule, which is either absent or present;

L is a linker, which is either absent or present;

Zy is a protease-cleavable substrate;

Bx is a self-immolative spacer;

Pep1 is a polypeptide; and,

Pep2 is a polypeptide, which is either absent or present; wherein, Pep1 or Pep2 comprises a clotting factor or a fragment thereof, or a synthetic procoagulant peptide.

In some embodiments, the self-immolative spacer in the procoagulant compound of the invention undergoes 1,4 elimination after the enzymatic cleavage of the protease-cleavable substrate. In some embodiments, the self-immolative spacer in the procoagulant compound of the invention undergoes 1,6 elimination after the enzymatic cleavage of the protease-cleavable substrate. In some embodiments, the self-immolative spacer is a p-amino benzyl carbamate (PABC), a p-amino benzyl ether (PABE), or a p-amino benzyl carbonate. In certain embodiments, the self-immolative spacer comprises an aromatic group. In some embodiments, the aromatic group is selected from the group consisting of benzyl, cinnamyl, naphthyl, and biphenyl. In some embodiments, the aromatic group is heterocyclic. In other embodiments, the aromatic group comprises at least one substituent. In some embodiments, at least one substituent is selected from F, Cl, I, Br, OH, methyl, methoxy, $NO_2$, $NH_2$, $NO^{3+}$, $NHCOCH_3$, $N(CH_3)_2$, $NHCOCF_3$, alkyl, haloalkyl, $C_1$-$C_8$ alkylhalide, carboxylate, sulfate, sulfamate, sulfonate, or any combinations thereof. In other embodiments, at least one C in the aromatic group is substituted with N, O or C—$R_1$, wherein $R_1$ is independently selected from H, F, Cl, I, Br, OH, methyl, methoxy, $NO_2$, $NH_2$, $NO^{3+}$, $NHCOCH_3$, $N(CH_3)_2$, $NHCOCF_3$, alkyl, haloalkyl, $C_1$-$C_8$ alkylhalide, carboxylate, sulfate, sulfamate, and sulfonate.

In some embodiments, the protease-cleavable substrate in the procoagulant compound of the invention comprises a coagulation cascade protease substrate. In some embodiments, the coagulation cascade protease is selected from thrombin, thromboplastin, Factor Va, Factor VIIa, Factor VIIIa, Factor IXa, Factor Xa, Factor XIa, Factor XIIa, or any combinations thereof. In other embodiments, the coagulation cascade protease substrate is a thrombin substrate. In some embodiments, the thrombin substrate is a synthetic thrombin substrate. In other embodiments, the synthetic thrombin substrate comprises the sequence of D-Phe-Pip-Arg. In some embodiments, the thrombin substrate is selected from D-Phe-Pro-Arg, D-Ala-Leu-Val-Pro-Arg (SEQ ID NO: 17), Ala-Leu-Val-Pro-Arg (SEQ ID NO: 17), Leu-Val-Pro-Arg (SEQ ID NO: 18), or Ala-Leu-Arg-Pro-Arg (SEQ ID NO: 90).

In some embodiments, the protease-cleavable substrate comprises a cleavage site for a protease selected from neprilysin (CALLA or CD10), thimet oligopeptidase (TOP), leukotriene A4 hydrolase, endothelin converting enzymes, ste24 protease, neurolysin, mitochondrial intermediate peptidase, interstitial collagenases, collagenases, stromelysins, macrophage elastase, matrilysin, gelatinases, meprins, procollagen C-endopeptidases, procollagen N-endopeptidases, ADAMs and ADAMTs metalloproteinases, myelin associated metalloproteinases, enamelysin, tumor necrosis factor α-converting enzyme, insulysin, nardilysin, mitochondrial processing peptidase, magnolysin, dactylysin-like metalloproteases, neutrophil collagenase, matrix metallopeptidases, membrane-type matrix metalloproteinases, SP2 endopeptidase, prostate specific antigen (PSA), plasmin, urokinase, human fibroblast activation protein (FAPα), trypsin, chymotrypsins, caldecrin, pancreatic elastases, pancreatic endopeptidase, enteropeptidase, leukocyte elastase, myeloblasts, chymases, tryptase, granzyme, stratum corneum chymotryptic enzyme, acrosin, kallikreins, complement components and factors, alternative-complement pathway c3/c5 convertase, mannose-binding protein-associated serine protease, coagulation factors, thrombin, protein c, u and t-type plasminogen activator, cathepsin G, hepsin, prostasin, hepatocyte growth factor-activating endopeptidase, subtilisin/kexin type proprotein convertases, furin, proprotein convertases, prolyl peptidases, acylaminoacyl peptidase, peptidyl-glycaminase, signal peptidase, n-terminal nucleophile aminohydrolases, 20s proteasome, γ-glutamyl transpeptidase, mitochondrial endopeptidase, mitochondrial endopeptidase Ia, htra2 peptidase, matriptase, site 1 protease, legumain, cathepsins, cysteine cathepsins, calpains, ubiquitin isopeptidase T, caspases, glycosylphosphatidylinositoliprotein transamidase, cancer procoagulant, prohormone thiol protease, γ-Glutamyl hydrolase, bleomycin hydrolase, seprase, cathepsin D, pepsins, chymosyn, gastricsin, renin, yapsin and/or memapsins, Prostate-Specific antigen (PSA), or any combinations thereof.

In some embodiments, Pep1 and Pep2 are different. In other embodiments, Pep1 and Pep2 are the same. In some embodiments, Pep1 is a clotting factor or a fragment thereof. In other embodiments, wherein Pep2 is a clotting factor or a fragment thereof. In certain embodiments, both Pep1 and Pep2 are clotting factors or fragments thereof.

In some embodiments, Pep1 is a heavy chain of a clotting factor and Pep2 is a light chain of the clotting factor. In other embodiments, the clotting factor is selected from FVII, FVIIa, FVIII, FIX, FX, FXa, vWF, or any combinations thereof. In other embodiments, Pep1 is a synthetic procoagulant peptide. In other embodiments, Pep2 is a synthetic procoagulant peptide. In some embodiments, both Pep1 and Pep2 are synthetic procoagulant peptides.

In some embodiments, the linker (L) is a peptide linker. In some embodiments, the peptide linker comprises at least two amino, at least three, at least four, at least five, at least 10, at least 20, at least 30, at least 40, at least 50, at least 60, at least 70, at least 80, at least 90, or at least 100 amino acids. In other embodiments, the peptide linker comprises at least 200, at least 300, at least 400, at least 500, at least 600, at least 700, at least 800, at least 900, or at least 1,000 amino acids. In some embodiments, the peptide linker comprises a peptide having the formula $[(Gly)_x\text{-}Ser_y]_z$ where x is from 1 to 4, y is 0 or 1, and z is from 1 to 50. In some embodiments, the linker (L) comprises a non-peptide linker.

In some embodiments, the linker (L) consists of a non-peptide linker. In other embodiments, the non-peptide linker is selected from MC, MP, MPEG, SMCC, MBS, SMPT, LC-SPDP, SMPB, or any combinations thereof.

In some embodiments, the heterologous moiety comprises a half-life extending moiety. In other embodiments, the half-life extending moiety is a low-complexity polypeptide. In other embodiments, the half-life extending moiety comprises albumin, albumin binding polypeptide or fatty acid, Fc, transferrin, PAS, the C-terminal peptide (CTP) of the β subunit of human chorionic gonadotropin, polyethylene glycol (PEG), hydroxyethyl starch (HES), albumin-binding small molecules, vWF, XTEN, or any combinations thereof. In some embodiments, the half-life extending moiety comprises a clearance receptor or fragment thereof which blocks binding of the procoagulant compound to a clearance receptor. In some embodiments, the clearance receptor is LRP1.

In some embodiments, the heterologous moiety comprises a peptide or a polypeptide which enables visualization or localization of the procoagulant compound or a fragment thereof. In some embodiments, the visualization or localization is enabled in vitro, in vivo, ex vivo or any combination thereof. In some embodiments, the peptide or the polypeptide which enables visualization or localization is selected from a biotin acceptor peptide, a lipoic acid acceptor peptide, a fluorescent protein, a cysteine-containing peptide for ligation of a biarsenical dye or for conjugating metastable technetium, a peptide for conjugating europium clathrates for fluorescence resonance energy transfer (FRET)-based proximity assays, or any combination thereof.

In some embodiments, the fluorescent protein is selected from GFP, RFP, YFP, EGFP, EYFP, or any combination thereof. In some embodiments, the biarsenical dye is 4',5'-bis(1,3,2-dithioarsolan-2-yl)fluorescein (FlAsH). In some embodiments, the biotin acceptor peptide facilitates conjugation of avidin- and streptavidin-based reagents. In some embodiments, the lipoic acid acceptor peptide facilitates conjugation of thiol-reactive probes to bound lipoic acid or direct ligation of fluorescent lipoic acid analogs.

In some embodiments, the heterologous moiety comprises a non-peptidic active agent. In some embodiments, the non-peptidic active agent is a procoagulant molecule. In some embodiments, the non-peptidic active agent is a small molecule drug. In some embodiments, the heterologous moiety comprises a targeting or ligand binding moiety. In some embodiments, the heterologous moiety comprises an anchor or scaffolding molecule. In some embodiments, the anchor or scaffolding molecule is a lipid, a carbohydrate, or a sulfhydryl group.

In some embodiments, the procoagulant compound of the invention comprises the formula Het-L-Zy-Bx-Peb1, wherein:

Het is cysteine,

L is a peptide linker,

Zy is a synthetic thrombin substrate,

Bx is the self-immolative spacer, and

Pep1 is procoagulant peptide.

In some embodiments, the peptide linker comprises a GGGG amino acid sequence, the synthetic thrombin substrate comprises the sequence DPhe-Pip-Arg, the self-immolative spacer is PABC, and the procoagulant peptide comprises the sequence:

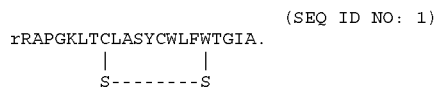

In some embodiments, the procoagulant compound of the invention comprises the formula Zy-Bx-Pep1, wherein: Zy is a synthetic thrombin substrate, Bx is a self-immolative spacer, and Pep1 is a clotting factor. In some embodiments, the synthetic thrombin substrate comprises the sequence DPhe-Pip-Arg, the self-immolative spacer is PABC, and the clotting factor is Factor Xa or FVIIa.

In some embodiments, the procoagulant activity of the procoagulant compounds of the invention is measured using a method selected from an activated partial thromboplastin time (aPTT) assay, a modified activated partial thromboplastin time (aPTT*) assay, a thrombin generation assay (TGA), and a ROTEM assay.

The present disclosure also provides a pharmaceutical composition comprising a procoagulant compound of the invention, and a pharmaceutically acceptable carrier.

Also provided is a method for treating, ameliorating, or preventing a bleeding disease or disorder in a subject, comprising administering to the subject an effective amount of a procoagulant compound of the invention or a pharmaceutical composition comprising the procoagulant compound of the invention. In some embodiments, the bleeding disease or disorder is caused by a blood coagulation disorder. In some embodiments, the blood coagulation disorder is selected from hemophilia and von Willebrand disease (vWD). In some embodiments, the blood coagulation disorder is hemophilia A or hemophilia B. In some embodiments, the bleeding disease or disorder is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

The present disclosure also provides a method of treating, ameliorating, or preventing a deficiency in at least one blood coagulation factor in mammalian subject, wherein the blood coagulation factor is selected from FV, FVII, FVIIa, FVIII, FIX, FX, FXI, and vWF, the method comprising administering to the subject an effective amount of the procoagulant compound of the invention or a pharmaceutical composition comprising the procoagulant compound. In some embodiments, the subject is a human subject.

In some embodiments, the procoagulant compound of the invention or a pharmaceutical formulation comprising the procoagulant compound of the invention are used for treating a subject having a blood coagulation disorder. In some embodiments, the subject is a human subject. In some embodiments, the procoagulant compound of the invention or a pharmaceutical formulation comprising the procoagulant compound of the invention are used for the manufacture of a medicament for the treatment, prevention, or amelioration of a blood coagulation disorder.

Also provided in the present disclosure is a method for making the procoagulant compound of the invention comprising using solid-phase peptide synthesis. In some embodiments, the method uses orthogonal solid-phase peptide synthesis.

The present disclosure also provides a method of enhancing in vivo efficacy of a procoagulant polypeptide comprising coupling the polypeptide to a self-immolative spacer, wherein said self-immolative spacer is coupled to a protease-cleavable substrate moiety. In some embodiments, the self-immolative spacer comprises a PABC group. In some embodiments, the protease-cleavable substrate moiety comprises a synthetic thrombin substrate. In some embodiments, the procoagulant polypeptide is a clotting factor or a procoagulant peptide. In some embodiments, the procoagulant peptide is synthetic.

The present disclosure also provides a method of increasing the efficacy of the cleavage of a protease substrate operably linked to a procoagulant peptide or clotting factor comprising conjugating a self-immolative linker to said procoagulant polypeptide, wherein said self-immolative linker is interposed between the protease substrate and the procoagulant peptide or clotting factor. Also disclosed is a method of activating a procoagulant peptide comprising contacting a procoagulant compound of the invention with a protease specific for the protease-cleavable substrate moiety in said procoagulant compound, wherein the activated procoagulant peptide is released upon proteolytic cleavage of the protease-cleavable substrate moiety.

Also provided is a method of activating a clotting factor comprising contacting a procoagulant compound of the invention with a protease specific for the protease-cleavable substrate moiety in said procoagulant compound, wherein the activated clotting factor is released upon proteolytic cleavage of the protease-cleavable substrate moiety. The instant disclosure also provides a method of releasing a procoagulant peptide from a heterologous moiety comprising contacting a procoagulant compound of the invention with a protease specific for the protease-cleavable substrate in said procoagulant compound, wherein the activated procoagulant polypeptide is released upon proteolytic cleavage of the protease-cleavable substrate.

The present disclosure also provides a method of releasing a clotting factor from a heterologous moiety comprising contacting a procoagulant compound of the invention with a protease specific for the protease-cleavable substrate in said procoagulant compound, wherein the activated clotting factor is released upon proteolytic cleavage of the protease-cleavable substrate. In some embodiments, the procoagulant compound is cleaved by a protease specific for the protease-cleavable substrate moiety at least 2-fold, at least 3-fold, at least 4-fold, at least 5-fold, at least 6-fold, at least 7-fold, at least 8-fold, at least 9-fold or at least 10-fold-faster when compared to a reference procoagulant compound with the same sequence but without a self-immolative linker. In some embodiments, the procoagulant compound is cleaved by a protease specific for the protease-cleavable substrate moiety at least 20-fold, at least 30-fold, at least 40-fold, at least 50-fold, at least 60-fold, at least 70-fold, at least 80-fold, at least 90-fold or at least 100-fold-faster when compared to a reference procoagulant compound with the same sequence but without a self-immolative linker.

In some embodiments, the procoagulant compound of the invention comprises a self-immolative spacer comprising an exosite binding peptide.

BRIEF DESCRIPTION OF THE DRAWINGS/FIGURES

FIG. 1A shows the general organization of a protease-activatable procoagulant compound of the invention. Het2, Pep2, Het1 and L are independently optional components. Pep1 and Pep2 are polypeptides, at least one of which is a clotting factor or a procoagulant peptide. Het1 and Het are heterologous moieties. L is a linker. Additional linkers can connect the different moieties; for example, a linker could be located between Pep2 and Het1 (as shown in the diagram). Additional protease cleavable substrate and self-immolative spacer groups can be inserted at the N-terminus of other moieties such as polypeptides or heterologous moieties. The diagram shows the optional insertion of such a group at the N-terminus of Pep2.

FIG. 1B is a representation of an exemplary procoagulant compound of the invention comprising a protease cleavable substrate ($Aa_1Aa_2Aa_3Aa_4$), a self-immolative spacer and a protein of interest (POI; e.g., a clotting factor or procoagulant peptide); illustrating the fragmentation of the compound and the release of the peptide or protein of interest after proteolytic cleavage of the cleavable substrate and 1,6 spontaneous fragmentation.

FIG. 2 is a representation of an alternative exemplary protease-activatable procoagulant compound of the invention which comprises an exosite binding peptide (M). The diagram illustrates the release of the peptide or protein of interest (POI; e.g., a clotting factor or procoagulant peptide) and the exosite binding peptide after proteolytic cleavage of a cleavable substrate ($Aa_1Aa_2Aa_3Aa_4$) and 1,6 spontaneous fragmentation.

FIG. 3 and FIG. 4 show the general synthesis scheme for protease-activatable procoagulant compound of the invention. The diagrams correspond to the synthesis of Compound 7. FIG. 3 shows the reactions leading to the synthesis of the compound comprising the protease cleavable substrate (thrombin substrate) and the self-immolative spacer (PABC). FIG. 4 shows the conjugation of the substrate/PABC compound to the synthetic procoagulant peptide and the deprotection of the resulting product to yield Compound 7.

FIG. 5 presents a schematic representation of the cleavage of Compound 7 by thrombin.

Figure 1A:
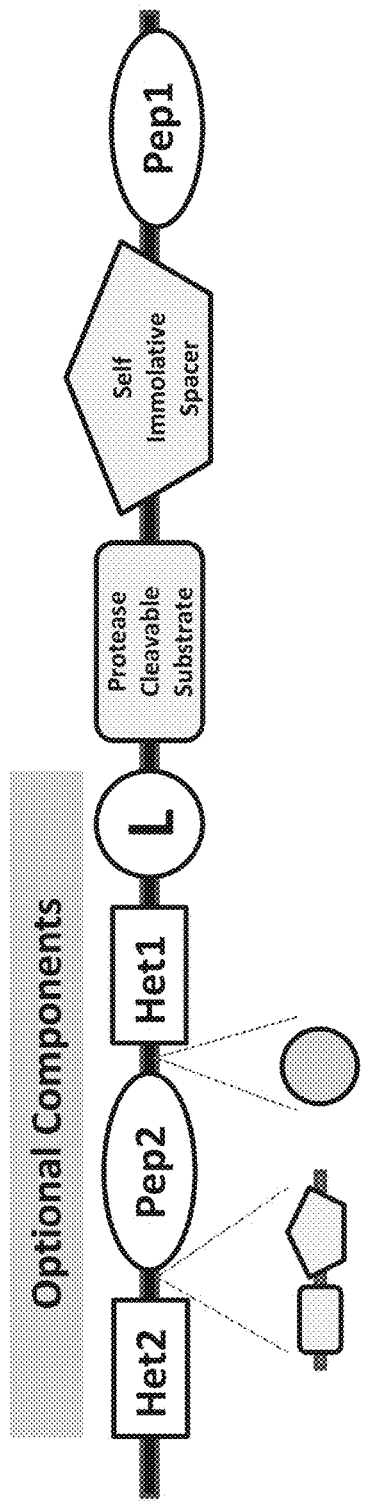

FIGS. 14A-14 show a flow diagram of a cleavable polypeptide, FVII-186 (FIG. 14A) that can be processed by a proprotein convertase (e.g., PACE) to a processed cleavable polypeptide (FIG. 14B). FIG. 14A shows a cleavable polypeptide comprising FVIILC (FVII light chain)-Proprotein Convertase Processing site by a proprotein convertase (e.g., PACE processing site, e.g., 2X(RKR) (SEQ ID NO: 88))-Linker1-SUMO-Truncated FVIIHC (FVII heavy chain without IVGGKV (SEQ ID NO: 83) at the N-terminus)-Linker2-Fc Region2-Linker3-Fc Region2. FIG. 14B shows a schematic diagram of a cleavable polypeptide that has been processed by PACE. The processed cleavable polypeptide comprises two polypeptide chains, the first chain comprising FVIILC linked to the Proprotein Convertase processing site and the second chain comprising Linker1-SUMO-Truncated FVIIHC (FVII heavy chain without IVGGKV (SEQ ID NO: 83) at the N-terminus)-Linker2-Fc Region1-Linker3-Fc Region2. FIG. 14C demonstrates non-reduced (lane 1) or reduced (lane 2) SDS-PAGE, showing the above constructs and chains. (-) indicates a peptide bond.

FIGS. 15A-15D show a flow diagram of (i) FVII-186 cleavage by a SUMO protease (FIG. 15B) and (ii) its fusion to a thioester peptide (FIG. 14C). FIG. 15A is identical to the construct in FIG. 14B. FIG. 15B shows that, after FVII-186 is cleaved by a SUMO protease, the resulting cleaved polypeptide construct comprises two chains, the first chain comprising FVIILC and Proprotein Convertase Site and the second chain comprising Truncated FVIIHC (FVII heavy chain without IVGGKV (SEQ ID NO: 83) at the N-terminus)-Linker2-Fc Region1-Linker3-Fc Region2. The first chain and the second chain are linked by a disulfide bond. FIG. 15C shows that after the cleaved polypeptide construct in FIG. 15B is ligated with a thioester peptide (Biotin-Pra-GGGG-D-Phe-Pip-Arg-PABC-IVGGKV-COSBn (SEQ ID NO: 79)), the resulting construct comprises two polypeptide chains, the first chain comprising FVIILC and Proprotein Convertase Processing Site and the second chain comprising Thrombin cleavage site-FVIIHC (FVII heavy chain)-Linker2-Fc Region1-Linker3-Fc Region2 (TA-FVII-186). FIG. 15D shows reducing SDS-PAGE indicating the constructs and chains: lane 1 shows marker; lane 2 shows FVII-186; lane 3 shows FVII-186 with SUMO protease reaction; lane 3 shows FVII-186 with SUMO protease reaction and conjugation with a positive control peptide; and lane 5 shows FVII-186 with SUMO protease reaction and conjugation with PABC peptide. (-) indicates a peptide bond.

Figure 16:
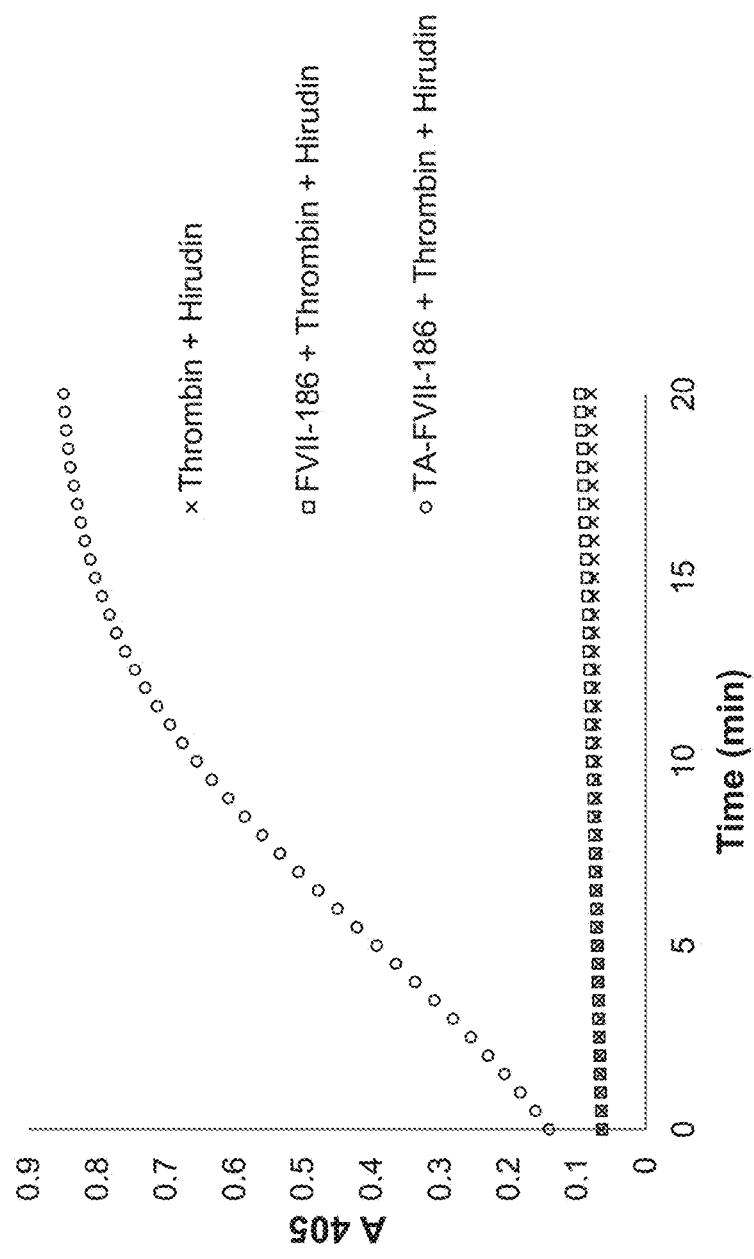

FIG. 16 shows FVIIa chromogenic assay after thrombin activation of TA-FVII-186. X axis indicates time (min), and Y axis indicates Absorbance (A405) measurement for FVIIa activity. (x) shows FVIIa activity of a mixture of thrombin and hirudin. (□) indicates FVIIa activity of a mixture of FVII-186, thrombin, and hirudin. (○) indicates FVIIa activity of a mixture of TA-FVII-186, thrombin, and hirudin.

Figures 17A, 17B, 17C:
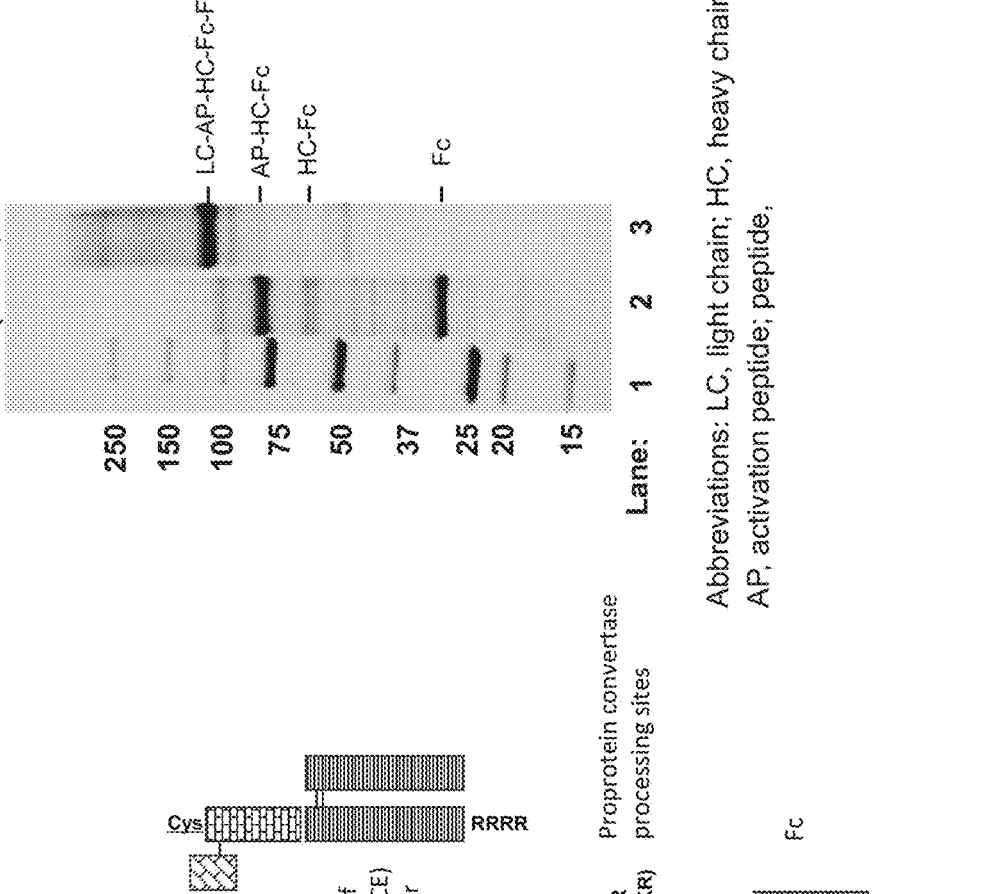

FIGS. 17A-17 show a flow diagram of FX-011 expression by a proprotein convertase (e.g., PACE). FIG. 17A shows a cleavable polypeptide construct comprising FXLC (Factor X light chain)-AP (activation peptide)-Proprotein Convertase Processing Site1 (e.g., 2X(RKR) SEQ ID NO: 88))-Truncated FXHC (Factor X heavy chain without six amino acids (i.e., IVGGQE (SEQ ID NO: 85)) at the N-terminus)-Fc Region1-Proprotein Convertase Processing Site2 (e.g., RRRR (SEQ ID NO: 89))-Linker-Fc Region2. When the cleavable construct of FIG. 16A is expressed, the initial construct can be processed by a proprotein convertase (e.g., PACE) to three polypeptide chains construct, the first chain comprising FXLC, the second chain comprising Truncated FXHC (Factor X heavy chain without six amino acids (i.e., IVGGQE (SEQ ID NO: 85) at the N-terminus)-Fc Region1-Proprotein Convertase Processing Site2, and the third chain comprising Fc Region2. FIG. 17C shows reduced (lane 2) and non-reduced (lane 3) SDS-PAGE showing the chains and constructs. (-) indicates a peptide bond.

FIGS. 18A-18 show a flow diagram of thrombin-cleavable Factor X molecule synthesis. FIG. 18A construct, identical to FIG. 17B contruct (FX-011), is incubated with a thioester peptide (GG-D-Phe-Pip-Arg-PABC-IVGGQE- COSBn (SEQ ID NO: 80)). The resulting construct (TA-FX-011) comprises three chains, the first chain comprising FXLC, the second chain comprising Thrombin Cleavage Site (D-Phe-Pip-Arg-PABC)-FXHC-Fc Region1-Proprotein Convertase Processing Site, and the third chain comprising Fc Region 2. The first chain and the second chain are bound by a disulfide bond, and the second and the third chains are bound by two disulfide bonds. FIG. 18C shows the constructs and chains in SDS-PAGE. (-) indicates a peptide bond.

Figure 19:
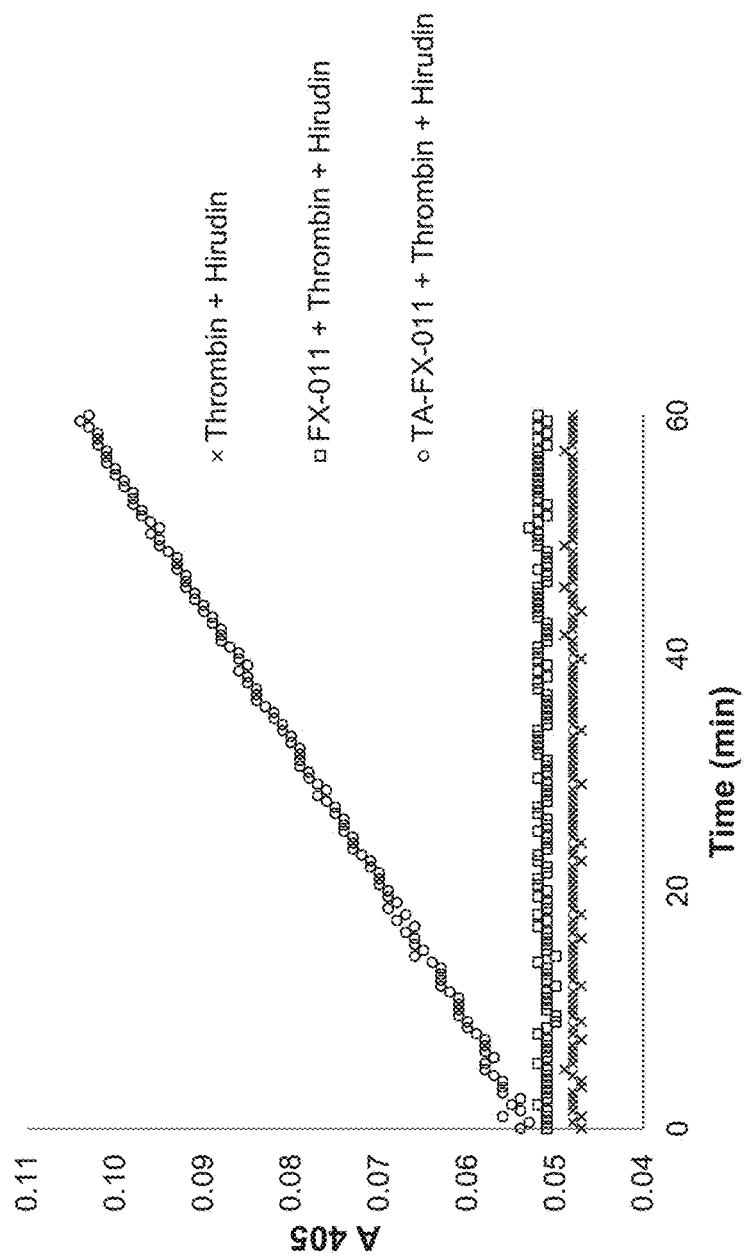

FIG. 19 shows FXa chromogenic assay after thrombin activation of TA-FX-011. X axis indicates time (min), and Y axis indicates Absorbance (A405) measurement for FXa activity. (x) shows FXa activity of a mixture of thrombin and hirudin. (□) indicates FXa activity of a mixture of FX-011, thrombin, and hirudin. (○) indicates FXa activity of a mixture of TA-FXa-011, thrombin, and hirudin.

FIGS. 20A-20C show a flow diagram of a cleavable FX polypeptide construct (FX-012). FIG. 20A shows a cleavable polypeptide comprising FXLC-SUMO-Truncated FXHC (Factor X heavy chain without six amino acids, i.e., IVGGQE (SEQ ID NO: 85) at the N-terminus)-Fc Region1-Proprotein Convertase Processing Site1-Linker-Proprotein Converase Processing Site2-Fc Region2. The FIG. 20A construct can be intracellularly processed by a proprotein convertase (e.g., PACE) to result in the FIG. 20B construct. FIG. 20B shows a processed cleavable FX polypeptide comprising three chains (FX-012), the first chain comprising FXLC, the second chain comprising SUMO-Truncated FXHC-Fc Region1-Proprotein Convertase Processing Site1, and the third chain comprising Fc Region2. The first chain and the second chain are bound by a disulfide bond. The second chain and the third chain are bound by two disulfide bonds. FIG. 20C shows a western blot of FX-012 under non-reduced (Lane 2) and reduced (Lane 3) conditions, compared to a molecular weight marker (Lane 1).

Figures 21A, 21B, 21C, 21D:
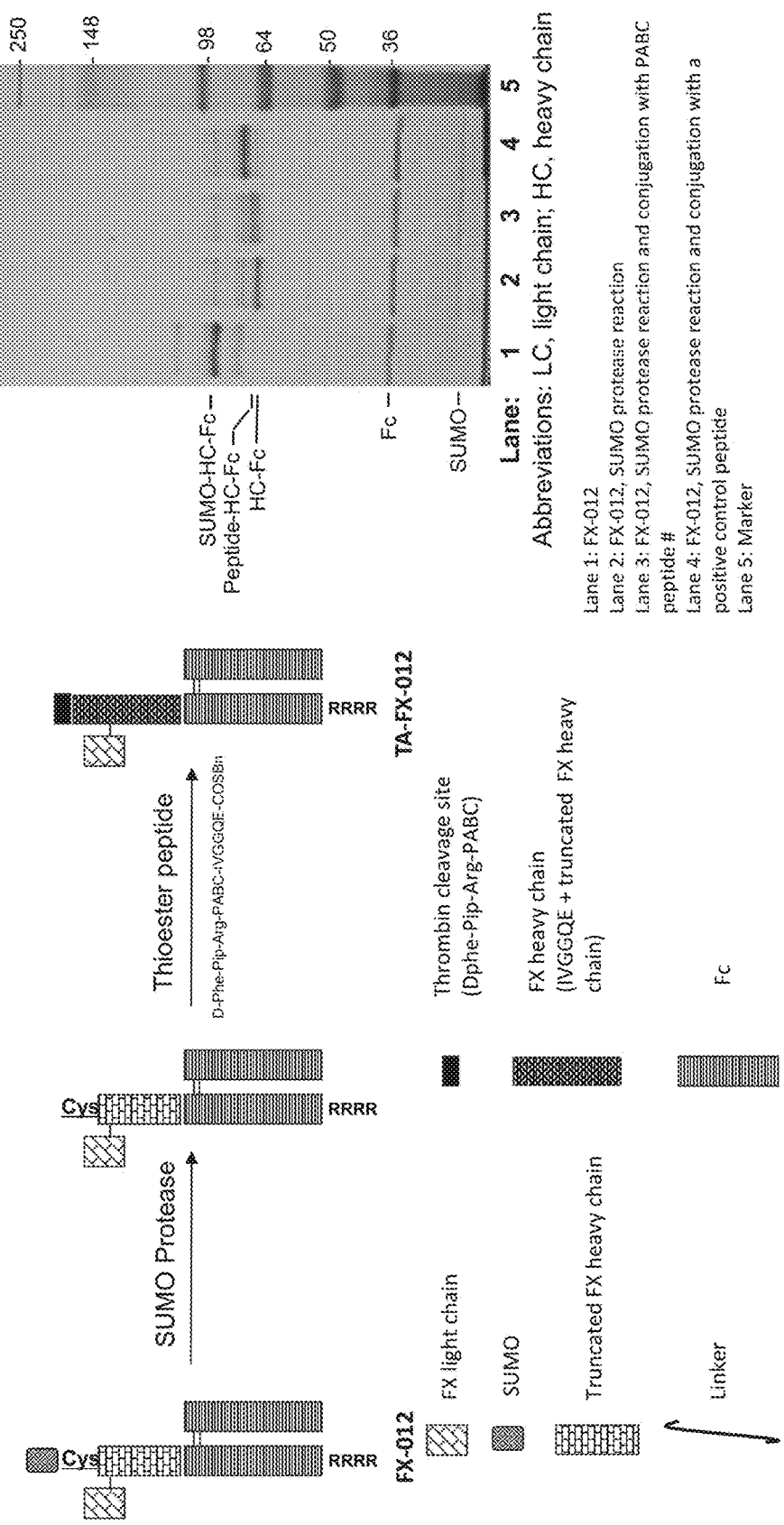

FIGS. 21A-21D show a flow diagram of (i) FX-012 cleavage by a SUMO protease (FIG. 21B) and (ii) its fusion to a thioester peptide (FIG. 21C). FIG. 21A is identical to the construct in FIG. 20B. FIG. 21B shows that, after FX-012 is cleaved by a SUMO protease, the resulting, cleaved polypeptide construct comprises three polypeptide chains, the first chain comprising FXLC, the second chain comprising Truncated FXHC (Factor X heavy chain without six amino acids (i.e., IVGGQE (SEQ ID NO: 85)) at the N-terminus)-Fc Region1-Proprotein Convertase Processing Site2, and the third chain comprising Fc Region2. The first chain and the second chain are bound by a disulfide bond, and the second and the third chains are bound by two disulfide bonds. FIG. 21C shows that after the cleaved polypeptide construct in FIG. 21B is ligated with a thioester peptide (D-Phe-Pip-Arg-PABC-IVGGQE-COSBn (SEQ ID NO: 90)). The resulting construct (TA-FX-012) comprises three chains, the first chain comprising FXLC, the second chain comprising Thrombin Cleavage Site (D-Phe-Pip-Arg-PABC)-FXHC-Fc Region1-Proprotein Convertase Processing Site, and the third chain comprising Fc Region 2. The first chain and the second chain are bound by a disulfide bond, and the second and the third chains are bound by two disulfide bonds. FIG. 21D shows reducing SDS-PAGE indicating the constructs and chains: lane 1 shows FX-012; lane 2 shows FX-012 with SUMO protease reaction; lane 3 shows FX-012 with SUMO protease reaction and conjugation with PABC peptide, lane 4 shows FX-012 with SUMO protease reaction and conjugation with a positive control peptide; and lane 5 shows marker. (-) indicates a peptide bond.

Figure 22:
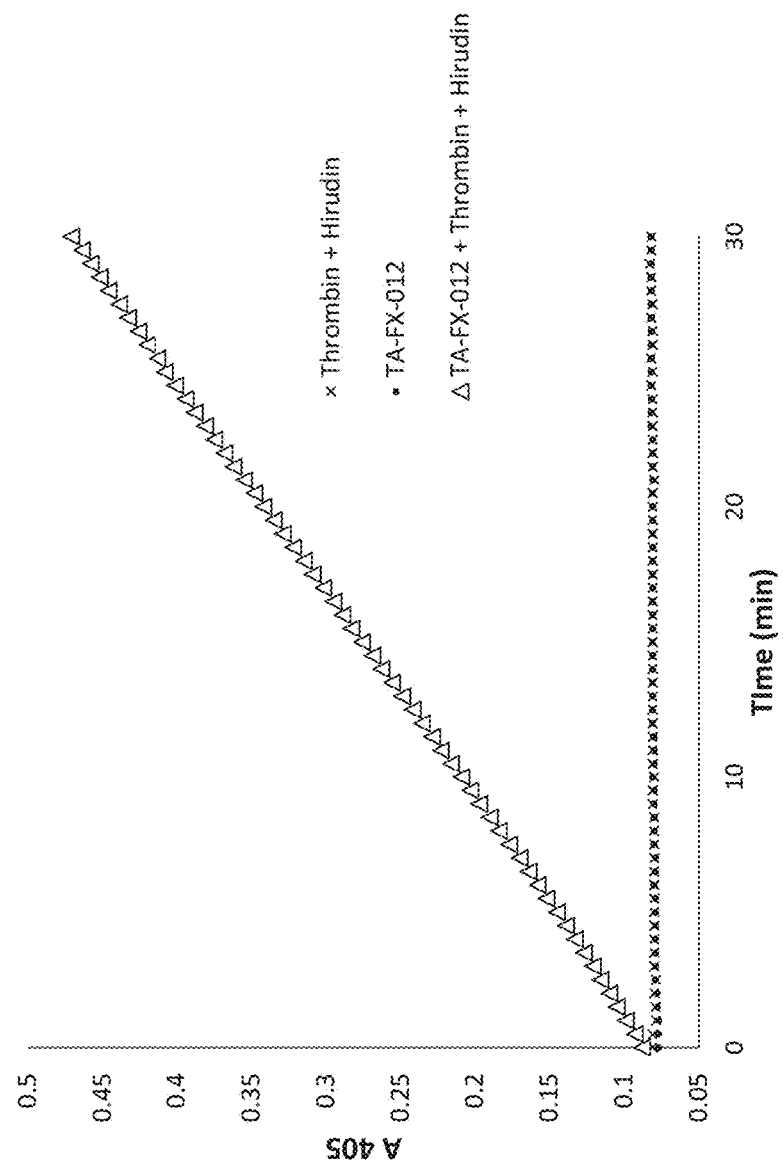

FIG. 22 shows FXa chromogenic assay after thrombin activation of TA-FX-012. X axis indicates time (min), and Y axis indicates Absorbance (A405) measurement for FXa activity. (x) shows FXa activity of a mixture of thrombin and hirudin. (•) indicates FXa activity of TA-FX-012 without thrombin and hirudin. (Δ) indicates FXa activity of a mixture of TA-FXa-012, thrombin, and hirudin.

DETAILED DESCRIPTION

The present disclosure provides procoagulant compounds comprising a protease-cleavable substrate (e.g., a synthetic thrombin substrate) and a self-immolative spacer (e.g., PABC) linked to a procoagulant polypeptide, e.g., a clotting factor or a procoagulant peptide. The protease-cleavable substrate can incorporate, e.g., the best known thrombin substrate, D-PhePipArg. Upon cleavage of the protease-cleavable substrate by a protease such as thrombin, the self-immolative spacer allows the release of the polypeptide via spontaneous fragmentation.

I. Definitions

It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising," otherwise analogous embodiments described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, RC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various embodiments of the disclosure, which can be had by reference to the specification as a whole. Accordingly, the terms defined immediately below are more fully defined by reference to the specification in its entirety. Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The term "sequence" as used to refer to a protein sequence, a peptide sequence, a polypeptide sequence, or an amino acid sequence means a linear representation of the amino acid constituents in the polypeptide in an amino-terminal to carboxyl-terminal direction in which residues that neighbor each other in the representation are contiguous in the primary structure of the polypeptide.

By a "protein" or "polypeptide" is meant any sequence of two or more amino acids linearly linked by amide bonds (peptide bonds) regardless of length, post-translation modification, or function. As used herein, the term "polypeptide" is intended to encompass a singular "polypeptide" as well as plural "polypeptides." "Polypeptide," "peptide," and "protein" are used interchangeably herein. Thus, peptides, dipeptides, tripeptides, or oligopeptides are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. A polypeptide can be generated in any manner, including by chemical synthesis. Also included as polypeptides of the present invention are fragments, derivatives, analogs, or variants of the foregoing polypeptides, and any combination thereof.

The term "fragment" when referring to polypeptides and proteins of the present invention include any polypeptides or proteins which retain at least some of the properties of the reference polypeptide or protein. E.g., in the case of procoagulant polypeptides such as clotting factors and procoagulant peptides, a term fragment would refer to any polypeptides or proteins which retain at least some of the procoagulant activity of the reference polypeptide or protein. Fragments of polypeptides include proteolytic fragments, as well as deletion fragments.

The term "variant" as used herein refers to a polypeptide sequence that differs from that of a parent polypeptide sequence by virtue of at least one amino acid modification. Variants can occur naturally or be non-naturally occurring. Non-naturally occurring variants can be produced using art-known mutagenesis techniques. Variant polypeptides can comprise conservative or non-conservative amino acid substitutions, deletions, or additions.

"Derivatives" of polypeptides or proteins of the invention are polypeptides or proteins which have been altered so as to exhibit additional features not found on the native polypeptide or protein. Also included as "derivatives" are those peptides that contain one or more naturally occurring amino acid derivatives of the twenty standard amino acids. A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide can have one or more mutations relative to the starting polypeptide, e.g., one or more amino acid residues which have been substituted with another amino acid residue or which has one or more amino acid residue insertions or deletions. Preferably, the polypeptide comprises an amino acid sequence which is not naturally occurring. Such variants necessarily have less than 100% sequence identity or similarity with the starting antibody. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule. In one embodiment, there is one amino acid difference between a starting polypeptide sequence and the sequence derived therefrom. Identity or similarity with respect to this sequence is defined herein as the percentage of amino acid residues in the candidate sequence that are identical (i.e. same residue) with the starting amino acid residues, after aligning the sequences and intro-ducing gaps, if necessary, to achieve the maximum percent sequence identity.

A polypeptide which is "isolated" is a polypeptide which is in a form not found in nature. Isolated polypeptides include those which have been purified to a degree that they are no longer in a form in which they are found in nature. In some embodiments, a polypeptide which is isolated is substantially pure.

A "recombinant" polypeptide or protein refers to a polypeptide or protein produced via recombinant DNA technology. Recombinantly produced polypeptides and proteins expressed in host cells are considered isolated for the purpose of the invention, as are native or recombinant polypeptides which have been separated, fractionated, or partially or substantially purified by any suitable technique. The polypeptides disclosed herein, e.g., clotting factors or procoagulant peptides, can be recombinantly produced using methods known in the art. Alternatively, proteins and peptides disclosed herein can be chemically synthesized.

A "conservative amino acid substitution" is one in which the amino acid residue is replaced with an amino acid residue having a similar side chain. Families of amino acid residues having similar side chains have been defined in the art, including basic side chains (e.g., Lys, Arg, His), acidic side chains (e.g., Asp, Glu), uncharged polar side chains (e.g., Gly, Asn, Gln, Ser, Thr, Tyr, Cys), nonpolar side chains (e.g., Ala, Val, Leu, Ile, Pro, Phe, Met, Trp), beta-branched side chains (e.g., Thr, Val, Ile) and aromatic side chains (e.g., Tyr, Phe, Trp, His). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, Ile, Phe or Trp) is substituted for, or by, one having a smaller side chain (e.g., Ala, Ser) or no side chain (e.g., Gly).

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain embodiments, the percentage identity "X" of a first amino acid sequence to a second sequence amino acid is calculated as 100× (Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at tcoffee.org, and alternatively available, e.g., from the EBI. It will also be appreciated that the final alignment used to calculate percent sequence identity can be curated either automatically or manually.

As used herein, the term "half-life" refers to a biological half-life of a particular polypeptide (e.g., clotting factor or procoagulant peptide) or procoagulant compound of the invention in vivo. Half-life can be represented by the time required for half the quantity administered to a subject to be cleared from the circulation and/or other tissues in the animal. When a clearance curve of a given polypeptide or procoagulant compound of the invention is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, procoagulant compounds of the invention are monophasic, and thus do not have an alpha phase, but just the single beta phase. Therefore, in certain embodiments, the term half-life as used herein refers to the half-life of the procoagulant compound in the β-phase. The typical β phase half-life of a human antibody in humans is 21 days.

The terms "heterologous" and "heterologous moiety" mean that a polynucleotide, polypeptide, or any other moiety which is derived from a distinct entity from that of the entity to which it is being compared. For instance, a heterologous polypeptide can be synthetic, or derived from a different species, different cell type of an individual, or the same or different type of cell of distinct individuals. In one embodiment, a heterologous moiety can be a polypeptide fused to another polypeptide to produce a fusion polypeptide or protein. In another embodiment, a heterologous moiety can be a non-polypeptide such as PEG conjugated to a polypeptide or protein.

As used herein, the terms "linked," "fused", "fusion," or "connected" refer to linkage via a peptide bond (e.g., genetic fusion), chemical conjugation, or other means. For example, one way in which molecules or moieties can be linked employs polypeptide linkers which link the molecules or moieties via peptide bonds. The terms "genetically fused," "genetically linked" or "genetic fusion" are used interchangeably and refer to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence. Preferred genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs.

As used herein the term "moiety" refers to a component part or constituent of a procoagulant compound of the invention.

As used herein, the term "targeting moiety" refers to heterologous moiety which localizes or directs the procoagulant compound of the invention to a desired site or cell. In one embodiment, the procoagulant compound of the invention comprises a "targeting moiety" which enhances the activity of the procoagulant compound, e.g., by localizing it to a desired site. Such a moiety can be, e.g., an antibody or variant thereof (e.g., and scFv) or a peptide. In another embodiment, the procoagulant compound of the invention comprises a targeting moiety which can be a polypeptide, a receptor binding portion of a ligand, or a ligand binding portion of a receptor and binds to the desired target, e.g., on a cell or tissue. In some embodiments, the procoagulant compound of the invention comprises a targeting moiety which is genetically fused, chemically conjugated, or linked to the construct via a linker or other moiety. Exemplary targeting moieties are described in more detail below. In one embodiment a targeting moiety for use in a procoagulant compound of the invention comprises an antibody or antibody variant. The term "antibody variant" or "modified antibody" includes an antibody which does not occur in nature and which has an amino acid sequence or amino acid side chain chemistry which differs from that of a naturally-derived antibody by at least one amino acid or amino acid modification as described herein. As used herein, the term "antibody variant" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules; single-chain antibodies; diabodies; triabodies; and antibodies with altered effector function and the like.

As used herein the term "scFv molecule" includes binding molecules which consist of one light chain variable domain (VL) or portion thereof, and one heavy chain variable domain (VH) or portion thereof, wherein each variable domain (or portion thereof) is derived from the same or different antibodies. scFv molecules preferably comprise an scFv linker interposed between the VH domain and the VL domain. ScFv molecules are known in the art and are described, e.g., in U.S. Pat. No. 5,892,019, Ho et al. 1989. *Gene* 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

A "scFv linker" as used herein refers to a moiety interposed between the VL and VH domains of the scFv. scFv linkers preferably maintain the scFv molecule in a antigen binding conformation. In one embodiment, a scFv linker comprises or consists of an scFv linker peptide. In certain embodiments, a scFv linker peptide comprises or consists of a gly-ser polypeptide linker. In other embodiments, a scFv linker comprises a disulfide bond.

As used herein, the term "protease-cleavable substrate" refers to peptide sequence comprising a site recognized by a protease enzyme. Certain cleavage sites comprise an intracellular processing site. In one embodiment, a procoagulant compound of the invention comprises a protease-cleavable substrate cleaved by an enzyme that is activated during the dotting cascade, such that cleavage of such sites occurs at the site of clot formation. Exemplary protease-cleavable substrates include, e.g., those recognized by thrombin, Factor XIa or Factor Xa. Exemplary FXIa cleavage sites include, e.g., TQSFNDFTR (SEQ ID NO: 2) and SVSQTSKLTR (SEQ ID NO: 3). Exemplary thrombin cleavage sites include, e.g., DFLAEGGGVR (SEQ ID NO: 4), TTKIKPR (SEQ ID NO: 5), LVPRG (SEQ ID NO: 6) and ALRPR (SEQ ID NO: 7). Other enzymatic cleavage sites are known in the art. Protease-cleavable substrates can comprise natural or non-natural amino acids, e.g., D-amino acids.

The term "bleeding disease or disorder," as used herein, means a genetically inherited or acquired condition characterized by a tendency to hemorrhage, either spontaneously or as a result of trauma, due to an impaired ability or inability to form a fibrin clot. Examples of such disorders include hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this can increase bleeding risk.

The phrase "effective amount" as used herein refers to that amount of a procoagulant compound or pharmaceutical composition of the present invention, which is effective for producing a desired effect, at a reasonable benefit/risk ratio applicable to any medical treatment. For example, an "effective amount" is an amount effective to reduce or lessen at least one symptom of the disease or disorder being treated or to reduce or delay onset of one or more clinical markers or symptoms associated with the disease or disorder, or to modify or reverse the disease process.

As used herein, the term "pharmaceutically acceptable" means approved by a regulatory agency of U.S. or E.U. or other government or listed in the U.S. Pharmacopeia or other generally recognized pharmacopeia for use in humans. Hence, the term "pharmaceutically acceptable" refers to those properties and/or substances that are acceptable to a patient (e.g., a human patient) from a toxicological and/or safety point of view.

The term "administering," as used herein, means to give a procoagulant compound of the present invention, or pharmaceutical composition containing a procoagulant compound of the present invention, to a subject (e.g., human subject) in need thereof via a pharmaceutically acceptable route of administration. In some embodiments, the route of administration is intravenous, e.g., intravenous injection or intravenous infusion. In other embodiments, the route of administration is selected from subcutaneous, intramuscular, oral, nasal, and pulmonary administration. The procoagulant compounds of the invention can be administered as part of a pharmaceutical composition comprising at least one pharmaceutically acceptable carrier.

The term "prophylactic treatment," as used herein, means administering a procoagulant compound of the present invention to a subject over a course of time to increase the level of activity in a subject's plasma. Preferably, the increased level is sufficient to decrease the incidence of spontaneous bleeding or to prevent bleeding, e.g., in the event of an unforeseen injury. Preferably, during prophylactic treatment, the plasma protein level in the subject does not fall below the baseline level for that subject, or below the level that characterizes severe hemophilia.

The term "subject," as used herein means a human or a non-human mammal. Non-human mammals include, e.g., mice, dogs, primates, monkeys, cats, horses, cows, pigs, and other domestic animals and small animals.

The term "therapeutic dose," as used herein, means a dose that achieves a therapeutic goal, as described herein. The therapeutic doses that can be used in the methods of the invention are about 10-100 mg/kg, more specifically, 10-20, 20-30, 30-40, 40-50, 50-60, 60-70, 70-80, 80-90, or 90-100 mg/kg, and more specifically, 10, 15, 20, 25, 30, 35, 40, 45, 50, 55, 60, 65, 70, 75, 80, 85, 90, 95, or 100 mg/kg. Additional therapeutic doses that can be used in the methods of the invention are about 10 to about 150 mg/kg, more specifically, about 100-110, 110-120, 120-130, 130-140, 140-150 mg/kg, and more specifically, about 110, 115, 120, 125, 130, 135, 140, 145, or 150 mg/kg.

"About," as used herein for a range, modifies both ends of the range. Thus, "about 10-20" means "about 10 to about 20."

The term "selective" as used in connection with proteolytic cleavage means a greater rate of cleavage of a protease-cleavable substrate relative to cleavage of a peptide substrate which comprises a random sequence of amino acids. The term "selective" also indicates that the procoagulant compound comprising the protease-cleavable substrate is cleaved at the site where it is coupled to the amino group of the self-immolative spacer.

The term "D-amino acid" as used herein, refers to an amino acid having a D-configuration (e.g., D-Phe). A D-amino acid can be a naturally occurring amino acid or an unnatural amino acid.

The term "self-immolative spacer" as used herein refers to a bifunctional chemical moiety which is capable of covalently linking together two spaced moieties (e.g., a clotting factor or a procoagulant peptide and a protein-cleavable substrate) into a normally stable tripartate molecule. The self-immolative spacer will spontaneously separate from the second moiety (e.g., a clotting factor or a procoagulant peptide) if its bond to the first moiety (e.g., a protein-cleavable substrate) is cleaved.

II. Procoagulant Compounds

The present disclosure provides procoagulant compounds comprising a clotting factor or a fragment, variant, or derivative thereof, or a procoagulant peptide (e.g., a synthetic procoagulant peptide) connected to a protease-cleavable substrate (e.g., a thrombin substrate) via a self-immolative spacer (e.g., PABC). The PABC self-immolative spacer allows the release of any peptides and proteins containing at least one amine, phenol, carboxylic acid, or thiol functionality upon cleavage of the protease-cleavable substrate by endogenous or exogenous proteases and 1,6-spontaneous fragmentation. Cleavage kinetics is independent of the identity of released amine, phenol, carboxylic acid, or thiol molecules. Moreover, PABC can enhance the cleavage rate due to the presence of the p-aminobenzyl group.

In some embodiments, the disclosure provides a procoagulant compound represented by the following general formula:

(Het2)-(Pep2)-(Het1)-(L)-Zy-Bx-Peb1    (Formula I)

wherein:
Het1 is a first heterologous molecule, which is either absent or present;
Het2 is a second heterologous molecule, which is either absent or present;
L is a linker, which is either absent or present;
Zy is a protease-cleavable substrate;
Bx is a self-immolative spacer;
Pep1 is a first polypeptide; and,
Pep2 is a second polypeptide, which is either absent or present;
wherein, Pep1 or Pep2 is a clotting factor or a fragment thereof, or a procoagulant peptide (for example, a synthetic procoagulant peptide) (see FIG. 1A).

In various embodiments, the present disclosure provides, inter alia, procoagulant compounds which are selectively activatable at the site of injury; procoagulant compounds that are selectively activatable by clotting cascade proteases; methods of treatment of bleeding disorders comprising the administration of the procoagulant compounds of the disclosure; methods for the production of the procoagulant compounds of the disclosure; and pharmaceutical compositions comprising the procoagulant compounds of the disclosure.

In some embodiments, the procoagulant compounds disclosed herein are stable and pharmacologically inactive in the absence of the protease targeting the protease-cleavable substrate. However, upon action of the protease, or any other suitable cleavage conditions, the protease-cleavable substrate is cleaved and the self-immolative spacer undergoes a spontaneous reaction, resulting in the release of an active procoagulant polypeptide (e.g., an active clotting factor or a procoagulant peptide). In some embodiments, the procoagulant compound of the invention is a zymogen.

In some aspects, a procoagulant protein of the invention comprises a formula selected from:
(a) Zy-Bx-Peb1;
(b) Het1-Zy-Bx-Peb1;
(c) Het1-L-Zy-Bx-Peb1;
(d) Pep2-Zy-Bx-Peb1;
(e) Pep2-L-Zy-Bx-Pep1;
(f) Pep2-Het1-L-Zy-Bx-Peb1;
(g) Pep2-Het1-Zy-Bx-Peb1;
(h) Het2-Het1-L-Zy-Bx-Peb1;
(i) Het2-Het1-Zy-Bx-Peb1;
(j) Het2-Pep2-Het1-L-Zy-Bx-Peb1;
(k) Het2-Pep2-L-Zy-Bx-Pep1;
(l) Het2-Pep2-Het1-Zy-Bx-Peb1; or,
(m) Het2-Pep2-Zy-Bx-Pep1,
wherein:
Het1 is a first heterologous molecule;
Het2 is a second heterologous molecule;
L is a linker;
Zy is a protease-cleavable substrate;
Bx is a self-immolative spacer;
Pep1 is a first polypeptide; and,
Pep2 is a second polypeptide;
wherein, Pep1 or Pep2 is a clotting factor or a fragment thereof, or a procoagulant peptide (for example, a synthetic procoagulant peptide).

In some embodiments, the formulas described herein can comprise additional sequences between the two moieties, e.g., linkers. For example, linkers can be situated between Het2 and Pep2, or between Pep2 and Het1. In some embodiments, additional Zy-Bx groups are present at the N-terminus of peptides (e.g., Pep1 or Pep2) and/or heterologous molecules (e.g., Het1 or Het2) to facilitate the clean release of such peptides and/or heterologous moieties. Accordingly, in some embodiments, a procoagulant protein of the invention comprises a formula selected from:
(n) Pep2-Zy-Bx-L-Zy-Bx-Pep1;
(o) Pep2-Zy-Bx-Het1-L-Zy-Bx-Pep1;
(p) Pep2-Zy-Bx-Het1-Zy-Bx-Peb1;
(q) Het2-Zy-Bx-Pep2-Zy-Bx-Het1-L-Zy-Bx-Pep1;
(r) Het2-Zy-Bx-Pep2-Zy-Bx-L-Zy-Bx-Pep1;
(s) Het2-Zy-Bx-Pep2-Zy-Bx-Het1-Zy-Bx-Pep1, or,
(t) Het2-Zy-Bx-Pep2-Zy-Bx-Pep1,
wherein:
Het1 is a first heterologous molecule;
Het2 is a second heterologous molecule;
L is a linker;
Zy is a protease-cleavable substrate;
Bx is a self-immolative spacer;
Pep1 is a first polypeptide; and,
Pep2 is a second polypeptide;
wherein, Pep1 or Pep2 is a clotting factor or a fragment thereof, or a procoagulant peptide (e.g., a synthetic procoagulant peptide).

The orientation of the procoagulant compounds formulas herein is listed from N-terminus (left) to C-terminus (right). For example, formula Pep2-Zy-Bx-Pep1 means formula $NH_2$-Pep2-Zy-Bx-Pep1-COOH. Formulas (a) to (t) shown above are included herein merely as non-limiting examples of procoagulant compounds of the present invention. For example, the formula Het2-Pep2-Het1-L-Zy-Bx-Pep1 can further comprise sequences at the free end of Het2, between Het2 and Pep2, between Pep2 and Het1, between Het1 and Sp, between L and Zy, between Zy and Bx, between Bx and Pep1, or at the C-terminus of Pep1. In another embodiment, the hyphen (-) indicates a peptide bond or one or more amino acids.

In some embodiments, the procoagulant compound comprises a clotting factor or fragment thereof and a heterologous moiety. In some embodiments, the heterologous moiety comprises a half-life extending moiety selected, e.g., from the group consisting of an immunoglobulin constant region or portion thereof (e.g., an Fc region), a PAS sequence, HES, and albumin, fragment, or variant thereof, or an XTEN. In yet other embodiments, the procoagulant compound comprises a clotting factor or fragment thereof, a second clotting factor or fragment thereof, and a PEG heterologous moiety, wherein the procoagulant compound further comprises a heterologous moiety selected from an immunoglobulin constant region or portion thereof (e.g., an Fc region), a PAS sequence, HES, and albumin, fragment, or variant thereof, or an XTEN.

In other embodiments, the procoagulant compound comprises a clotting factor or fragment thereof, a synthetic procoagulant polypeptide, and a heterologous moiety, wherein the procoagulant compound further comprises a second heterologous moiety selected from an immunoglobulin constant region or portion thereof (e.g., an Fc region), a PAS sequence, HES, and albumin, fragment, or variant thereof, XTEN, or any combinations thereof. In other embodiments, the procoagulant compound comprises two synthetic procoagulant peptides and a heterologous moiety, wherein the procoagulant compound further comprises a second heterologous moiety selected from an immunoglobulin constant region or portion thereof (e.g., an Fc region), a PAS sequence, HES, and albumin, fragment, or variant thereof, XTEN, or any combinations thereof. In yet another embodiment, the procoagulant compound comprises a clotting factor or fragment thereof, a clotting factor cofactor (e.g., Factor Va if the clotting factor in Factor X; or Tissue Factor if the clotting factor is Factor VII), and a heterologous moiety, wherein the procoagulant compound further comprises a second heterologous moiety selected from an immunoglobulin constant region or portion thereof (e.g., an Fc region), a PAS sequence, HES, and albumin, fragment, or variant thereof, XTEN, or any combinations thereof.

In specific aspects of the invention, a procoagulant compound of the invention comprises the formula wherein Het1-L-Zy-Bx-Pep1, wherein Pep1 comprises a procoagulant peptide comprising the sequence rRAPGKLT-CLASYCWLFWTGIA, Bx comprises a PABC self-immolative spacer, Zy comprises a thrombin-cleavable substrate comprising the sequence D-Phe-Pip-Arg, L comprises a linker comprising the sequence GGGG, and Het1 comprises a scaffold heterologous moiety comprising a cysteine amino acid.

In a specific aspect of the invention, a procoagulant compound of the invention comprises the formula wherein Zy-Bx-Pep1, wherein Pep1 comprises a FXa clotting factor, Bx comprises a PABC self-immolative spacer, and Zy comprises a thrombin-cleavable substrate comprising the sequence D-Phe-Pip-Arg.

In a specific aspect of the invention, a procoagulant compound of the invention comprises the formula wherein Zy-Bx-Pep1, wherein Pep1 comprises a FVIIa clotting factor, Bx comprises a PABC self-immolative spacer, and Zy comprises a thrombin-cleavable substrate comprising the sequence D-Phe-Pip-Arg.

Figure 11:
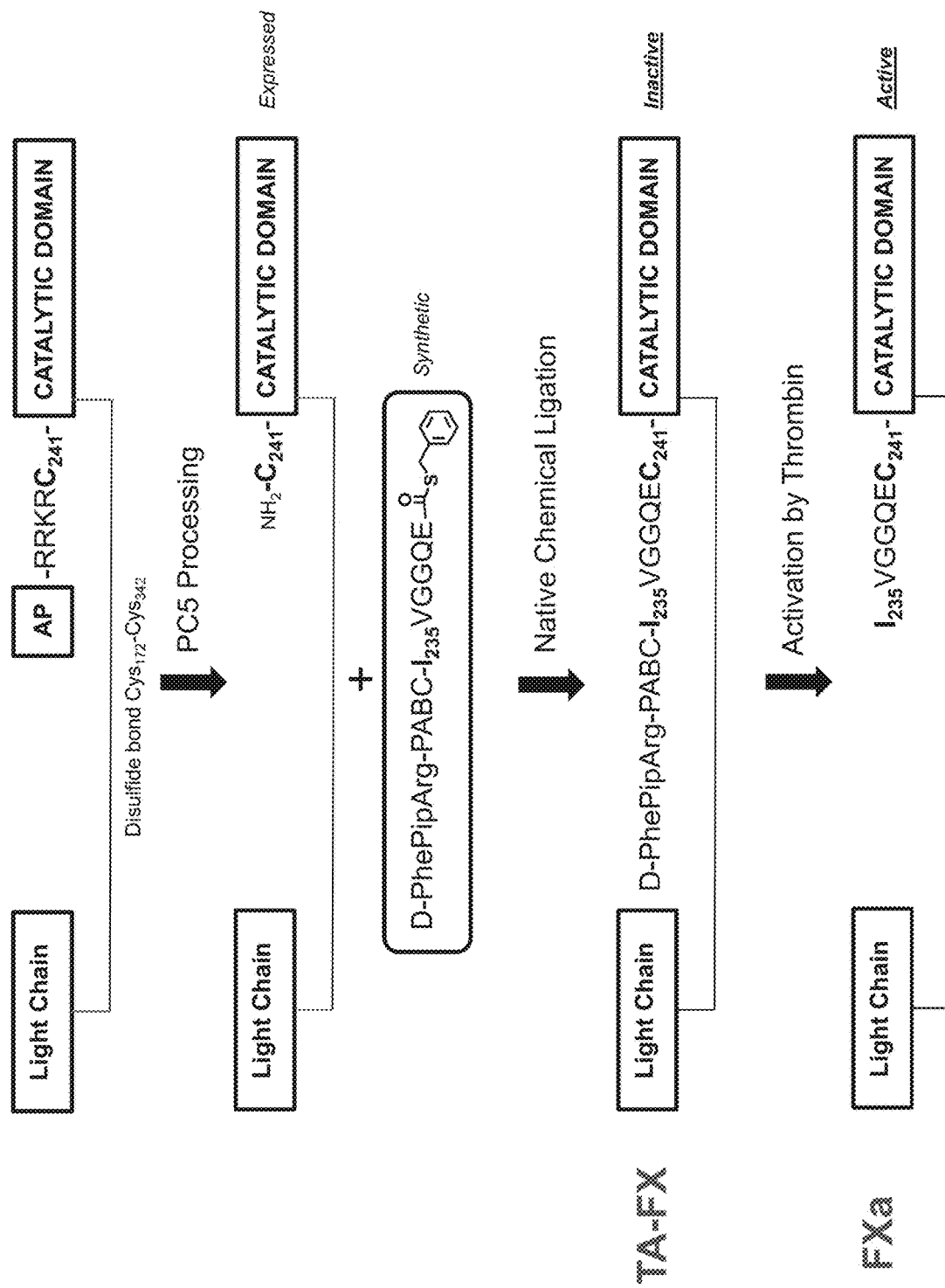
FIG. 11 is a representation of exemplary procoagulant compounds of the invention comprising FXa clotting factor.
Figure 12:
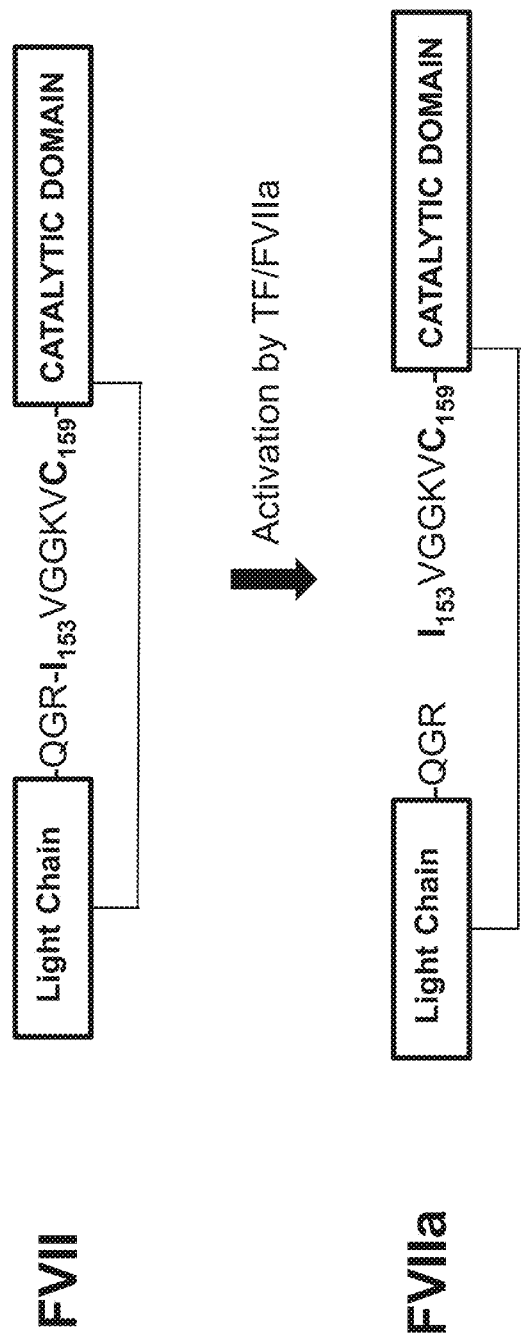
FIG. 12 shows the natural processing of factor VII to yield activated factor VII (FVIIa).
Figure 13:
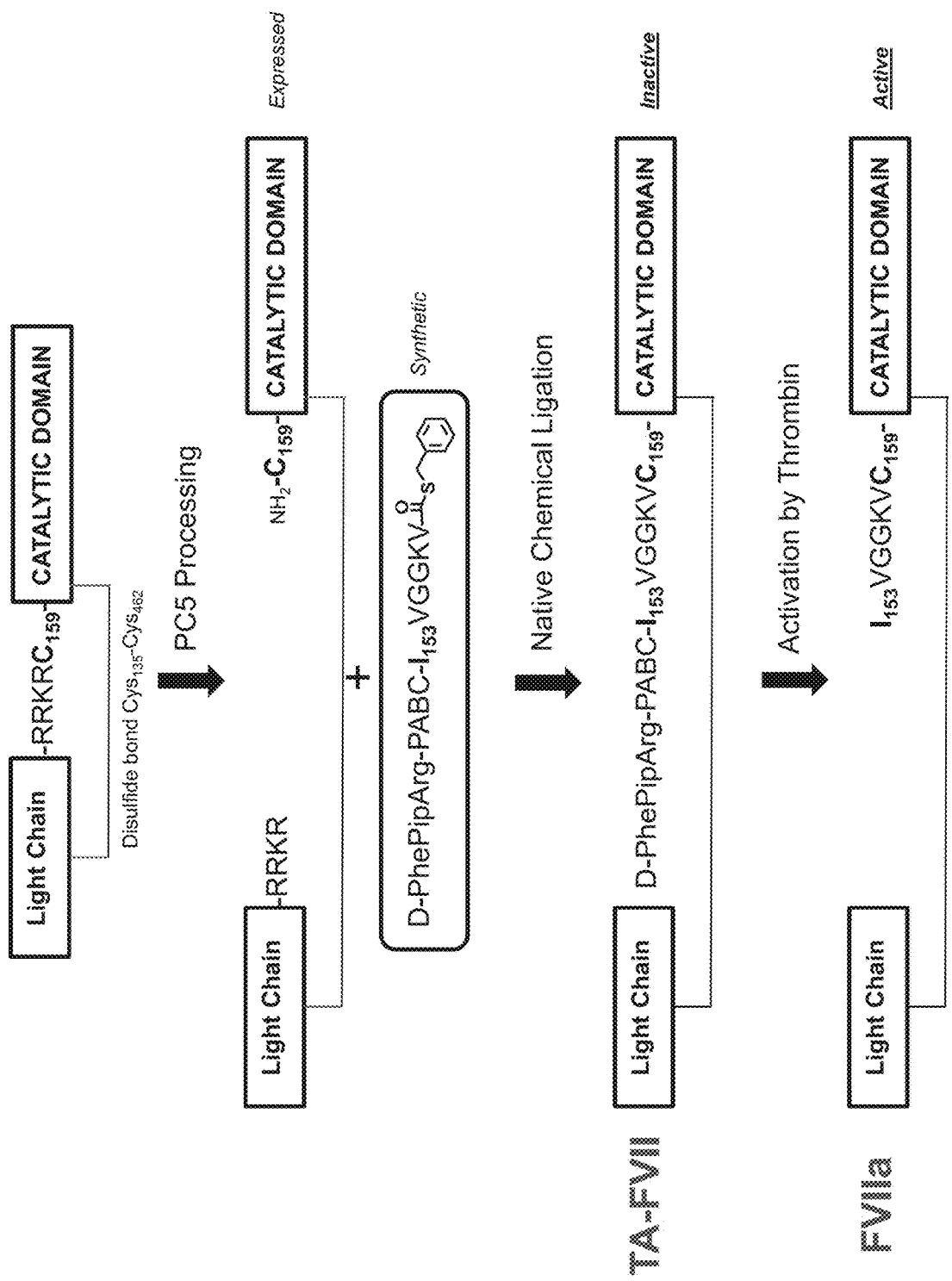
FIG. 13 is a representation of exemplary procoagulant compounds of the invention comprising FVIIa clotting factor.

In another specific aspect of the invention, a procoagulant compound of the invention comprises the formula wherein Pep2-Zy-Bx-Pep1, wherein Pep1 comprises a FX clotting factor, Bx comprises a PABC self-immolative spacer, Zy comprises a thrombin-cleavable substrate comprising the sequence D-Phe-Pip-Arg, and Pep2 is an activation peptide, wherein cleavage of the thrombin-cleavable substrate causes the release of the activation peptide and the activation of the clotting factor (see FIG. 11). In some embodiments according to such formula, the clotting factor is FIXa and the activation peptide is FVIIIa. In other embodiments, the clotting factor is FVIIa and the activation peptide is Tissue Factor. In some embodiments, the activation peptide can be a procoagulant peptide.

In some specific aspects of the invention, a procoagulant compound of the invention comprises the formula Pep1-Het3-Het2-Bx-Het1, wherein Pep1 comprises a clotting factor, Het3 is a scaffold heterologous moiety, Het2 is a heterologous moiety, Bx is a self-immolative spacer, and Het1 is a second heterologous moiety. In some embodiments according to such formula, Pep1 comprises a FVIII clotting factor, Het3 is a cysteine, Het2 comprises an Fc heterologous moiety, Bx comprises a PABC self-immolative spacer, and Het1 comprises an XTEN.

In some specific aspects of the invention, a procoagulant compound of the invention comprises the formula Pep1-Het2-Bx-Het1, wherein Pep1 comprises a clotting factor, Het2 is a scaffold heterologous moiety, Bx is a self-immolative spacer, and Het1 is a second heterologous moiety. In some embodiments according to such formula, Pep1 comprises a FVIII clotting factor, Het2 is a cysteine, Bx comprises a PABC self-immolative spacer, and Het) comprises an XTEN.

For a better understand of the procoagulant compounds of the disclosure their components will be discussed individually below:

A. Polypeptides (e.g., Pep1, Pep2, . . . , Pep$_n$)

1. Clotting Factors and Procoagulant Peptides

The procoagulant compounds the invention comprise at least one polypeptide moiety (Pep1 or Pep2) which is (i) a clotting factor, or (ii) a procoagulant peptide (e.g., a synthetic procoagulant peptide).

The term "clotting factor," as used herein encompasses clotting factors (e.g., vWF, FV, FVa, FVII, FVIIa, FVIII, FVIIIa, FIX, FIXa, FX, FXa, FXI, FXIa, FXII, FXIIa, FXIII, or FXIIIa), fragments, variants, analogs, or derivatives thereof, naturally occurring, recombinantly produced, or synthetically produced which prevent or decrease the duration of a bleeding episode in a subject. In other words, it means molecules having procoagulant activity. In some embodiments, the procoagulant compound of the invention comprises a FVII or activated FVII (FVIIa) clotting factor. In other embodiments, the procoagulant compound of the invention comprises a FVIII or activated FVIII (FVIIIa) clotting factor. In some embodiments, the procoagulant compound of the invention comprises a FIX or activated FIX (FIXa) clotting factor. In other embodiments, the procoagulant compound of the invention comprises a FX or activated FX (FXa) clotting factor. In some embodiments, the procoagulant compound of the invention comprises vWF. The term "procoagulant peptide" as used herein refers to any peptide that has procoagulant activity. In particular, the term refers to peptides that initiate or accelerate the process of blood coagulation through the transformation of soluble circulating fibrinogen to an insoluble cross-linked fibrin network.

A "synthetic procoagulant peptide" as used herein refers to a procoagulant polypeptide that has been produced using solid phase peptide synthesis.

By "procoagulant activity" is meant the ability to promote thrombin generation and/or fibrin deposition in a suitable test system. A number of tests are available to assess the function of the coagulation system: activated partial thromboplastin time (aPTT) test, chromogenic assay, ROTEM assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphosholipid antibodies, D-dimer, genetic tests (e.g. factor V Leiden, prothrombin mutation G20210A), dilute Russell's viper venom time (dRVVT), miscellaneous platelet function tests, thromboelastography (TEG or Sonoclot), thromboelastometry (TEM®, e.g, ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

In some embodiments, the procoagulant compound comprises a single clotting factor. In some embodiments, the single clotting factor is Pep1. In other embodiments, the single clotting factor is Pep2. In other embodiments, the procoagulant compound comprises two clotting factors. In some embodiments, the two clotting factors are the same. In other embodiments, the two clotting factors are different. In some embodiments, one clotting factor is a fragment of a clotting factor (e.g., the heavy chain of a clotting factor such as FVIII) and the second clotting factor is a fragment of the same clotting factor (e.g., the light chain of a clotting factor such as FVIII). In some embodiments, the procoagulant compound comprises more than two clotting factors.

In some embodiments, a clotting factor's amino terminus is linked to a self-immolative spacer, which in turn is linked to a protease-cleavable substrate. In some embodiments, a procoagulant compound of the invention comprises two clotting factors (e.g., two different clotting factors or the heavy and light chains of a clotting factor) wherein only one of them has its amino terminus linked to a self-immolative spacer, which in turn is linked to a protease-cleavable substrate. In other embodiments, a procoagulant compound of the invention comprises two clotting factors (e.g., two different clotting factors or the heavy and light chains of a clotting factor) wherein both of them have its amino terminus linked to a self-immolative spacer, which in turn is linked to a protease-cleavable substrate.

In some embodiments, the procoagulant compound comprises a procoagulant peptide (e.g., a procoagulant synthetic peptide). In some embodiments, the procoagulant compound comprises two procoagulant peptides. In some embodiments, the two procoagulant peptides can be the same. In other embodiments, the two procoagulant peptides can be different. In some embodiments, at least one procoagulant peptide is a synthetic procoagulant peptide. In some embodiments, both procoagulant peptides are synthetic. In some embodiments, the procoagulant compound comprises more than two procoagulant peptides.

In some embodiments, the procoagulant compound comprises a clotting factor and a procoagulant peptide, e.g. a synthetic procoagulant peptide. In some embodiments, Pep1 is a clotting factor and Pep2 is a procoagulant peptide, e.g., a synthetic procoagulant peptide. In other embodiments, Pep1 is a procoagulant peptide, e.g., a synthetic procoagulant peptide, and Pep2 is a clotting factor.

In some embodiments, Pep1 and Pep2 are a clotting factor-clotting cofactor pair, e.g., FVIIa and tissue factor, FVIII and FIX, FVIII and vWF, FIXa and FVIIIa, etc.

Suitable clotting factors and procoagulant peptides to incorporate as Pep1 and/or Pep2 in procoagulant compounds of the invention are disclosed for example in WO2011/069164; WO 2012/006624; WO 2004/101740; WO/2007/112005; and WO 2012/006633; and in U.S. Provisional Patent Applications 61/491,762; 61/467,880; 61/442,029; 61/363,186; 61/599,305; 61/586,654; 61/586,099; 61/622,789; 61/586,443; 61/569,158; 61/541,561; 61/522,647; 61/506,015; 61/496,542; 61/496,541; 61/496,544; 61/496,543; or 3480000; all of which are herein incorporated by reference in their entireties.

(i) Clotting Factors

In some embodiments, Pep1 and/or Pep2 are clotting factors, e.g., Factor VII, Factor VIII, Factor IX, and Factor X. Active forms of Factors VII, IX, and X are comprised of dimeric molecules in which the heavy and light chain are linked only by a disulfide bond. Methods for activating clotting factors are known in the art.

a. Factor VII

In some embodiments, a clotting factor is a mature form of Factor VII or a variant thereof. Factor VII (FVII, F7; also referred to as Factor 7, coagulation factor VII, serum factor VII, serum prothrombin conversion accelerator, SPCA, proconvertin and eptacog alpha) is a serine protease that is part of the coagulation cascade. FVII includes a Gla domain, two EGF domains (EGF-1 and EGF-2), and a serine protease domain (or peptidase S1 domain) that is highly conserved among all members of the peptidase S1 family of serine proteases, such as for example with chymotrypsin. FVII occurs as a single chain zymogen, an activated zymogen-like two-chain polypeptide and a fully activated two-chain form.

As used herein, a "zymogen-like" protein or polypeptide refers to a protein that has been activated by proteolytic cleavage, but still exhibits properties that are associated with a zymogen, such as, for example, low or no activity, or a conformation that resembles the conformation of the zymogen form of the protein. For example, when it is not bound to tissue factor, the two-chain activated form of FVII is a zymogen-like protein; it retains a conformation similar to the uncleaved FVII zymogen, and, thus, exhibits very low activity. Upon binding to tissue factor, the two-chain activated form of FVII undergoes conformational change and acquires its full activity as a coagulation factor.

Exemplary FVII variants include those with increased specific activity, e.g., mutations that increase the activity of FVII by increasing its enzymatic activity (Kcat or Km). Such variants have been described in the art and include, e.g., mutant forms of the molecule as described for example in Persson et al. 2001. PNAS 98:13583; Petrovan and Ruf. 2001. J. Biol. Chem. 276:6616; Persson et al. 2001 J. Biol. Chem. 276:29195; Soejima et al. 2001. J. Biol. Chem. 276:17229; Soejima et al. 2002. J. Biol. Chem. 247:49027.

In one embodiment, a variant form of FVII includes the mutations Exemplary mutations include V158D-E296V-M298Q. In another embodiment, a variant form of FVII includes a replacement of amino acids 608-619 (LQQSRKVGDSPN, corresponding to the 170-loop) from the FVII mature sequence with amino acids EASYPGK from the 170-loop of trypsin. High specific activity variants of FIX are also known in the art. For example, Simioni et al. (2009 N.E. Journal of Medicine 361:1671) describe an R338L mutation. Chang et al. (1988 JBC 273:12089) and Pierri et al. (2009 Human Gene Therapy 20:479) describe an R338A mutation. Other mutations are known in the art and include those described, e.g., in Zogg and Brandstetter. 2009 Structure 17:1669; Sichler et al. 2003. J. Biol. Chem. 278:4121; and Sturzebecher et al. 1997. FEBS Lett 412:295. The contents of these references are incorporated herein by reference.

Full activation, which occurs upon conformational change from a zymogen-like form, occurs upon binding to is cofactor tissue factor. Also, mutations can be introduced that result in the conformation change in the absence of tissue factor. Hence, reference to FVIIa includes both two-chain forms thereof: the zymogen-like form, and the fully activated two-chain form.

b. Factor VIII

In one embodiment, a clotting factor is a mature form of Factor VIII or a variant thereof. FVIII functions in the intrinsic pathway of blood coagulation as a cofactor to accelerate the activation of factor X by factor IXa, a reaction that occurs on a negatively charged phospholipid surface in the presence of calcium ions. FVIII is synthesized as a 2351 amino acid single-chain polypeptide having the domain structure A1-A2-B-A3-C1-C2. Wehar, G. A. et al., Nature 312:337-342 (1984) and Toole, J. J. et al., Nature 312:342-347 (1984).

The domain structure of FVIII is identical to that of the homologous coagulation factor, factor V (FV). Kane, W. H. et al., PNAS (USA) 83:6800-6804 (1986) and Jenny, R. J. et al., PNAS (USA) 84:4846-4850 (1987). The FVIII A-domains are 330 amino acids and have 40% amino acid identity with each other and to the A-domain of FV and the plasma copper-binding protein ceruloplasmin. Takahashi, N. et al., PNAS (USA) 81:390-394 (1984). Each C-domain is 150 amino acids and exhibits 40% identity to the C-domains of FV, and to proteins that bind glycoconjugates and negatively charged phospholipids. Stubbs, J. D. et al., PNAS (USA) 87:8417-8421 (1990). The FVIII B-domain is encoded by a single exon and exhibits little homology to any known protein including FV B-domain. Gitschier, J. et al., Nature 312:326-330 (1984) and Cripe, L. D. et al., Biochemistry 31:3777-3785 (1992).

FVIII is secreted into plasma as a heterodimer of a heavy chain (domains A1-A2-B) and a light chain (domains A3-C1-C2) associated through a divalent metal ion linkage between the A1- and A3-domains. In plasma, FVIII is stabilized by binding to von Willebrand factor. More specifically, the FVIII light chain is bound by noncovalent interactions to a primary binding site in the amino terminus of von Willebrand factor.

Upon proteolytic activation by thrombin, FVIII is activated to a heterotrimer of 2 heavy chain fragments (A1, a 50 kDa fragment, and A2, a 43 kDa fragment) and the light chain (A3-C1-C2, a 73 kDa chain). The active form of FVIII (FVIIIa) thus consists of an A1-subunit associated through the divalent metal ion linkage to a thrombin-cleaved A3-C1-C2 light chain and a free A2 subunit associated with the A1 domain through an ion association. Eaton, D. et al., Biochemistry 25: 505 (1986); Lollar, P. et al., J. Biol. Chem. 266: 12481 (1991); and Fay, P. J. et al., J. Biol. Chem. 266: 8957 (1991). This FVIIIa heterotrimer is unstable and subject to rapid inactivation through dissociation of the A2 subunit under physiological conditions.

In one embodiment, a clotting factor comprises a B-domain deleted version of factor VIII. "B-domain" of Factor VIII, as used herein, is the same as the B-domain known in the art that is defined by internal amino acid sequence identity and sites of proteolytic cleavage, e.g., residues Ser741-Arg1648 of full-length human Factor VIII. The other human Factor VIII domains are defined by the following amino acid residues: A1, residues Ala1-Arg372; A2, residues Ser373-Arg740; A3, residues Ser1690-Asn2019; C1, residues Lys2020-Asn2172; 2, residues Ser2173-Tyr2332. The A3-C1-C2 sequence includes residues Ser1690-Tyr2332. The remaining sequence, residues Glu1649-Arg1689, is usually referred to as the a3 acidic region.

The locations of the boundaries for all of the domains, including the B-domains, for porcine, mouse and canine Factor VIII are also known in the art. In one embodiment, the B domain of Factor VIII is deleted ("B-domain-deleted factor VIII" or "BDD FVIII"). An example of a BDD FVIII is REFACTO® (recombinant BDD FVIII with S743/Q1638 fusion), which is known in the art.

A "B-domain-deleted Factor VIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B-domain-deleted Factor VIII sequence comprises any one of the deletions disclosed at col. 4, line 4 to col. 5, line 28 and examples 1-5 of U.S. Pat. No. 6,316,226 (also in U.S. Pat. No. 6,346,513).

In another embodiment, a B-domain deleted Factor VIII is the S743/Q1638 B-domain deleted Factor VIII (SQ version Factor VIII) (e.g., Factor VIII having a deletion from amino acid 744 to amino acid 1637, e.g., Factor VIII having amino acids 1-743 and amino acids 1638-2332). In some embodiments, a B-domain-deleted Factor VIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620).

Figure 2:
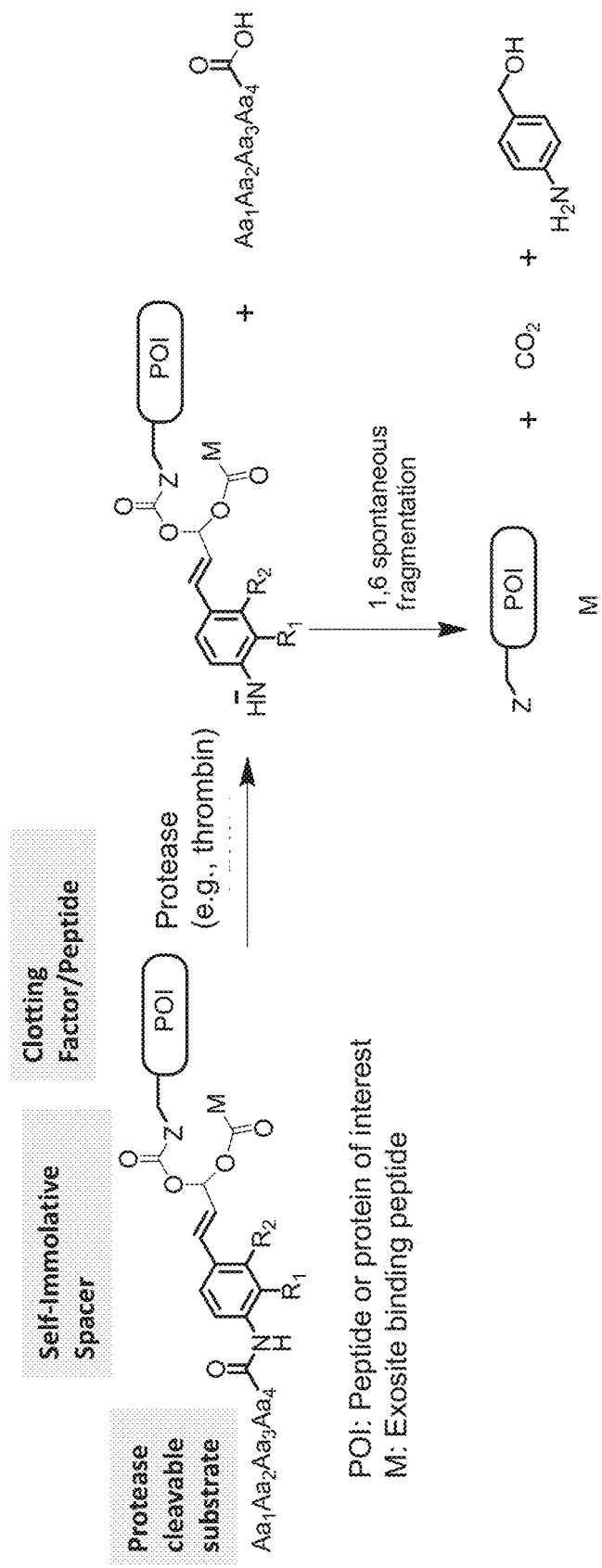

In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563.

In some embodiments, a B-domain-deleted Factor VIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B-domain-deleted Factor VIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety.

A B-domain-deleted Factor VIII can also contain a deletion of amino acids 771-1666 or amino acids 868-1562 of Factor VIII. Meulien P., et al. *Protein Eng.* 2(4): 301-6 (1988), incorporated herein by reference in its entirety. Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., *DNA* (1987) 6:553-564)), 741 though 1648 (Pasek (PCT application No. 88/00831)), or 816 through 1598 or 741 through 1648 (Lagner (Behring Inst. Mitt. (1988) No 82:16-25, EP 295597)), each of which is incorporated herein by reference in its entirety. Each of the foregoing deletions can be made in any Factor VIII sequence.

c. Factor IX

In one embodiment, a clotting factor is a mature form of Factor IX or a variant thereof. Factor IX circulates as a 415 amino acid, single chain plasma zymogen (A. Vysotchin et al., J. Biol. Chem. 268, 8436 (1993)). The zymogen of FIX is activated by FXIa or by the tissue factor/FVIIa complex. Specific cleavages between arginine-alanine 145-146 and arginine-valine 180-181 result in a light chain and a heavy chain linked by a single disulfide bond between cysteine 132 and cysteine 289 (S. Bajaj et al., Biochemistry 22, 4047 (1983)).

The structural organization of FIX is similar to that of the vitamin K-dependent blood clotting proteins FVII, FX and protein C (B. Furie and B. Furie, supra). The approximately 45 amino acids of the amino terminus comprise the gamma-carboxyglutamic acid, or Gla, domain. This is followed by two epidermal growth factor homology domains (EGF), an activation peptide and the catalytic "heavy chain" which is a member of the serine protease family (A. Vysotchin et al., J. Biol. Chem. 268, 8436 (1993); S. Spitzer et al., Biochemical Journal 265, 219 (1990); H. Brandstetter et al., Proc. Natl. Acad Sci. USA 92, 9796 (1995)).

d. Factor X

In one embodiment, a clotting factor is a mature form of Factor X. Factor X is a vitamin-K dependent glycoprotein of a molecular weight of 58.5 kDa, which is secreted from liver cells into the plasma as a zymogen. Initially factor X is produced as a prepropeptide with a signal peptide consisting in total of 488 amino acids. The signal peptide is cleaved off by signal peptidase during export into the endoplasmatic reticulum, the propeptide sequence is cleaved off after gamma carboxylation took place at the first 11 glutamic acid residues at the N-terminus of the mature N-terminal chain. A further processing step occurs by cleavage between Arg182 and Ser183. This processing step also leads concomitantly to the deletion of the tripeptide Arg180-Lys181-Arg182. The resulting secreted factor X zymogen consists of an N-terminal light chain of 139 amino acids (M, 16,200) and a C-terminal heavy chain of 306 amino acids (M, 42,000) which are covalently linked via a disulfide bridge between Cys172 and Cys342. Further posttranslational processing steps include the β-hydroxylation of Asp103 as well as N- and O-type glycosylation.

It will be understood that in addition to wild type (WT) versions of these clotting factors or biologically active portions thereof, the present invention can also employ precursor truncated forms thereof that have activity, allelic variants and species variants, variants encoded by splice variants, and other variants, including polypeptides that have at least 40%, 45%, 50%, 55%, 65%, 70%, 75%, 80%, 85%, 90%, 95%, 96%, 97%, 98%, 99% or more sequence identity to the mature form of the clotting factor and which retain the ability to promote clot formation. For example, modified FVII polypeptides and variants thereof which retain at least one activity of a FVII, such as TF binding, factor X binding, phospholipid binding, and/or coagulant activity of a FVII can be employed. By retaining activity, the activity can be altered, such as reduced or increased, as compared to a wild-type clotting factor so long as the level of activity retained is sufficient to yield a detectable effect.

Exemplary modified polypeptides include, but are not limited to, tissue-specific isoforms and allelic variants thereof, synthetic molecules prepared by translation of nucleic acids, proteins generated by chemical synthesis, such as syntheses that include ligation of shorter polypeptides, through recombinant methods, proteins isolated from human and non-human tissue and cells, chimeric polypeptides and modified forms thereof. The instant clotting factors can also consist of fragments or portions of WT molecules that are of sufficient length or include appropriate regions to retain at least one activity (upon activation if needed) of a full-length mature polypeptide. Exemplary clotting factor variants are known in the art.

As used herein, the term "Gla domain" refers to the conserved membrane binding motif which is present In vitamin K-dependent proteins, such as as prothrombin, coagulation factors VII, IX and X, proteins C, S, and Z. These proteins require vitamin K for the posttranslational synthesis of g-carboxyglutamic acid, an amino acid clustered in the N-terminal Gla domain of these proteins. All glutamic residues present in the domain are potential carboxylation sites and many of them are therefore modified by carboxylation. In the presence of calcium ions, the Gla domain interacts with phospholipid membranes that include phosphatidylserine. The Gla domain also plays a role in binding to the FVIIa cofactor, tissue factor (TF). Complexed with TF, the Gla domain of FVIIa is loaded with seven Ca2+ ions, projects three hydrophobic side chains in the direction of the cell membrane for interaction with phospholipids on the cell surface, and has significant contact with the C-terminal domain of TF.

The Gla domain of factor VII comprises the uncommon amino acid_-carboxyglutamic acid (Gla), which plays a vital role in the binding of clotting factors to negatively charged phospholipid surfaces.

The GLA domain is responsible for the high-affinity binding of calcium ions. It starts at the N-terminal extremity of the mature form of proteins and ends with a conserved aromatic residue. A conserved Gla-x(3)-Gla-x-Cys motif is found in the middle of the domain which seems to be important for substrate recognition by the carboxylase.

Using stopped-flow fluorescence kinetic measurements in combination with surface plasmon resonance analysis, the Gla domain has been found to be important in the sequence of events whereby the protease domain of FVIIa initiates contact with sTF (Biochemical and Biophysical Research Communications. 2005. 337:1276). In addition, clearance of clotting factors can be significantly mediated through Gla interactions, e.g., on liver cells and clearance receptors, e.g., EPCR.

In one embodiment, targeted clotting factors are modified to lack a Gla domain. The Gla domain is responsible for mediating clearance of clotting factors via multiple pathways, such as binding to liver cells, clearance receptors such as EPCR, etc. Thus, eliminating the Gla domain has beneficial effects on half life of clotting factors. Though Gla domain is also generally required for activity by localizing clotting factors to sites of coagulation, the inclusion of a platelet targeting domain moiety targets the Gla deleted clotting factor to platelets. In one embodiment, a clotting factor comprises a targeting moiety and lacks a Gla domain. For example, in the case of Factor VII, the Gla domain is present at the amino terminus of the light chain and consists of amino acids 1-35. The Gla domains of exemplary clotting factors are indicated in the accompanying sequence listing. This domain can be removed using standard molecular biology techniques, replaced with a targeting domain, and the modified light chain incorporated into a construct of the invention. In one embodiment, a cleavage site can be introduced into constructs lacking a Gla domain to facilitate activation of the molecule. For example, in one embodiment, such a cleavage site can be introduced between the amino acids that are cleaved when the clotting factor is activated (e.g., between amino acids 152 and 153 in the case of Factor VII).

In one embodiment, a cleavage site can be introduced into constructs lacking a Gla domain to facilitate activation of the molecule. For example, in one embodiment, such a cleavage site can be introduced between the amino acids that are cleaved when the clotting factor is activated (e.g., between amino acids 152 and 153 in the case of Factor VII). Exemplary clotting factors lacking a Gla domain are shown in the accompanying figures.

Exemplary clotting factors are those of mammalian, e.g., human, origin.

(ii) Procoagulant Peptides

Suitable procoagulant peptides to incorporate as Pep1 and/or Pep2 in procoagulant compounds of the invention are disclosed, for example, in U.S. Provisional Application Nos. 61/495,818; 61/600,237; and, 61/605,540 which are herein incorporated by reference in their entireties.

Exemplary synthetic procoagulant peptides include, for example:

```
                                        (SEQ ID NO: 8)
KLTCLASYCWLF;

(SEQ ID NO: 9)
RRAPGKLTCLASYCWLFWTGIA;

(SEQ ID NO: 10)
RRAPGKLQCLASYCWLFWTGIA;

(SEQ ID NO: 11)
PRIRTVGPGSRSASGKLTCLASYCWLFWTGIA;

(SEQ ID NO: 12)
SKQGRPISPDRRAAGKLTCLASYCWLFWTGIA;

(SEQ ID NO: 13)
PRIRTVGPGSRSASGKSTCLASYCWLFWTGIA;

(SEQ ID NO: 14)
SRIRTVSPGSRSASGKSTCLASYCWLFWTGIA;
or
                                        (SEQ ID NO: 15)
PRSRTVGPGSRSASGKSTCLASYCWLFWTGIA.
```

2. Other Polypeptides

In some embodiments, the procoagulant compound comprises at least one polypeptide (e.g., Pep1 or Pep2) that is not a clotting factor or a synthetic procoagulant peptide. In some embodiments, the procoagulant compound comprises a Pep1 or Pep2 polypeptide which is clotting cascade cofactor, e.g., tissue factor, or a derivative, fragment, or variant thereof.

In other embodiments, the procoagulant compound comprises a Pep1 or Pep2 polypeptide comprising a ligand binding moiety. In some embodiments, such ligand binding moiety is an antibody or an antigen binding fragment thereof.

B. Self-Immolative Spacer (Bx)

Procoagulant compounds according to the present disclosure comprise a self-immolative spacer. In some aspects, the self-immolative spacer comprises an aminobenzyl carbamate group, an aminobenzyl ether group, or an aminobenzyl carbonate group. In one aspect, the self-immolative spacer is p-amino benzyl carbamate (PABC).

Figure 1B:
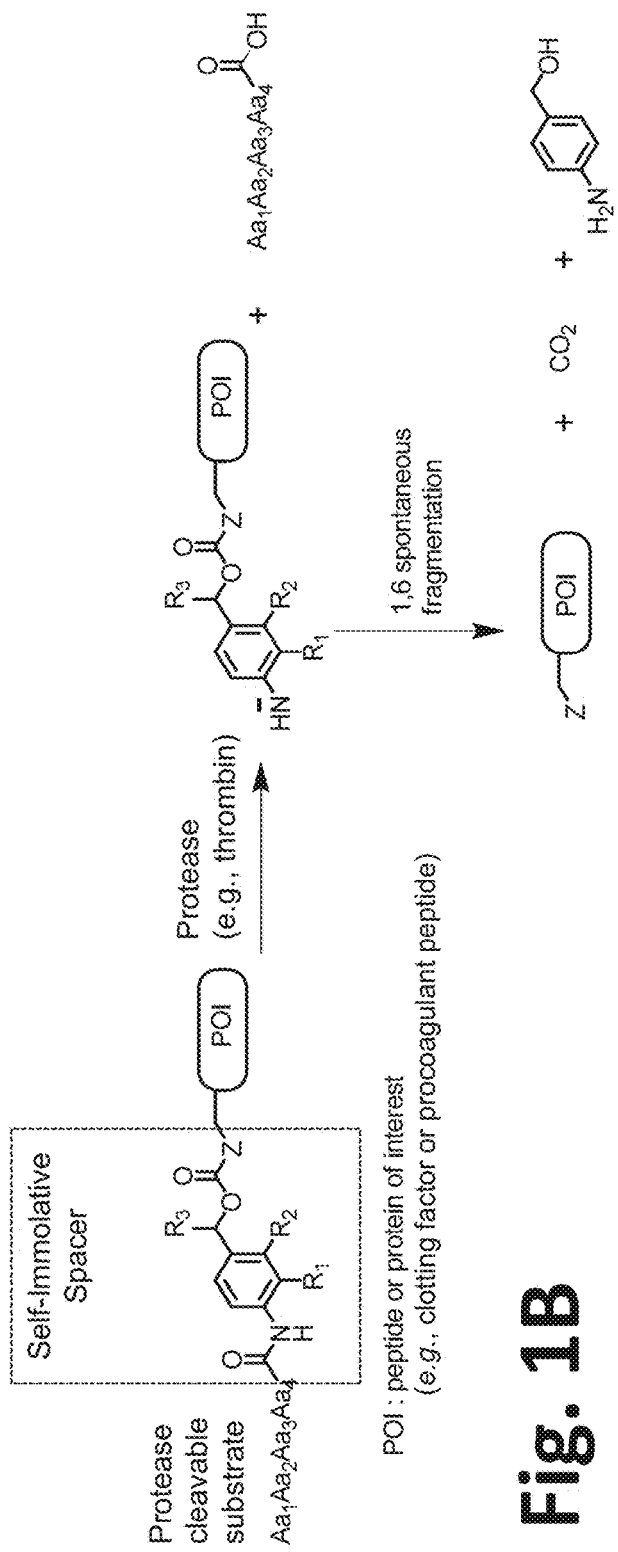

P-amino benzyl carbamate (PABC) is the most efficient and most widespread connector linkage for self-immolative site-specific prodrug activation (see, e.g., Carl et al. J. Med. Chem. 24:479-480 (1981); WO 1981/001145; Rautio et al, Nature Reviews Drug Discovery 7:255-270 (2008); Simplicio et al., Molecules 13:519-547 (2008). PABC allows the release of any amine drugs, peptides, and proteins upon cleavage by a protease and 1,6 spontaneous fragmentation (see FIG. 1).

In some embodiments, the self-immolative spacer connects a polypeptide of interest (e.g., a clotting factor or fragment thereof, or a synthetic procoagulant peptide) to a protease-cleavable substrate (e.g., a thrombin substrate). In specific aspects, the carbamate group of a PABC self-immolative spacer is connected to the N-terminus of a polypeptide of interest (e.g., a clotting factor or fragment thereof, or a synthetic procoagulant peptide), and the amino group of the PABC self-immolative spacer is connected to a protease-cleavable substrate (e.g., a thrombin substrate).

The aromatic ring of the aminobenzyl group can optionally be substituted with one or more (e.g., $R_1$ and/or $R_2$) substituents on the aromatic ring, which replace a hydrogen that is otherwise attached to one of the four non-substituted carbons that form the ring. As used herein, the symbol "$R_x$" (e.g., $R_1$, $R_2$, $R_3$, $R_4$) is a general abbreviation that represents a substituent group as described herein.

Substituent groups can improve the self-immolative ability of the p-aminobenzyl group (Hay et al., J. Chem Soc., Perkin Trans. 1:2759-2770 (1999); see also, Sykes et al. J. Chem. Soc., Perkin Trans. 1:1601-1608 (2000)).

The following formula shows the general topology of a p-amino benzyl immolative linker and the relative locations of an exemplary protease-cleavable substrate ($Aa_1Aa_2Aa_3Aa_4$) and a peptide or protein of interest (POI), which could be Pep1, Pep2, a polypeptide heterologous moiety, or linker comprising a peptide linker. The formula indicates possible locations of R substituent groups ($R_1$, $R_2$, $R_3$).

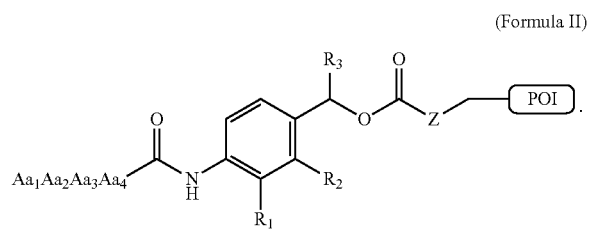

(Formula II)

The substituents, which can be a single atom, e.g., a halogen, or a multi-atom group, e.g., methyl, are selected in order to impact the stability of the aminobenzyl or the decomposition product thereof. Electron withdrawal from the ring can be used to facilitate the spontaneous decomposition of the aminobenzyl group from the drug after cleavage of the bond between the amino group of the aminobenzyl group and the adjacent peptide linkage. Exemplary aromatic group $R_1$, $R_2$, or $R_3$ substituents include, for example, F, Cl, I, Br, OH, methyl, methoxy, $NO_2$, $NH_2$, $NO^{3+}$, $NHCOCH_3$, $N(CH_3)_2$, $NHCOCF_3$, alkyl, haloalkyl, $C_1$-$C_8$ alkylhalide, carboxylate, sulfate, sulfamate, sulfonate, etc. (see, e.g., U.S. Pat. Nos. 7,091,186 and 7,659,241). The p-aminobenzyl linker can comprise a heteroatom Z connected to the amino terminus of the peptide or protein of interest protein. The term heteroatom, as used herein, includes oxygen (O), nitrogen (N), sulfur (S), silicon (Si), boron (B) and phosphorus (P). In one embodiment, the heteroatoms in Z are O, S or N.

As illustrated below, in some aspects the self-immolative linker comprises an M group comprising an exosite binding peptide which binds to the exosite of its respective clotting factor.

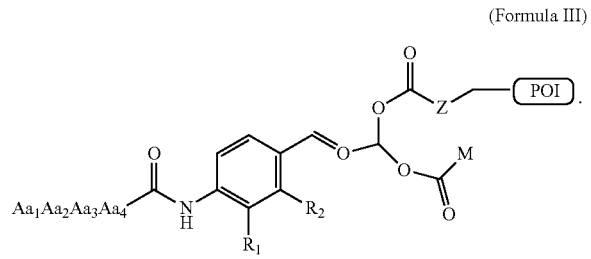

(Formula III)

Many exosite binding motifs are known in the art. Insertion of an exosite binding motifs can increase the cleavage rate. Upon cleavage, both the exosite binding motif and the peptide or protein of interest (e.g., a clotting factor or fragment thereof, or a procoagulant peptide) are released (see FIG. 2).

In some embodiments, only one of the four non-substituted carbons in the p-aminobenzyl ring is substituted. In some other embodiments, two of the four non-substituted carbons in the p-aminobenzyl ring are substituted. In other embodiments, three of the four non-substituted carbons in the p-aminobenzyl ring are substituted. In some embodiments, the four non-substituted carbons in the p-aminobenzyl ring are substituted.

Self-immolative elimination can take place, e.g., via 1,4 elimination, 1,6 elimination (e.g., PABC), 1,8 elimination (e.g., p-amino-cinnamyl alcohol), β-elimination, cyclisation-elimination (e.g., 4-aminobutanol ester and ethylenediamines), cyclization/lactonization, cyclization/lactolization, etc. See, e.g., Singh et al. Curr. Med. Chem. 15:1802-1826 (2008); Greenwald et al. J. Med. Chem. 43:475-487 (2000).

In some aspects, the self-immolative spacer can comprise, e.g., an cinnamyl, naphthyl, or biphenyl groups (see, e.g., Blencowe et al. Polym. Chem. 2:773-790 (2011)). In some aspects, the self-immolative spacer comprises a heterocyclic ring (see, e.g., U.S. Pat. Nos. 7,375,078; 7,754,681). Numerous homoaromatic (see, e.g., Carl et al. J. Med. Chem. 24:479 (1981); Senter et al. J. Org. Chem. 55:2975 (1990); Taylor et al. J. Org. Chem. 43:1197 (1978); Andrianomenjanahary et al. Bioorg. Med. Chem. Lett. 2:1903 (1992)), and coumarin (see, e.g., Weinstein et al. Chem. Commun. 46:553 (2010)), furan, thiophene, thiazole, oxazole, isoxazole, pyrrole, pyrazole (see, e.g., Hay et al. J. Med. Chem. 46:5533 (2003)), pyridine (see, e.g., Perry-Feigenbaum et al. Org. Biomol. Chem. 7:4825 (2009)), imidazone (see, e.g., Nailor et al. Bioorg. Med. Chem. Lett. Z:1267 (1999); Hay and Denny, Tetrahedron Lett. 38:8425 (1997)), and triazole (see, e.g., Bertrand and Gesson, J. Org. Chem. 72:3596 (2007)) based heteroaromatic groups that are self-immolative under both aqueous and physiological conditions are known in the art. See also, U.S. Pat Nos. 7,691,962; 7,091,186; U.S. Pat. Publ. Nos. US2006/0269480; US2010/0092496; US2010/0145036; US2003/0130189; US2005/0256030).

In some embodiments, a procoagulant compound of the invention comprises more than one self-immolative spacer in tandem, e.g., two or more PABC units. See, e.g., de Groot et al. J. Org. Chem. 66:8815-8830 (2001). In some embodiments, a procoagulant compound of the invention can comprise a self-immolative spacer (e.g., a p-aminobenzylalcohol or a hemithioaminal derivative of p-carboxybenzaldehyde or glyoxilic acid) linked to a fluorigenic probe (see, e.g., Meyer et al. Org. Biomol. Chem. 8:1777-1780 (2010)).

Where substituent groups in the self-immolative linkers are specified by their conventional chemical formulae, written from left to right, they equally encompass the chemically identical substituents, which would result from writing the structure from right to left. For example, "—$CH_2O$—" is intended to also recite "—$OCH_2$—". Substituent groups in self-immolative, for example, $R_1$ and/or $R_2$ substituents in a p-aminobenzyl self-immolative linker as discuss above can include, e.g., alkyl, alkylene, alkenyl, alkynyl, alkoxy, alkylamino, alkylthio, heteroalkyl, cycloalkyl, heterocycloalkyl, aryl, arylalkyl, aryloxy, heteroaryl, etc. When a compound of the present disclosure includes more than one substituent, then each of the substituents is independently chosen.

The term "alkyl," by itself or as part of another substituent, means, unless otherwise stated, a straight or branched chain hydrocarbon radical having the number of carbon atoms designated (e.g., $C_1$-$C_{10}$ means one to ten carbon atoms). Typically, an alkyl group will have from 1 to 24 carbon atoms, for example having from 1 to 10 carbon atoms, from 1 to 8 carbon atoms or from 1 to 6 carbon atoms. A "lower alkyl" group is an alkyl group having from 1 to 4 carbon atoms. The term "alkyl" includes di- and multivalent radicals. For example, the term "alkyl" includes "alkylene" wherever appropriate, e.g., when the formula indicates that the alkyl group is divalent or when substituents are joined to form a ring. Examples of alkyl radicals include, but are not limited to, methyl, ethyl, n-propyl, iso-propyl, n-butyl, tert-butyl, iso-butyl, sec-butyl, as well as homologs and isomers of, for example, n-pentyl, n-hexyl, n-heptyl and n-octyl.

The term "alkylene" by itself or as part of another substituent means a divalent (diradical) alkyl group, wherein alkyl is defined herein. "Alkylene" is exemplified, but not limited, by —$CH_2H_2H_2H_2$—. Typically, an "alkylene" group will have from 1 to 24 carbon atoms, for example, having 10 or fewer carbon atoms (e.g., 1 to 8 or 1 to 6 carbon atoms). A "lower alkylene" group is an alkylene group having from 1 to 4 carbon atoms.

The term "alkenyl" by itself or as part of another substituent refers to a straight or branched chain hydrocarbon radical having from 2 to 24 carbon atoms and at least one double bond. A typical alkenyl group has from 2 to 10 carbon atoms and at least one double bond. In one embodiment, alkenyl groups have from 2 to 8 carbon atoms or from 2 to 6 carbon atoms and from 1 to 3 double bonds. Exemplary alkenyl groups include vinyl, 2-propenyl, 1-but-3-enyl, crotyl, 2-(butadienyl), 2,4-pentadienyl, 3-(1,4-pentadienyl), 2-isopentenyl, 1-pent-3-enyl, 1-hex-5-enyl and the like.

The term "alkynyl" by itself or as part of another substituent refers to a straight or branched chain, unsaturated or polyunsaturated hydrocarbon radical having from 2 to 24 carbon atoms and at least one triple bond. A typical "alkynyl" group has from 2 to 10 carbon atoms and at least one triple bond. In one aspect of the disclosure, alkynyl groups have from 2 to 6 carbon atoms and at least one triple bond. Exemplary alkynyl groups include prop-1-ynyl, prop-2-ynyl (i.e., propargyl), ethynyl and 3-butynyl.

The terms "alkoxy," "alkylamino" and "alkylthio" (or thioalkoxy) are used in their conventional sense, and refer to alkyl groups that are attached to the remainder of the molecule via an oxygen atom, an amino group, or a sulfur atom, respectively.

The term "heteroalkyl," by itself or in combination with another term, means a stable, straight or branched chain hydrocarbon radical consisting of the stated number of carbon atoms (e.g., $C_2$-$C_{10}$, or $C_2$-$C_8$) and at least one heteroatom chosen, e.g., from N, O S, Si, B and P (in one embodiment, N, O and S), wherein the nitrogen, sulfur and phosphorus atoms are optionally oxidized, and the nitrogen atom(s) are optionally quaternized. The heteroatom(s) is/are placed at any interior position of the heteroalkyl group. Examples of heteroalkyl groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—Si($CH_3$)$_3$, —$CH_2$—CH=N—$OCH_3$, and —CH=CH—N($CH_3$)—$CH_3$. Up to two heteroatoms can be consecutive, such as, for example, —$CH_2$—NH—$OCH_3$ and —$CH_2$—O—Si($CH_3$)$_3$.

Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. Typically, a heteroalkyl group will have from 3 to 24 atoms (carbon and heteroatoms, excluding hydrogen) (3- to 24-membered heteroalkyl). In another example, the heteroalkyl group has a total of 3 to 10 atoms (3- to 10-membered heteroalkyl) or from 3 to 8 atoms (3- to 8-membered heteroalkyl). The term "heteroalkyl" includes "heteroalkylene" wherever appropriate, e.g., when the formula indicates that the heteroalkyl group is divalent or when substituents are joined to form a ring.

The term "cycloalkyl" by itself or in combination with other terms, represents a saturated or unsaturated, non-aromatic carbocyclic radical having from 3 to 24 carbon atoms, for example, having from 3 to 12 carbon atoms (e.g., $C_3$-$C_8$ cycloalkyl or $C_3$-$C_6$ cycloalkyl). Examples of cycloalkyl include, but are not limited to, cyclopropyl, cyclobutyl, cyclopentyl, cyclohexyl, cycloheptyl, 1-cyclohexenyl, 3-cyclohexenyl, cycloheptyl and the like. The term "cycloalkyl" also includes bridged, polycyclic (e.g., bicyclic) structures, such as norbornyl, adamantyl and bicyclo[2.2.1]heptyl. The "cycloalkyl" group can be fused to at least one (e.g., 1 to 3) other ring selected from aryl (e.g., phenyl), heteroaryl (e.g., pyridyl) and non-aromatic (e.g., carbocyclic or heterocyclic) rings. When the "cycloalkyl" group includes a fused aryl, heteroaryl or heterocyclic ring, then the "cycloalkyl" group is attached to the remainder of the molecule via the carbocyclic ring.

The term "heterocycloalkyl," "heterocyclic," "heterocycle," or "heterocyclyl," by itself or in combination with other terms, represents a carbocyclic, non-aromatic ring (e.g., 3- to 8-membered ring and for example, 4-, 5-, 6- or 7-membered ring) containing at least one and up to 5 heteroatoms selected from, e.g., N, O S, Si, B and P (for example, N, O and S), wherein the nitrogen, sulfur and phosphorus atoms are optionally oxidized, and the nitrogen atom(s) are optionally quaternized (e.g., from 1 to 4 heteroatoms selected from nitrogen, oxygen and sulfur), or a fused ring system of 4- to 8-membered rings, containing at least one and up to 10 heteroatoms (e.g., from 1 to 5 heteroatoms selected from N, O and S) in stable combinations known to those of skill in the art. Exemplary heterocycloalkyl groups include a fused phenyl ring. When the "heterocyclic" group includes a fused aryl, heteroaryl or cycloalkyl ring, then the "heterocyclic" group is attached to the remainder of the molecule via a heterocycle. A heteroatom can occupy the position at which the heterocycle is attached to the remainder of the molecule.

Exemplary heterocycloalkyl or heterocyclic groups of the present disclosure include morpholinyl, thiomorpholinyl, thiomorpholinyl S-oxide, thiomorpholinyl S,S-dioxide, piperazinyl, homopiperazinyl, pyrrolidinyl, pyrrolinyl, imidazolidinyl, tetrahydropyranyl, piperidinyl, tetrahydrofuranyl, tetrahydrothienyl, piperidinyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazolyl, dihydropyridyl, dihydropyrimidinyl, dihydrofuryl, dihydropyranyl, tetrahydrothienyl S-oxide, tetrahydrothienyl S,S-dioxide, homothiomorpholinyl S-oxide, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

By "aryl" is meant a 5-, 6- or 7-membered, aromatic carbocyclic group having a single ring (e.g., phenyl) or being fused to other aromatic or non-aromatic rings (e.g., from 1 to 3 other rings). When the "aryl" group includes a non-aromatic ring (such as in 1,2,3,4-tetrahydronaphthyl) or heteroaryl group then the "aryl" group is bonded to the remainder of the molecule via an aryl ring (e.g., a phenyl ring). The aryl group is optionally substituted (e.g., with 1 to 5 substituents described herein). In one example, the aryl group has from 6 to 10 carbon atoms. Non-limiting examples of aryl groups include phenyl, 1-naphthyl, 2-naphthyl, quinoline, indanyl, indenyl, dihydronaphthyl, fluorenyl, tetralinyl, benzo[d][1,3]dioxolyl or 6,7,8,9-tetrahydro-5H-benzo[a]cycloheptenyl. In one embodiment, the aryl group is selected from phenyl, benzo[d][1,3]dioxolyl and naphthyl. The aryl group, in yet another embodiment, is phenyl.

The term "arylalkyl" or "aralkyl" is meant to include those radicals in which an aryl group or heteroaryl group is attached to an alkyl group to create the radicals -alkyl-aryl and -alkyl-heteroaryl, wherein alkyl, aryl and heteroaryl are defined herein. Exemplary "arylalkyl" or "aralkyl" groups include benzyl, phenethyl, pyridylmethyl and the like.

By "aryloxy" is meant the group-O-aryl, where aryl is as defined herein. In one example, the aryl portion of the aryloxy group is phenyl or naphthyl. The aryl portion of the aryloxy group, in one embodiment, is phenyl.

The term "heteroaryl" or "heteroaromatic" refers to a polyunsaturated, 5-, 6- or 7-membered aromatic moiety containing at least one heteroatom (e.g., 1 to 5 heteroatoms, such as 1-3 heteroatoms) selected from N, O, S, Si and B (for example, N, O and S), wherein the nitrogen and sulfur atoms are optionally oxidized, and the nitrogen atom(s) are optionally quaternized. The "heteroaryl" group can be a single ring or be fused to other aryl, heteroaryl, cycloalkyl or heterocycloalkyl rings (e.g., from 1 to 3 other rings). When the "heteroaryl" group includes a fused aryl, cycloalkyl or heterocycloalkyl ring, then the "heteroaryl" group is attached to the remainder of the molecule via the heteroaryl ring. A heteroaryl group can be attached to the remainder of the molecule through a carbon- or heteroatom.

In one example, the heteroaryl group has from 4 to 10 carbon atoms and from 1 to 5 heteroatoms selected from O, S and N. Non-limiting examples of heteroaryl groups include pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridyl, benzotetrahydrofuranyl, benzotetrahydrothienyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Exemplary heteroaryl groups include imidazolyl, pyrazolyl, thiadiazolyl, triazolyl, isoxazolyl, isothiazolyl, imidazolyl, thiazolyl, oxadiazolyl, and pyridyl.

Other exemplary heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, pyridin-4-yl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from acceptable aryl group substituents described below.

C. Protease-Cleavable Substrate (Zy)

The procoagulant compounds of the invention comprise a protease-cleavable substrate (Zy) linked to a self-immolative spacer (Bx). In some embodiments, the procoagulant compound of the invention comprises a single protease-cleavable substrate. In other embodiments, particularly embodiments where more that one procoagulant polypeptide (e.g., a clotting factor o procoagulant peptide) or one or more heterologous moieties comprising polypeptide sequences are present, additional protease-cleavable substrate moieties (alone or in tandem with self-immolative spacers), can be linked to the N-terminus of the sequence of the procoagulant polypeptide or heterogous moiety. In some embodiments, protease-cleavable substrate moieties (alone or in tandem with self-immolative spacers), can be linked to the N-terminus of linkers (L) comprising peptide linkers.

Accordingly, procoagulant compounds of the invention can comprise a Zy-Bx-Pep1 module and further comprise, e.g., one or more of the following additional modules:

Zy-Het (wherein Het is Het1 or Het2),

Zy-Bx-Het (wherein Het is Het1 or Het2),

Zy-Pep (wherein Pep is Pep2 or an additional polypeptide if the procoagulant compound comprises more than two polypeptides)

Zy-Bx-Pep (wherein Pep is Pep2 or an additional polypeptide if the procoagulant compound comprises more than two polypeptides), wherein the additional module is covalently linked to the N-terminus or the C-terminus of the Zy-Bx-Pep1 module, with optionally one or more linkers or heterologous moieties interposed between the Zy-Bx-Pep1 and the additional module.

In some embodiments, when more that one protease-cleavable substrate is present, the substrates can be cleaved by the same or by different proteases. In embodiments where the protease-cleavable substrates are cleaved by the same protease, the protease-cleavable substrate can be the same or they can be different.

In some embodiments, the protease-cleavable substrate is a selective substrate for enzymatic cleavage by one or more proteases, e.g., blood-coagulation cascade proteases. Blood-coagulating cascade proteases include, but are not necessarily limited to, thrombin, FVIIa, FIXa, FXa, FXIa, and FXIIa.

The term "blood-coagulation cascade" used herein refers to the intrinsic, extrinsic, and common pathways. The intrinsic coagulation pathway leads to the formation of FIXa, that in conjunction with FVIIIa and FX, phospholipid and $Ca^{2+}$ gives FXa. The extrinsic pathway gives FXa and FIXa after the combination of tissue factor and FVII. The common coagulation pathway interacts with the blood coagulation factors FV, FVIII, FIX and FX to cleave prothrombin to thrombin (FIIa), which is then able to cleave fibrinogen to fibrin.

In some embodiments, the protease-cleavable substrate comprise a cleavage site for a protease selected from neprilysin (CALLA or CD10), thimet oligopeptidase (TOP), leukotriene A4 hydrolase, endothelin converting enzymes, ste24 protease, neurolysin, mitochondrial intermediate peptidase, interstitial collagenases, collagenases, stromelysins, macrophage elastase, matrilysin, gelatinases, meprins, procollagen C-endopeptidases, procollagen N-endopeptidases, ADAMs and ADAMTs metalloproteinases, myelin associated metalloproteinases. enamelysin, tumor necrosis factor α-converting enzyme, insulysin, nardilysin, mitochondrial processing peptidase, magnolysin, dactylysin-like metal loproteases, neutrophil collagenase, matrix metallopeptidases, membrane-type matrix metalloproteinases, SP2 endopeptidase, prostate specific antigen (PSA), plasmin, urokinase, human fibroblast activation protein (FAPα), trypsin, chymotrypsins, caldecrin, pancreatic elastases, pancreatic endopeptidase, enteropeptidase, leukocyte elastase, myeloblasts, chymases, tryptase, granzyme, stratum corneum chymotryptic enzyme, acrosin, kallikreins, complement components and factors, alternative-complement pathway c3/c5 convertase, mannose-binding protein-associated serine protease, coagulation factors, thrombin, protein c, u and t-type plasminogen activator, cathepsin G, hepsin, prostasin, hepatocyte growth factor-activating endopeptidase, subtilisin/kexin type proprotein convertases, furin, proprotein convertases, prolyl peptidases, acylaminoacyl peptidase, peptidyl-glycaminase, signal peptidase, n-terminal nucleophile aminohydrolases, 20s proteasome, γ-glutamyl transpeptidase, mitochondrial endopeptidase, mitochondrial endopeptidase Ia, htra2 peptidase, matriptase, site 1 protease, legumain, cathepsins, cysteine cathepsins, calpains, ubiquitin isopeptidase T, caspases, glycosylphosphatidylinositoliprotein transamidase, cancer procoagulant, prohormone thiol protease, γ-Glutamyl hydrolase, bleomycin hydrolase, seprase, cathepsin D, pepsins, chymosyn, gastricsin, renin, yapsin and/or memapsins, Prostate-Specific antigen (PSA), or any combinations thereof. See, e.g., Kohchi et al. Bioorganic & Medicinal Chemistry Letters 17:2241-2245 (2007); Brady et al. J. Med. Chem. 45:4706-4715 (2002).

In specific embodiments, the protease-cleavable substrate is selectively cleaved by thrombin at the site of injury. In some embodiments, the protease-cleavable substrate is selectively cleaved by thrombin in vitro, for example, when the procoagulant peptides of the invention are used for diagnosis or visualization. Non-limiting exemplary thrombin-cleavable substrates include, e.g., DFLAEGGGVR (SEQ ID NO: 4), TTKIKPR (SEQ ID NO: 5), or LVPRG (SEQ ID NO: 6), or a sequence comprising, consisting essentially of, or consisting of ALRPR (SEQ ID NO: 7) (e.g., ALRPRVVGGA (SEQ ID NO: 16)).

In specific embodiments, the thrombin-cleavable substrate comprises the sequence ALRPR (SEQ ID NO: 7), ALVPR (SEQ ID NO: 17), LVPR (SEQ ID NO: 18), D-Phe-Pro-Arg (SEQ ID NO: 19), D-Ala-Leu-Val-Pro-Arg (SEQ ID NO: 20), or D-Phe-Pip-Arg (Pip=pipecolic acid) (SEQ ID NO: 21) (see, e.g., Tung et al., ChemBioChem 3:207-2011 (2002); Jaffer et al. Arterioscler. Thromb. Vasc. Biol. 22:1929-1935 (2002); Rijkers et al. Thrombosis Research 79: 491-499 (1995)). Numerous synthetic thrombin-cleavable substrates are known in the art (see, e.g., Izquierdo & Burguillo, Int. J. Biochem. 21:579-592 (1989); WO1992/007869). The consensus cleavage site for thrombin has been identified as P3-hydrophobic, P2-Pro, Pip, P3-Arg, or isosteric and isoelectronic with Arg; e.g., D-Phe-Pip-Lys (SEQ ID NO: 22), D-Phe-Pro-Lys (SEQ ID NO: 23), D-Phe-Pip-Orn (SEQ ID NO: 24). See also, Gallwitz et al. PLoS ONE 7(2): e31756. doi:10.1371/journal.pone.0031756 (2012); Tanihara et al. Peptides 19:421-425 (1998); Rijkers et al. Thrombosis 79:491-499 (1995).

In some embodiments, the protease-cleavable substrate comprises a FXIa cleavage site (e.g., KLTRIAET (SEQ ID NO: 25)), a FXIa cleavage site (e.g., DFTR↓VVG (SEQ ID NO: 26)), a FXIIa cleavage site (e.g., TMTR↓IVGG (SEQ ID NO: 27)), a kallikrein cleavage site (e.g., SPFRISTGG (SEQ ID NO: 28)), a FVIIa cleavage site (e.g., LQVR↓IVGG (SEQ ID NO: 29)), a FIXa cleavage site (e.g., PLGR↓IVGG (SEQ ID NO: 30)), a FXa cleavage site (e.g., IEGR↓TVGG (SEQ ID NO: 31)), a FIIa (thrombin) cleavage site (e.g., LTPR₁SLLV (SEQ ID NO: 32)), a Elastase-2 cleavage site (e.g., LGPV↓SGVP (SEQ ID NO: 33)), a Granzyme-B cleavage site (e.g, VAGD↓SLEE (SEQ ID NO: 34)), a MMP-12 cleavage site (e.g., GPAG↓LGGA (SEQ ID NO: 35)), a MMP-13 cleavage site (e.g., GPAG↓LRGA (SEQ ID NO: 36)), a MMP-17 cleavage site (e.g., APLG↓LRLR (SEQ ID NO: 37)), a MMP-20 cleavage site (e.g., PALP↓LVAQ (SEQ ID NO: 38)), a TEV cleavage site (e.g., ENLYFQ↓G (SEQ ID NO: 39)), a Enterokinase cleavage site (e.g., DDDK↓IVGG (SEQ ID NO: 40)), a Protease 3 (PRESCISSION™) cleavage site (e.g., LEVLFQ↓GP (SEQ ID NO: 41)), and a Sortase A cleavage site (e.g., LPKT↓GSES) (SEQ ID NO: 42). In certain embodiments, the FXIa cleavage sites include, but are not limited to, e.g., TQSFNDFTR (SEQ ID NO: 2) and SVSQTSKLTR (SEQ ID NO: 3).

D. Linkers (L)

As described above, the procoagulant compounds of the invention can comprise one or more linkers. As used herein, the term "linker" (represented as L in the formulas disclosed herein) refers to a peptide or polypeptide sequence (e.g., a synthetic peptide or polypeptide sequence), or a non-peptide linker for which its main function is to connect two moieties (e.g., Het1, Het2, Pep1, Pep2, Bx) in a procoagulant compound of the invention. A linker can be present between any two moieties or non-linker elements of the procoagulant compounds of the invention. For example, one or more linkers can be present between a protease-cleavable substrate (e.g., a thrombin-cleavable substrate) and a heterologous moiety, or between a protease-cleavable substrate and a polypeptide (e.g., a procoagulant peptide, a clotting factor, or a non-procoagulant polypeptide), or between a first polypeptide and a second polypeptide, or between a first heterologous moiety and a second heterologous moiety. In some embodiments, two or more linkers can be linked in tandem.

When multiple linkers are present in a procoagulant compound of the invention, each of the linkers can be the same or different. Generally, linkers provide flexibility to the polypeptide molecule. Linkers are not typically cleaved; however in certain embodiments, such cleavage can be desirable. Accordingly, in some embodiments a linker can comprise one or more protease-cleavable sites, which can be located within the sequence of the linker or flanking the linker at either end of the linker sequence.

In one embodiment, the linker is a peptide linker. In some embodiments, the peptide linker can comprise at least two amino, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Examples of peptide linkers are well known in the art, for example peptide linkers according to the formula [(Gly)$_x$-Ser$_y$]$_z$ where x is from 1 to 4, y is 0 or 1, and z is from 1 to 50. In one embodiment, the peptide linker comprises the sequence G$_n$, where n can be an integer from 1 to 100. In a specific embodiment, the specific embodiment, the sequence of the peptide linker is GGGG. The peptide linker can comprise the sequence (GA)$_n$. The peptide linker can comprise the sequence (GGS)$_n$. In other embodiments, the peptide linker comprises the sequence (GGGS)$_n$ (SEQ ID NO: 43). In still other embodiments, the peptide linker comprises the sequence (GGS)$_n$(GGGGS)$_n$ (SEQ ID NO: 44). In these instances, n can be an integer from 1-100. In other instances, n can be an integer from 1-20, i.e., 1, 2, 3, 4, 5, 6, 7, 8, 9, 10, 11, 12, 13, 14, 15, 16, 17, 18, 19, or 20. Examples of linkers include, but are not limited to, GGG, SGGSGGS (SEQ ID NO: 45), GGSGGSGGSGGSGGG (SEQ ID NO:46), GGSGGSGGSGGSGGGG (SEQ ID NO:47), GGSGGSGGSGGSGGSGGS (SEQ ID NO:48), or GGGGSGGGGSGGGGS (SEQ ID NO:49). In other embodiments, the linker is a poly-G sequence (GGGG)$_n$ (SEQ ID NO: 50), where n can be an integer from 1-100.

In one embodiment, the peptide linker is synthetic, i.e., non-naturally occurring. In one embodiment, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one embodiment the peptide linker can comprise non-naturally occurring polypeptides which are modified forms of naturally occurring polypeptides (e.g., comprising a mutation such as an addition, substitution or deletion). In another embodiment, the peptide linker can comprise non-naturally occurring amino acids. In another embodiment, the peptide linker can comprise naturally occurring amino acids occurring in a linear sequence that does not occur in nature. In still another embodiment, the peptide linker can comprise a naturally occurring polypeptide sequence.

In some embodiments, the linker comprises a non-peptide linker. In other embodiments, the linker consists of a non-peptide linker. In some embodiments, the non-peptide linker can be, e.g., maleimido caproyl (MC), maleimido propanoyl (MP), methoxyl polyethyleneglycol (MPEG), succinimidyl 4-(N-maleimidomethyl)-cyclohexane-1-carboxylate (SMCC), m-maleimidobenzoyl-N-hydroxysuccinimide ester (MBS), succinimidyl 4-(p-maleimidophenyl)butyrate (SMPB), N-succinimidyl(4-iodoacetyl)aminobenzonate (SIAB), succinimidyl 6-[3-(2-pyridyldithio)-propionamide] hexanoate (LC-SPDP), 4-succinimidyloxycarbonyl-alpha-methyl-alpha-(2-pyridyldithio)toluene (SMPT), etc. (see, e.g., U.S. Pat. No. 7,375,078).

Linkers can be introduced into polypeptide sequences using techniques known in the art (e.g., chemical conjugation, recombinant techniques, or peptide synthesis). Modifications can be confirmed by DNA sequence analysis. In some embodiments, the linkers can be introduced using recombinant techniques. In other embodiments, the linkers can be introduced using solid phase peptide synthesis. In certain embodiments, a procoagulant compound of the invention can contain simultaneously one or more linkers that have been introduced using recombinant techniques and one or more linkers that have been introduced using solid phase peptide synthesis or methods of chemical conjugation known in the art.

E. Heterologous Moieties (e.g., Het1, Het2, . . . , Het$_n$)

In some embodiments, the procoagulant compound of the invention can comprise one heterologous moiety (indicated herein as "Het1" or "Het2"). In other embodiments, the procoagulant compound of the invention can comprise two heterologous moieties ("Het1" and "Het2"). In yet other embodiments, the procoagulant compound of the invention can comprise more than two heterologous moieties, e.g., three, four, five, or more than five heterologous moieties. In some embodiments, all the heterologous moieties are identical. In some embodiments, at least one heterologous moiety is different from the other heterologous moieties. In some embodiments, the procoagulant compound of the invention can comprise two, three or more than three heterologous moieties in tandem. In other embodiments, the procoagulant compound of the invention can comprise two, three, or more than heterologous moieties wherein at least an additional moiety (e.g., a procoagulant polypeptide, a linker, a protease-cleavable substrate, a self-immolative spacer, or combinations thereof) is interposed between two heterologous moieties.

A heterologous moiety can comprise a heterologous polypeptide moiety, or a heterologous non-polypeptide moiety, or both. In one specific embodiment, Het1 is a first heterologous moiety, e.g., a half-life extending molecule which is known in the art. In some embodiments, Het2 is a second heterologous moiety that can also be a half-life extending molecule which is known in the art. In some aspects, the heterologous moiety comprises a combination of a heterologous polypeptide and a non-polypeptide moiety.

In certain embodiments, the first heterologous moiety (e.g., a first Fc region) and the second heterologous moiety (e.g., a second Fc region) are associated with each other to form a dimer. In one embodiment, the second heterologous moiety is a second Fc region, wherein the second Fc region is linked to or associated with the first heterologous moiety, e.g., the first Fc region. For example, the second heterologous moiety (e.g., the second Fc region) can be linked to the first heterologous moiety (e.g., the first Fc region) by a linker or associated with the first heterologous moiety by a covalent or non-covalent bond.

In some embodiments, the Het1 and Het2 heterologous moieties are peptides and polypeptides with either unstructured or structured characteristics that are associated with the prolongation of in vivo half-life when incorporated in a procoagulant compound of the invention. Non-limiting examples include albumin, albumin fragments, Fc fragments of immunoglobulins, the β subunit of the C-terminal peptide (CTP) of the β subunit of human chorionic gonadotropin, a HAP sequence, XTEN, a transferrin or a fragment thereof, a PAS polypeptide, polyglycine linkers, polyserine linkers, albumin-binding moieties, or any fragments, derivatives, variants, or combinations of these polypeptides. In other related aspects a heterologous moiety can include an attachment site (e.g., a cysteine amino acid) for a non-polypeptide moiety such as polyethylene glycol (PEG), hydroxyethyl starch (HES), polysialic acid, or any derivatives, variants, or combinations of these elements. In some aspects, a heterologous moiety consisting of a cysteine amino acid that function as an attachment site for a non-polypeptide moiety such as polyethylene glycol (PEG), hydroxyethyl starch (HES), polysialic acid, XTEN, or any derivatives, variants, or combinations of these elements.

In some embodiments, the heterologous moiety is a polypeptide comprising, consisting essentially of, or consisting of at least about 10, 100, 200, 300, 400, 500, 600, 700, 800, 900, 1000, 1100, 1200, 1300, 1400, 1500, 1600, 1700, 1800, 1900, 2000, 2500, 3000, or 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In certain embodiments, a heterologous moiety improves one or more pharmacokinetic properties of the procoagulation compound without significantly affecting the biological activity or function of the Pep1 and/or Pep2 polypeptides (e.g., procoagulant activity of a clotting factor or a fragment thereof, or of procoagulant activity of a procoagulant synthetic peptide).

In certain embodiments, a heterologous moiety increases the in vivo and/or in vitro half-life of the procoagulant compound of the invention. In other embodiments, a heterologous moiety facilitates visualization or localization of the procoagulant compound of the invention or a fragment thereof (e.g., a fragment comprising a heterologous moiety after proteolytic cleavage of the protease-cleavable substrate Zy). Visualization and/or location of the procoagulant compound of the invention or a fragment thereof can be in vivo, in vitro, ex vivo, or combinations thereof.

In other embodiments, a heterologous moiety increases stability of the procoagulant compound of the invention or a fragment thereof (e.g., a fragment comprising a heterologous moiety after proteolytic cleavage of the protease-cleavable substrate Zy). As used herein, the term "stability" refers to an art-recognized measure of the maintenance of one or more physical properties of the procoagulant compound in response to an environmental condition (e.g., an elevated or lowered temperature). In certain aspects, the physical property can be the maintenance of the covalent structure of the procoagulant compound (e.g., the absence of proteolytic cleavage, unwanted oxidation or deamidation). In other aspects, the physical property can also be the presence of the procoagulant compound in a properly folded state (e.g., the absence of soluble or insoluble aggregates or precipitates). In one aspect, the stability of the procoagulant compound is measured by assaying a biophysical property of the procoagulant compound, for example thermal stability, pH unfolding profile, stable removal of glycosylation, solubility, biochemical function (e.g., ability to bind to a protein, receptor or ligand), etc., and/or combinations thereof. In another aspect, biochemical function is demonstrated by the binding affinity of the interaction. In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

1. Half-Life Extending Heterologous Moieties

In certain aspects, a procoagulant compound of the invention comprises at least one half-life extending moiety, i.e., a heterologous moiety which increases the in vivo half-life of the procoagulant compound with respect to the in vivo half-life of the corresponding procoagulant compound lacking such heterologous moiety. In vivo half-life of a procoagulant compound can be determined by any method known to those of skill in the art, e.g., activity assays (chromogenic assay or one stage clotting aPTT assay), ELISA, etc.

In some embodiments, the presence of one or more half-life extending moieties results in the half-life of the procoagulant compound to be increased compared to the half life of the corresponding procoagulant compound lacking such one or more half-life extending moieties. The half-life of the procoagulant compound comprising a half-life extending moiety is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding procoagulant compound lacking such half-life extending moiety.

In one embodiment, the half-life of the procoagulant compound comprising a half-life extending moiety is about 1.5-fold to about 20-fold, about 1.5 fold to about 15 fold, or about 1.5 fold to about 10 fold longer than the in vivo half-life of the corresponding procoagulant compound lacking such half-life extending moiety. In another embodiment, the half-life of procoagulant compound comprising a half-life extending moiety is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding procoagulant compound lacking such half-life extending moiety.

In other embodiments, the half-life of the procoagulant compound comprising a half-life extending moiety is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In still other embodiments, the half-life of the procoagulant compound comprising a half-life extending moiety is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life per subject of the procoagulant compound comprising a half-life extending moiety is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

(a) Low Complexity Polypeptides

In certain aspects, a procoagulant compound of the invention comprises at least one heterologous moiety comprising a polypeptide with low compositional and/or structural complexity (e.g., a disordered polypeptide with no secondary or tertiary structure in solution under physiologic conditions).

(b) CTP

In certain aspects, a procoagulant compound of the invention comprises at least a heterologous moiety comprising one C-terminal peptide (CTP) of the β subunit of human chorionic gonadotropin, or fragment, variant, or derivative thereof. One or more CTP peptides inserted into a recombinant protein is known to increase the in vivo half-life of that protein. See, e.g., U.S. Pat. No. 5,712,122, incorporated by reference herein in its entirety.

Exemplary CTP peptides include DPRFQDSSSSKAPPPSLPSPSRLPGPSDTPIL (SEQ ID NO: 51) or SSSSKAPPPSLPSPSRLPGPSDTPILPQ. (SEQ ID NO: 52). See, e.g., U.S. Patent Application Publication No. US 2009/0087411 A1, incorporated by reference.

(c) Immunoglobulin Constant Region (Fc) or Portion Thereof

In certain aspects, a procoagulant compound of the invention comprises at least one Fc region. The term "Fc" or "Fc region" as used herein, means a functional neonatal Fc receptor (FcRn) binding partner comprising an Fc domain, variant, or fragment thereof which maintain the desirable properties of an Fc region in a chimeric protein, e.g., an increase in in vivo half-life. Myriad mutants, fragments, variants, and derivatives are described, e.g., in PCT Publication Nos. WO 2011/069164 A2, WO 2012/006623 A2, WO 2012/006635 A2, or WO 2012/006633 A2, all of which are incorporated herein by reference in their entireties. An Fc region is comprised of domains denoted CH (constant heavy) domains (CH1, H2, etc.). Depending on the isotype, (i.e. IgG, IgM, IgA IgD, or IgE), the Fc region can be comprised of three or four CH domains. Some isotypes (e.g. IgG) Fc regions also contain a hinge region. See Janeway et al. 2001, *Immunobiology*, Garland Publishing, N.Y., N.Y.

An Fc region or a portion thereof for producing the procoagulant compound of the present invention can be obtained from a number of different sources. In some embodiments, an Fc region or a portion thereof is derived from a human immunoglobulin. It is understood, however, that the Fc region or a portion thereof can be derived from an immunoglobulin of another mammalian species, including for example, a rodent (e.g. a mouse, rat, rabbit, guinea pig) or non-human primate (e.g. chimpanzee, macaque) species. Moreover, the Fc region or a portion thereof can be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

Procoagulant compounds comprising an Fc region of an immunoglobulin bestow several desirable properties on a chimeric protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

In certain embodiments, a procoagulant compound of the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region in a procoagulant compound of the invention can comprise or consist of an FcRn binding portion. FcRn binding portions can be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

An Fc in a procoagulant compound of the invention can include, for example, a change (e.g., a substitution) at one or more of the amino acid positions disclosed in Int'l. PCT Publs. WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/

085967A2; U.S. Pat. Publ. Nos. US 2007/0231329, US2007/0231329, US2007/0237765, US2007/0237766, US2007/0237767, US2007/0243188, US2007/0248603, US2007/0286859, US2008/0057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein in its entirety. In one embodiment, the specific change (e.g., the specific substitution of one or more amino acids disclosed in the art) can be made at one or more of the disclosed amino acid positions. In another embodiment, a different change at one or more of the disclosed amino acid positions (e.g., the different substitution of one or more amino acid position disclosed in the art) can be made.

An Fc region used in the invention can also comprise an art recognized amino acid substitution which alters the glycosylation of the chimeric protein. For example, the Fc region of the procoagulant compound can comprise an Fc region having a mutation leading to reduced glycosylation (e.g., N- or O-linked glycosylation) or can comprise an altered glycoform of the wild-type Fc moiety (e.g., a low fucose or fucose-free glycan).

(d) Albumin or Fragment, or Variant Thereof

In certain embodiments, the procoagulant compound of the invention comprises a heterologous moiety comprising albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

In one embodiment, the procoagulant compound of the invention comprises albumin, a fragment, or a variant thereof which is further linked to a heterologous moiety selected from an immunoglobulin constant region or portion thereof (e.g., an Fc region), a PAS sequence, HES, XTEN, PEG, or any combinations thereof.

(e) Albumin Binding Moiety

In certain embodiments, the heterologous moiety is an albumin binding moiety, which comprises an albumin binding peptide, a bacterial albumin binding domain, an albumin-binding antibody fragment, a fatty acid, or any combinations thereof.

For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, H is, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis et al. (2002) *J. Biol. Chem.* 277, 35035-35043).

Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO: 53). See, e.g., Dennis et al., J. Biol. Chem. 2002, 277: 35035-35043 (2002). Some examples of albumin-binding peptides are:

```
                                    (SEQ ID NO: 54)
        RLIEDICLPRWGCLWEDD, (SEQ ID NO: 55)
        QRLMEDICLPRWGCLWEDDF, (SEQ ID NO: 56)
        QGLIGDICLPRWGCLWGDSVK,
        or (SEQ ID NO: 57)
        GEWWEDICLPRWGCLWEEED.
```

Examples of albumin-binding antibody fragments are disclosed in Muller and Kontermann, Curr. Opin. Mol. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties. An example of such albumin binding moiety is 2-(3-maleimidopropanamido)-6-(4-(4-iodophenyl)butanamido) hexanoate ("Albu" tag) as disclosed by Trussel et al., Bioconjugate Chem. 20:2286-2292 (2009).

Fatty acids, in particular long chain fatty acids (LCFA) and long chain fatty acid-like albumin-binding compounds can be used to extend the in vivo half-life of procoagulant compounds of the invention. An example of a LCFA-like albumin-binding compound is 16-(1-(3-(9-(((2,5-dioxopyrrolidin-1-yloxy) carbonyloxy)-methyl)-7-sulfo-9H-fluoren-2-ylamino)-3-oxopropyl)-2,5-dioxopyrrolidin-3-ylthio) hexadecanoic acid (see, e.g., WO 2010/140148).

(f) PAS Sequence

In other embodiments, at least one heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the procoagulant compound. Yet, the skilled person is aware that an amino acid polymer also can form random coil conformation when residues other than alanine, serine, and proline are added as a minor constituent in the PAS sequence.

The term "minor constituent" as used herein means that amino acids other than alanine, serine, and proline can be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline can be selected from Arg, Asn, Asp, Cys, Gln, Glu, Gly, His, Ile, Leu, Lys, Met, Phe, Thr, Trp, Tyr, or Val.

Under physiological conditions, the PAS sequence stretch forms a random coil conformation and thereby can mediate an increased in vivo and/or in vitro stability to procoagulant compound. Since the random coil domain does not adopt a stable structure or function by itself, the biological activity mediated by the Pep1 and/or Pep2 polypeptides in the procoagulant compound is essentially preserved. In other embodiments, the PAS sequences that form random coil domain are biologically inert, especially with respect to proteolysis in blood plasma, immunogenicity, isoelectric point/electrostatic behavior, binding to cell surface receptors or internalization, but are still biodegradable, which provides clear advantages over synthetic polymers such as PEG.

Non-limiting examples of the PAS sequences forming random coil conformation comprise an amino acid sequence selected from ASPAAPAPASPAAPAPSAPA (SEQ ID NO:58), AAPASPAPAAPSAPAPAAPS (SEQ ID NO:59), APSSPSPSAPSSPSPASPSS (SEQ ID NO:60), APSSPSP-SAPSSPSPASPS (SEQ ID NO: 61), SSP-SAPSPSSPASPSPSSPA (SEQ ID NO: 62), AASPAAPSAP-PAAASPAAPSAPPA (SEQ ID NO: 63), ASAAAPAAASAAASAPSAAA (SEQ ID NO: 64) or any combinations thereof. Additional examples of PAS sequences are known from, e.g., US Pat. Publ. No. 2010/0292130 A1 and PCT Appl. Publ. No. WO 2008/155134 A1.

(g) HAP Sequence

In certain embodiments, at least one heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to (Gly)$_n$, (Gly$_4$Ser)$_n$ or S(Gly$_4$Ser)$_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

(h) XTEN

In certain aspects, a procoagulant compound of the invention comprises at least one heterologous moiety comprising an XTEN polypeptide or fragment, variant, or derivative thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half life extension moiety. In addition, XTEN can provide desirable properties including but are not limited to enhanced pharmacokinetic parameters and solubility characteristics.

The incorporation of a heterologous moiety comprising an XTEN sequence into a procoagulant compound of the invention can confer to the procoagulant compound one or more of the following advantageous properties: conformational flexibility, enhanced aqueous solubility, high degree of protease resistance, low immunogenicity, low binding to mammalian receptors, or increased hydrodynamic (or Stokes) radii.

In certain aspects, an XTEN sequence can increase pharmacokinetic properties such as longer in vivo half-life or increased area under the curve (AUC), so that a procoagulant compound of the invention stays in vivo and has procoagulant activity for an increased period of time compared to a procoagulant compound with the same but without the XTEN heterogous moiety.

Examples of XTEN sequences that can be used as heterologous moieties in procoagulant compounds of the invention are disclosed, e.g., in U.S. Pat Nos. 7,855,279 and 7,846,445, U.S. Patent Publication Nos. 2009/0092582 A1, 2010/0239554 A1, 2010/0323956 A1, 2011/0046060 A1, 2011/0046061 A1, 2011/0077199 A1, or 2011/0172146 A1, 2013/0017997 A1, or 2012/0263701 A1, or International Patent Publication Nos. WO 2010091122 A1, WO 2010144502 A2, WO 2010144508 A1, WO 2011028228 A1, WO 2011028229 A1, or WO 2011028344 A2, or International Application No. PCT/US2011/48517, filed Aug. 19, 2011, each of which is incorporated by reference herein in its entirety.

(i) Transferrin or Fragment Thereof

In certain embodiments, at least one heterologous moiety is transferrin or a fragment thereof. Any transferrin can be used to make the procoagulant compounds of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and 595936 (ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, $C_2$ domain or any combinations thereof.

(j) Polymer, e.g., Polyethylene Glycol (PEG)

In other embodiments, at least one heterologous moiety is a soluble polymer known in the art, including, but not limited to, polyethylene glycol, ethylene glycol/propylene glycol copolymers, carboxymethylcellulose, dextran, or polyvinyl alcohol. In some embodiments, the procoagulant compound comprising a PEG heterologous moiety further comprises a heterologous moiety selected from an immunoglobulin constant region or portion thereof (e.g., an Fc region), a PAS sequence, HES, and albumin, fragment, or variant thereof, an XTEN, or any combinations thereof. In still other embodiments, the procoagulant compound comprises a clotting factor or fragment thereof and a PEG heterologous moiety, wherein the procoagulant compound further comprises a heterologous moiety selected from an immunoglobulin constant region or portion thereof (e.g., an Fc region), a PAS sequence, HES, and albumin, fragment, or variant thereof, an XTEN, or any combinations thereof.

In yet other embodiments, the procoagulant compound comprises a clotting factor or fragment thereof, a second clotting factor or fragment thereof, and a PEG heterologous moiety, wherein the procoagulant compound further comprises a heterologous moiety selected from an immunoglobulin constant region or portion thereof (e.g., an Fc region), a PAS sequence, HES, and albumin, fragment, or variant thereof, an XTEN, or any combinations thereof. In other embodiments, the procoagulant compound comprises a clotting factor or fragment thereof, a synthetic procoagulant polypeptide, and a PEG heterologous moiety, wherein the procoagulant compound further comprises a heterologous moiety selected from an immunoglobulin constant region or portion thereof (e.g., an Fc region), a PAS sequence, HES, and albumin, fragment, or variant thereof, an XTEN, or any combinations thereof.

In other embodiments, the procoagulant compound comprises two synthetic procoagulant peptides and a PEG heterologous moiety, wherein the procoagulant compound further comprises a heterologous moiety selected from an immunoglobulin constant region or portion thereof (e.g., an Fc region), a PAS sequence, HES, and albumin, fragment, or variant thereof, an XTEN, or any combinations thereof. In yet another embodiment, the procoagulant compound comprises a clotting factor or fragment thereof, a clotting factor cofactor (e.g., Factor Va if the clotting factor in Factor X; or Tissue Factor if the clotting factor is Factor VII), and a PEG heterologous moiety, wherein the procoagulant compound further comprises a heterologous moiety selected from an immunoglobulin constant region or portion thereof (e.g., an Fc region), a PAS sequence, HES, and albumin, fragment, or variant thereof, an XTEN, or any combinations thereof.

Also provided by the invention are procoagulant compounds of the invention comprising heterologous moieties which can provide additional advantages such as increased solubility, stability and circulating time of the polypeptide, or decreased immunogenicity (see U.S. Pat. No. 4,179,337). Such heterologous moieties for modification can be selected from water soluble polymers including, but not limited to, polyethylene glycol, ethylene glycol/propylene glycol copolymers, carboxymethylcellulose, dextran, polyvinyl alcohol, or any combinations thereof.

The polymer can be of any molecular weight, and can be branched or unbranched. For polyethylene glycol, in one embodiment, the molecular weight is between about 1 kDa and about 100 kDa for ease in handling and manufacturing. Other sizes can be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol can have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

In some embodiments, the polyethylene glycol can have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), each of which is incorporated herein by reference in its entirety.

The number of polyethylene glycol moieties attached to each procoagulant compound of the invention (i.e., the degree of substitution) can also vary. For example, the PEGylated procoagulant compound can be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

In some embodiments, the procoagulant compound can be PEGylated. A PEGylated procoagulant compound comprises at least one polyethylene glycol (PEG) molecule. In other embodiments, the polymer can be water-soluble. Non-limiting examples of the polymer can be poly(alkylene oxide), poly(vinyl pyrrolidone), poly(vinyl alcohol), polyoxazoline, or poly(acryloylmorpholine). Additional types of polymer-conjugation to clotting factors are disclosed in U.S. Pat. No. 7,199,223. See also, Singh et al. Curr. Med. Chem. 15:1802-1826 (2008).

(k) Hydroxyethyl Starch (HES)

In certain embodiments, at least one heterologous moiety is a polymer, e.g., hydroxyethyl starch (HES) or a derivative thereof. Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie*, 8(8), 271-278 (1987); and Weidler et al., *Arzneim.-Forschung/Drug Res.*, 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., *Krankenhauspharmazie*, 8(8), 271-278 (1987), as cited above, in particular p. 273.

In one embodiment, hydroxyethyl starch has a mean molecular weight (weight mean) of from 1 to 300 kD, from 2 to 200 kD, from 3 to 100 kD, or from 4 to 70 kD. hydroxyethyl starch can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7.

In a specific embodiment, HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolemia. The characteristics of VOLUVEN® are a mean molecular weight of 130,000+/−20,000 D, a molar substitution of 0.4 and a C2:C6 ratio of about 9:1. In other embodiments, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD.

In still other embodiments, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain embodiments, the heterologous moiety can be a mixture of hydroxyethyl starches having different mean molecular weights and/or different degrees of substitution and/or different ratios of C2:C6 substitution. Therefore, mixtures of hydroxyethyl starches can be employed having different mean molecular weights and different degrees of substitution and different ratios of C2:C6 substitution, or having different mean molecular weights and different degrees of substitution and the same or about the same ratio of C2:C6 substitution, or having different mean molecular weights and the same or about the same degree of substitution and different ratios of C2:C6 substitution, or having the same or about the same mean molecular weight and different degrees of substitution and different ratios of C2:C6 substitution, or having different mean molecular weights and the same or about the same degree of substitution and the same or about the same ratio of C2:C6 substitution, or having the same or about the same mean molecular weights and different degrees of substitution and the same or about the same ratio of C2:C6 substitution, or having the same or about the same mean molecular weight and the same or about the same degree of substitution and different ratios of C2:C6 substitution, or having about the same mean molecular weight and about the same degree of substitution and about the same ratio of C2:C6 substitution.

(l) Polysialic Acids (PSA)

In certain embodiments, at least one heterologous moiety is a polymer, e.g., polysialic acids (PSAs) or a derivative thereof. Polysialic acids (PSAs) are naturally occurring unbranched polymers of sialic acid produced by certain bacterial strains and in mammals in certain cells Roth J., et al. (1993) in *Polysialic Acid: From Microbes to Man*, eds Roth J., Rutishauser U., Troy F. A. (Birkhäuser Verlag, Basel, Switzerland), pp 335-348. They can be produced in various degrees of polymerisation from n=about 80 or more sialic acid residues down to n=2 by limited acid hydrolysis or by digestion with neuraminidases, or by fractionation of the natural, bacterially derived forms of the polymer.

The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist—such as the alternating alpha-2,8 alpha-2,9 polysialic acid of *E. coli* strain K92 and group C polysaccharides of *N. meningitidis*. Sialic acid can also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during foetal development (wherein the polymer has an anti-adhesive function) Cho and Troy, *P.N.A.S., USA*, 91 (1994) 11427-11431, although there are no known receptors for polysialic acids in mammals.

The alpha-2,8-linked polysialic acid of *E. coli* strain K1 is also known as 'colominic acid' and is used (in various lengths) to exemplify the present invention. Various methods of attaching or conjugating polysialic acids to a polypeptide have been described (for example, see U.S. Pat. No. 5,846,951; WO-A-0187922, and US 2007/0191597 A1, which are incorporated herein by reference in their entireties.

(m) Clearance Receptors

In certain aspects, the in vivo half-life of a therapeutic polypeptide in a procoagulant compound of the invention can be extended where the procoagulant compound comprises at least one heterologous molecule comprising a clearance receptor, fragment, variant, or derivative thereof. In specific aspects wherein the therapeutic peptide is Factor VIII, Factor IX or Factor X, soluble forms of clearance receptors, such as the low density lipoprotein-related protein receptor LRP1, or fragments thereof, can block binding of Factor VIII, Factor IX or Factor X to clearance receptors and thereby extend its in vivo half-life.

LRP1 is a 600 kDa integral membrane protein that is implicated in the receptor-mediate clearance of a variety of proteins, such as Factor VIII. See, e.g., Lenting et al., Haemophilia 16:6-16 (2010). LRP1 also mediates clearance of Factor Xa (see, e.g., Narita et al., Blood 91:555-560 (1998)) and Factor IX (see, e.g., Strickland & Medved. J. Thromb. Haemostat. 4:1484-1486 (2006).

Other suitable FVIII clearance receptors are, e.g., LDLR (low-density lipoprotein receptor), VLDLR (very low-density lipoprotein receptor), and megalin (LRP-2), or fragments thereof. See, e.g.,Bovenschen et al., Blood 106:906-912 (2005); Bovenschen, Blood 116:5439-5440 (2010); Martinelli et al., Blood 116:5688-5697 (2010).

2. Visualization and Location

In certain embodiments, a heterologous moiety facilitates visualization or localization of the procoagulant compounds of the invention. Myriad peptides and other moieties for insertion or conjugation into a compound which facilitate visualization or localization are known in the art. Such moieties can be used to facilitate visualization or localization in vitro, in vivo, ex vivo or any combination thereof.

Since thrombin plays a central role in the coagulation cascade, detection of imaging of its activity in vivo is highly desired. Accordingly, various heterologous moiety facilitates visualization or localization of the procoagulant compounds of the invention (e.g., fluorescent dyes) can be engineered into the procoagulant compounds of the invention. In some embodiments, fluorescent dyes can be engineered to be non-fluorescent until their amines are regenerated upon thrombin cleavage.

Non-limiting examples of peptides or polypeptides which enable visualization or localization include biotin acceptor peptides which can facilitate conjugation of avidin- and streptavidin-based reagents, lipoic acid acceptor peptides which can facilitate conjugation of thiol-reactive probes to bound lipoic acid or direct ligation of fluorescent lipoic acid analogs, fluorescent proteins, e.g., green fluorescent protein (GFP) and variants thereof (e.g., EGFP, YFP such as EYFP, mVenus, YPet or Citrine, or CFP such as Cerulean or ECFP) or red fluorescent protein (RFP), cysteine-containing peptides for ligation of biarsenical dyes such as 4',5'-bis(1,3,2-dithioarsolan-2-yl)fluorescein (FlAsH), or for conjugating metastable technetium, peptides for conjugating europium clathrates for fluorescence resonance energy transfer (FRET)-based proximity assays, any variants, thereof, and any combination thereof.

Procoagulant compounds of the present disclosure labeled by these techniques can be used, for example, for 3-D imaging of pathological thrombus formation and dissolution, tumor imaging in procoagulant malignancies, flow cytometric quantitation and characterization of procoagulant microparticles in blood and plasma, monitoring of thrombus formation by intravital microscopy.

3. Targeting Moieties, Anchors and Other Moieties

In some embodiments, procoagulant compounds of the invention can comprise a heterologous moiety that targets the compound to specific location, e.g., to platelets to enhance the efficacy of the compound by localizing the clotting factor or procoagulation peptide of the compound to the site of coagulation (a "targeting moiety"). In some embodiment, the targeting moiety binds to a target molecule expressed on platelets. Preferably the targeted molecules are not expressed on cells or tissues other than platelets, i.e., the targeting moieties specifically bind to platelets.

In one embodiment, receptors/conformations found on resting platelets are targeted. By doing so, sites for coagulation could be primed for enhanced efficacy. Targeting such molecule can also extend half life of the clotting factor and/or prevent clearance. Examples of such targets include GpIb of the GpIb/V/IX complex, and GpVI and nonactive form of GPIIb/IIIa. See, e.g., Schwarz et al. Circulation Research. 99:25-33 (2006); U.S. Pat. Publ. 20070218067; Peterson et al. Hemostasis, Thrombosis, and Vascular Biology 101:937 (2003); WO 2010115866; Lin et al. Journal of Thrombosis and Haemostasis 8:1773 (2010).

The procoagulant compound of the invention can comprise one or more than one targeting moiety. In some embodiments, two or more targeting moieties can be linked to each other (e.g., via a linker). When two or more targeting moieties are present in a procoagulant compound of the invention, the targeting moieties can be the same or different.

In one embodiment, a targeting moiety is fused to a procoagulant compound of the invention by a protease cleavable linker which can be cleaved to remove the targeting moiety at the site of a clot. In another embodiment, a targeting moiety is not attached via a cleavable linker and, therefore, is not cleaved at the site of a clot.

In one embodiment, the targeting moiety is located on the N- or C-terminus of the procoagulant compound. In one embodiment, a targeting moiety is not genetically fused directly to a procoagulant compound of the invention, but rather is chemically linked via a linker or a chemical bond to the construct (see, e.g., U.S. Pat. No. 7,381,408).

In one embodiment, a procoagulant compound of the invention comprises at least an antigen binding site (e.g., an antigen binding site of an antibody, antibody variant, or antibody fragment), a polypeptide, a receptor binding portion of ligand, or a ligand binding portion of a receptor which specifically binds to platelets, e.g., resting or activated platelets. Exemplary targeting moieties include scFv molecules or peptides which bind to molecules to be targeted.

In some embodiments, a procoagulant compound of the invention comprises an anchor or scaffolding molecule, e.g., a lipid, a carbohydrate, or a sulfhydryl group. For example, a sulfhydryl group in an N-terminal cysteine can be used to anchor a procoagulant compound of the invention to another molecule, cell, or other surface. For example, a lipid anchor can be used to anchor a procoagulant compound of the invention to a cell surface or a lipid bilayer (e.g., a liposome).

In some embodiments, a procoagulant compound of the invention can comprise a heterogous molecule comprising a non-peptidic active agent useful for the treatment of bleeding disorders. In some embodiments, the non-peptidic active agent is a procoagulant molecule. In some embodiments, the non-peptidic active agent is a small molecule drug.

III. Pharmaceutical Compositions

The invention also provides pharmaceutical compositions containing at least one procoagulant compound of the present and a pharmaceutically acceptable carrier.

The term "pharmaceutically acceptable carrier" means all pharmaceutically acceptable ingredients known to those of skill in the art, which are typically considered non-active ingredients. The term "pharmaceutically acceptable carrier" includes, e.g., solvents, solid or liquid diluents, additives, vehicles, adjuvants, excipients, glidants, binders, granulating agents, dispersing agents, suspending agents, wetting agents, lubricating agents, disintegrants, solubilizers, stabilizers, preservatives, emulsifiers, fillers, preservatives (e.g., anti-oxidants), flavoring agents, sweetening agents, thickening agents, buffering agents, coloring agents and the like, as well as any mixtures thereof. Exemplary carriers (i.e., excipients) are described in, e.g., Handbook of Pharmaceutical Manufacturing Formulations, Volumes 1-6, Niazi, Sarfaraz K., Taylor & Francis Group 2005, which is incorporated herein by reference in its entirety.

Pharmaceutical compositions can additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives.

Pharmaceutical compositions can be formulated for any appropriate manner of administration, including, for example, topical (e.g., transdermal or ocular), oral, buccal, nasal, vaginal, rectal or parenteral administration.

The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. It is preferred that subcutaneous, intraperitoneal, buccal, intravenous and other parenteral formulations are sterile and endotoxin free. Procoagulant compounds of the present disclosure can be administered parenterally in a sterile medium.

The procoagulant compound, depending on the vehicle and concentration used, can either be suspended or dissolved in the vehicle. In one embodiment, adjuvants such as local anesthetics, preservatives and buffering agents can be dissolved in the vehicle. In one example, the procoagulant compounds of the present invention are administered to the subject using a non-intravenous route, e.g., by subcutaneous, nasal, buccal, oral or pulmonary delivery.

Forms suitable for oral use include, for example, tablets, troches, lozenges, aqueous or oily suspensions, dispersible powders or granules, emulsion, hard or soft capsules, or syrups or elixirs. Compositions provided herein can be formulated as a lyophilizate.

The pharmaceutical composition can be also for example a suspension, emulsion, sustained release formulation, cream, gel or powder. The pharmaceutical composition can be formulated as a suppository, with traditional binders and carriers such as triglycerides.

In one example, the pharmaceutical composition is a liquid formulation, e.g., a buffered, isotonic, aqueous solution. In one example, the pharmaceutical composition has a pH that is physiologic, or close to physiologic. In another example, the aqueous formulation has a physiologic or close to physiologic osmolarity and salinity. It can contain sodium chloride and/or sodium acetate.

Pharmaceutical compositions intended for oral use can be prepared according to any method known for the manufacture of pharmaceutical compositions. Such pharmaceutical compositions can contain one or more agents chosen from the group consisting of sweetening agents, flavoring agents, coloring agents and preservative agents in order to provide pharmaceutically elegant and palatable preparations. Tablets can contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period (i.e., tablets can be enterically coated). For example, a time delay material such as glyceryl monosterate or glyceryl distearate can be employed.

Pharmaceutical compositions for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. In another example, the active ingredient is formulated in capsules containing optionally coated microtablets or micropellets. Pharmaceutical compositions for oral use can also be presented as lozenges.

Aqueous suspensions contain the active ingredient(s) in admixture with excipients suitable for the manufacture of aqueous suspensions. Such excipients include suspending agents (e.g., sodium carboxymethylcellulose, methylcellulose, hydropropyl methylcellulose, sodium alginate, polyvinyl-pyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions can also comprise one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water can provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the present disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, a flavoring agent or a coloring agent. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The procoagulant compounds of the present disclosure can also be administered in the form of suppositories, e.g., for rectal administration of the drug. These pharmaceutical compositions can be prepared by mixing the drug with a suitable non-irritating excipient that is solid at ordinary temperatures but liquid at the rectal temperature and will therefore melt in the rectum to release the drug. Such materials include cocoa butter and poly ethylene glycols.

Procoagulant compounds of the present disclosure can be formulated for local or topical administration, such as for topical application to the skin, wounds or mucous membranes, such as in the eye. Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices.

A composition can further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations can comprise microcapsules, such as hydroxymethylcellulose or gelatin-microcapsules, liposomes, albumin microspheres, microemulsions, nanoparticles or nanocapsules.

Pharmaceutical compositions suitable for topical administration to the eye also include eye drops wherein the active ingredients are dissolved or suspended in suitable carrier, especially an aqueous solvent for the active ingredients. The anti-inflammatory active ingredients may, for example, be present in such formulations in a concentration of 0.5 to 20%, such as 0.5 to 10%, for example about 1.5% w/w. For therapeutic purposes, the active compounds of the present disclosure are ordinarily combined with one or more adjuvants appropriate to the indicated route of administration. The compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose.

Formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Alternatively, the active ingredients can be formulated in a cream with an oil-in-water cream base. If desired, the aqueous phase of the cream base can include, for example at least 30% w/w of a polyhydric alcohol such as propylene glycol, butane-1,3-diol, mannitol, sorbitol, glycerol, polyethylene glycol and mixtures thereof. The topical formulation can desirably include a compound, which enhances absorption or penetration of the active ingredient through the skin or other affected areas. Examples of such dermal penetration enhancers include dimethylsulfoxide and related analogs. The compounds of this present disclosure can also be administered by a transdermal device. In one embodiment, topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient.

If the active agent is absorbed through the skin, a controlled and predetermined flow of the active agent is administered to the recipient. In the case of microcapsules, the encapsulating agent can also function as the membrane. The transdermal patch can include the compound in a suitable solvent system with an adhesive system, such as an acrylic emulsion, and a polyester patch. The oily phase of the emulsions of this present disclosure can be constituted from known ingredients in a known manner. While the phase can comprise merely an emulsifier, it can comprise a mixture of at least one emulsifier with a fat or oil or with both a fat and an oil. In one embodiment, a hydrophilic emulsifier is included together with a lipophilic emulsifier, which acts as a stabilizer. The phase may, for example, include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations.

Emulsifiers and emulsion stabilizers suitable for use in the formulation of the present disclosure include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream may, for example, be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters can be used. These can be used alone or in combination depending on the properties required. Alternatively, high melting point lipids such as white soft paraffin and/or liquid paraffin or other mineral oils can be used.

A pharmaceutical composition can be formulated as inhaled formulations, including sprays, mists, or aerosols. For inhalation formulations, the compounds provided herein can be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and can be filled into conventional aerosol containers that are closed by a suitable metering valve.

Formulations suitable for inhalation or insufflation include solutions and suspensions in pharmaceutically acceptable aqueous or organic solvents, or mixtures thereof, and powders. The liquid or solid compositions can contain suitable pharmaceutically acceptable excipients as describe above. The compositions can be administered by oral or nasal respiratory route for local or systemic effect. Compositions can be nebulized by use of inert gases or vaporized, and breathed directly from the nebulizing/vaporizing device or the nebulizing device can be attached to a facemask tent or intermittent positive pressure-breathing machine.

Inhalant compositions can comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations or compositions suitable for nasal administration, wherein the carrier is a solid, include a coarse powder having a particle size, for example, in the range of 20 to 500 microns which is administered in the manner in which snuff is administered (i.e., by rapid inhalation through the nasal passage from a container of the powder held close up to the nose). Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which can be inserted by the patient into a device that punctures the capsule and blows the powder out in a steady stream suitable for inhalation.

Pharmaceutical compositions can be formulated as sustained release formulations (i.e., a formulation such as a capsule that effects a slow release of modulator following administration). Such formulations can generally be prepared using well known technology and administered by, for example, oral, rectal or subcutaneous implantation, or by implantation at the desired target site. Carriers for use within such formulations are biocompatible, and can also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In one example, the pharmaceutical formulations provided herein can include one or more additional active agent (i.e., other biologically active ingredient). In one example, the additional active agent is selected from known drugs approved for the treatment of a coagulation disorder, such as hemophilia A. For example, the pharmaceutical formulation can further include a blood coagulation factor.

Pharmaceutical compositions can be formulated with an agent to improve bioavailability, such an as organic solvent. For example, Cremophor EL® (Product No. 00647/1/63; BASF Aktiengesellschaft, Germany) is a polyethoxylated castor oil which is prepared by reacting 35 moles of ethylene oxide with each mole of castor oil. It can be used to stabilize emulsions of non-polar materials in aqueous systems. Alternatively, peptide, peptide derivative or dual peptide can be incorporated within or bound to a proteinaceous micro or nano-particle for improved bioavailability.

Suitable micro- and nano-particles are described in U.S. Pat. No. 5,439,686 (Desai et al; Vivorx Pharmaceuticals, Inc., CA) and U.S. Pat. No. 5,498,421 (Grinstaff et al; Vivorx Pharmaceuticals, Inc., CA). Suitably, the proteinaceous nano-particle comprises human serum albumin, particularly human serum albumin or a recombinant form thereof. WO 2007/077561 (Gabbai; Do-Coop Technologies Ltd., Israel) describe another suitable carrier comprising nanostructures and a liquid, referred to therein as NEOWATER™.

For veterinary use, a compound of the present disclosure is administered as a suitably acceptable formulation in accordance with normal veterinary practice and the veterinary surgeon will determine the dosing regimen and route of administration which will be most appropriate for a particular animal. For administration to non-human animals, the composition can be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

Dosage levels of the order of from about 0.005 mg to about 80 mg per kilogram of body weight per day are useful in the treatment of the diseases and conditions described herein (e.g., about 0.35 mg to about 5.6 g per human patient per day, based on an average adult person weight of 70 kg). The amount of active ingredient that can be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may, for example, be applied as a topical preparation of compounds of this present disclosure on the affected area one to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

IV. Methods of Making

The procoagulant compounds of the present disclosure can be produced by chemical synthesis, recombinant DNA technology, biochemical or enzymatic fragmentation of larger molecules, combinations of the foregoing or by any other method.

In one example, the method comprises forming the amino acid sequence of the compound, or a retro-, inverso- or retro-inverso variant thereof using solid-phase peptide synthesis. Exemplary methods of making procoagulant compounds of the invention are described herein in Example 1. Other methods to form synthetic peptides are known to those of skill in the art.

For example, the procoagulant compounds of the present disclosure can be synthesized using solid-phase peptide synthesis as described in "*Fmoc Solid Phase Peptide Synthesis—A Practical Approach*", edited by W. C. Chan, P. D. White, Oxford University Press, New York 2000 and references therein. Temporary N-amino group protection is afforded, e.g., by a 9-fluorenylmethyloxycarbonyl (Fmoc) group. Repetitive cleavage of this highly base-labile protecting group is effected, e.g., using 20% piperidine in N,N-dimethylformamide. Side-chain functionalities can be protected as their butyl ethers (in the case of serine, threonine and tyrosine), butyl esters (in the case of glutamic acid and aspartic acid), butyloxycarbonyl derivative (in the case of lysine and histidine), trityl derivative (in the case of cysteine, asparagine and glutamine) and 4-methoxy-2,3,6-trimethylbenzenesulphonyl derivative (in the case of arginine).

The solid-phase support can be based on a polydimethylacrylamide polymer constituted from the three monomers dimethylacrylamide (backbone-monomer), bisacryloylethylene diamine (cross linker) and acryloylsarcosine methyl ester (functionalising agent), or can be based on polyethylene glycol (PEG), such as Rink Amide resin (e.g., NovaPEG Rink Amide). The peptide-to-resin cleavable linked agent can be the acid-labile 4-hydroxymethyl-phenoxyacetic acid derivative, or in case of C-terminal amides, the Rink-amide linker. All amino acid derivatives can be added as their preformed symmetrical anhydride derivatives with the exception of asparagine and glutamine, which are added using a reversed N,N-dicyclohexyl-carbodiimide/1-hydroxybenzotriazole mediated coupling procedure.

Alternatively, other peptide coupling reagents, such as O-benzotriazole-N,N,N',N'-tetramethyl-uronium-hexafluoro-phosphate (HBTU) or 2-(6-chloro-1-H-benzotriazole-1-yl)-1,1,3,3-tetramethylaminium haxafluorophosphate (HCTU) can be used (e.g., in site). Coupling and deprotection reactions can be monitored using ninhydrin, trinitrobenzene sulphonic acid or isotin test procedures. Upon completion of synthesis, peptides are cleaved from the resin support with concomitant removal of side-chain protecting groups, e.g., by treatment with 95% trifluoroacetic acid containing about 5-50% scavenger. Scavengers commonly used are TIPS (triisopropylsilane), ethanedithiol, phenol, anisole water, and mixtures thereof. The exact choice depends on the constituent amino acids of the peptide being synthesised. For methionine containing peptides one can use, e.g., a mixture of TIPS (e.g., 2-5%) and ethanedithiol (e.g., 2-5%).

Trifluoroacetic acid can subsequently be removed by evaporation in vacuo, with subsequent trituration with diethyl ether affording the crude peptide. Any scavengers present can be removed by a simple extraction procedure which on lyophilisation of the aqueous phase affords the crude peptide free of scavengers.

Reagents for peptide synthesis are generally available, e.g., from Calbiochem-Novabiochem (UK), or EMD4Biosciences (U.S.).

Purification of the peptides can be effected by any one, or a combination of, techniques such as size exclusion chromatography, ion-exchange chromatography, affinity chromatography, differential solubility, and reverse-phase high performance liquid chromatography. Analysis of peptides can be carried out using thin layer chromatography, reverse-phase high performance liquid chromatography, mass spectroscopy (e.g., LC-MS), amino-acid analysis after acid hydrolysis and by fast atom bombardment (FAB) mass spectrometry.

SPOT-synthesis, which allows the positional addressable, chemical synthesis of peptides on continuous cellulose membranes can be also used (see, e.g., R. Frank, *Tetrahedron* (1992) 48, 9217).

When the procoagulant peptide is particularly large, e.g., larger than 50 amino acids, or larger than 100 amino acids, the procoagulant compounds of the present disclosure can be made semirecombinantly (see, e.g., U.S. Pat. No. 7,381,408; Dawson et al. *Ann. Rev. Biochem.* 69: 923-9600 (2000); Mei, B. et. al., *Blood* 116:270-279 (2010); and U.S. Pat. Appl. Publ. US2006/0115876, each of which is incorporated herein in its entirety). In one embodiment, a clotting factor or procoagulant polypeptide is produced recombinantly, and then attached to an intermediate compound comprising the cleavable substrate and self-immolative spacer via chemical ligation as described herein in Example 1. Chemical ligation can be performed using established organic chemistry techniques and commercially available reagents.

The procoagulant compounds of the invention can be assembled by conjugating the different moieties disclosed herein (e.g., polypeptides, heterologous moieties, linkers, protease-cleavable substrates, etc.) using orthogonal conjugation strategies know in the art. In some embodiments, such strategies include, e.g., alkyne, azide, N-terminal Cys, strained alkyne, ketone, aldehyde, tetrazine-trans-cyclooctene, and combinations thereof.

In one aspect, the procoagulant compounds of the invention can be produced by using a cleavable polypeptide comprising a protease cleavable site, e.g., SUMO. Small Ubiquitin-like Modifier (or SUMO) is a member of the ubiquitin (Ub) and ubiquitin-like (Ubl) family. Post-translational attachment of SUMO to target proteins occurs through an enzymatic cascade analogous to the ubiquitin conjugation cascade (E1-E2-E3 enzymes), ultimately resulting in formation of an isopeptide bond between the Ub/Ubl C-terminal residue and substrate lysine residue.

SUMO Protease, a highly active cysteinyl protease also known as Ulp, is a recombinant fragment of Ulp1 (Ubl-specific protease 1) from *Saccharomyces cerevisiae*. SUMO Protease cleaves in a highly specific manner, recognizing the tertiary structure of the ubiquitin-like (UBL) protein, SUMO, rather than an amino acid sequence. The protease can be used to cleave SUMO from recombinant fusion proteins. The sequence of the SUMO protein comprises:

```
                                         (SEQ ID NO: 90)
SLQDSEVNQEAKPEVKPETHINLKVSDGSSEIFFKIKKTTPLRRLM
EAFAKRQGKEMDSLRFLYDGIRIQADQAPEDLDMEDNDIIEAHREQIGG
```

In one embodiment, a cleavable polypeptide useful for the invention comprises a light chain of a clotting factor, a truncated heavy chain of the clotting factor, and a protease cleavable site, wherein the protease cleavable site is inserted between the truncated heavy chain of the clotting factor and the light chain of the clotting factor. In another embodiment, the cleavable polypeptide further comprises an intracellular processing site (also referred herein as proprotein convertase processing site) between the protease cleavable site and the light chain of the clotting factor. In other embodiments, a cleavable polypeptide comprises a light chain of a clotting factor, a protease cleavable site, a truncated heavy chain of the clotting factor, and a heterologous moiety, wherein the protease cleavable site is inserted between the light chain and the truncated heavy chain of the clotting factor, and the heterologous moiety is linked to the truncated heavy chain of the clotting factor by an optional linker. In still other embodiments, the protease cleavable site comprises SUMO, which can be cleaved by a SUMO protease.

In some embodiments, the heterologous moiety comprises a half-life extending moiety. Non-limiting examples of the half-life extending moiety are disclosed elsewhere herein. In certain embodiments, the clotting factor for the cleavable polypeptide comprises FVII or FX. In some embodiments, the truncated heavy chain of the clotting factor does not comprise one or more amino acids at the N-terminus of the truncated heavy chain compared to the wild-type heavy chain of the clotting factor. In certain embodiments, the one or more amino acids deleted from the truncated heavy chain of the clotting factor are two amino acids, three amino acids, four amino acids, five amino acids, six amino acids, seven amino acids, eight amino acids, nine amino acids, ten amino acids, eleven amino acids, twelve amino acids, thirteen amino acids, fourteen amino acids, or fifteen amino acids corresponding to the N-terminus of the heavy chain that are missing from the truncated heavy chain of the clotting factor. In one example, the clotting factor for the cleavable polypeptide is Factor VII and the one or more amino acids are IVGGKV (SEQ ID NO: 83). In another example, the clotting factor for the cleavable polypeptide is Factor X and the one or more amino acids are IVGGQE (SEQ ID NO: 85).

In certain embodiments, the invention is directed to a method of making a cleavable polypeptide comprising transfecting a host cell with a polynucleotide or a vector encoding a cleavable polypeptide under a condition sufficient to express the polypeptide. In some embodiments, the host cell further expresses a proprotein convertase, e.g., PACE or PC5, that can process any intracellular processing sites, e.g., 2X (RKR) (SEQ ID NO: 88) or RRRR (SEQ ID NO: 89).

In some aspects, a cleavable polypeptide comprising a light chain of a clotting factor, a protease cleavable site, and a truncated heavy chain of the clotting factor is cleaved by a protease. After the cleavage, the resulting construct therefore can comprise at least two chains, the first chain comprising the light chain of the clotting factor and the second chain comprising the truncated heavy chain of the clotting factor. In some embodiments, the truncated heavy chain of the clotting factor lacks one or more amino acids at the end of the N-terminus compared to the wild-type clotting factor, thereby exposing Cysteine at the N-terminus for chemical ligation. In one embodiment, the amino acids missing from the truncated heavy chain are six amino acids, e.g., IVGGKV (SEQ ID NO: 83) for FVII or IVGGQE (SEQ ID NO 85) for FX. In another embodiment, the amino acids missing from the heavy chain are 11 amino acids, e.g., IVGGKVCPKGE (SEQ ID NO: 84) for FVII or IVGGQECKDGE (SEQ ID NO: 86) for FX). In some embodiments, the protease cleavable site comprises SUMO.

In one aspect, the invention comprises a method of making a procoagulant compound comprising combining the cleavable polypeptide with a protease under a condition sufficient to cleave the protease cleavable site. In another embodiment, the method further comprises adding a thioester peptide to the cleaved polypeptide. The thioester peptide can then be fused to the N-terminus of the truncated heavy chain of the clotting factor, forming activatable clotting factor. In one example, the thioester peptide comprises a protease-cleavable substrate (Zy). In another embodiment, the thioester peptide comprises a protease-cleavable substrate and a self-immolative spacer (Bx), wherein the self-immolative spancer is inserted between the protease-cleavable substrate and the truncated heavy chain. In other embodiments, the thioester peptide comprises a protease-cleavable substrate, a self-immolative spacer, and one or more amino acids (W), wherein the self-immolative spacer is inserted between the protease-cleavable substrate and the one or more amino acids (W). In one aspect, the one or more amino acids comprise the N-terminus amino acid sequence missing from the truncated heavy chain of the clotting factor compared to the wild-type heavy chain. Therefore, in certain embodiments, the thioester peptide comprising a protease-cleavable substrate, a self-immolative moiety, and one or amino acids (e.g., six amino acids corresponding to wild-type heavy chain) forms protease-cleavable clotting factor, which comprises the protease-cleavable substrate, the self-immolative moiety, and full-length heavy chain. In some embodiments, the one or more amino acids comprise IVGGKV (SEQ ID NO: 83), wherein the clotting factor comprises Factor VII. In certain embodiments, the one or more amino acids comprise IVGGQE (SEQ ID NO: 85), wherein the clotting factor comprises Factor X. In other embodiments, the one or more amino acids comprise 11 amino acids, e.g., IVGGKVCPKGE (SEQ ID NO: 84) for FVII or IVGGQECKDGE (SEQ ID NO: 86) for FX). In yet other embodiments, the thioester peptide comprises a formula: Zy-Bx-W, wherein Zy is a protease-cleavable substrate; Bx is a self-immolative spacer; and W is one or more amino acids that are missing from the truncated heavy chain of the clotting factor. In a particular embodiment, the one or more amino acids and the truncated heavy chain of the clotting factor, when fused, result in the complete heavy chain of the clotting factor. In still other embodiments, the protease-cleavable substrate comprises a thrombin cleavage site, e.g., D-Phe-Pip-Arg. In yet other embodiments, the self-immolative spacer comprises PABC.

A variety of methods are available for recombinantly producing a clotting factor or procoagulant peptide for subsequent incorporation in a procoagulant compound of the invention. For recombinant production, a polynucleotide sequence encoding the clotting factor or procoagulant peptide is inserted into an appropriate expression vehicle, i.e., a vector which contains the necessary elements for the transcription and translation of the inserted coding sequence, or in the case of an RNA viral vector, the necessary elements for replication and translation. The nucleic acid encoding the clotting factor or procoagulant peptide is inserted into the vector in proper reading frame. The expression vector is then transfected into a suitable target cell which will express the procoagulant polypeptide. Transfection techniques known in the art include, but are not limited to, calcium phosphate precipitation (Wigler et al. 1978, Cell 14: 725) and electroporation (Neumann et al. 1982, EMBO, J. 1: 841). A variety of host-expression vector systems can be utilized to express the procoagulant polypeptides described herein in eukaryotic cells. In one embodiment, the eukaryotic cell is an animal cell, including mammalian cells (e.g. 293 cells, PerC6, HO, BHK, Cos, HeLa cells).

V. Methods of Treatment

The present invention further provides methods for treating, ameliorating or preventing a bleeding disease or disorder in a subject (e.g., a human subject). An exemplary method comprises administering to the subject in need thereof a therapeutically effective amount of a procoagulant compound or a pharmaceutical composition/formulation of the present disclosure. In some embodiments, the procoagulant compounds or the pharmaceutical composition of the invention is administered to the subject orally.

The procoagulant compounds and pharmaceutical compositions of the invention can be used prophylactically. As used herein the term "prophylactic treatment" refers to the administration of a molecule prior to a bleeding episode. In one embodiment, the subject in need of a general hemostatic agent is undergoing, or is about to undergo, surgery. The procoagulant compound or pharmaceutical composition of the invention can be administered prior to or after surgery as a prophylactic. The procoagulant compound or pharmaceutical composition of the invention can be administered during or after surgery to control an acute bleeding episode. The surgery can include, but is not limited to, liver transplantation, liver resection, dental procedures, or stem cell transplantation.

The procoagulant compound or pharmaceutical composition of the invention can also used for on-demand treatment. The term "on-demand treatment" refers to the administration of a procoagulant compound or pharmaceutical composition of the invention in response to symptoms of a bleeding episode or before an activity that can cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

Treat, treatment, treating, as used herein refers to, e.g., the reduction in severity of a disease or disorder; the reduction in the duration of a disease course; the amelioration of one or more symptoms associated with a disease or disorder; the provision of beneficial effects to a subject with a disease or disorder, without necessarily curing the disease or disorder, or the prophylaxis of one or more symptoms associated with a disease or disorder.

In one example according to any of the above embodiments, the bleeding disease or disorder is caused by a blood coagulation disorder. A blood coagulation disorder can also be referred to as a coagulopathy. In a particular example, the blood coagulation disorder, which can be treated with a compound or a pharmaceutical composition of the current disclosure, is hemophilia or von Willebrand disease (vWD). In a particular example, the blood coagulation disorder, which can be treated with a compound or a pharmaceutical composition of the present disclosure is hemophilia A.

In another example, the type of bleeding associated with the bleeding disease or disorder is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

In another example, the subject suffering from a bleeding disease or disorder is in need of treatment for surgery, including, e.g., surgical prophylaxis or pen-operative management. In one example, the surgery is selected from minor surgery and major surgery. Exemplary surgical procedures include tooth extraction, tonsillectomy, inguinal herniotomy, synovectomy, craniotomy, osteosynthesis, trauma surgery, intracranial surgery, intra-abdominal surgery, intrathoracic surgery, joint replacement surgery (e.g., total knee replacement, hip replacement, and the like), heart surgery, and caesarean section.

A coagulation disorder can be caused by a deficiency in at least one blood coagulation factor (e.g., FVIII). The current disclosure provides a method of treating a subject (e.g., a human subject) having a deficiency in at least one blood coagulation factor selected from von Willebrand Factor (vWF), FV, FVII, FVIIa, FVIII, FIX, FIXa, FX, FXI, and FXa (e.g., for both the prophylaxis and for the treatment of acute bleeds). An exemplary method comprises administering to the subject a therapeutically effective amount of a procoagulant compound or a pharmaceutical composition of the present disclosure.

In one example according to any of the above embodiments, the subject is a human subject (i.e., a human patient). In another example according to any of the above embodiments, the subject (e.g, human patient) is concomitantly treated with at least one additional active agent, e.g., a drug approved for the treatment of coagulation disorders. In one example, the additional active agent is administered to the subject at the same time that the procoagulant compound or pharmaceutical composition of the present disclosure is administered to the subject. For example, the at least one additional active agent is contained in a pharmaceutical composition that also contains the compound of the present disclosure. In another example, the additional active agent is administered to the subject at a different time but within the treatment period for the compound of the present disclosure. For example, the additional active agent is administered alternatingly with the procoagulant compound or pharmaceutical composition of the present disclosure.

For oral and parenteral administration to patients, including human patients, the daily dosage level of the procoagulant compound of the current disclosure will usually be from 2 to 2000 mg per adult (i.e. from about 0.03 to 30 mg/kg), administered in single or divided doses.

A unit dosage form (for example tablet or capsule) can contain from 2 mg to 2000 mg of procoagulant compound. The unit dosage form can be administered once, twice or more times per day as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

VI. Other Methods

The invention further provides a method of increasing the efficacy of the cleavage of a protease-cleavage substrate (e.g., a thrombin-cleavable substrate) operably linked to a procoagulant polypeptide (e.g., a synthetic procoagulant peptide or clotting factor) comprising conjugating a self-immolative linker (e.g., PABC) to the procoagulant polypeptide, wherein the self-immolative linker is interposed between the protease-cleavage substrate and the procoagulant polypeptide.

In some embodiments, the efficacy of cleavage is increased by at least about 10%, by at least about 20%, by at least about 30%, by at least about 40%, by at least about 50%, by at least about 60%, by at least 70%, by at least about 80%, by at least 90% or by at least about 100% when compared to a reference procoagulant compound with the same sequence but without a self-immolative linker. In some embodiments, the efficacy of cleavage is increased by at least 100% when compared to a reference procoagulant compound with the same sequence but without a self-immolative linker.

In some embodiments, the efficacy of cleavage is at least about 2-fold, at least about 3-fold, at least about 4-fold, at least about 5-fold, at least about 6-fold, at least about 7-fold, at least about 8-fold, at least about 9-fold, or at least about 10-fold when compared to a reference procoagulant compound with the same sequence but without a self-immolative linker. In some embodiments, the efficacy of cleavage is at least about 20-fold, at least about 30-fold, at least about 40-fold, at least about 50-fold, at least about 60-fold, at least about 70-fold, at least about 80-fold, at least about 90-fold, or at least about 100-fold when compared to a reference procoagulant compound with the same sequence but without a self-immolative linker.

In some embodiments, wherein the procoagulant compound is cleaved by a protease specific for the protease-cleavable substrate moiety at least 10% faster when compared to a reference procoagulant compound with the same sequence but without a self-immolative linker. In some embodiments, cleavage is at least about 10%, at least about 20%, at least about 30%, at least about 40%, at least about 50%, at least about 60%, at least about 70%, at least about 80%, at least 90% or at least about 100% faster when compared to a reference procoagulant compound with the same sequence but without a self-immolative linker. In some embodiments, the cleavage is faster by at least 100% when compared to a reference procoagulant compound with the same sequence but without a self-immolative linker. In some embodiments, the cleavage is at least about 2-fold, at least about 3-fold, at least about 4-fold, at least about 5-fold, at least about 6-fold, at least about 7-fold, at least about 8-fold, at least about 9-fold, or at least about 10-fold faster when compared to a reference procoagulant compound with the same sequence but without a self-immolative linker.

Also provided in the present disclosure is a method of activating a procoagulant peptide, comprising contacting a procoagulant compound of the invention a protease specific for the protease-cleavable substrate moiety in said procoagulant compound, wherein the activated procoagulant peptide is released upon proteolytic cleavage of the protease-cleavable substrate moiety.

The disclosure also provides a method of activating a clotting factor comprising contacting a procoagulant compound of the invention with a protease specific for the protease-cleavable substrate moiety in said procoagulant compound, wherein the activated clotting factor is released upon proteolytic cleavage of the protease-cleavable substrate moiety. In some embodiments, more than one clotting factor (e.g., an activated clotting factor), clotting factor fragment (e.g., a heavy chain or a light chain), procoagulant peptide (e.g., a synthetic procoagulant peptide) or combinations thereof can be released upon proteolytic cleavage of the procoagulant compound of the invention.

The disclosure also provides a method of releasing a procoagulant peptide from a heterologous moiety comprising contacting a procoagulant compound of the invention with a protease specific for the protease-cleavable substrate in said procoagulant compound, wherein the activated procoagulant polypeptide is released upon proteolytic cleavage of the protease-cleavable substrate.

The disclosure also provides a method of releasing a clotting factor from a heterologous moiety comprising contacting a procoagulant compound of the invention with a protease specific for the protease-cleavable substrate in said procoagulant compound, wherein the activated clotting factor is released upon proteolytic cleavage of the protease-cleavable substrate. In some embodiments, more than one clotting factor (e.g., an activated clotting factor), clotting factor fragment (e.g., a heavy chain or a light chain), procoagulant peptide (e.g., a synthetic procoagulant peptide) or combinations thereof can be released upon proteolytic cleavage of the procoagulant compound of the invention from one or more heterologous moieties (e.g., PEG). In some embodiments, the release of the one or more than one clotting factor (e.g., an activated clotting factor), clotting factor fragment (e.g., a heavy chain or a light chain), procoagulant peptide (e.g., a synthetic procoagulant peptide) or combinations thereof factor and the heterologous moiety takes place simultaneously. In some embodiments, the release of the release of the one or more than one clotting factor (e.g., an activated clotting factor), clotting factor fragment (e.g., a heavy chain or a light chain), procoagulant peptide (e.g., a synthetic procoagulant peptide) or combinations thereof factor and the release of the heterologous moiety takes place sequentially.

Also provided in the disclosure is a method of releasing at least one heterologous moiety from a procoagulant compound of the invention, prior or concurrently with the release of one or more clotting factors, clotting factor fragments (e.g., a heavy chain or a light chain), procoagulant peptides (e.g., a synthetic procoagulant peptide) or combinations thereof by treatment with one or more proteases, comprising contacting a procoagulant compound of the invention with one or more proteases specific for the one or more than one protease-cleavable substrate in said procoagulant compound. In some embodiments, the release of one, two, three or more than three heterologous moieties takes place prior to the proteolytic release of clotting factors, clotting factor fragments (e.g., a heavy chain or a light chain), procoagulant peptides (e.g., a synthetic procoagulant peptide) or combinations thereof. In other embodiments, the release of one, two, three or more than three heterologous moieties takes place concurrently with the proteolytic release of clotting factors, clotting factor fragments (e.g., a heavy chain or a light chain), procoagulant peptides (e.g., a synthetic procoagulant peptide) or combinations thereof. In some embodiments, the release of two, three or more than three heterologous moieties takes place simultaneously. In some embodiments, the release of two, three or more than three heterologous moieties takes place sequentially.

Having now described the present invention in detail, the same will be more clearly understood by reference to the following examples, which are included herewith for purposes of illustration only and are not intended to be limiting of the invention. All patents, patent application, patent application publications, and other publications referred to herein are expressly incorporated by reference in their entireties.

EXAMPLES

Materials and Methods

The materials and methods for peptide synthesis, purification, and characterization described below are used in the Examples below unless otherwise stated.
1. Solid Phase Peptide Synthesis Synthetic procoagulant peptides of the present disclosure were synthesized by solid phase peptide synthesis using 9-fluorenylmethoxycarbonyl/tertiary-butyl (Fmoc/tBu) chemistry. Heating was accomplished using a microwave oven or other means. In most cases, the peptides were synthesized in 0.1 mmol scale using NovaPEG Rink Amide resin (Novabiochem) or NovaPEG TGT resin (Novabiochem) in a 35 mL reaction vessel. Standard methods for resin load, amino acid coupling, Fmoc deprotection and washing steps were performed on a CEM Liberty peptide synthesizer (CEM Corp.), whereas the trifluoroacetic acid (TFA) cleavage of the peptide was performed manually.

Briefly, 5 equivalent of Fmoc protected amino acids dissolved in N,N-dimethylformamide (DMF) were linked subsequently to the resin in the presence of 5 equivalents of 2(6-chloro-1H-benzotriazole-1-yl)-1,1,3,3-tetramethylaminium hexafluoro phosphate (HCTU) and 10 equivalents of diisopropylethylamine (DIPEA). The microwave method used for the coupling step was single coupling at 75° C. (20 W for 300 seconds), except for cysteine and histidine, which were coupled at 50° C. (0 W for 120 sec, 20 W for 240 seconds). Arginine was double coupled at 75° C. (0 W for 1500 sec, 20 W for 300 seconds). The Fmoc deprotection was performed with 5% piperazine, 0.1M 1-hydroxybenzotriazole (HOBt) in DMF at 75° C. (45 W for 30 seconds, 45 W for 180 seconds). Most amino acids and coupling reagents were purchased from Novabiochem® EMD (EMD Millipore Chemicals).

Following the automated peptide synthesis, the peptides were cleaved from the resin with 95% TFA and 5% triisopropylsilane (TIPS) for 2 hours or 30% hexafluoroisopropanol (HFIP) in DCM. Next, the peptides were filtered into round bottom reaction flasks. The solvents were removed in vacuo, and the concentrates containing the peptides were precipitated and further triturated with ice cold diethyl ether ($Et_2O$). The identity of the synthesized peptides was confirmed by mass spectral analysis.

2. Peptide Purification

The synthesized peptides were purified by preparative reverse phase high performance liquid chromatography (RP-HPLC) using Waters 600 controller and pump system equipped with a Waters 2489 UV/Visible detector and a Water Fraction Collector III (Waters Corp.). The purifications were typically performed on a Phenomenex Jupiter C18 10 micron 250×21.20 mm RP-HPLC column (Phenomenex, Inc.) with a flow rate of 20 mL/min. The acetonitrile/water (0.1% TFA) gradient was modified for each specific peptide based on hydrophobicity. The peptides were detected at two wavelengths, 228 nm and 280 nm, and the fractions were further analyzed by liquid chromatography mass spectrometry (LC-MS). Fractions containing peptide of adequate purity were pooled, flash frozen and lyophilized.

3. Peptide Characterization

The peptides were characterized by LC-MS (Agilent LC-MS TOF 6220 with 1200 series pump, auto handler and UV detection system). The LC separation was performed on a Phenomenex Jupiter C18 5 micron 250×2.00 mm column using a mobile phase of A (water+0.08% formic acid+0.02% trifluoroacetic acid) and B (acetonitrile+0.08% formic acid+0.02% trifluoroacetic acid). The general LC method had a gradient from 0-70% B over 12 min. Mass determination was achieved by electrospray ionization in positive mode. The purity of the peptides was determined by measuring the absorbance of UV light at 228 nm over the chromatogram.

Example 1

Thrombin-Activatable Procoagulant Compounds with PABC Self-Immolative Linker

Seven different peptides, designated Compound 1 to 7, were used in the experiments disclosed herein (TABLE 1). The sequence Ile-Val-Gly-Gly-Gln-Glu in Compounds 1 to 6 corresponds to the six N-terminal amino acid residues of the heavy chain of the FXa clotting factor. These compounds reproduce the coupling of a thrombin cleavable substrate and a self-immolative spacer to the N-terminus of a clotting factor or a fragment thereof, in this specific example, FX. Compound 7 corresponds to a synthetic procoagulant peptide fused to PABC and to a thrombin-cleavable substrate, and further including a linker and a scaffolding amino acid heterologous moiety (Cys) for attachment of half-life extending moieties such as PEG.

TABLE 1

| Compound | Structure |
|---|---|
| 1 | (D-Phe)-Pip-Arg-PABC-Ile-Val-Gly-Gly-Gln-Glu-$NH_2$ |
| 2 | (D-Phe)-Pip-Arg-Ile-Val-Gly-Gly-Gln-Glu-$NH_2$ |
| 3 | Ala-Leu-Arg-Pro-Arg-Ile-Val-Gly-Gly-Gln-Glu-$NH_2$ |
| 4 | (D-Phe)-Pro-Arg-PABC-Ile-Val-Gly-Gly-Gln-Glu-$NH_2$ |
| 5 | Ala-Leu-Val-Pro-Arg-PABC-Ile-Val-Gly-Gly-Gln-Glu-$NH_2$ |
| 6 | Ala-Leu-Val-Pro-Arg-Ile-Val-Gly-Gly-Gln-Glu-$NH_2$ |
| 7 | *C(Acm)-GGGG-*(D-Phe)-Pip-Arg-PABC-r-Arg-Ala-Pro-Gly-Lys-Leu-Thr-Cys-Leu-Ala-Ser-Tyr-Cys-Trp-Leu-Phe-Trp-Thr-Gly-Ile-Ala-$NH_2$ |

TABLE 1-continued

| Compound | Structure |
|---|---|

Pip is pipecolic acid. (D-Phe) is D-Phenyl alanine. The sequences of the thrombin substrate are underlined. The location of the PABC self-immolative linker is indicated by a box.

1. Synthesis of PABC Peptides (Compound 1, 4, 5, and 7)

Figure 5:
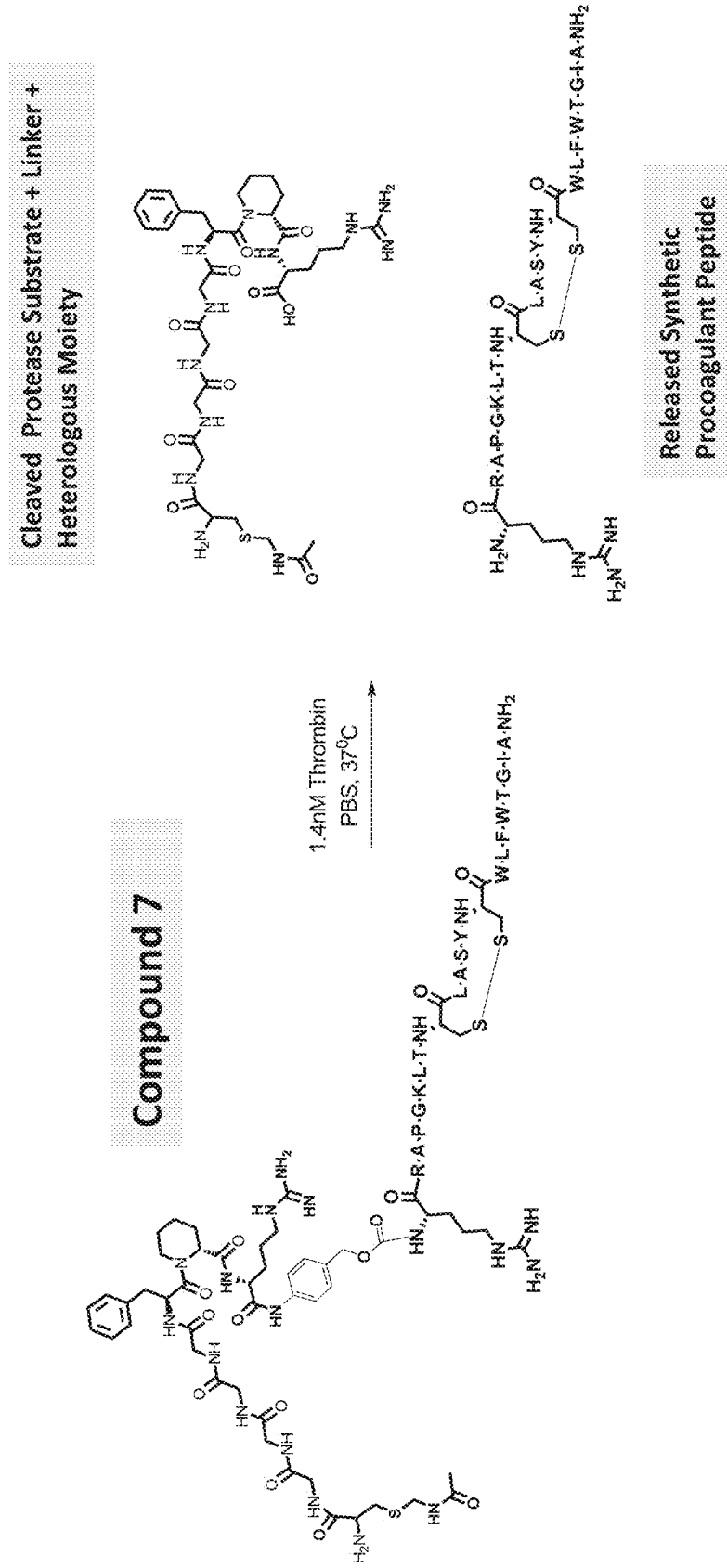
Figure 6:
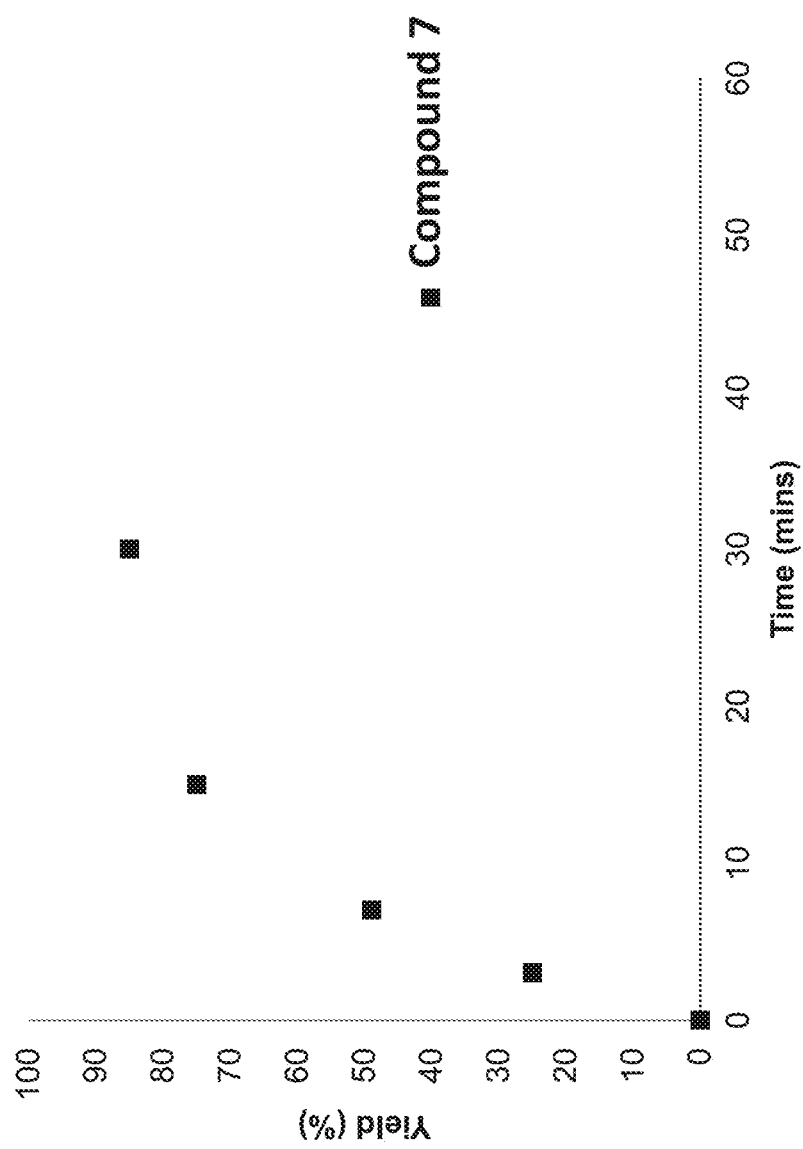
FIG. 6 shows the kinetics of the cleavage of Compound 7 by thrombin.

The synthesis process for Compound 7 is shown in FIG. 5 and FIG. 6, and explained in detailed below. The synthesis of Compounds 1, 4, and 5 was outsourced, and followed a similar synthesis procedure. Compounds 2, 3, 6 were synthesized as described in the Materials and Methods section, supra.

Figure 3:
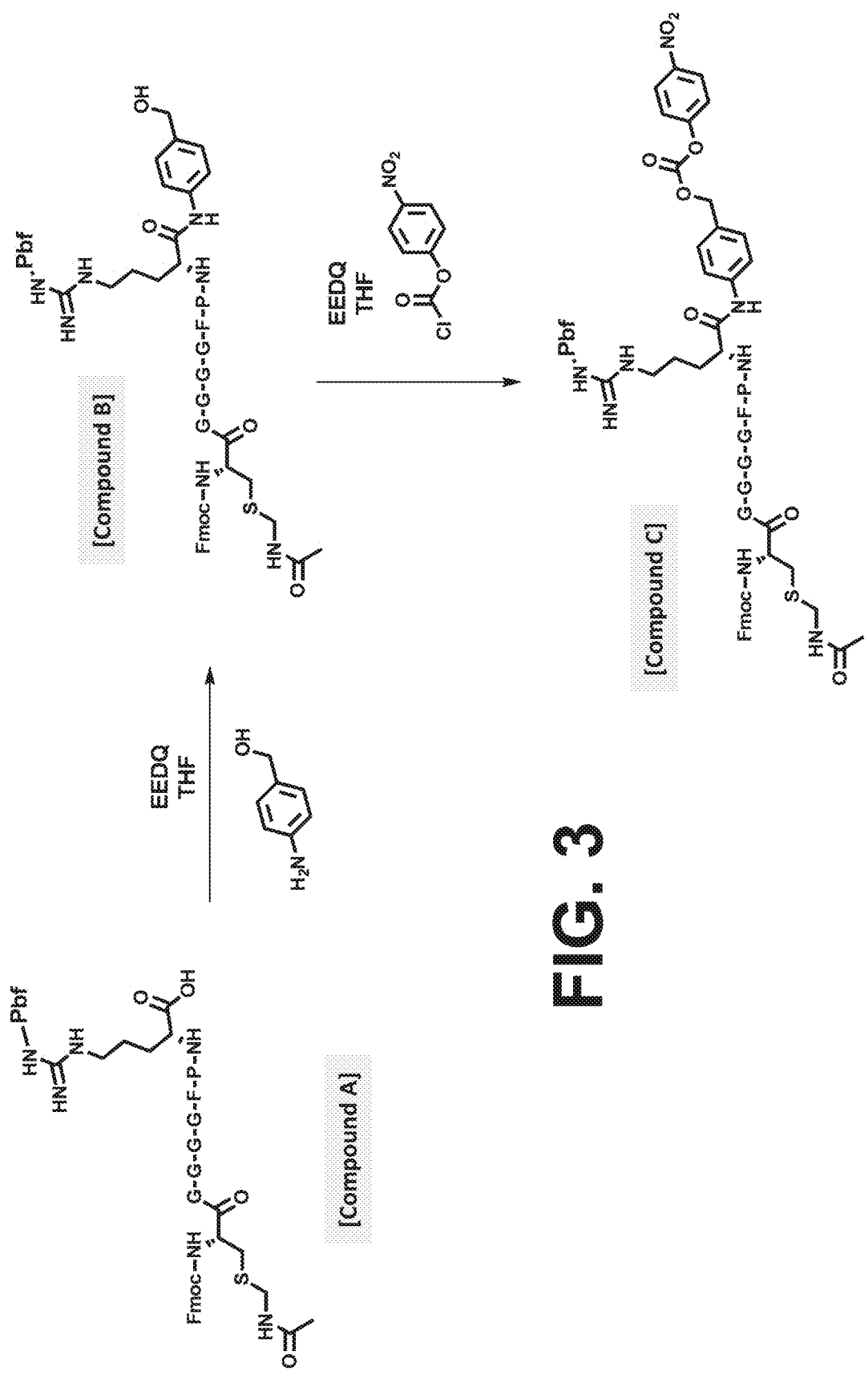

The first two steps in the synthesis of Compound 7 after cleavage from the resin are shown in FIG. 3:

Compound A Synthesis

Fmoc-Cys(Acm)-Gly-Gly-Gly-Gly-Dphe-Pip-Arg(Pbf)

The chemically synthesized and fully protected Compound A peptide (Fmoc-Cys(Acm)-Gly-Gly-Gly-Gly-Dphe-Pip-Arg(Pbf)) was cleaved from the NovaPEG TGT resin by 30% HFIP/DCM and filtered into a round bottom reaction flask. The solvents were removed in vacuo, and the concentrate containing the peptide was precipitated and further triturated with ice cold diethyl ether (Et$_2$O). This material was directly used without further purification. ESI-MS m/z: 1309.51 (MH)$^+$.

Compound B Synthesis

Fmoc-Cys(Acm)-Gly-Gly-Gly-Gly-Dphe-Pip-Arg(Pbf)-PABOH (p-Amino Benzyl Alcohol)

A stirred solution of Fmoc-Cys(Acm)-Gly-Gly-Gly-Gly-Dphe-Pip-Arg(Pbf) (Compound A) (268 mg, 0.2 mmol) and p-amino benzyl alcohol (28 mg, 1.1 equivalents) in THF (2 mL) at room temperature was treated with EEDQ (55.6 mg, 1.1 equivalents). After 16 hours, the mixture was evaporated to dryness, and the residue was triturated with ether. The resulting white solid product, comprising Compound B (Fmoc-Cys(Acm)-Gly-Gly-Gly-Gly-Dphe-Pip-Arg(Pbf)-PABOH (p-amino benzyl alcohol)) was collected by centrifugation and dried in vacuo (200 mg, 70%). ESI-MS m/z: 1414.61 (MH)$^+$.

Compound C Synthesis

Fmoc-Cys(Acm)-Gly-Gly-Gly-Gly-Dphe-Pip-Arg(Pbf)-PABC-PNP

A stirred solution of Fmoc-Cys(Acm)-Gly-Gly-Gly-Gly-Dphe-Pip-Arg(Pbf)-PABOH (Compound B) (180 mg, 0.127 mmol) in dry THF (4 mL) and DCM (4 mL) at room temperature was treated with PNP chloroformate (38.5 mg, 1.5 equivalents) and dry pyridine (15 mg, 1.5 equivalents). After 16 hours, the mixture was concentrated to 1 mL, and the product was precipitated and triturated with cold ether. The resulting white solid product, comprising Compound C (Fmoc-Cys(Acm)-Gly-Gly-Gly-Gly-Dphe-Pip-Arg(Pbf)-PABC-PNP) was collected by centrifugation and dried in vacuo (150 mg, 75%). ESI-MS m/z: 1579.61 (MH)$^+$.

Figure 4:
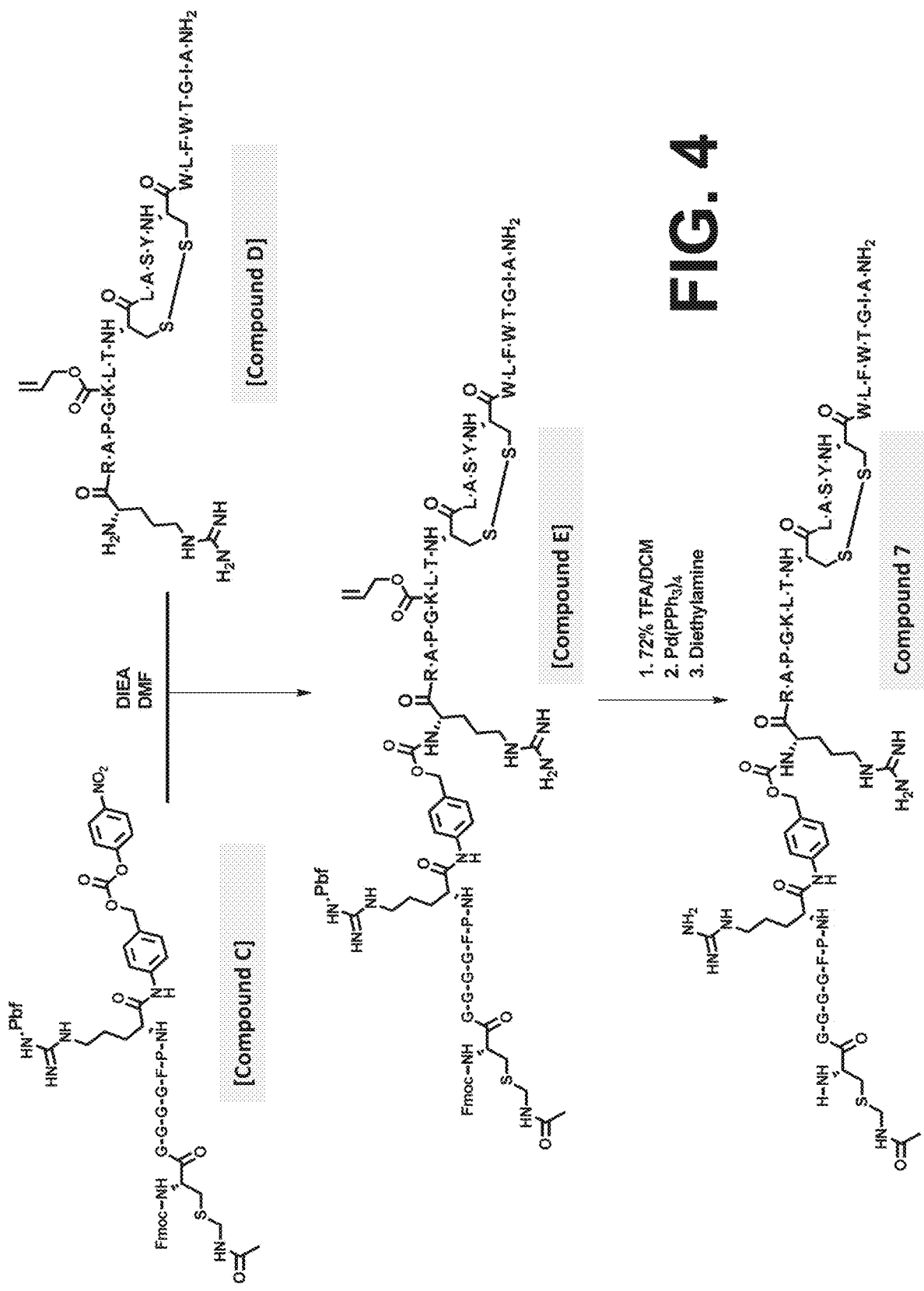

The remaining steps in the synthesis of Compound 7, comprising the conjugation of the protease-cleavable substrate/self-immolative spacer to the synthetic procoagulant peptide are depicted in FIG. 4.

Compound D Synthesis rRAPGK(Alloc)LTCLASYCWLFWTGIA-NH$_2$ (disulfide)

The linear peptide was synthesized on NovaPEG Rink Amide resin (0.2 mmol) as described in the general method. The Cys-Cys disulfidic bond was formed by stirring the crude peptide in 50% DMSO/H$_2$O overnight at 37° C. 35 mg of peptide was obtained after purification by preparative HPLC. ESI-MS m/z: 1298.17 (MH$_2$)$^{2+}$, 865.78 (MH$_3$)$^{3+}$.

Compound E Synthesis

Fmoc-Cys(Acm)-Gly-Gly-Gly-Gly-Dphe-Pip-Arg(Pbf)-PABC-rRAPGK(Alloc)LTCLA SYCWLFWTGIA-NH$_2$ (disulfide)

Fmoc-Cys(Acm)-Gly-Gly-Gly-Gly-Dphe-Pip-Arg(Pbf)-PABC-PNP (Compound C) (12.5 mg, 0.008 mmol) and rRAPGK(Alloc)LTCLASYCWLFWTGIA (Compound D) (30 mg, 0.011 mmol) in DMF (1 mL) at room temperature were treated with DIEA (6.5 µL, 5 equivalents). The mixture was allowed to stand in the dark overnight. The crude product was precipitated, and triturated with cold ether. The resulting crude product was collect by centrifugation, dried in vacuo, and used for next step without further purification. ESI-MS m/z: 2018.32 $(MH_2)^{2+}$, 1345.86 $(MH_3)^{3+}$.
Compound 7 Synthesis
Step 1
Fmoc-Cys(Acm)-Gly-Gly-Gly-Gly-Dphe-Pip-Arg-PABC-rRAPGK(Alloc)LTCLA SYCWLFWTGIA-NH$_2$ (disulfide)

Pbf deprotection of Fmoc-Cys(Acm)-Gly-Gly-Gly-Gly-Dphe-Pip-Arg(Pbf)-PABC-rRAPGK(Alloc)LTCLA SYCWLFWTGIA from the previous step was carried out in 1 mL of solvent mixture (72% TFA, 5% DMF, 5% H$_2$O, 18% DCM) for 75 minutes. Since the PABC linker was unstable under this condition, aliquots were taken at various time points to monitor progress of the reaction. At 75 minutes, cold ether (50 mL) was added to stop the reaction. The resulting solid was purified by preparative HPLC, to give a white powder (8 mg, 25% for 2 steps). ESI-MS m/z: 1261.83 $(MH_3)^{3+}$.
Step 2
Fmoc-Cys(Acm)-Gly-Gly-Gly-Gly-Dphe-Pip-Arg-PABC-rRAPGKLTCLA SYCWLFWTGIA-NH$_2$ (disulfide)

Fmoc-Cys (Acm)-Gly-Gly-Gly-Gly-Dphe-Pip-Arg-PABC-rRAPGK(Alloc)LTCLASYCWLFWTGIA (8 mg, 0.002 mmol) in MeOH/Dioxane (1:1, 180 µL) under N$_2$ at room temperature was treated with Pd(PPh$_3$)$_4$ (0.0002 mmol, 0.1 equivalents, 20 µL of a THF solution of Pd(PPh$_3$)$_4$ (23 mg/mL), followed by PhSiH$_3$ (0.01 mmol, 5 equivalents). After 20 minutes, the crude mixture was precipitated and triturated with cold ether. The resulting crude product was used for the next step without purification. ESI-MS m/z: 1233.82 $(MH_3)^{3+}$.
Step 3
Cys(Acm)-Gly-Gly-Gly-Gly-Dphe-Pip-Arg-PABC-rRAPGKLTCLASYCWLFWTGIA-NH$_2$ (disulfide) (Compound 7)

Fmoc deprotection of Fmoc-Cys(Acm)-Gly-Gly-Gly-Gly-Dphe-Pip-Arg-PABC-rRAPGKLTCLASYCWLFWTGIA from the previous step was carried out in DMSO (200 µL) with Et$_2$NH (50 µL, excess). After 20 minutes, the reaction was complete and the mixture was purified by preparative HPLC, to give a white powder SYN 4018 (0.83 mg, 12% over 2 steps). ESI-MS m/z: 1159.80 $(MH_3)^{3+}$, 870.09 $(MH_4)^{4+}$.
2. Thrombin Cleavage of Compound 7

FIG. 5 depicts the cleavage of Compound 7 by thrombin. Upon cleavage with 1.4 nM thrombin in PBS, the clean synthetic procoagulant peptide is released, as well as the portion of the molecule comprising the thrombin substrate, the GGGG linker, and the N-terminal cysteine. To conduct the reaction, 21 µL of peptide (0.24 mM) in water was added to 476.5 µL PBS. The mixture was incubated at 37° C. for 30 min, followed by 2.5 µL of thrombin (278 nM, 10 µg/mL), giving the following approximate initial concentrations: thrombin=1.4 nM, peptide=10 µM. The mixture was incubated at 37° C. Aliquots (60 µL) at various time points were quenched with 1 µL of hirudin (10 µM) and injected into the HPLC (C-18 column, CH$_3$CN/H$_2$O, 0 to 70% over 12 minutes, 60° C. 0.5 mL/min, $\lambda$ =280 nm). The kinetics of the cleavage of Compound 7 is shown in FIG. 6. Compound 7 was cleaved rapidly by 1.4 nm thrombin. Approximately 90% of Compound 7 was cleaved after 30 minutes.

Figure 7:
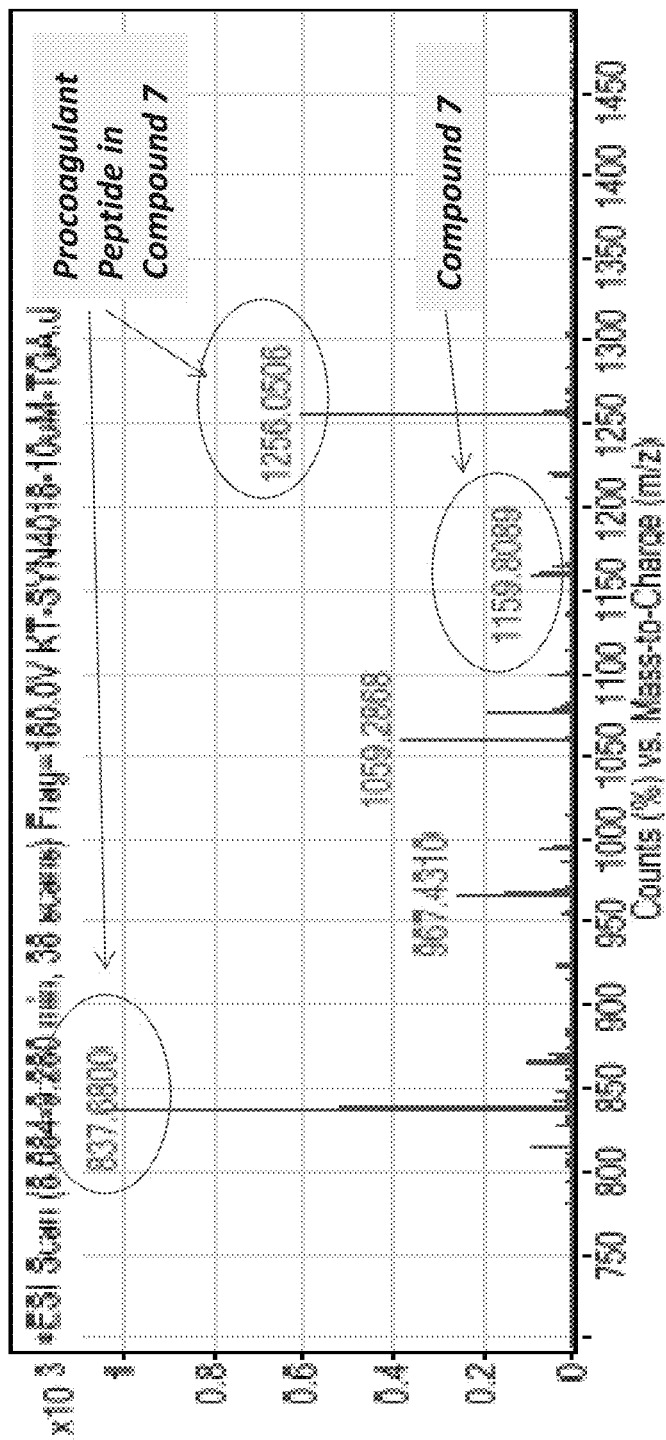
FIG. 7 shows the cleavage of Compound 7 during the course of a TGA assay.

Compound 7 was also cleaved completely during the course of a TGA assay (FIG. 7). Plasma at the end of TGA assay for Compound 7 was transferred into cold CH$_3$CN (1 mL) and centrifuged at 13 k rpm for 10 min. Supernatant (1.1 mL) was transferred to a new vial and dried by speedvac. The resulting solid was reconstituted with 30 µL of H$_2$O and injected into the HPLC for analysis. FIG. 7 shows peaks corresponding to the procoagulant peptide in Compound 7, indicating that Compound 7 was completely cleaved in the course of the TGA assay.
3. Thrombin Cleavage of Compounds 1, 2, and 3

Figure 8:
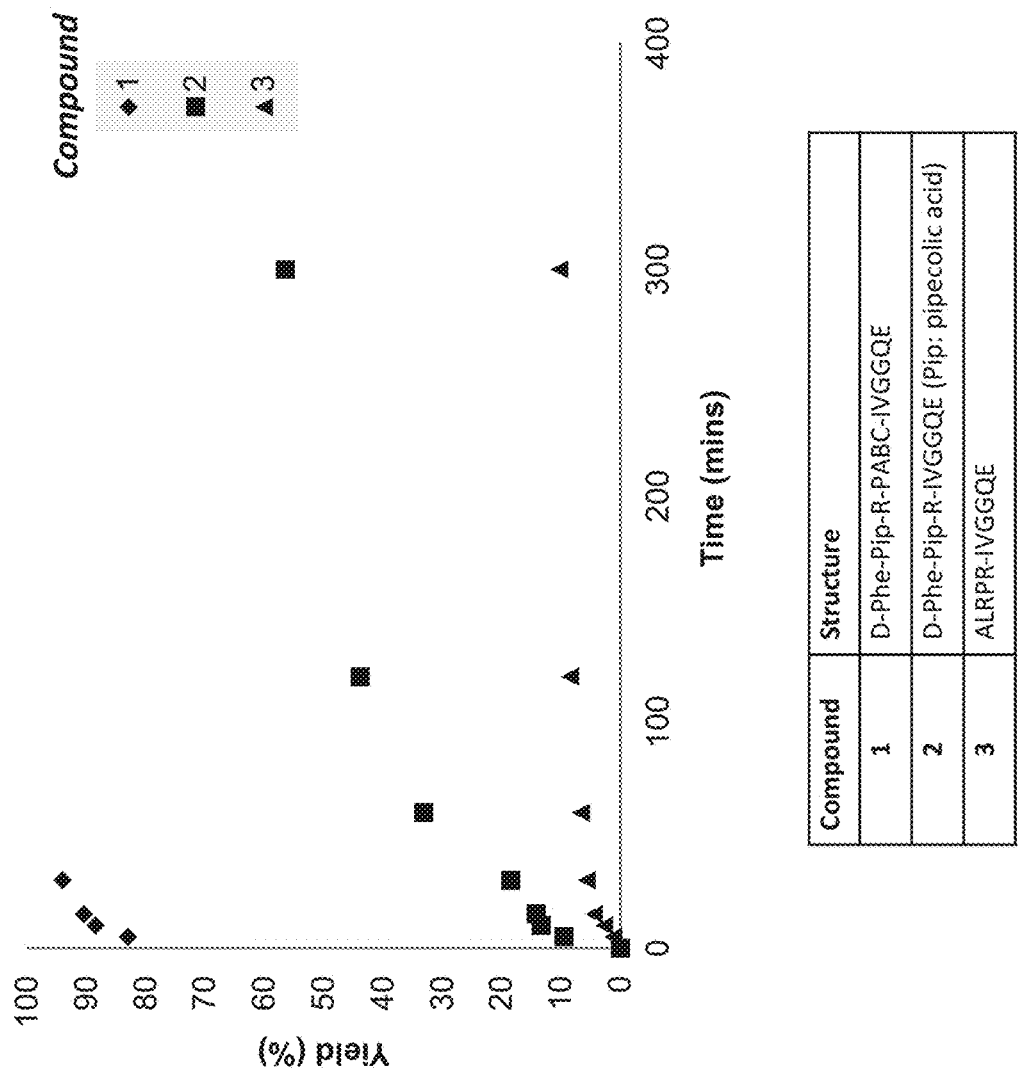
FIG. 8 shows the release kinetics of the peptide IVGGQE (SEQ ID NO: 85), which corresponds to the six N-terminal amino acid residues of the heavy chain of the FXa clotting factor, from different procoagulant compounds (Compounds 1, 2, and 3) following treatment with 14 nM thrombin.

FIG. 8 depicts the cleavage of Compounds 1, 2 and 3 by 14 nM thrombin. These compounds, as discussed above, comprise the six N-terminal amino acid residues of the heavy chain of the FXa clotting factor, and function as a model to show the applicability of the procoagulant compound design disclosed herein to clotting factors.

In this specific example, 50 µL of peptide (1 mM) in water was added to 900 µL PBS, followed by 50 µL of thrombin (278 nM, 10 µg/mL), giving the following approximate initial concentrations: thrombin=14 nM, peptide=50 µM. The mixture was incubated at room temperature. Aliquots (95 µL) at various time points were quenched with 5 µL of hirudin (2 µM) and injected into the HPLC (C-18 column, CH$_3$CN/H$_2$O, 0 to 70% over 12 minutes, 60° C. 0.5 mL/min, $\lambda$ =280 nm). The decreases of peptide peak areas were used to calculate yield.

Compared to Compounds 2 and 3, the construct incorporating the thrombin-cleavable synthetic substrate D-Phe-Pip-Arg (SEQ ID NO: 21) and the self-immolative spacer PABC (Compound 1) was a better substrate for thrombin. The incorporation of PABC to Compound 1 led to at least 10-fold increase in cleavage rate compared to that of Compound 2.
4. Thrombin Cleavage of Compounds 1, 4, 5 and 6

Figure 9:
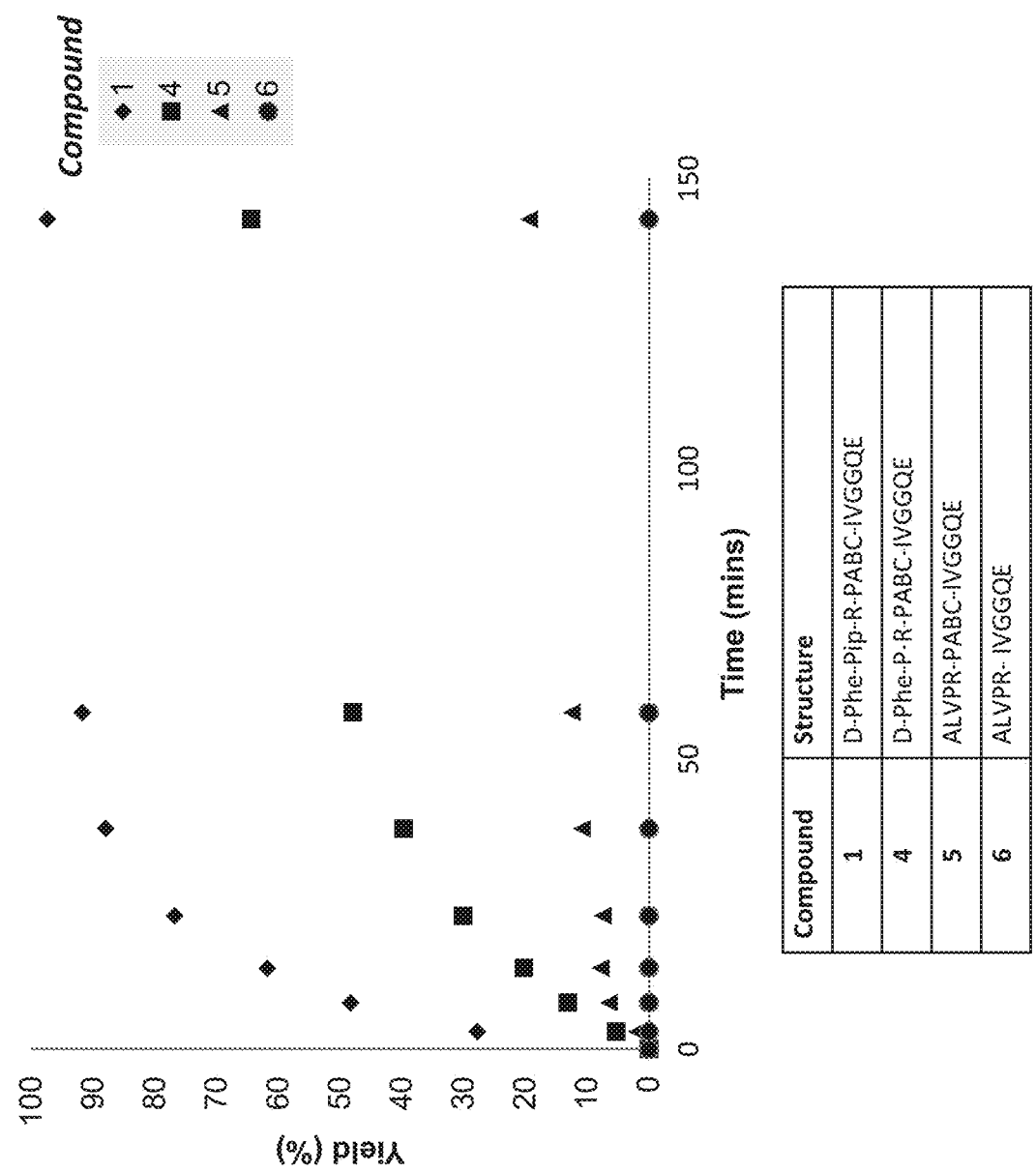
FIG. 9 shows the release kinetics of the peptide IVGGQE (SEQ ID NO: 85), which corresponds to the six N-terminal amino acid residues of the heavy chain of the FXa clotting factor, from different procoagulant compounds (Compounds 1, 4, 5 and 6) following treatment with 1.4 nM thrombin.

FIG. 9 depicts the cleavage of Compounds 1, 4, 5 and 6 by 1.4 nM thrombin. Compounds 1, 4 and 5 incorporate PABC and different thrombin-cleavable substrates.

50 µL of peptide (1 mM) in water was added to 900 µL PBS. The mixture was incubated at 37° C. for 30 min, followed by 50 µL of thrombin (27.8 nM, 1 µg/mL), giving the following approximate initial concentrations: thrombin=1.4 nM, peptide=50 µM. The mixture was incubated at 37° C. Aliquots (95 µL) at various time points were quenched with 5 µL of hirudin (2 µM) and injected into the HPLC (C-18 column, CH$_3$CN/H$_2$O, 0 to 70% over 12 minutes, 60° C. 0.5 mL/min, $\lambda$ =280 nm). The decreases of peptide peak areas were used to calculate yield.

Compound 1 was a better substrate for thrombin than Compounds 4 and 5. At 1.4 nM, a physiological relevant concentration of thrombin, 30% of Compound 1 was quickly cleaved and released. In contrast, thrombin-mediated release of peptide IVGGQE (SEQ ID NO: 85) from Compound 6 without PABC linker was not observed.

Example 2

Thrombin-Activatable FX with PABC Self-Immolative Linker

Peptide synthesis method equivalents to those described above, standard recombinant protein production methods, and standard chemical conjugation techniques are used to generate the procoagulant compound described in this example.

Figure 10:
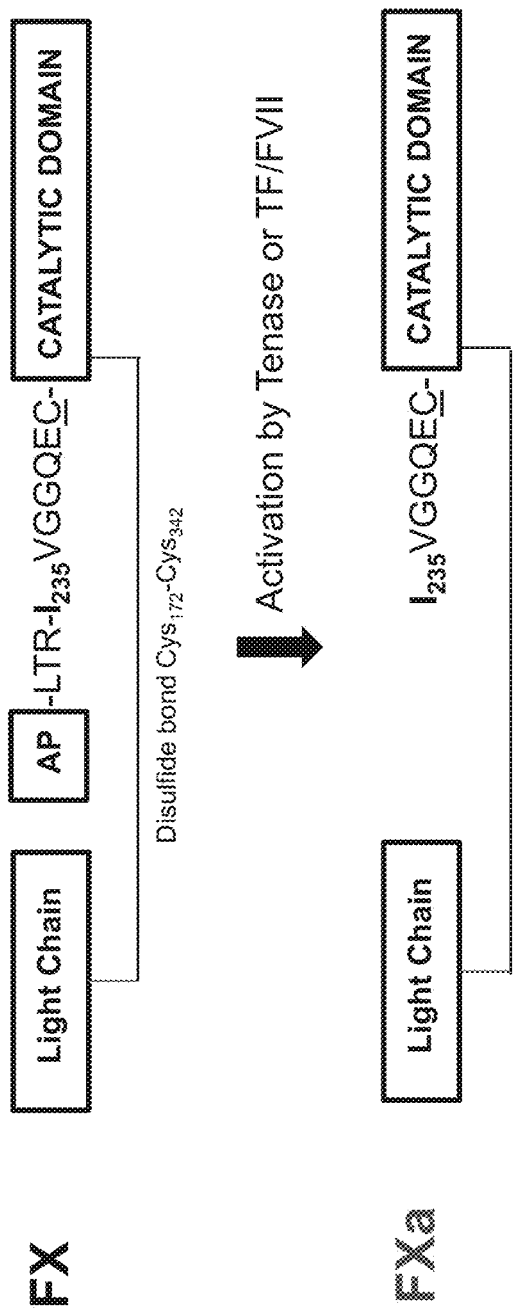
FIG. 10 shows the natural processing of factor X to yield activated factor X (FXa).

Factor X consists of two polypeptide chains linked by a disulfide bridge (Cys172-Cys342): the 139 amino acid light chain in composed of the Gla domain and the two EGFs; the 306 amino acid heavy chain is composed of the activation peptide joined to the catalytic domain. The activation of factor X requires proteolytic cleavage between the activation peptide and the catalytic domain. The tensase complex and the FVIIa-TF complex perform this cleavage between the Arg234 and Ile235 residues (FIG. 10). As in all serine proteases, the N-terminal residues of the catalytic chain of activated factor X are involved in the enzymatic activity. The generated N-terminal Ile235 in particular plays a fundamental role in the catalytic mechanism of the enzyme.

PCT Publ. No. WO 2004/005347 proposed replacement of the native site for activation by the tenase complex with a site for cleavage by thrombin. However, since the efficiency of cleavage is conditioned by the nature of the amino acids framing the cleavage site, these thrombin-activatable FX (TA-FX) analogs suffered from slow activation and undesired efficacy. It is therefore desirable to have other TA-FX analogs which would exhibit faster cleavage kinetics.

The present disclosure provides TA-FX analogs comprising a synthetic thrombin substrate and a self-immolative spacer (e.g., PABC) linked to FXa (FIG. 11). After proteolytic cleavage of the thrombin substrate (D-PhePipArg) and 1,6 spontaneous fragmentation, the natural sequence of FXa is released (FIG. 10). The TA-FX is generated semi-synthetically using native chemical ligation chemistry. This process involves the reaction of a recombinantly produced FX fragment containing an N terminal cysteine residue 241 on the catalytic domain (CysFX) with a synthetically produced thioester peptide to generate a native amide bond at the linkage site. To generate the CysFX protein, the sequence comprising the six N-terminal amino acid residues of the heavy chain IVGGQE (SEQ ID NO: 85) is truncated from the FX; and the native site for activation by tensase complex is replaced with a cleavage site, e.g., for cleavage by PC5.

Example 3

Thrombin-Activatable FVII with PABC Self-Immolative Linker

Peptide synthesis method equivalent to those described above, standard recombinant protein production methods, and standard chemical conjugation techniques are used to generate the procoagulant compounds described in this example.

The present disclosure provides thrombin-activatable FVII (TA-FVII) analogs comprising a synthetic thrombin substrate and a self-immolative spacer (e.g., PABC) linked to FVIIa (FIG. 13). After proteolytic cleavage of the thrombin substrate (D-PhePipArg) and 1,6 spontaneous fragmentation, the natural sequence of FVIIa is released (FIG. 10). The TA-FVII is generated semi-synthetically using native chemical ligation chemistry. This process involves the reaction of a recombinantly produced FVII fragment containing an N terminal cysteine residue 159 on the catalytic domain (CysFVII) with a synthetically produced thioester peptide to generate a native amide bond at the linkage site. To generate the CysFVII protein, the sequence comprising the six N-terminal amino acid residues of the heavy chain IVGGKV (SEQ ID NO: 83) is truncated from the FVII; and the native site for activation by FXa is replaced with a cleavage site, e.g., for cleavage by PC5.

Example 4

Thrombin Activatable FVII-186 with SUMO Cleavage Site

For cloning of FVII-186, synthesis of the DNA sequence comprising nucleotides from the HindIII site to the EcoRI site of FVII-186 (Table 2) was outsourced. The DNA was subcloned into the HindIII/EcoRI sites of pcDNA.

To transiently express FVII-186, HEK-293-F cells were grown in suspension in FREESTYLE® media (Invitrogen) supplemented with vitamin K3 (Sigma Aldrich, St. Louis, Mo.) to 2 μg/liter (growth media) as suspension cells at 37° C./10% $CO_2$. Cells were subcultured every three to four days by seeding at cell density of $5\times10^5$ cells/ml. Twenty-four hours prior to transfection, cells were seeded at a density of $7\times10^5$ cells/ml in growth media. On the day of transfection, a transfection solution was made with a volume equal to 5% of the total volume of the cell culture to be transfected. In the transfection solution, DNA was added (final concentration 20 mg/L) to a freshly made solution of PEI (60 mg/L) in growth media. The solution was swirled for 30 seconds and incubated for five minutes at room temperature before adding directly to the cell culture. Four hours later a volume equal to the cell culture volume of OPTICHO™ (Invitrogen) supplemented with vitamin K3 and 200 mM L-glutamine was added to the cells. The cell culture was allowed to grow as shown above and daily media samples were taken to assess protein expression. On the day of harvest, the cells were spun down, and the media filtered in preparation for protein purification or protein analysis by protein A pulldown. For expression of FVII-186, a plasmid encoding FVII-186 was contransfected with a plasmid encoding the proprotein convertase PACE to ensure intracellular processing and cleavage of the proprotein convertase cleavage sites (2X(RKR) SEQ ID NO: 88) in the linker connecting the FVII light chain to SUMO (FIG. 14).

To purify FVII-186, conditioned medium was loaded onto a 25-mL column of Q SEPHAROSE® Fast Flow (GE HealthCare Life Sciences) after adjustment of pH to 7.4 with 2.0 M Tris, pH 8.0. column was washed with 10 mM MES, 50 mM NaCl, pH 6.5. The protein was eluted with 10 mM MES, 100 mM NaCl, 20 mM $CaCl_2$, pH 6.5. The fractions containing FVII-186 were pooled and loaded onto a 25-mL column of rhFcRn-sepharose after adjustment of pH to 6.2 with 0.5 M MES, pH 5.5. After washing with 50 mM MES, 100 mM NaCl, pH 6.2, the bound material was eluted with 10 mM Tris, 250 mM NaCl, pH 8.0 and analyzed with SDS-PAGE.

FVII-186 was cleaved by a SUMO protease as follows. FVII-186 (0.83 mg/mL, 10 μL) was incubated with 10 μL of 100 mM HEPES, 20 mM $CaCl_2$, 0.004% Tween 80 containing 0.4 mM oxidized Glutathione (GSSG), 20 mM Glutathione (GSH), 0.2 U/μL SUMO protease (Invitrogen Cat. No. 12588-018) for 48 hours at room temperature. Reducing SDS-PAGE (FIG. 15, lane 3) showed almost complete conversion of FVII-186 to the desired FVIIHC.

For SUMO protease cleavage of FVII-186 and native chemical ligation with a thioester peptide, FVII-186 (0.83 mg/mL, 10 μL) was incubated with 10 μL of 100 mM HEPES, 20 mM $CaCl_2$, 0.004% Tween 80 containing 0.4 mM SYN470 as a positive control peptide, 0.4 mM GSSG, 20 mM GSH, 0.2 U/μL SUMO protease (Invitrogen Cat. No. 12588-018) for 48 hours at room temperature. Reducing SDS-PAGE (FIG. 15, lane 4) showed complete disappearance of the FVIIHC band and a single new band as the conjugate of the positive peptide control and the FVIIHC.

In order to synthesize Thrombin Activatable FVII-186 (TA-FVII-186), FVII-186 (0.83 mg/mL, 200 μL) was incubated with 200 μL of 100 mM HEPES, 20 mM $CaCl_2$, 0.004% Tween 80 containing 0.4 mM FVII-PABC peptide (i.e., Biotin-Pra-GGGG-D-Phe-Pip-Arg-PABC-IVGGKV-COSBn) (SEQ ID NO: 79), 0.4 mM GSSG, 20 mM GSH, 0.2 U/μL SUMO protease (Invitrogen Cat. No. 12588-018)

for 48 hours at room temperature and analyzed by reducing SDS-PAGE (FIG. 15, lane 5). Reaction mixture was placed in a 0.5 mL dialysis cassette with 10 k MWCO and dialyzed against 1 L of 10 mM Tris, 250 mM NaCl, pH 8.0 containing 0.4 mM GSSG, 2 mM GSH for 24 hours at 4° C. The conjugate was further purified by rhFcRn-sepharose column as described.

FVIIa Chromogenic assay was performed after Thrombin cleavage and activation of TA-FVII-186 (FIG. 16). This assay measures the FX activation activity by measuring the ability of FVIIa to activate FX, as determined by measuring levels of a chromogenic substrate that is cleaved by activated FX (FXa). TA-FVII-186 (200 nM) was activated with Thrombin (140 nM) for 20 minutes at 37° C. Hirudin was added to quench Thrombin. sTF-PL mixture (A STACLOT® FVII-rTF kit), FX, and PEFACHROME® FXa substrate were added and reaction was monitored by measuring absorbance at 405 nm. FVII-186 missing the six N-terminal amino acids was not active in the presence of thrombin. Only TA-FVII-186 with a thrombin cleavage site connected to the complete heavy chain FVII (which includes FVIIa-PABC peptide) showed activity after thrombin cleavage. The resulted activity demonstrated that the FVIIa-PABC peptide was successfully conjugated to the N-terminal cysteine residue of the truncated heavy chain of FVIIa, the crucial N-terminal isoleucine residue was generated upon cleavage by thrombin, and the formed protein had the essential structure for activity.

Example 5

Thrombin Activatable FX-011 with PACE Cleavage Site

For cloning of FX-011, synthesis of the DNA sequence comprising nucleotides from the HindIII site to the NotI site of FX-011 (Table 4) was outsourced. The DNA was subcloned into the HindIII/NotI sites of pcDNA.

For transient expression of FX-011, HEK-293-F cells were transfected essentially as described above to obtain expression of FX-011. A plasmid encoding FX-011 was cotransfected with a plasmid encoding the proprotein convertase PACE (20%) to ensure intracellular processing and cleavage of the proprotein convertase cleavage sites in the linkers and removal of linkers (FIG. 17) In order to analyze the protein from transient transfections, conditioned media were subjected to protein A immunoprecipitation. Briefly, cell culture supernatant was mixed with approximately 50 µl of protein A-Sepharose 50% slurry and incubated at 4° C. with rocking for 1 hour, then centrifuged to pellet the protein A beads. Beads were washed twice by resuspending in 1 ml of PBS, spinning and aspirating. The beads were resuspended with SDS-PAGE buffer under reducing or nonreducing conditions, heated for 5 minutes at 95° C., spun down, loaded on SDS-PAGE gels, and run according to standard protocols. Under non-reducing conditions, 1 band with the expected molecular weight for the FX-011 was observed (FIG. 17, lane 3). Under reducing conditions, 3 major bands were observed representing the incompletely processed activation peptide-heavy chain FX-Fc subunit, the desired heavy chain FX-Fc subunit, and the Fc subunit (FIG. 17, lane 2). Proteins were transferred onto a cellulose membrane and the band corresponding to heavy chain FX-Fc subunit was collected and analyzed. N-terminal sequencing confirmed the existing N-terminal cysteine (Cys) residue as expected after cleavage by PACE.

For purification of FX-011, conditioned medium (200 mL) was concentrated to 10 mL by 15 mL centrifugal filter units 30,000 MWCO (catalog #UFC 903008). After adjustment of pH to 6.2 with 0.5 M MES, pH 5.5, the concentrated medium was loaded onto a 0.5 mL rhFcRn-sepharose resin bed equilibrated with 50 mM MES, 100 mM NaCl, pH 6.2 buffer. After washing with 50 mM MES, 100 mM NaCl, pH 6.2, the bound material was eluted with 10 mM Tris, 250 mM NaCl, pH 8.0. Before conjugation, FX-011 was transferred to a 20 mM HEPES, 500 mM NaCl, 5 mM CaCl$_2$, pH 7.4 buffer by dialysis.

For semisynthesis of Thrombin Activatable FX-011 (TA-FX-011) by native chemical ligation with a thioester peptide, FX-011 (0.5 mg/mL) was incubated with 0.5 mM FX-PABC peptide (i.e., GG-D-Phe-Pip-Arg-PABC-IVGGQE-COSBn) (SEQ ID No. _____) and 20 mM sodium 2-sulfanylethane-sulfonate (MESNA) in 20 mM HEPES, 500 mM NaCl, 5 mM CaCl$_2$, pH 7.4 buffer for 16 hours at room temperature. Reaction was analyzed by SDS-PAGE gel (FIG. 18, lane 3). Excess peptides and MESNA were removed by gel filtration. The pooled fractions containing TA-FX-011 were placed in a 0.5 mL dialysis cassette with 10 k MWCO and dialyzed against 1 L of 20 mM HEPES, 500 mM NaCl, 5 mM CaCl$_2$, pH 7.4 for 24 hours at 4° C.

FXa chromogenic assay was performed after Thrombin cleavage of TA-FX-011 (FIG. 19). TA-FX-011 (200 nM) was activated with Thrombin (140 nM) for 20 minutes at 37° C. Hirudin was added to quench Thrombin. FXa substrate was added and reaction was monitored by measuring absorbance at 405 nm. FX-011 missing the six N-terminal amino acids was not active in the presence of thrombin. Only TA-FX-011 with a thrombin cleavage site connected to the complete heavy chain FX (which includes FXa-PABC peptide) showed activity after thrombin cleavage. The resulted activity demonstrated that the FX PABC peptide was successfully conjugated to the N-terminal cysteine residue of the truncated heavy chain of FX, the crucial N-terminal isoleucine residue was generated upon cleavage by thrombin, and the formed protein had the essential structure for activity.

Example 6

Thrombin Activatable FX-012 with SUMO Cleavage Site

For cloning of FX-012, synthesis of the DNA sequence comprising nucleotides from the HindIII site to the NotI site of FX-012 (Table 6) was outsourced. The DNA was subcloned into the HindIII/NotI sites of pcDNA.

Transient expression and protein purification of FX-012 was essentially as described for FVII-186. Under non-reducing conditions, the major band with the expected molecular weight for the FX-012 was observed (FIG. 20, lane 2). Under reducing conditions, 2 major bands were observed representing the desired SUMO-heavy chain FX-Fc subunit and the Fc subunit (FIG. 20, lane 3). The LC band was not visible.

FX-012 was cleaved by a SUMO protease as follows. FX-012 (0.35 mg/mL) was incubated with 0.1 U/µL SUMO protease (Invitrogen Cat. No. 12588-018), 20 mM GSH in 50 mM HEPES, 10 mM CaCl$_2$, pH 7.4 buffer for 24 hours at room temperature. Reducing SDS-PAGE (FIG. 21, lane 2) showed almost complete conversion of FX-012 to the desired FXHC-Fc.

For SUMO protease cleavage of FX-012 and native chemical ligation with a thioester peptide, FX-012 (0.35 mg/mL) was incubated with 0.4 mM SYN470 as a positive control peptide, 0.1 U/μL SUMO protease (Invitrogen Cat. No. 12588-018), 20 mM GSH in 50 mM HEPES, 10 mM $CaCl_2$, pH 7.4 buffer for 24 hours at room temperature. Reducing SDS-PAGE (FIG. 21, lane 4) showed complete disappearance of the FXHC-Fc band and a single new band as the conjugate of the positive peptide control and the FXHC-Fc.

For semisynthesis of Thrombin Activatable FX-012 (TA-FX-012) by native chemical ligation with a thioester peptide, FX-012 (0.35 mg/mL) was incubated with 0.4 mM FX-PABC peptide (i.e., D-Phe-Pip-Arg-PABC-IVGGQE-COSBn) (SEQ ID NO: 90), 0.1 U/μL SUMO protease (Invitrogen Cat. No. 12588-018), 20 mM GSH in 50 mM HEPES, 10 mM $CaCl_2$, pH 7.4 buffer for 24 hours at room temperature. Reducing SDS-PAGE (FIG. 21, lane 3) showed a new band as the desired conjugate of the FX-PABC peptide and the FXHC-Fc. Reaction mixture was placed in a 0.5 mL dialysis cassette with 10 k MWCO and dialyzed against 1 L of 10 mM Tris, 250 mM NaCl, pH 8.0 containing 0.4 mM GSSG, 2 mM GSH for 24 hours at 4° C. The conjugate was further purified by rhFcRn-sepharose column as described.

FXa chromogenic assay was performed after Thrombin cleavage of TA-FX-012 (FIG. 22). TA-FX-012 (200 nM) was activated with Thrombin (140 nM) for 20 minutes at 37° C. Hirudin was added to quench Thrombin. FXa substrate was added and reaction was monitored by measuring absorbance at 405 nm. FX-012 missing the six N-terminal amino acids was not active in the presence of thrombin. Only TA-FX-012 with a thrombin cleavage site connected to the complete heavy chain FX (which includes FXa-PABC peptide) showed activity after thrombin cleavage. The resulted activity demonstrated that the FX PABC peptide was successfully conjugated to the N-terminal cysteine residue of the truncated heavy chain of FX, the crucial N-terminal isoleucine residue was generated upon cleavage by thrombin, and the formed protein had the essential structure for activity.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

Tables

TABLE 2

| DNA sequence of FVII-186 (SEQ ID NO: 65) | | | | |
|---|---|---|---|---|
| 1 | AAGCTTGCCG CCACCATGGT | CTCCCAGGCC | CTCAGGCTCC | TCTGCCTTCT GCTTGGGCTT |
|  | TTCGAACGGC GGTGGTACCA | GAGGGTCCGG | GAGTCCGAGG | AGACGGAAGA CGAACCCGAA |
| 61 | CAGGGCTGCC TGGCTGCAGT | CTTCGTAACC | CAGGAGGAAG | CCCACGGCGT CCTGCACCGG |
|  | GTCCCGACGG ACCGACGTCA | GAAGCATTGG | GTCCTCCTTC | GGGTGCCGCA GGACGTGGCC |
| 121 | CGCCGGCGCG CCAACGCGTT | CCTGGAGGAG | CTGCGGCCGG | GCTCCCTGGA GAGGGAGTGC |
|  | GCGGCCGCGC GGTTGCGCAA | GGACCTCCTC | GACGCCGGCC | CGAGGGACCT CTCCCTCACG |
| 181 | AAGGAGGAGC AGTGCTCCTT | CGAGGAGGCC | CGGGAGATCT | TCAAGGACGG GGAGAGGACG |
|  | TTCCTCCTCG TCACGAGGAA | GCTCCTCCGG | GCCCTCTAGA | AGTTCCTGCG CCTCTCCTGC |
| 241 | AAGCTGTTCT GGATTTCTTA | CAGTGATGGG | GACCAGTGTG | CCTCAAGTCC ATGCCAGAAT |
|  | TTCGACAAGA CCTAAAGAAT | GTCACTACCC | CTGGTCACAC | GGAGTTCAGG TACGGTCTTA |
| 301 | GGGGGCTCCT GCAAGGACCA | GCTCCAGTCC | TATATCTGCT | TCTGCCTCCC TGCCTTCGAG |
|  | CCCCCGAGGA CGTTCCTGGT | CGAGGTCAGG | ATATAGACGA | AGACGGAGGG ACGGAAGCTC |
| 361 | GGCCGGAACT GTGAGACGCA | CAAGGATGAC | CAGCTGATCT | GTGTGAACGA GAACGGCGGC |
|  | CCGGCCTTGA CACTCTGCGT | GTTCCTACTG | GTCGACTAGA | CACACTTGCT CTTGCCGCCG |
| 421 | TGTGAGCAGT ACTGCAGTGA | CCACACGGGC | ACCAAGCGCT | CCTGTCGGTG CCACGAGGGG |
|  | ACACTCGTCA TGACGTCACT | GGTGTGCCCG | TGGTTCGCGA | GGACAGCCAC GGTGCTCCCC |
| 481 | TACTCTCTGC TGGCAGACGG | GGTGTCCTGC | ACACCCACAG | TTGAATATCC ATGTGGAAAA |
|  | ATGAGAGACG ACCGTCTGCC | CCACAGGACG | TGTGGGTGTC | AACTTATAGG TACACCTTTT |
| 541 | ATACCTATTC TAGAAAAAAG | AAATGCCAGC | AAACCCCAAG | GCCGAAAGAG GAGGAAGAGG |
|  | TATGGATAAG ATCTTTTTTC | TTTACGGTCG | TTTGGGGTTC | CGGCTTTCTC CTCCTTCTCC |
| 601 | GGTGGCGGCG GATCAGGTGG | GGGTGGATCA | GGCGGTGGAG | GTTCCCTGCA GGACTCAGAA |
|  | CCACCGCCGC CTAGTCCACC | CCCACCTAGT | CCGCCACCTC | CAAGGGACGT CCTGAGTCTT |

TABLE 2-continued

DNA sequence of FVII-186 (SEQ ID NO: 65)

```
 661   GTCAATCAAG AAGCTAAGCC AGAGGTCAAG CCAGAAGTCA AGCCTGAGAC TCACATCAAT
       CAGTTAGTTC TTCGATTCGG TCTCCAGTTC GGTCTTCAGT TCGGACTCTG AGTGTAGTTA

721   TTAAAGGTGT CCGATGGATC TTCAGAGATC TTCTTCAAGA TCAAAAAGAC CACTCCTTTA
       AATTTCCACA GGCTACCTAG AAGTCTCTAG AAGAAGTTCT AGTTTTTCTG GTGAGGAAAT

781   AGAAGGCTGA TGGAAGCGTT CGCTAAAAGA CAGGGTAAGG AAATGGACTC CTTAAGATTC
       TCTTCCGACT ACCTTCGCAA GCGATTTTCT GTCCCATTCC TTTACCTGAG GAATTCTAAG

841   TTGTACGACG GTATTAGAAT TCAAGCTGAT CAGGCCCCTG AAGATTTGGA CATGGAGGAT
       AACATGCTGC CATAATCTTA AGTTCGACTA GTCCGGGGAC TTCTAAACCT GTACCTCCTA

901   AACGATATTA TTGAGGCTCA CCGCGAACAG ATTGGAGGTT GCCCCAAAGG GGAGTGTCCA
       TTGCTATAAT AACTCCGAGT GGCGCTTGTC TAACCTCCAA CGGGGTTTCC CCTCACAGGT

961   TGGCAGGTCC TGTTGTTGGT GAATGGAGCT CAGTTGTGTG GGGGGACCCT GATCAACACC
       ACCGTCCAGG ACAACAACCA CTTACCTCGA GTCAACACAC CCCCCTGGGA CTAGTTGTGG

1021   ATCTGGGTGG TCTCCGCGGC CCACTGTTTC GACAAAATCA GAACTGGAG GAACCTGATC
       TAGACCCACC AGAGGCGCCG GGTGACAAAG CTGTTTTAGT TCTTGACCTC CTTGGACTAG

1081   GCGGTGCTGG CGAGCACGA CCTCAGCGAG CACGACGGGG ATGAGCAGAG CCGGCGGGTG
       CGCCACGACC CGCTCGTGCT GGAGTCGCTC GTGCTGCCCC TACTCGTCTC GGCCGCCCAC

1141   GCGCAGGTCA TCATCCCCAG CACGTACGTC CCGGGCACCA CCAACCACGA CATCGCGCTG
       CGCGTCCAGT AGTAGGGGTC GTGCATGCAG GGCCCGTGGT GGTTGGTGCT GTAGCGCGAC

1201   CTCCGCCTGC ACCAGCCCGT GGTCCTCACT GACCATGTGG TGCCCCTCTG CCTGCCCGAA
       GAGGCGGACG TGGTCGGGCA CCAGGAGTGA CTGGTACACC ACGGGGAGAC GGACGGGCTT

1261   CGGACGTTCT CTGAGAGGAC GCTGGCCTTC GTGCGCTTCT CATTGGTCAG CGGCTGGGGC
       GCCTGCAAGA GACTCTCCTG CGACCGGAAG CACGCGAAGA GTAACCAGTC GCCGACCCCG

1321   CAGCTGCTGG ACCGTGGCGC CACGGCCCTG GAGCTCATGG TCCTCAACGT GCCCCGGCTG
       GTCGACGACC TGGCACCGCG GTGCCGGGAC CTCGAGTACC AGGAGTTGCA CGGGGCCGAC

1381   ATGACCCAGG ACTGCCTGCA GCAGTCACGG AAGGTGGGAG ACTCCCCAAA TATCACGGAG
       TACTGGGTCC TGACGGACGT CGTCAGTGCC TTCCACCCTC TGAGGGGTTT ATAGTGCCTC

1441   TACATGTTCT GTGCCGGCTA CTCGGATGGC AGCAAGGACT CCTGCAAGGG GGACAGTGGA
       ATGTACAAGA CACGGCCGAT GAGCCTACCG TCGTTCCTGA GGACGTTCCC CCTGTCACCT

1501   GGCCCACATG CCACCCACTA CCGGGGCACG TGGTACCTGA CGGGCATCGT CAGCTGGGGC
       CCGGGTGTAC GGTGGGTGAT GGCCCCGTGC ACCATGGACT GCCCGTAGCA GTCGACCCCG

1561   CAGGGCTGCG CAACCGTGGG CCACTTTGGG GTGTACACCA GGGTCTCCCA GTACATCGAG
       GTCCCGACGC GTTGGCACCC GGTGAAACCC CACATGTGGT CCCAGAGGGT CATGTAGCTC

1621   TGGCTGCAAA AGCTCATGCG CTCAGAGCCA CGCCCAGGAG TCCTCCTGCG AGCCCCATTT
       ACCGACGTTT TCGAGTACGC GAGTCTCGGT GCGGGTCCTC AGGAGGACGC TCGGGGTAAA

1681   CCCGGTGGCG GTGGCTCCGG CGGAGGTGGG TCCGGTGGCG GCGGATCAGG TGGGGGTGGA
       GGGCCACCGC CACCGAGGCC GCCTCCACCC AGGCCACCGC CGCCTAGTCC ACCCCCACCT

1741   TCAGGCGGTG GAGGTTCCGG TGGCGGGGGA TCCGACAAAA CTCACACATG CCCACCGTGC
       AGTCCGCCAC CTCCAAGGCC ACCGCCCCCT AGGCTGTTTT GAGTGTGTAC GGGTGGCACG

1801   CCAGCTCCGG AACTCCTGGG CGGACCGTCA GTCTTCCTCT TCCCCCCAAA ACCCAAGGAC
       GGTCGAGGCC TTGAGGACCC GCCTGGCAGT CAGAAGGAGA AGGGGGGTTT TGGGTTCCTG

1861   ACCCTCATGA TCTCCCGGAC CCCTGAGGTC ACATGCGTGG TGGTGGACGT GAGCCACGAA
       TGGGAGTACT AGAGGGCCTG GGGACTCCAG TGTACGCACC ACCACCTGCA CTCGGTGCTT

1921   GACCCTGAGG TCAAGTTCAA CTGGTACGTG GACGGCGTGG AGGTGCATAA TGCCAAGACA
       CTGGGACTCC AGTTCAAGTT GACCATGCAC CTGCCGCACC TCCACGTATT ACGGTTCTGT

1981   AAGCCGCGGG AGGAGCAGTA CAACAGCACG TACCGTGTGG TCAGCGTCCT CACCGTCCTG
       TTCGGCGCCC TCCTCGTCAT GTTGTCGTGC ATGGCACACC AGTCGCAGGA GTGGCAGGAC

2041   CACCAGGACT GGCTGAATGG CAAGGAGTAC AAGTGCAAGG TCTCCAACAA AGCCCTCCCA
       GTGGTCCTGA CCGACTTACC GTTCCTCATG TTCACGTTCC AGAGGTTGTT TCGGGAGGGT

2101   GCCCCCATCG AGAAAACCAT CTCCAAAGCC AAAGGGCAGC CCCGAGAACC ACAGGTGTAC
       CGGGGGTAGC TCTTTTGGTA GAGGTTTCGG TTTCCCGTCG GGGCTCTTGG TGTCCACATG

2161   ACCCTGCCCC CATCCCGGGA TGAGCTGACC AAGAACCAGG TCAGCCTGAC CTGCCTGGTC
       TGGGACGGGG GTAGGGCCCT ACTCGACTGG TTCTTGGTCC AGTCGGACTG GACGGACCAG
```

TABLE 2-continued

DNA sequence of FVII-186 (SEQ ID NO: 65)

```
2221  AAAGGCTTCT ATCCCAGCGA CATCGCCGTG GAGTGGGAGA GCAATGGGCA GCCGGAGAAC
      TTTCCGAAGA TAGGGTCGCT GTAGCGGCAC CTCACCCTCT CGTTACCCGT CGGCCTCTTG

2281  AACTACAAGA CCACGCCTCC CGTGTTGGAC TCCGACGGCT CCTTCTTCCT CTACAGCAAG
      TTGATGTTCT GGTGCGGAGG GCACAACCTG AGGCTGCCGA GGAAGAAGGA GATGTCGTTC

2341  CTCACCGTGG ACAAGAGCAG GTGGCAGCAG GGAACGTCT TCTCATGCTC CGTGATGCAT
      GAGTGGCACC TGTTCTCGTC CACCGTCGTC CCCTTGCAGA AGAGTACGAG GCACTACGTA

2401  GAGGCTCTGC ACAACCACTA CACGCAGAAG AGCCTCTCCC TGTCTCCGGG TAAAGGTGGC
      CTCCGAGACG TGTTGGTGAT GTGCGTCTTC TCGGAGAGGG ACAGAGGCCC ATTTCCACCG

2461  GGCGGATCAG GTGGGGGTGG ATCAGGCGGT GGAGGTTCCG GTGGCGGGGG ATCAGACAAA
      CCGCCTAGTC CACCCCCACC TAGTCCGCCA CCTCCAAGGC CACCGCCCCC TAGTCTGTTT

2521  ACTCACACAT GCCCACCGTG CCCAGCACCT GAACTCCTGG GAGGACCGTC AGTCTTCCTC
      TGAGTGTGTA CGGGTGGCAC GGGTCGTGGA CTTGAGGACC CTCCTGGCAG TCAGAAGGAG

2581  TTCCCCCCAA AACCCAAGGA CACCCTCATG ATCTCCCGGA CCCCTGAGGT CACATGCGTG
      AAGGGGGGTT TTGGGTTCCT GTGGGAGTAC TAGAGGGCCT GGGGACTCCA GTGTACGCAC

2641  GTGGTGGACG TGAGCCACGA AGACCCTGAG GTCAAGTTCA ACTGGTACGT GGACGGCGTG
      CACCACCTGC ACTCGGTGCT TCTGGGACTC CAGTTCAAGT TGACCATGCA CCTGCCGCAC

2701  GAGGTGCATA ATGCCAAGAC AAAGCCGCGG GAGGAGCAGT ACAACAGCAC GTACCGTGTG
      CTCCACGTAT TACGGTTCTG TTTCGGCGCC CTCCTCGTCA TGTTGTCGTG CATGGCACAC

2761  GTCAGCGTCC TCACCGTCCT GCACCAGGAC TGGCTGAATG GCAAGGAGTA CAAGTGCAAG
      CAGTCGCAGG AGTGGCAGGA CGTGGTCCTG ACCGACTTAC CGTTCCTCAT GTTCACGTTC

2821  GTCTCCAACA AAGCCCTCCC AGCCCCCATC GAGAAAACCA TCTCCAAAGC CAAGGGCAG
      CAGAGGTTGT TTCGGGAGGG TCGGGGGTAG CTCTTTTGGT AGAGGTTTCG GTTCCCGTC

2881  CCCCGAGAAC CACAGGTGTA CACCCTGCCC CCATCCCGCG ATGAGCTGAC CAAGAACCAG
      GGGGCTCTTG GTGTCCACAT GTGGGACGGG GGTAGGGCGC TACTCGACTG GTTCTTGGTC

2941  GTCAGCCTGA CCTGCCTGGT CAAAGGCTTC TATCCCAGCG ACATCGCCGT GGAGTGGGAG
      CAGTCGGACT GGACGGACCA GTTTCCGAAG ATAGGGTCGC TGTAGCGGCA CCTCACCCTC

3001  AGCAATGGGC AGCCGGAGAA CAACTACAAG ACCACGCCTC CCGTGTTGGA CTCCGACGGC
      TCGTTACCCG TCGGCCTCTT GTTGATGTTC TGGTGCGGAG GGCACAACCT GAGGCTGCCG

3061  TCCTTCTTCC TCTACAGCAA GCTCACCGTG GACAAGAGCA GGTGGCAGCA GGGGAACGTC
      AGGAAGAAGG AGATGTCGTT CGAGTGGCAC CTGTTCTCGT CCACCGTCGT CCCCTTGCAG

3121  TTCTCATGCT CCGTGATGCA TGAGGCTCTG CACAACCACT ACACGCAGAA GAGCCTCTCC
      AAGAGTACGA GGCACTACGT ACTCCGAGAC GTGTTGGTGA TGTGCGTCTT CTCGGAGAGG

3181  CTGTCTCCGG GTAAATGAGA ATTC
      GACAGAGGCC CATTTACTCT TAAG
```

TABLE 3

FVII-186 amino acid sequence. Signal sequence is shown in dotted underline,
propeptide is double underlined, linker with proprotein convertase
processing sites connecting the FVII light chain to SUMO is underlined,
SUMO sequence is in dashed underline, SUMO region connecting
FVII to Fc region is in italic, and linker connecting the two
Fc fragments is shown in bold (SEQ ID NO: 66)

```
  1  MVSQALRLLC LLLGLQGCLA AVFVTQEEAH GVLHRRRRAN AFLEELRPGS LERECKEEQC

61  SFEEAREIFK DAERTKLFWI SYSDGDQCAS SPCQNGGSCK DQLQSYICFC LPAFEGRNCE

121  THKDDQLICV NENGGCEQYC SDHTGTKRSC RCHEGYSLLA DGVSCTPTVE YPCGKIPILE

181  KRNASKPQGR KRRKRGGGGS GGGGSGGGGS LQDSEVNQEA KPEVKPEVKP ETHINLKVSD

241  GSSEIFFKIK KTTPLRRLME AFAKRQKGEM DSLRFLYDGI RIQADQAPED LDMEDNDIIE

301  AHREQIGGCP KGECPWQVLL LVNGAQLCGG TLINTIWVVS AAHCFDKIKN WRNLIAVLGE
```

TABLE 3-continued

FVII-186 amino acid sequence. Signal sequence is shown in dotted underline, propeptide is double underlined, linker with proprotein convertase processing sites connecting the FVII light chain to SUMO is underlined, SUMO sequence is in dashed underline, linker region connecting FVII to Fc region is in italic, and linker connecting the two Fc fragments is shown in bold (SEQ ID NO: 66)

```
 361 HDLSEHDGDE QSRRVAQVII PSTYVPGTTN HDIALLRLHQ PVVLTDHVVP LCLPERTFSE

421 RTLAFVRFSL VSGWGQLLDR GATALELMVL NVPRLMTQDC LQQSRKVGDS PNITEYMFCA

481 GYSDGSKDSC KGDSGGPHAT HYRGTWYLTG IVSWGQGCAT VGHFGVYTRV SQYIEWLQKL

541 MRSEPRPGVL LRAPFPGGGG SGGGGSGGGG SGGGGSGGGG SGGGGSDKTH TCPPCPAPEL

601 LGGPSVFLFP PKPKDTLMIS RTPEVTCVVV DVSHEDPEVK FNWYVDGVEV HNAKTKPREE

661 QYNSTYRVVS VLTVLHQDWL NGKEYKCKVS NKALPAPIEK TISKAKGQPR EPQVYTLPPS

721 RDELTKNQVS LTCLVKGFYP SDIAVEWESN GQPENNYKTT PPVLDSDGSF FLYSKLTVDK

781 SRWQQGNVFS CSVMHEALHN HYTQKSLSLS PGKGGGGSGG GGSGGGGSGG GGSDKTHTCP

841 PCPAPELLGG PSVFLFPPKP KDTLMISRTP EVTCVVVDVS HEDPEVKFNW YVDGVEVHNA

901 KTKPREEQYN STYRVVSVLT VLHQDWLNGK EYKCKVSNKA LPAPIEKTIS KAKGQPREPQ

961 VYTLPPSRDE LTKNQVSLTC LVKGFYPSDI AVEWESNGQP ENNYKTTPPV LDSDGSFFLY

1021 SKLTVDKSRW QQGNVFSCSV MHEALHNHYT QKSLSLSPGK*
```

TABLE 4

DNA sequence of FX-011 (SEQ ID NO: 67)

```
   1 AAGCTTATGG GTCGTCCACT GCACCTCGTC CTGCTCAGTG CCTCCCTGGC TGGCCTCCTG
     TTCGAATACC CAGCAGGTGA CGTGGAGCAG GACGAGTCAC GGAGGGACCG ACCGGAGGAC

61 CTGCTCGGGG AAAGTCTGTT CATCCGCAGG GAGCAGGCCA ACAACATCCT GGCGAGGGTC
     GACGAGCCCC TTTCAGACAA GTAGGCGTCC CTCGTCCGGT TGTTGTAGGA CCGCTCCCAG

121 AGGAGGGCCA ATTCCTTTCT TGAAGAGATG AAGAAAGGAC ACCTCGAAAG AGAGTGCATG
     TCCTCCCGGT TAAGGAAAGA ACTTCTCTAC TTCTTTCCTG TGGAGCTTTC TCTCACGTAC

181 GAAGAGACCT GCTCATACGA AGAGGCCCGC GAGGTCTTTG AGGACAGCGA CAAGACGAAT
     CTTCTCTGGA CGAGTATGCT TCTCCGGGCG CTCCAGAAAC TCCTGTCGCT GTTCTGCTTA

241 GAATTCTGGA ATAAATACAA AGATGGCGAC CAGTGTGAGA CCAGTCCTTG CCAGAACCAG
     CTTAAGACCT TATTTATGTT TCTACCGCTG GTCACACTCT GGTCAGGAAC GGTCTTGGTC

301 GGCAAATGTA AAGACGGCCT CGGGGAATAC ACCTGCACCT GTTTAGAAGG ATTCGAAGGC
     CCGTTTACAT TTCTGCCGGA GCCCCTTATG TGGACGTGGA CAAATCTTCC TAAGCTTCCG

361 AAAAACTGTG AATTATTCAC ACGGAAGCTC TGCAGCCTGG ACAACGGGGA CTGTGACCAG
     TTTTTGACAC TTAATAAGTG TGCCTTCGAG ACGTCGGACC TGTTGCCCCT GACACTGGTC

421 TTCTGCCACG AGGAACAGAA CTCTGTGGTG TGCTCCTGCG CCCGCGGGTA CACCCTGGCT
     AAGACGGTGC TCCTTGTCTT GAGACACCAC ACGAGGACGC GGGCGCCCAT GTGGGACCGA

481 GACAACGGCA AGGCCTGCAT TCCCACAGGG CCCTACCCCT GTGGGAAACA GACCCTGGAA
     CTGTTGCCGT TCCGGACGTA AGGGTGTCCC GGGATGGGGA CACCCTTTGT CTGGGACCTT

541 CGCAGGAAGA GGTCAGTGGC CCAGGCCACC AGCAGCAGCG GGGAGGCCCC TGACAGCATC
     GCGTCCTTCT CCAGTCACCG GGTCCGGTGG TCGTCGTCGC CCCTCCGGGG ACTGTCGTAG

601 ACATGGAAGC CATATGATGC AGCCGACCTG GACCCCACCG AGAACCCCTT CGACCTGCTT
     TGTACCTTCG GTATACTACG TCGGCTGGAC CTGGGGTGGC TCTTGGGGAA GCTGGACGAA

661 GACTTCAACC AGACGCAGCC TGAGAGGGGC GACAACAACG GTGGCGGCGG ATCAGGTGGG
     CTGAAGTTGG TCTGCGTCGG ACTCTCCCCG CTGTTGTTGC CACCGCCGCC TAGTCCACCC

721 GGTGGATCAG GCGGTGGAGG TTCCGGTGGC GGGGGATCCA GGAAGAGGAG GAAGAGGTGC
     CCACCTAGTC CGCCACCTCC AAGGCCACCG CCCCTAGGT CCTTCTCCTC CTTCTCCACG

781 AAGGACGGGG AGTGTCCCTG GCAGGCCCTG CTCATCAATG AGGAAAACGA GGGTTTTTGT
     TTCCTGCCCC TCACAGGGAC CGTCCGGGAC GAGTAGTTAC TCCTTTTGCT CCCAAAAACA
```

TABLE 4-continued

DNA sequence of FX-011 (SEQ ID NO: 67)

```
 841   GGAGGTACCA TTCTGAGCGA GTTCTACATC CTAACGGCAG CCCACTGTCT CTACCAAGCC
       CCTCCATGGT AAGACTCGCT CAAGATGTAG GATTGCCGTC GGGTGACAGA GATGGTTCGG

901   AAGAGATTCA AGGTGAGGGT AGGGGACCGG AACACGGAGC AGGAGGAGGG CGGTGAGGCG
       TTCTCTAAGT TCCACTCCCA TCCCCTGGCC TTGTGCCTCG TCCTCCTCCC GCCACTCCGC

961   GTGCACGAGG TGGAGGTGGT CATCAAGCAC AACCGGTTCA CAAAGGAGAC CTATGACTTC
       CACGTGCTCC ACCTCCACCA GTAGTTCGTG TTGGCCAAGT GTTTCCTCTG GATACTGAAG

1021   GACATCGCCG TGCTCCGGCT CAAGACCCCC ATCACCTTCC GCATGAACGT GGCGCCTGCC
       CTGTAGCGGC ACGAGGCCGA GTTCTGGGGG TAGTGGAAGG CGTACTTGCA CCGCGGACGG

1081   TGCCTCCCCG AGCGTGACTG GGCCGAGTCC ACGCTGATGA CGCAGAAGAC GGGGATTGTG
       ACGGAGGGGC TCGCACTGAC CCGGCTCAGG TGCGACTACT GCGTCTTCTG CCCCTAACAC

1141   AGCGGCTTCG GGCGCACCCA CGAGAAGGGC CGGCAGTCCA CCAGGCTCAA GATGCTGGAG
       TCGCCGAAGC CCGCGTGGGT GCTCTTCCCG GCCGTCAGGT GGTCCGAGTT CTACGACCTC

1201   GTGCCCTACG TGGACCGCAA CAGCTGCAAG CTGTCCAGCA GCTTCATCAT CACCCAGAAC
       CACGGGATGC ACCTGGCGTT GTCGACGTTC GACAGGTCGT CGAAGTAGTA GTGGGTCTTG

1261   ATGTTCTGTG CCGGCTACGA CACCAAGCAG GAGGATGCCT GCCAGGGGGA CAGCGGGGGC
       TACAAGACAC GGCCGATGCT GTGGTTCGTC CTCCTACGGA CGGTCCCCCT GTCGCCCCCG

1321   CCGCACGTCA CCCGCTTCAA GGACACCTAC TTCGTGACAG GCATCGTCAG CTGGGGAGAG
       GGCGTGCAGT GGGCGAAGTT CCTGTGGATG AAGCACTGTC CGTAGCAGTC GACCCCTCTC

1381   GGCTGTGCCC GTAAGGGGAA GTACGGGATC TACACCAAGG TCACCGCCTT CCTCAAGTGG
       CCGACACGGG CATTCCCCTT CATGCCCTAG ATGTGGTTCC AGTGGCGGAA GGAGTTCACC

1441   ATCGACAGGT CCATGAAAAC CAGGGGCTTG CCCAAGGCCA AGAGCCATGC CCCGGAGGTC
       TAGCTGTCCA GGTACTTTTG GTCCCCGAAC GGGTTCCGGT TCTCGGTACG GGGCCTCCAG

1501   ATAACGTCCT CTCCATTAAA AGAAGACCAA GTAGATCCGG GCTCATTGA TGGTAAGGAC
       TATTGCAGGA GAGGTAATTT TCTTCTGGTT CATCTAGGCG CCGAGTAACT ACCATTCCTG

1561   AAAACTCACA CATGCCCACC GTGCCCAGCT CCGGAACTCC TGGGAGGACC GTCAGTCTTC
       TTTTGAGTGT GTACGGGTGG CACGGGTCGA GGCCTTGAGG ACCCTCCTGG CAGTCAGAAG

1621   CTCTTCCCCC CAAAACCCAA GGACACCCTC ATGATCTCCC GGACCCCTGA GGTCACATGC
       GAGAAGGGGG GTTTTGGGTT CCTGTGGGAG TACTAGAGGG CCTGGGGACT CCAGTGTACG

1681   GTGGTGGTGG ACGTGAGCCA CGAAGACCCT GAGGTCAAGT TCAACTGGTA CGTGGACGGC
       CACCACCACC TGCACTCGGT GCTTCTGGGA CTCCAGTTCA AGTTGACCAT GCACCTGCCG

1741   GTGGAGGTGC ATAATGCCAA GACAAAGCCG CGGGAGGAGC AGTACAACAG CACGTACCGT
       CACCTCCACG TATTACGGTT CTGTTTCGGC GCCCTCCTCG TCATGTTGTC GTGCATGGCA

1801   GTGGTCAGCG TCCTCACCGT CCTGCACCAG GACTGGCTGA ATGGCAAGGA GTACAAGTGC
       CACCAGTCGC AGGAGTGGCA GGACGTGGTC CTGACCGACT TACCGTTCCT CATGTTCACG

1861   AAGGTCTCCA ACAAAGCCCT CCCAGCCCCC ATCGAGAAAA CCATCTCCAA AGCCAAAGGG
       TTCCAGAGGT TGTTTCGGGA GGGTCGGGGG TAGCTCTTTT GGTAGAGGTT TCGGTTTCCC

1921   CAGCCCCGAG AACCACAGGT GTACACCCTG CCCCCATCCC GGGATGAGCT GACCAAGAAC
       GTCGGGGCTC TTGGTGTCCA CATGTGGGAC GGGGGTAGGG CCCTACTCGA CTGGTTCTTG

1981   CAGGTCAGCC TGACCTGCCT GGTCAAAGGC TTCTATCCCA GCGACATCGC CGTGGAGTGG
       GTCCAGTCGG ACTGGACGGA CCAGTTTCCG AAGATAGGGT CGCTGTAGCG GCACCTCACC

2041   GAGAGCAATG GGCAGCCGGA GAACAACTAC AAGACCACGC CTCCCGTGTT GGACTCCGAC
       CTCTCGTTAC CCGTCGGCCT CTTGTTGATG TTCTGGTGCG GAGGGCACAA CCTGAGGCTG

2101   GGCTCCTTCT TCCTCTACAG CAAGCTCACC GTCGACAAGA GCAGGTGGCA GCAGGGGAAC
       CCGAGGAAGA AGGAGATGTC GTTCGAGTGG CAGCTGTTCT CGTCCACCGT CGTCCCCTTG

2161   GTCTTCTCAT GCTCCGTGAT GCATGAGGCT CTGCACAACC ACTACACGCA GAAGAGCCTC
       CAGAAGAGTA CGAGGCACTA CGTACTCCGA GACGTGTTGG TGATGTGCGT CTTCTCGGAG

2221   TCCCTGTCTC CGGGTAAACG CGCCGCCGG AGCGGTGGCG GCGGATCAGG TGGGGGTGGA
       AGGGACAGAG GCCCATTTGC GCGGCGGCC TCGCCACCGC CGCCTAGTCC ACCCCCACCT

2281   TCAGGCGGTG GAGGTTCCGG TGGCGGGGA TCCAGGAAGA GGAGGAAGAG GGACAAAACT
       AGTCCGCCAC CTCCAAGGCC ACCGCCCCCT AGGTCCTTCT CCTCCTTCTC CCTGTTTTGA

2341   CACACATGCC CACCGTGCCC AGCACCGGAA CTCCTGGGCG GACCGTCAGT CTTCCTCTTC
       GTGTGTACGG GTGGCACGGG TCGTGGCCTT GAGGACCCGC CTGGCAGTCA GAAGGAGAAG
```

TABLE 4-continued

DNA sequence of FX-011 (SEQ ID NO: 67)

```
2401  CCCCCAAAAC CCAAGGACAC CCTCATGATC TCCCGGACCC CTGAGGTCAC ATGCGTGGTG
      GGGGGTTTTG GGTTCCTGTG GGAGTACTAG AGGGCCTGGG GACTCCAGTG TACGCACCAC

2461  GTGGACGTGA GCCACGAAGA CCCTGAGGTC AAGTTCAACT GGTACGTGGA CGGCGTGGAG
      CACCTGCACT CGGTGCTTCT GGGACTCCAG TTCAAGTTGA CCATGCACCT GCCGCACCTC

2521  GTGCATAATG CCAAGACAAA GCCGCGGGAG GAGCAGTACA ACAGCACGTA CCGTGTGGTC
      CACGTATTAC GGTTCTGTTT CGGCGCCCTC CTCGTCATGT TGTCGTGCAT GGCACACCAG

2581  AGCGTCCTCA CCGTCCTGCA CCAGGACTGG CTGAATGGCA AGGAGTACAA GTGCAAGGTC
      TCGCAGGAGT GGCAGGACGT GGTCCTGACC GACTTACCGT TCCTCATGTT CACGTTCCAG

2641  TCCAACAAAG CCCTCCCAGC CCCCATCGAG AAACCATCT CCAAAGCCAA AGGGCAGCCC
      AGGTTGTTTC GGGAGGGTCG GGGGTAGCTC TTTTGGTAGA GGTTTCGGTT TCCCGTCGGG

2701  CGAGAACCAC AGGTGTACAC CCTGCCCCCA TCCCGGGATG AGCTGACCAA GAACCAGGTC
      GCTCTTGGTG TCCACATGTG GGACGGGGGT AGGGCCCTAC TCGACTGGTT CTTGGTCCAG

2761  AGCCTGACCT GCCTGGTCAA AGGCTTCTAT CCCAGCGACA TCGCCGTGGA GTGGGAGAGC
      TCGGACTGGA CGGACCAGTT TCCGAAGATA GGGTCGCTGT AGCGGCACCT CACCCTCTCG

2821  AATGGGCAGC CGGAGAACAA CTACAAGACC ACGCCTCCCG TGTTGGACTC CGACGGCTCC
      TTACCCGTCG GCCTCTTGTT GATGTTCTGG TGCGGAGGGC ACAACCTGAG GCTGCCGAGG

2881  TTCTTCCTCT ACAGCAAGCT CACCGTGGAC AAGAGCAGGT GGCAGCAGGG GAACGTCTTC
      AAGAAGGAGA TGTCGTTCGA GTGGCACCTG TTCTCGTCCA CCGTCGTCCC CTTGCAGAAG

2941  TCATGCTCCG TGATGCATGA GGCTCTGCAC AACCACTACA CGCAGAAGAG CCTCTCCCTG
      AGTACGAGGC ACTACGTACT CCGAGACGTG TTGGTGATGT GCGTCTTCTC GGAGAGGGAC

3001  TCTCCGGGTA AATGAGCGGC CGC
      AGAGGCCCAT TTACTCGCCG GCG
```

TABLE 5

FX-011 amino acid sequence. Signal sequence is shown in dotted underline, propeptide is double underlined, linker region connecting FX activation peptide to FX heavy chain is underlined, and linker with proprotein convertase processing sites connecting the two Fc fragments is shown in bold (SEQ ID NO: 68)

```
  1  MGRPLHLVLL SASLAGLLLL GESLFIRREQ ANNILARVRR ANSFLEEMKK GHLERECMEE

61  TCSYEEAREV FEDSDKTNEF WNKYKDGDQC ETSPCQNQGK CKDGLGEYTC TCLEGFEGKN

121  CELFTRKLCS LDNGDCDQFC HEEQNSVVCS CARGYTLADN GKACIPTGPY PCGKQTLERR

181  KRSVAQATSS SGEAPDSITW KPYDAADLDP TENPFDLLDF NQTQPERGDN NGGGGSGGGG

241  SGGGGSGGGG SRKRRKRCKD GECPWQALLI NEENEGFCGG TILSEFYILT AAHCLYQAKR

301  FKVRVGDRNT EQEEGGEAVH EVEVVIKHNR FTKETYDFDI AVLRLKTPIT FRMNVAPACL

361  PERDWAESTL MTQKTGIVSG FGRTHEKGRQ STRLKMLEVP YVDRNSCKLS SSFIITQNMF

421  CAGYDTKQED ACQGDSGGPH VTRFKDTYFV TGIVSWGEGC ARKGKYGIYT KVTAFLKWID

481  RSMKTRGLPK AKSHAPEVIT SSPLKEDQVD PRLIDGKDKT HTCPPCPAPE LLGGPSVFLF

541  PPKPKDTLMI SRTPEVTCVV VDVSHEDPEV KFNWYVDGVE VHNAKTKPRE EQYNSTYRVV

601  SVLTVLHQDW LNGKEYKCKV SNKALPAPIE KTISKAKGQP REPQVYTLPP SRDELTKNQV

661  SLTCLVKGFY PSDIAVEWES NGQPENNYKT TPPVLDSDGS FFLYSKLTVD KSRWQQGNVF

721  SCSVMHEALH NHYTQKSLSL SPGKRRRRSG GGGSGGGGSG GGGSGGGGSR KRRKRDKTHT

781  CPPCPAPELL GGPSVFLFPP KPKDTLMISR TPEVTCVVVD VSHEDPEVKF NWYVDGVEVH

841  NAKTKPREEQ YNSTYRVVSV LTVLHQDWLN GKEYKCKVSN KALPAPIEKT ISKAKGQPRE
```

TABLE 5-continued

FX-011 amino acid sequence. Signal sequence is shown in dotted underline, propeptide is double underlined, linker region connecting FX activation peptide to FX heavy chain is underlined, and linker with proprotein convertase processing sites connecting the two Fc fragments is shown in bold (SEQ ID NO: 68)

```
901  PQVYTLPPSR DELTKNQVSL TCLVKGFYPS DIAVEWESNG QPENNYKTTP PVLDSDGSFF

961  LYSKLTVDKS RWQQGNVFSC SVMHEALHNH YTQKSLSLSP GK*
```

TABLE 6

| DNA sequence of FX-012 (SEQ ID NO: 69) |
|---|

```
   1  AAGCTTATGG GTCGTCCACT GCACCTCGTC CTGCTCAGTG CCTCCCTGGC TGGCCTCCTG
      TTCGAATACC CAGCAGGTGA CGTGGAGCAG GACGAGTCAC GGAGGGACCG ACCGGAGGAC

61  CTGCTCGGGG AAAGTCTGTT CATCCGCAGG GAGCAGGCCA CAACATCCT GGCGAGGGTC
      GACGAGCCCC TTTCAGACAA GTAGGCGTCC CTCGTCCGGT TGTTGTAGGA CCGCTCCCAG

121  AGGAGGGCCA ATTCCTTTCT TGAAGAGATG AAGAAAGGAC ACCTCGAAAG AGAGTGCATG
      TCCTCCCGGT TAAGGAAAGA ACTTCTCTAC TTCTTTCCTG TGGAGCTTTC TCTCACGTAC

181  GAAGAGACCT GCTCATACGA AGAGGCCCGC GAGGTCTTTG AGGACAGCGA CAAGACGAAT
      CTTCTCTGGA CGAGTATGCT TCTCCGGGCG CTCCAGAAAC TCCTGTCGCT GTTCTGCTTA

241  GAATTCTGGA ATAAATACAA AGATGGCGAC CAGTGTGAGA CCAGTCCTTG CCAGAACCAG
      CTTAAGACCT TATTTATGTT TCTACCGCTG GTCACACTCT GGTCAGGAAC GGTCTTGGTC

301  GGCAAATGTA AAGACGGCCT CGGGGAATAC ACCTGCACCT GTTTAGAAGG ATTCGAAGGC
      CCGTTTACAT TTCTGCCGGA GCCCCTTATG TGGACGTGGA CAAATCTTCC TAAGCTTCCG

361  AAAAACTGTG AATTATTCAC ACGGAAGCTC TGCAGCCTGG ACAACGGGGA CTGTGACCAG
      TTTTTGACAC TTAATAAGTG TGCCTTCGAG ACGTCGGACC TGTTGCCCCT GACACTGGTC

421  TTCTGCCACG AGGAACAGAA CTCTGTGGTG TGCTCCTGCG CCCGCGGGTA CACCCTGGCT
      AAGACGGTGC TCCTTGTCTT GAGACACCAC ACGAGGACGC GGGCGCCCAT GTGGGACCGA

481  GACAACGGCA AGGCCTGCAT TCCCACAGGG CCCTACCCCT GTGGGAAACA GACCCTGGAA
      CTGTTGCCGT TCCGGACGTA AGGGTGTCCC GGGATGGGGA CACCCTTTGT CTGGGACCTT

541  CGCAGGAAGA GGGGTGGGGG TGGATCAGGC GGTGGAGGTT CCGGTGGCGG GGGATCCTCC
      GCGTCCTTCT CCCCACCCCC ACCTAGTCCG CCACCTCCAA GGCCACCGCC CCCTAGGAGG

601  CTGCAGGACT CAGAAGTCAA TCAAGAAGCT AAGCCAGAGG TCAAGCCAGA AGTCAAGCCT
      GACGTCCTGA GTCTTCAGTT AGTTCTTCGA TTCGGTCTCC AGTTCGGTCT TCAGTTCGGA

661  GAGACTCACA TCAATTTAAA GGTGTCCGAT GGATCTTCAG AGATCTTCTT CAAGATCAAA
      CTCTGAGTGT AGTTAAATTT CCACAGGCTA CCTAGAAGTC TCTAGAAGAA GTTCTAGTTT

721  AAGACCACTC CTTTAAGAAG GCTGATGGAA GCGTTCGCTA AAAGACAGGG TAAGGAAATG
      TTCTGGTGAG GAAATTCTTC CGACTACCTT CGCAAGCGAT TTTCTGTCCC ATTCCTTTAC

781  GACTCCTTAA GATTCTTGTA CGACGGTATT AGAATTCAAG CTGATCAGGC CCCTGAAGAT
      CTGAGGAATT CTAAGAACAT GCTGCCATAA TCTTAAGTTC GACTAGTCCG GGGACTTCTA

841  TTGGACATGG AGGATAACGA TATTATTGAG GCTCACCGCG AACAGATTGG AGGTTGCAAG
      AACCTGTACC TCCTATTGCT ATAATAACTC CGAGTGGCGC TTGTCTAACC TCCAACGTTC

901  GACGGGAGT GTCCCTGGCA GGCCCTGCTC ATCAATGAGG AAAACGAGGG TTTTTGTGGA
      CTGCCCCTCA CAGGGACCGT CCGGGACGAG TAGTTACTCC TTTTGCTCCC AAAAACACCT

961  GGTACCATTC TGAGCGAGTT CTACATCCTA ACGGCAGCCC ACTGTCTCTA CCAAGCCAAG
      CCATGGTAAG ACTCGCTCAA GATGTAGGAT TGCCGTCGGG TGACAGAGAT GGTTCGGTTC

1021  AGATTCAAGG TGAGGGTAGG GGACCGGAAC ACGGAGCAGG AGGAGGGCGG TGAGGCGGTG
      TCTAAGTTCC ACTCCCATCC CCTGGCCTTG TGCCTCGTCC TCCTCCCGCC ACTCCGCCAC

1081  CACGAGGTGG AAGTGGTCAT CAAGCACAAC CGGTTCACAA AGGAGACCTA TGACTTCGAC
      GTGCTCCACC TTCACCAGTA GTTCGTGTTG GCCAAGTGTT TCCTCTGGAT ACTGAAGCTG

1141  ATCGCCGTGC TCCGGCTCAA GACCCCCATC ACCTTCCGCA TGAACGTGGC GCCTGCCTGC
      TAGCGGCACG AGGCCGAGTT CTGGGGGTAG TGGAAGGCGT ACTTGCACCG CGGACGGACG

1201  CTCCCCGAGC GTGACTGGGC CGAGTCCACG CTGATGACGC AGAAGACGGG GATTGTGAGC
      GAGGGGCTCG CACTGACCCG GCTCAGGTGC GACTACTGCG TCTTCTGCCC CTAACACTCG
```

TABLE 6-continued

DNA sequence of FX-012 (SEQ ID NO: 69)

```
1261  GGCTTCGGGC GCACCCACGA GAAGGGCCGG CAGTCCACCA GGCTCAAGAT GCTGGAGGTG
      CCGAAGCCCG CGTGGGTGCT CTTCCCGGCC GTCAGGTGGT CCGAGTTCTA CGACCTCCAC

1321  CCCTACGTGG ACCGCAACAG CTGCAAGCTG TCCAGCAGCT TCATCATCAC CCAGAACATG
      GGGATGCACC TGGCGTTGTC GACGTTCGAC AGGTCGTCGA AGTAGTAGTG GGTCTTGTAC

1381  TTCTGTGCCG GCTACGACAC CAAGCAGGAG GATGCCTGCC AGGGGGACAG CGGGGGCCCG
      AAGACACGGC CGATGCTGTG GTTCGTCCTC CTACGGACGG TCCCCCTGTC GCCCCCGGGC

1441  CACGTCACCC GCTTCAAGGA CACCTACTTC GTGACAGGCA TCGTCAGCTG GGGAGAGGGC
      GTGCAGTGGG CGAAGTTCCT GTGGATGAAG CACTGTCCGT AGCAGTCGAC CCCTCTCCCG

1501  TGTGCCCGTA AGGGGAAGTA CGGGATCTAC ACCAAGGTCA CCGCCTTCCT CAAGTGGATC
      ACACGGGCAT TCCCCTTCAT GCCCTAGATG TGGTTCCAGT GGCGGAAGGA GTTCACCTAG

1561  GACAGGTCCA TGAAAACCAG GGGCTTGCCC AAGGCCAAGA GCCATGCCCC GGAGGTCATA
      CTGTCCAGGT ACTTTTGGTC CCCGAACGGG TTCCGGTTCT CGGTACGGGG CCTCCAGTAT

1621  ACGTCCTCTC CATTAAAAGA AGACCAAGTA GATCCGCGGC TCATTGATGG TAAGGACAAA
      TGCAGGAGAG GTAATTTTCT TCTGGTTCAT CTAGGCGCCG AGTAACTACC ATTCCTGTTT

1681  ACTCACACAT GCCCACCGTG CCCAGCTCCG GAACTCCTGG GAGGACCGTC AGTCTTCCTC
      TGAGTGTGTA CGGGTGGCAC GGGTCGAGGC CTTGAGGACC CTCCTGGCAG TCAGAAGGAG

1741  TTCCCCCCAA AACCCAAGGA CACCCTCATG ATCTCCCGGA CCCCTGAGGT CACATGCGTG
      AAGGGGGGTT TTGGGTTCCT GTGGGAGTAC TAGAGGGCCT GGGGACTCCA GTGTACGCAC

1801  GTGGTGGACG TGAGCCACGA AGACCCTGAG GTCAAGTTCA ACTGGTACGT GGACGGCGTG
      CACCACCTGC ACTCGGTGCT TCTGGGACTC CAGTTCAAGT TGACCATGCA CCTGCCGCAC

1861  GAGGTGCATA ATGCCAAGAC AAAGCCGCGG GAGGAGCAGT ACAACAGCAC GTACCGTGTG
      CTCCACGTAT TACGGTTCTG TTTCGGCGCC CTCCTCGTCA TGTTGTCGTG CATGGCACAC

1921  GTCAGCGTCC TCACCGTCCT GCACCAGGAC TGGCTGAATG GCAAGGAGTA CAAGTGCAAG
      CAGTCGCAGG AGTGGCAGGA CGTGGTCCTG ACCGACTTAC CGTTCCTCAT GTTCACGTTC

1981  GTCTCCAACA AAGCCCTCCC AGCCCCCATC GAGAAAACCA TCTCCAAAGC CAAAGGGCAG
      CAGAGGTTGT TTCGGGAGGG TCGGGGGTAG CTCTTTTGGT AGAGGTTTCG GTTTCCCGTC

2041  CCCCGAGAAC CACAGGTGTA CACCCTGCCC CCATCCCGGG ATGAGCTGAC CAAGAACCAG
      GGGGCTCTTG GTGTCCACAT GTGGGACGGG GGTAGGGCCC TACTCGACTG GTTCTTGGTC

2101  GTCAGCCTGA CCTGCCTGGT CAAAGGCTTC TATCCCAGCG ACATCGCCGT GGAGTGGGAG
      CAGTCGGACT GGACGGACCA GTTTCCGAAG ATAGGGTCGC TGTAGCGGCA CCTCACCCTC

2161  AGCAATGGGC AGCCGGAGAA CAACTACAAG ACCACGCCTC CCGTGTTGGA CTCCGACGGC
      TCGTTACCCG TCGGCCTCTT GTTGATGTTC TGGTGCGGAG GGCACAACCT GAGGCTGCCG

2221  TCCTTCTTCC TCTACAGCAA GCTCACCGTC GACAAGAGCA GGTGGCAGCA GGGGAACGTC
      AGGAAGAAGG AGATGTCGTT CGAGTGGCAG CTGTTCTCGT CCACCGTCGT CCCCTTGCAG

2281  TTCTCATGCT CCGTGATGCA TGAGGCTCTG CACAACCACT ACACGCAGAA GAGCCTCTCC
      AAGAGTACGA GGCACTACGT ACTCCGAGAC GTGTTGGTGA TGTGCGTCTT CTCGGAGAGG

2341  CTGTCTCCGG GTAAACGGCG CCGCCGGAGC GGTGGCGGCG GATCAGGTGG GGGTGGATCA
      GACAGAGGCC CATTTGCCGC GGCGGCCTCG CCACCGCCGC CTAGTCCACC CCCACCTAGT

2401  GGCGGTGGAG GTTCCGGTGG CGGGGGATCC AGGAAGAGGA GGAAGAGGGA CAAAACTCAC
      CCGCCACCTC CAAGGCCACC GCCCCCTAGG TCCTTCTCCT CCTTCTCCCT GTTTTGAGTG

2461  ACATGCCCAC CGTGCCCAGC ACCGGAACTC CTGGGCGGAC CGTCAGTCTT CCTCTTCCCC
      TGTACGGGTG GCACGGGTCG TGGCCTTGAG GACCCGCCTG GCAGTCAGAA GGAGAAGGGG

2521  CCAAAACCCA AGGACACCCT CATGATCTCC CGGACCCCTG AGGTCACATG CGTGGTGGTG
      GGTTTTGGGT TCCTGTGGGA GTACTAGAGG GCCTGGGGAC TCCAGTGTAC GCACCACCAC

2581  GACGTGAGCC ACGAAGACCC TGAGGTCAAG TTCAACTGGT ACGTGGACGG CGTGGAGGTG
      CTGCACTCGG TGCTTCTGGG ACTCCAGTTC AAGTTGACCA TGCACCTGCC GCACCTCCAC

2641  CATAATGCCA AGACAAAGCC GCGGGAGGAG CAGTACAACA GCACGTACCG TGTGGTCAGC
      GTATTACGGT TCTGTTTCGG CGCCCTCCTC GTCATGTTGT CGTGCATGGC ACACCAGTCG

2701  GTCCTCACCG TCCTGCACCA GGACTGGCTG AATGGCAAGG AGTACAAGTG CAAGGTCTCC
      CAGGAGTGGC AGGACGTGGT CCTGACCGAC TTACCGTTCC TCATGTTCAC GTTCCAGAGG

2761  AACAAAGCCC TCCCAGCCCC CATCGAGAAA ACCATCTCCA AAGCCAAAGG GCAGCCCCGA
      TTGTTTCGGG AGGGTCGGGG GTAGCTCTTT TGGTAGAGGT TTCGGTTTCC CGTCGGGGCT
```

TABLE 6-continued

DNA sequence of FX-012 (SEQ ID NO: 69)

```
2821  GAACCACAGG TGTACACCCT GCCCCCATCC CGGGATGAGC TGACCAAGAA CCAGGTCAGC
      CTTGGTGTCC ACATGTGGGA CGGGGGTAGG GCCCTACTCG ACTGGTTCTT GGTCCAGTCG

2881  CTGACCTGCC TGGTCAAAGG CTTCTATCCC AGCGACATCC CCGTGGAGTG GGAGAGCAAT
      GACTGGACGG ACCAGTTTCC GAAGATAGGG TCGCTGTAGC GGCACCTCAC CCTCTCGTTA

2941  GGGCAGCCGG AGAACAACTA CAAGACCACG CCTCCCGTGT TGGACTCCGA CGGCTCCTTC
      CCCGTCGGCC TCTTGTTGAT GTTCTGGTGC GGAGGGCACA ACCTGAGGCT GCCGAGGAAG

3001  TTCCTCTACA GCAAGCTCAC CGTGGACAAG AGCAGGTGGC AGCAGGGGAA CGTCTTCTCA
      AAGGAGATGT CGTTCGAGTG GCACCTGTTC TCGTCCACCG TCGTCCCCTT GCAGAAGAGT

3061  TGCTCCGTGA TGCATGAGGC TCTGCACAAC CACTACACGC AGAAGAGCCT CTCCCTGTCT
      ACGAGGCACT ACGTACTCCG AGACGTGTTG GTGATGTGCG TCTTCTCGGA GAGGGACAGA

3121  CCGGGTAAAT GAGCGGCCGC
      GGCCCATTTA CTCGCCGGCG
```

TABLE 7

FX-012 amino acid sequence. Signal sequence is shown in dotted underline, propeptide is double underlined, linker region connecting FX light chain to SUMO is underlined, SUMO sequence is in dashed underline, and linker with proprotein convertase processing sites connecting the two Fc fragments is shown in bold (SEQ ID NO: 70)

```
   1 MGRPLHLVLL SASLAGLLLL GESLFIRREQ ANNILARVRR ANSFLEEMKK GHLERECMEE

61 TCSYEEAREV FEDSDKTNEF WNKYKDGDQC ETSPCQNQGK CKDGLGEYTC TCLEGFEGKN

121 CELFTRKLCS LDNGDCDQFC HEEQNSVVCS CARGYTLADN GKACIPTGPY PCGKQTLERR

181 KRGGGGSGGG GSGGGGSSLQ DSEVNQEAKP EVKPEVKPET HINLKVSDGS SEIFFKIKKT

241 TPLRRLMEAF AKRQGKEMDS LRFLYDGIRI QADQAPEDLD MEDNDIIEAH REQIGGCKDG

301 ECPWQALLIN EENEGFCGGT ILSEFYILTA AHCLYQAKRF KVRVGDRNTE QEEGGEAVHE

361 VEVVIKHNRF TKETYDFDIA VLRLKTPITF RMNVAPACLP ERDWAESTLM TQKTGIVSGF

421 GRTHEKGRQS TRLKMLEVPY VDRNSCKLSS SFIITQNMFC AGYDTKQEDA CQGDSGGPHV

481 TRFKDTYFVT GIVSWGEGCA RKGKYGIYTK VTAFLKWIDR SMKTRGLPKA KSHAPEVITS

541 SPLKEDQVDP RLIDGKDKTH TCPPCPAPEL LGGPSVFLFP PKPKDTLMIS RTPEVTCVVV

601 DVSHEDPEVK FNWYVDGVEV HNAKTKPREE QYNSTYRVVS VLTVLHQDWL NGKEYKCKVS

661 NKALPAPIEK TISKAKGQPR EPQVYTLPPS RDELTKNQVS LTCLVKGFYP SDIAVEWESN

721 GQPENNYKTT PPVLDSDGSF FLYSKLTVDK SRWQQGNVFS CSVMHEALHN HYTQKSLSLS

781 PGKRRRRSGG GGSGGGGSGG GGSGGGGSRK RRKRDKTHTC PPCPAPELLG GPSVFLFPPK

841 PKDTLMISRT PEVTCVVVDV SHEDPEVKFN WYVDGVEVHN AKTKPREEQY NSTYRVVSVL

901 TVLHQDWLNG KEYKCKVSNK ALPAPIEKTI SKAKGQPREP QVYTLPPSRD ELTKNQVSLT

961 CLVKGFYPSD IAVEWESNGQ PENNYKTTPP VLDSDGSFFL YSKLTVDKSR WQQGNVFSCS

1021 VMHEALHNHY TQKSLSLSPG K*
```

SEQUENCES

\>CTP peptide 1
SEQ ID NO: 51
DPRFQDSSSSKAPPPSLPSPSRLPGPSDTPIL

\>CTP peptide 2
SEQ ID NO: 52
SSSSKAPPPSLPSPSRLPGPSDTPILPQ

\>PAS peptide 1
SEQ ID NO: 58
ASPAAPAPASPAAPAPSAPA

\>PAS peptide 2
SEQ ID NO: 59
AAPASPAPAAPSAPAPAAPS

\>PAS peptide 3
SEQ ID NO: 60
APSSPSPSAPSSPSPASPSS

\>PAS peptide 4
SEQ ID NO: 61
APSSPSPSAPSSPSPASPS

\>PAS peptide 5
SEQ ID NO: 62
SSPSAPSPSSPASPSPSSPA

\>PAS peptide 6
SEQ ID NO: 63
AASPAAPSAPPAAASPAAPSAPPA

\>PAS peptide 7
SEQ ID NO: 64
ASAAAPAAASAAASAPSAAA

\>Albumin Binding Peptide Core Sequence
SEQ ID NO: 53
DICLPRWGCLW

\>GFP protein sequence (Genbank ID AAG34521.1)
SEQ ID NO: 71
MSKGEELFTGVVPILVELDGDVNGHKFSVSGEGEGDATYGKLTLKFICTTGKLPVPWPTL

VTTFGYGVQCFARYPDHMKQHDFFKSAMPEGYVQERTIFFKDDGNYKTRAEVKFEGDTLV

NRIELKGIDFKEDGNILGHKLEYNYNSHNVYIMADKQKNGIKVNFKIRHNIEDGSVQLAD

HYQQNTPIGDGPVLLPDNHYLSTQSALSKDPNEKRDHMVLLEFVTAAGITHGMDELYKSR

TSGSPGLQEFDIKLIDTVDLESCN

\>Example: Single-chain Human IgG1 Fc. (Fc sequences with
Gly/Ser linker underlined.)
SEQ ID NO: 72
DKTHTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK<u>GGGGSGGGGSGGG</u>

<u>GSGGGGS</u>DKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGK

\>Mature human albumin protein sequence (derived from NCBI
Ref. Sequence NP_000468):
SEQ ID NO: 73
RGVFRRDAHKSEVAHRFKDLGEENFKALVLIAFAQYLQQCPFEDHVKLVNEVTEFAKTCV

ADESAENCDKSLHTLFGDKLCTVATLRETYGEMADCCAKQEPERNECFLQHKDDNPNLPR

LVRPEVDVMCTAFHDNEETFLKKYLYEIARRHPYFYAPELLFFAKRYKAAFTECCQAADK

-continued

AACLLPKLDELRDEGKASSAKQRLKCASLQKFGERAFKAWAVARLSQRFPKAEFAEVSKL

VTDLTKVHTECCHGDLLECADDRADLAKYICENQDSISSKLKECCEKPLLEKSHCIAEVE

NDEMPADLPSLAADFVESKDVCKNYAEAKDVFLGMFLYEYARRHPDYSVVLLLRLAKTYE

TTLEKCCAAADPHECYAKVFDEFKPLVEEPQNLIKQNCELFEQLGEYKFQNALLVRYTKK

VPQVSTPTLVEVSRNLGKVGSKCCKHPEAKRMPCAEDYLSVVLNQLCVLHEKTPVSDRVT

KCCTESLVNRRPCFSALEVDETYVPKEFNAETFTFHADICTLSEKERQIKKQTALVELVK

HKPKATKEQLKAVMDDFAAFVEKCCKADDKETCFAEEGKKLVAASQAALGL

>Albumin binding peptide 1
SEQ ID NO: 54
RLIEDICLPRWGCLWEDD

>Albumin binding peptide 2
SEQ ID NO: 55
QRLMEDICLPRWGCLWEDDF

>Albumin binding peptide 3
SEQ ID NO: 56
QGLIGDICLPRWGCLWGDSVK

>Albumin binding peptide 4
SEQ ID NO: 74
GEWWEDICLPRWGCLWEEED

>Cysteine-containing peptide
SEQ ID NO: 75
GGGSGCGGGS

>Human LRP1 sequence (signal peptide and transmembrane
segment underlined; NCBI Reference Sequence: CAA32112)
SEQ ID NO: 76
<u>MLTPPLLLLLPLLSALVAA</u>AIDAPKTCSPKQFACRDQITCISKGWRCDGERDCPDGSDEA

PEICPQSKAQRCQPNEHNCLGTELCVPMSRLCNGVQDCMDGSDEGPHCRELQGNCSRLGC

QHHCVPTLDGPTCYCNSSFQLQADGKTCKDFDECSVYGTCSQLCTNTDGSFICGCVEGYL

LQPDNRSCKAKNEPVDRPPVLLIANSQNILATYLSGAQVSTITPTSTRQTTAMDFSYANE

TVCWVHVGDSAAQTQLKCARMPGLKGFVDEHTINISLSLHHVEQMAIDWLTGNFYFVDDI

DDRIFVCNRNGDTCVTLLDLELYNPKGIALDPAMGKVFFTDYGQIPKVERCDMDGQNRTK

LVDSKIVFPHGITLDLVSRLVYWADAYLDYIEVVDYEGKGRQTIIQGILIEHLYGLTVFE

NYLYATNSDNANAQQKTSVIRVNRFNSTEYQVVTRVDKGGALHIYHQRRQPRVRSHACEN

DQYGKPGGCSDICLLANSHKARTCRCRSGFSLGSDGKSCKKPEHELFLVYGKGRPGIIRG

MDMGAKVPDEHMIPIENLMNPRALDFHAETGFIYFADTTSYLIGRQKIDGTERETILKDG

IHNVEGVAVDWMGDNLYWTDDGPKKTISVARLEKAAQTRKTLIEGKMTHPRAIVVDPLNG

WMYWTDWEEDPKDSRRGRLERAWMDGSHRDIFVTSKTVLWPNGLSLDIPAGRLYWVDAFY

DRIETILLNGTDRKIVYEGPELNHAFGLCHHGNYLFWTEYRSGSVYRLERGVGGAPPTVT

LLRSERPPIFEIRMYDAQQQQVGTNKCRVNNGGCSSLCLATPGSRQCACAEDQVLDADGV

TCLANPSYVPPPQCQPGEFACANSRCIQERWKCDGDNDCLDNSDEAPALCHQHTCPSDRF

KCENNRCIPNRWLCDGDNDCGNSEDESNATCSARTCPPNQFSCASGRCIPISWTCDLDDD

CGDRSDESASCAYPTCFPLTQFTCNNGRCININWRCDNDNDCGDNSDEAGCSHSCSSTQF

KCNSGRCIPEHWTCDGDNDCGDYSDETHANCTNQATRPPGGCHTDEFQCRLDGLCIPLRW

RCDGDTDCMDSSDEKSCEGVTHVCDPSVKFGCKDSARCISKAWVCDGDNDCEDNSDEENC

ESLACRPPSHPCANNTSVCLPPDKLCDGNDDCGDGSDEGELCDQCSLNNGGCSHNCSVAP

GEGIVCSCPLGMELGPDNHTCQIQSYCAKHLKCSQKCDQNKFSVKCSCYEGWVLEPDGES

CRSLDPFKPFIIFSNRHEIRRIDLHKGDYSVLVPGLRNTIALDFHLSQSALYWTDVVEDK

-continued

```
IYRGKLLDNGALTSFEVVIQYGLATPEGLAVDWIAGNIYWVESNLDQIEVAKLDGTLRTT
LLAGDIEHPRAIALDPRDGILFWTDWDASLPRIEAASMSGAGRRTVHRETGSGGWPNGLT
VDYLEKRILWIDARSDAIYSARYDGSGHMEVLRGHEFLSHPFAVTLYGGEVYWTDWRTNT
LAKANKWTGHNVTVVQRTNTQPFDLQVYHPSRQPMAPNPCEANGGQGPCSHLCLINYNRT
VSCACPHLMKLHKDNTTCYEFKKFLLYARQMEIRGVDLDAPYYNYIISFTVPDIDNVTVL
DYDAREQRVYWSDVRTQAIKRAFINGTGVETVVSADLPNAHGLAVDWVSRNLFWTSYDTN
KKQINVARLDGSFKNAVVQGLEQPHGLVVHPLRGKLYWTDGDNISMANMDGSNRTLLFSG
QKGPVGLAIDFPESKLYWISSGNHTINRCNLDGSGLEVIDAMRSQLGKATALAIMGDKLW
WADQVSEKMGTCSKADGSGSVVLRNSTTLVMHMKVYDESIQLDHKGTNPCSVNNGDCSQL
CLPTSETTRSCMCTAGYSLRSGQQACEGVGSFLLYSVHEGIRGIPLDPNDKSDALVPVSG
TSLAVGIDFHAENDTIYWVDMGLSTISRAKRDQTWREDVVTNGIGRVEGIAVDWIAGNIY
WTDQGFDVIEVARLNGSFRYVVISQGLDKPRAITVHPEKGYLFWTEWGQYPRIERSRLDG
TERVVLVNVSISWPNGISVDYQDGKLYWCDARTDKIERIDLETGENREVVLSSNNMDMFS
VSVFEDFIYWSDRTHANGSIKRGSKDNATDSVPLRTGIGVQLKDIKVFNRDRQKGTNVCA
VANGGCQQLCLYRGRGQRACACAHGMLAEDGASCREYAGYLLYSERTILKSIHISDERNL
NAPVQPFEDPEHMKNVIALAFDYRAGTSPGTPNRIFFSDIHFGNIQQINDDGSRRITIVE
NVGSVEGLAYHRGWDTLYWTSYTTSTITRHTVDQTRPGAFERETVITMSGDDHPRAFVLD
ECQNLMFWTNWNEQHPSIMRAALSGANVLTLIEKDIRTPNGLAIDHRAEKLYFSDATLDK
IERCEYDGSHRYVILKSEPVHPFGLAVYGEHIFWTDWVRRAVQRANKHVGSNMKLLRVDI
PQQPMGIIAVANDTNSCELSPCRINNGGCQDLCLLTHQGHVNCSCRGGRILQDDLTCRAV
NSSCRAQDEFECANGECINFSLTCDGVPHCKDKSDEKPSYCNSRRCKKTFRQCSNGRCVS
NMLWCNGADDCGDGSDEIPCNKTACGVGEFRCRDGTCIGNSSRCNQFVDCEDASDEMNCS
ATDCSSYFRLGVKGVLFQPCERTSLCYAPSWVCDGANDCGDYSDERDCPGVKRPRCPLNY
FACPSGRCIPMSWTCDKEDDCEHGEDETHCNKFCSEAQFECQNHRCISKQWLCDGSDDCG
DGSDEAAHCEGKTCGPSSFSCPGTHVCVPERWLCDGDKDCADGADESIAAGCLYNSTCDD
REFMCQNRQCIPKHFVCDHDRDCADGSDESPECEYPTCGPSEFRCANGRCLSSRQWECDG
ENDCHDQSDEAPKNPHCTSPEHKCNASSQFLCSSGRCVAEALLCNGQDDCGDSSDERGCH
INECLSRKLSGCSQDCEDLKIGFKCRCRPGFRLKDDGRTCADVDECSTTFPCSQRCINTH
GSYKCLCVEGYAPRGGDPHSCKAVTDEEPFLIFANRYYLRKLNLDGSNYTLLKQGLNNAV
ALDFDYREQMIYWTDVTTQGSMIRRMHLNGSNVQVLHRTGLSNPDGLAVDWVGGNLYWCD
KGRDTIEVSKLNGAYRTVLVSSGLREPRALVVDVQNGYLYWTDWGDHSLIGRIGMDGSSR
SVIVDTKITWPNGLTLDYVTERIYWADAREDYIEFASLDGSNRHVVLSQDIPHIFALTLF
EDYVYWTDWETKSINRAHKTTGTNKTLLISTLHRPMDLHVFHALRQPDVPNHPCKVNNGG
CSNLCLLSPGGGHKCACPTNFYLGSDGRTCVSNCTASQFVCKNDKCIPFWWKCDTEDDCG
DHSDEPPDCPEFKCRPGQFQCSTGICTNPAFICDGDNDCQDNSDEANCDIHVCLPSQFKC
TNTNRCIPGIFRCNGQDNCGDEDERDCPEVTCAPNQFQCSITKRCIPRVWVCDRDNDCV
DGSDEPANCTQMTCGVDEFRCKDSGRCIPARWKCDGEDDCGDGSDEPKEECDERTCEPYQ
FRCKNNRCVPGRWQCDYDNDCGDNSDEESCTPRPCSESEFSCANGRCIAGRWKCDGDHDC
ADGSDEKDCTPRCDMDQFQCKSGHCIPLRWRCDADADCMDGSDEEACGTGVRTCPLDEFQ
CNNTLCKPLAWKCDGEDDCGDNSDENPEECARFVCPPNRPFRCKNDRVCLWIGRQCDGTD
NCGDGTDEEDCEPPTAHTTHCKDKKEFLCRNQRCLSSSLRCNMFDDCGDGSDEEDCSIDP
```

-continued

KLTSCATNASICGDEARCVRTEKAAYCACRSGFHTVPGQPGCQDINECLRFGTCSQLCNN

TKGGHLCSCARNFMKTHNTCKAEGSEYQVLYIADDNEIRSLFPGHPHSAYEQAFQGDESV

RIDAMDVHVKAGRVYWTNWHTGTISYRSLPPAAPPTTSNRHRRQIDRGVTHLNISGLKMP

RGIAIDWVAGNVYWTDSGRDVIEVAQMKGENRKTLISGMIDEPHAIVVDPLRGTMYWSDW

GNHPKIETAAMDGTLRETLVQDNIQWPTGLAVDYHNERLYWADAKLSVIGSIRLNGTDPI

VAADSKRGLSHPFSIDVFEDYIYGVTYINNRVFKIHKFGHSPLVNLTGGLSHASDVVLYH

QHKQPEVTNPCDRKKCEWLCLLSPSGPVCTCPNGKRLDNGTCVPVPSPTPPPDAPRPGTC

NLQCFNGGSCFLNARRQPKCRCQPRYTGDKCELDQCWEHCRNGGTCAASPSGMPTCRCPT

GFTGPKCTQQVCAGYCANNSTCTVNQGNQPQCRCLPGFLGDRCQYRQCSGYCENFGTCQM

AADGSRQCRCTAYFEGSRCEVNKCSRCLEGACVVNKQSGDVTCNCTDGRVAPSCLTCVGH

CSNGGSCTMNSKMMPECQCPPHMTGPRCEEHVFSQQQPGHIAS<u>ILIPLLLLLLLVLAGV</u>

<u>VFWY</u>KRRVQGAKGFQHQRMTNGAMNVEIGNPTYKMYEGGEPDDVGGLLDADFALDPDKPT

NFTNPVYATLYMGGHGSRHSLASTDEKRELLGRGPEDEIGDPLA

>Biotin Acceptor Peptide (BAP)                                SEQ ID NO: 77
LNDIFEAQKIEWH >Lipoate Acceptor Peptide 2 (LAP2)                            SEQ ID NO: 78
GFEIDKVWYDLDA >HAPylation motif, n = 1 to 400                               SEQ ID NO: 82
(Gly4Ser)n >CTP                                                          SEQ ID NO: 82
DSSSSKAPPPSLPSPSRLPGPSDTPILPQ >FVII-PABC peptide                                            SEQ ID NO: 79
Biotin-Pra-GGGG-DPhe-Pip-Arg-PABC-IVGGKV-COSBn,
Pra = L-Propargylglycine >FX-PABC peptide                                              SEQ ID NO: 80
GG-DPhe-Pip-Arg-PABC-IVGGQE-COSBn >SYN470                                                       SEQ ID NO: 81
IKPEAPGEDASPEELNRYYASLRHYLNLVTRQRY-PEG4-Gly-COSBn

---

What is claimed is:

1. A method for treating a bleeding disease or disorder selected from hemophilia A or hemophilia B in a subject, comprising administering to the subject an effective amount of a procoagulant compound consisting essentially of the formula:

Pep2-Zy-Bx-Pep1-Het1 wherein,

Zy is a synthetic thrombin substrate;

Bx is a self-immolative spacer;

Pep1 is a heavy chain of FVII; and

Pep2 is a light chain of FVII; and

Het1 is a half-life extending heterologous moiety.

2. The method of claim 1, wherein the self-immolative spacer undergoes 1,4 elimination or 1,6 elimination after enzymatic cleavage of the synthetic thrombin substrate.

3. The method of claim 1, wherein the self-immolative spacer comprises p-aminobenzyl carbamate (PABC).

4. The method of claim 1, wherein the synthetic thrombin substrate comprises D-Phe-Pip-Arg.

5. The method of claim 1, wherein the half-life extending heterologous moiety is albumin or an Fc region.

6. The method of claim 1, wherein the half-life extending heterologous moiety is conjugated to Pep1 via a linker.

7. The method of 1, wherein the half-life extending heterologous moiety is an Fc region.

8. The method of claim 1, wherein the bleeding disorder is hemophilia A.

9. The method of claim 1, wherein the bleeding disorder is hemophilia B.

10. The method of claim 1, wherein the procoagulant compound consists of the formula:

Pep2-Zy-Bx-Pep1-Het1 wherein,
Zy is a synthetic thrombin substrate;
Bx is a self-immolative spacer;
Pep1 is a heavy chain of FVII;
Pep2 is a light chain of FVII; and
Het1 is a half-life extending heterologous moiety.

11. The method of claim 1, wherein the half-life extending heterologous moiety is a low complexity polypeptide, albumin, albumin binding polypeptide or fatty acid, Fc, transferrin, a PAS sequence, the C-terminal peptide (CTP) of the β subunit of human chorionic gonadotropin, polyethylene glycol (PEG), hydroxyethyl starch (HES), albumin-binding small molecules, vWF, a clearance receptor or fragment thereof which blocks binding of the procoagulant compound to a clearance receptor, or any combination thereof.

12. The method of claim 10, wherein the half-life extending heterologous moiety is a low complexity polypeptide, albumin, albumin binding polypeptide or fatty acid, Fc, transferrin, a PAS sequence, the C-terminal peptide (CTP) of the β subunit of human chorionic gonadotropin, polyethylene glycol (PEG), hydroxyethyl starch (HES), albumin-binding small molecules, vWF, a clearance receptor or fragment thereof which blocks binding of the procoagulant compound to a clearance receptor, or any combination thereof.

* * * * *

SEQUENCE LISTING

<160> NUMBER OF SEQ ID NOS: 90

<210> SEQ ID NO 1

<400> SEQUENCE: 1

000

<210> SEQ ID NO 2
<211> LENGTH: 9
<212> TYPE: PRT
<213> ORGANISM: Artificial Sequence
<220> FEATURE:
<223> OTHER INFORMATION: FXIa cleavage site

<400> SEQUENCE: 2

Thr Gln Ser Phe Asn Asp Phe Thr Arg

```
1               5

<210> SEQ ID NO 3
<211> LENGTH: 10
<212> TYPE: PRT
<213> ORGANISM: Artificial Sequence
<220> FEATURE:
<223> OTHER INFORMATION: FXIa cleavage site

<400> SEQUENCE: 3

Ser Val Ser Gln Thr Ser Lys Leu Thr Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: thrombin cleavage site

<400> SEQUENCE: 4

Asp Phe Leu Ala Glu Gly Gly Gly Val Arg
1               5                   10

<210> SEQ ID NO 5
<211> LENGTH: 7
<212> TYPE: PRT
<213> ORGANISM: Artificial Sequence
<220> FEATURE:
<223> OTHER INFORMATION: thrombin cleavage site

<400> SEQUENCE: 5

Thr Thr Lys Ile Lys Pro Arg
1               5

<210> SEQ ID NO 6
<211> LENGTH: 5
<212> TYPE: PRT
<213> ORGANISM: Artificial Sequence
<220> FEATURE:
<223> OTHER INFORMATION: thrombin cleavage site

<400> SEQUENCE: 6

Leu Val Pro Arg Gly
1               5

<210> SEQ ID NO 7
<211> LENGTH: 5
<212> TYPE: PRT
<213> ORGANISM: Artificial Sequence
<220> FEATURE:
<223> OTHER INFORMATION: thrombin cleavage site

<400> SEQUENCE: 7

Ala Leu Arg Pro Arg
1               5

<210> SEQ ID NO 8
<211> LENGTH: 12
<212> TYPE: PRT
<213> ORGANISM: Artificial Sequence
<220> FEATURE:
<223> OTHER INFORMATION: synthetic procoagulant peptide

<400> SEQUENCE: 8

Lys Leu Thr Cys Leu Ala Ser Tyr Cys Trp Leu Phe
1               5

<210> SEQ ID NO 9
<211> LENGTH: 22
<212> TYPE: PRT
<213> ORGANISM: Artificial Sequence
<220> FEATURE:
<223> OTHER INFORMATION: synthetic procoagulant peptide

<400> SEQUENCE: 9

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 10
<211> LENGTH: 22
<212> TYPE: PRT
<213> ORGANISM: Artificial Sequence
<220> FEATURE:
<223> OTHER INFORMATION: synthetic procoagulant peptide

<400> SEQUENCE: 10

Arg Arg Ala Pro Gly Lys Leu Gln Cys Leu Ala Ser Tyr Cys Trp Leu
1               5                   10                  15

Phe Trp Thr Gly Ile Ala
            20

<210> SEQ ID NO 11
<211> LENGTH: 32
<212> TYPE: PRT
<213> ORGANISM: Artificial Sequence
<220> FEATURE:
<223> OTHER INFORMATION: synthetic procoagulant peptide

<400> SEQUENCE: 11

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: synthetic procoagulant peptide

<400> SEQUENCE: 12

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: synthetic procoagulant peptide

<400> SEQUENCE: 13

Pro Arg Ile Arg Thr Val Gly Pro Gly Ser Arg Ser Ala Ser Gly Lys
1               5                   10                  15

Ser Thr Cys Leu Ala Ser Tyr Cys Trp Leu Phe Trp Thr Gly Ile Ala

```
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: synthetic procoagulant peptide

<400> SEQUENCE: 14

Ser Arg Ile Arg Thr Val Ser Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: synthetic procoagulant peptide

<400> SEQUENCE: 15

Pro Arg Ser Arg Thr Val Gly Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 16
<211> LENGTH: 10
<212> TYPE: PRT
<213> ORGANISM: Artificial Sequence
<220> FEATURE:
<223> OTHER INFORMATION: thrombin-cleavable substrate

<400> SEQUENCE: 16

Ala Leu Arg Pro Arg Val Val Gly Gly Ala
1               5                   10

<210> SEQ ID NO 17
<211> LENGTH: 5
<212> TYPE: PRT
<213> ORGANISM: Artificial Sequence
<220> FEATURE:
<223> OTHER INFORMATION: thrombin-cleavable substrate

<400> SEQUENCE: 17

Ala Leu Val Pro Arg
1               5

<210> SEQ ID NO 18
<211> LENGTH: 4
<212> TYPE: PRT
<213> ORGANISM: Artificial Sequence
<220> FEATURE:
<223> OTHER INFORMATION: thrombin-cleavable substrate

<400> SEQUENCE: 18

Leu Val Pro Arg
1

<210> SEQ ID NO 19

<400> SEQUENCE: 19

000
```

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25
<211> LENGTH: 7
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: FXIa cleavage site

<400> SEQUENCE: 25

Lys Leu Thr Arg Ala Glu Thr
1               5

<210> SEQ ID NO 26
<211> LENGTH: 7
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: FXIa cleavage site

<400> SEQUENCE: 26

Asp Phe Thr Arg Val Val Gly
1               5

<210> SEQ ID NO 27
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE

```
<222> LOCATION: (4)..(5)
<223> OTHER INFORMATION: FXIIa cleavage site

<400> SEQUENCE: 27

Thr Met Thr Arg Ile Val Gly Gly
1               5

<210> SEQ ID NO 28
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: kallikrein cleavage site

<400> SEQUENCE: 28

Ser Pro Phe Arg Ser Thr Gly Gly
1               5

<210> SEQ ID NO 29
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: FVIIa cleavage site

<400> SEQUENCE: 29

Leu Gln Val Arg Ile Val Gly Gly
1               5

<210> SEQ ID NO 30
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: FIXa cleavage site

<400> SEQUENCE: 30

Pro Leu Gly Arg Ile Val Gly Gly
1               5

<210> SEQ ID NO 31
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: FXa cleavage site

<400> SEQUENCE: 31

Ile Glu Gly Arg Thr Val Gly Gly
1               5

<210> SEQ ID NO 32
<211> LENGTH: 8
```

```
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: FIIa (thrombin) cleavage site

<400> SEQUENCE: 32

Leu Thr Pro Arg Ser Leu Leu Val
1               5

<210> SEQ ID NO 33
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: Elastase-2 cleavage site

<400> SEQUENCE: 33

Leu Gly Pro Val Ser Gly Val Pro
1               5

<210> SEQ ID NO 34
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: Granzyme-B cleavage site

<400> SEQUENCE: 34

Val Ala Gly Asp Ser Leu Glu Glu
1               5

<210> SEQ ID NO 35
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: MMP-12 cleavage site

<400> SEQUENCE: 35

Gly Pro Ala Gly Leu Gly Gly Ala
1               5

<210> SEQ ID NO 36
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: MMP-13 cleavage site

<400> SEQUENCE: 36
```

```
Gly Pro Ala Gly Leu Arg Gly Ala
1               5

<210> SEQ ID NO 37
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: MMP-17 cleavage site

<400> SEQUENCE: 37

Ala Pro Leu Gly Leu Arg Leu Arg
1               5

<210> SEQ ID NO 38
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: MMP-20 cleavage site

<400> SEQUENCE: 38

Pro Ala Leu Pro Leu Val Ala Gln
1               5

<210> SEQ ID NO 39
<211> LENGTH: 7
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (6)..(7)
<223> OTHER INFORMATION: TEV cleavage site

<400> SEQUENCE: 39

Glu Asn Leu Tyr Phe Gln Gly
1               5

<210> SEQ ID NO 40
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: Enterokinase cleavage site

<400> SEQUENCE: 40

Asp Asp Asp Lys Ile Val Gly Gly
1               5

<210> SEQ ID NO 41
<211> LENGTH: 8
<212> TYPE: PRT
<213> ORGANISM: Artificial Sequence
<220> FEATURE:
<223> OTHER INFORMATION: protease-cleavable substrate
<220> FEATURE:
```

```
<221> NAME/KEY: SITE
<222> LOCATION: (6)..(7)
<223> OTHER INFORMATION: Protease 3C (PRESCISSION) cleavage site

<400> SEQUENCE: 41

Leu Glu Val Leu Phe Gln Gly Pro
1               5

<210> SEQ ID NO 42
<211> LENGTH: 8
<212> TYPE: PRT
<213> ORGANISM: Artificial Sequence
<220> FEATURE:
<223> OTHER INFORMATION: protease-cleavable substrate
<220> FEATURE:
<221> NAME/KEY: SITE
<222> LOCATION: (4)..(5)
<223> OTHER INFORMATION: Sortase A cleavage site

<400> SEQUENCE: 42

Leu Pro Lys Thr Gly Ser Glu Ser
1               5

<210> SEQ ID NO 43
<211> LENGTH: 4
<212> TYPE: PRT
<213> ORGANISM: Artificial Sequence
<220> FEATURE:
<223> OTHER INFORMATION: peptide linker
<220> FEATURE:
<221> NAME/KEY: REPEAT
<222> LOCATION: (1)..(4)
<223> OTHER INFORMATION: Repeat from 1-100

<400> SEQUENCE: 43

Gly Gly Gly Ser
1

<210> SEQ ID NO 44
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: REPEAT
<222> LOCATION: (1)..(3)
<223> OTHER INFORMATION: Repeat 1-100
<220> FEATURE:
<221> NAME/KEY: REPEAT
<222> LOCATION: (4)..(8)
<223> OTHER INFORMATION: Repeat 1-100

<400> SEQUENCE: 44

Gly Gly Ser Gly Gly Gly Gly Ser
1               5

<210> SEQ ID NO 45
<211> LENGTH: 7
<212> TYPE: PRT
<213> ORGANISM: Artificial Sequence
<220> FEATURE:
<223> OTHER INFORMATION: peptide linker

<400> SEQUENCE: 45

Ser Gly Gly Ser Gly Gly Ser
1               5

<210> SEQ ID NO 46
```

```
<211> LENGTH: 15
<212> TYPE: PRT
<213> ORGANISM: Artificial Sequence
<220> FEATURE:
<223> OTHER INFORMATION: peptide linker

<400> SEQUENCE: 46

Gly Gly Ser Gly Gly Ser Gly Gly Ser Gly Gly Ser Gly Gly Gly
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: peptide linker

<400> SEQUENCE: 47

Gly Gly Ser Gly Gly Ser Gly Gly Gly Gly Ser Gly Gly Gly Gly Ser
1               5                   10                  15

<210> SEQ ID NO 48
<211> LENGTH: 18
<212> TYPE: PRT
<213> ORGANISM: Artificial Sequence
<220> FEATURE:
<223> OTHER INFORMATION: peptide linker

<400> SEQUENCE: 48

Gly Gly Ser Gly Gly Ser Gly Gly Ser Gly Gly Ser Gly Gly Ser Gly
1               5                   10                  15

Gly Ser

<210> SEQ ID NO 49
<211> LENGTH: 15
<212> TYPE: PRT
<213> ORGANISM: Artificial Sequence
<220> FEATURE:
<223> OTHER INFORMATION: peptide linker

<400> SEQUENCE: 49

Gly Gly Gly Gly Ser Gly Gly Gly Gly Ser Gly Gly Gly Gly Ser
1               5                   10                  15

<210> SEQ ID NO 50
<211> LENGTH: 4
<212> TYPE: PRT
<213> ORGANISM: Artificial Sequence
<220> FEATURE:
<223> OTHER INFORMATION: peptide linker
<220> FEATURE:
<221> NAME/KEY: REPEAT
<222> LOCATION: (1)..(4)
<223> OTHER INFORMATION: Repeat from 1-100

<400> SEQUENCE: 50

Gly Gly Gly Gly
1

<210> SEQ ID NO 51
<211> LENGTH: 32
<212> TYPE: PRT
<213> ORGANISM: Artificial Sequence
<220> FEATURE:
<223> OTHER INFORMATION: CTP Peptide

<400> SEQUENCE: 51
```

```
Asp Pro Arg Phe Gln Asp Ser Ser Ser Lys Ala Pro Pro Ser
1               5                  10                  15

Leu Pro Ser Pro Ser Arg Leu Pro Gly Pro Ser Asp Thr Pro Ile Leu
            20                  25                  30
```

<210> SEQ ID NO 52
<211> LENGTH: 28
<212> TYPE: PRT
<213> ORGANISM: Artificial Sequence
<220> FEATURE:
<223> OTHER INFORMATION: CTP peptide

<400> SEQUENCE: 52

```
Ser Ser Ser Ser Lys Ala Pro Pro Ser Leu Pro Ser Pro Ser Arg
1               5                  10                  15

Leu Pro Gly Pro Ser Asp Thr Pro Ile Leu Pro Gln
            20                  25
```

<210> SEQ ID NO 53
<211> LENGTH: 11
<212> TYPE: PRT
<213> ORGANISM: Artificial Sequence
<220> FEATURE:
<223> OTHER INFORMATION: albumin-binding peptides

<400> SEQUENCE: 53

```
Asp Ile Cys Leu Pro Arg Trp Gly Cys Leu Trp
1               5                  10
```

<210> SEQ ID NO 54
<211> LENGTH: 18
<212> TYPE: PRT
<213> ORGANISM: Artificial Sequence
<220> FEATURE:
<223> OTHER INFORMATION: albumin-binding peptide

<400> SEQUENCE: 54

```
Arg Leu Ile Glu Asp Ile Cys Leu Pro Arg Trp Gly Cys Leu Trp Glu
1               5                  10                  15

Asp Asp
```

<210> SEQ ID NO 55
<211> LENGTH: 20
<212> TYPE: PRT
<213> ORGANISM: Artificial Sequence
<220> FEATURE:
<223> OTHER INFORMATION: albumin-binding peptide

<400> SEQUENCE: 55

```
Gln Arg Leu Met Glu Asp Ile Cys Leu Pro Arg Trp Gly Cys Leu Trp
1               5                  10                  15

Glu Asp Asp Phe
            20
```

<210> SEQ ID NO 56
<211> LENGTH: 21
<212> TYPE: PRT
<213> ORGANISM: Artificial Sequence
<220> FEATURE:
<223> OTHER INFORMATION: albumin-binding peptide

<400> SEQUENCE: 56

```
Gln Gly Leu Ile Gly Asp Ile Cys Leu Pro Arg Trp Gly Cys Leu Trp
1               5                  10                  15
```

```
Gly Asp Ser Val Lys
            20

<210> SEQ ID NO 57
<211> LENGTH: 20
<212> TYPE: PRT
<213> ORGANISM: Artificial Sequence
<220> FEATURE:
<223> OTHER INFORMATION: albumin-binding peptide

<400> SEQUENCE: 57

Gly Glu Trp Trp Glu Asp Ile Cys Leu Pro Arg Trp Gly Cys Leu Trp
1               5                   10                  15

Glu Glu Glu Asp
            20

<210> SEQ ID NO 58
<211> LENGTH: 20
<212> TYPE: PRT
<213> ORGANISM: Artificial Sequence
<220> FEATURE:
<223> OTHER INFORMATION: PAS Sequence

<400> SEQUENCE: 58

Ala Ser Pro Ala Ala Pro Ala Pro Ala Ser Pro Ala Ala Pro Ala Pro
1               5                   10                  15

Ser Ala Pro Ala
            20

<210> SEQ ID NO 59
<211> LENGTH: 20
<212> TYPE: PRT
<213> ORGANISM: Artificial Sequence
<220> FEATURE:
<223> OTHER INFORMATION: PAS Sequence

<400> SEQUENCE: 59

Ala Ala Pro Ala Ser Pro Ala Pro Ala Ala Pro Ser Ala Pro Ala Pro
1               5                   10                  15

Ala Ala Pro Ser
            20

<210> SEQ ID NO 60
<211> LENGTH: 20
<212> TYPE: PRT
<213> ORGANISM: Artificial Sequence
<220> FEATURE:
<223> OTHER INFORMATION: PAS sequence

<400> SEQUENCE: 60

Ala Pro Ser Ser Pro Ser Pro Ser Ala Pro Ser Ser Pro Ser Pro Ala
1               5                   10                  15

Ser Pro Ser Ser
            20

<210> SEQ ID NO 61
<211> LENGTH: 19
<212> TYPE: PRT
<213> ORGANISM: Artificial Sequence
<220> FEATURE:
<223> OTHER INFORMATION: PAS sequence

<400> SEQUENCE: 61

Ala Pro Ser Ser Pro Ser Pro Ser Ala Pro Ser Ser Pro Ser Pro Ala
1               5                   10                  15
```

-continued

Ser Pro Ser

<210> SEQ ID NO 62
<211> LENGTH: 20
<212> TYPE: PRT
<213> ORGANISM: Artificial Sequence
<220> FEATURE:
<223> OTHER INFORMATION: PAS sequence

<400> SEQUENCE: 62

Ser Ser Pro Ser Ala Pro Ser Pro Ser Ser Pro Ala Ser Pro Ser Pro
1               5                   10                  15

Ser Ser Pro Ala
            20

<210> SEQ ID NO 63
<211> LENGTH: 24
<212> TYPE: PRT
<213> ORGANISM: Artificial Sequence
<220> FEATURE:
<223> OTHER INFORMATION: PAS Sequence

<400> SEQUENCE: 63

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 64
<211> LENGTH: 20
<212> TYPE: PRT
<213> ORGANISM: Artificial Sequence
<220> FEATURE:
<223> OTHER INFORMATION: PAS Sequence

<400> SEQUENCE: 64

Ala Ser Ala Ala Ala Pro Ala Ala Ser Ala Ala Ala Ser Ala Pro
1               5                   10                  15

Ser Ala Ala Ala
            20

<210> SEQ ID NO 65
<211> LENGTH: 6408
<212> TYPE: DNA
<213> ORGANISM: Artificial Sequence
<220> FEATURE:
<223> OTHER INFORMATION: FVII-186

<400> SEQUENCE: 65
aagcttgccg ccaccatggt ctcccaggcc ctcaggctcc tctgccttct gcttgggctt    60
ttcgaacggc ggtggtacca gagggtccgg gagtccgagg agacggaaga cgaacccgaa   120
cagggctgcc tggctgcagt cttcgtaacc caggaggaag cccacggcgt cctgcaccgg   180
gtcccgacgg accgacgtca gaagcattgg gtcctccttc gggtgccgca ggacgtggcc   240
cgccggcgcg ccaacgcgtt cctggaggag ctgcggccgg gctccctgga gagggagtgc   300
gcggccgcgc ggttgcgcaa ggacctcctc gacgccggcc cgagggacct ctccctcacg   360
aaggaggagc agtgctccct tcgaggaggcc cgggagatct tcaaggacgc ggagaggacg   420
ttcctcctcg tcacgaggaa gctcctccgg gccctctaga agttcctgcg cctctcctgc   480
aagctgttct ggatttctta cagtgatggg gaccagtgtg cctcaagtcc atgccagaat   540

```
ttcgacaaga cctaaagaat gtcactaccc ctggtcacac ggagttcagg tacggtctta    600
gggggctcct gcaaggacca gctccagtcc tatatctgct tctgcctccc tgccttcgag    660
cccccgagga cgttcctggt cgaggtcagg atatagacga agacggaggg acggaagctc    720
ggccggaact gtgagacgca caaggatgac cagctgatct gtgtgaacga gaacggcggc    780
ccggccttga cactctgcgt gttcctactg gtcgactaga cacacttgct cttgccgccg    840
tgtgagcagt actgcagtga ccacacgggc accaagcgct cctgtcggtg ccacgagggg    900
acactcgtca tgacgtcact ggtgtgcccg tggttcgcga ggacagccac ggtgctcccc    960
tactctctgc tggcagacgg ggtgtcctgc acacccacag ttgaatatcc atgtggaaaa   1020
atgagagacg accgtctgcc ccacaggacg tgtgggtgtc aacttatagg tacaccttt    1080 atacctattc tagaaaaaag aaatgccagc aaacccaag gccgaaagag gaggaagagg    1140
tatggataag atcttttttc tttacggtcg tttggggttc cggctttctc ctccttctcc   1200
ggtggcggcg gatcaggtgg gggtggatca ggcggtggag gttccctgca ggactcagaa   1260
ccaccgccgc ctagtccacc cccacctagt ccgccacctc caaggacgt cctgagtctt   1320 gtcaatcaag aagctaagcc agaggtcaag ccagaagtca agcctgagac tcacatcaat   1380
cagttagttc ttcgattcgg tctccagttc ggtcttcagt tcggactctg agtgtagtta   1440
ttaaaggtgt ccgatggatc ttcagagatc ttcttcaaga tcaaaaagac cactccttta   1500
aatttccaca ggctacctag aagtctctag aagaagttct agttttttctg gtgaggaaat   1560 agaaggctga tggaagcgtt cgctaaaaga cagggtaagg aaatggactc cttaagattc   1620
tcttccgact accttcgcaa gcgatttttct gtcccattcc tttacctgag gaattctaag   1680
ttgtacgacg gtattagaat tcaagctgat caggcccctg aagatttgga catggaggat   1740
aacatgctgc cataatctta agttcgacta gtccggggac ttctaaacct gtacctccta   1800
aacgatatta ttgaggctca ccgcgaacag attggaggtt gccccaaagg ggagtgtcca   1860
ttgctataat aactccgagt ggcgcttgtc taacctccaa cggggtttcc cctcacaggt   1920
tggcaggtcc tgttgttggt gaatggagct cagttgtgtg ggggaccct gatcaacacc   1980 accgtccagg acaacaacca cttacctcga gtcaacacac ccccctggga ctagttgtgg   2040
atctgggtgg tctccgcggc ccactgtttc gacaaaatca agaactggag gaacctgatc   2100
tagacccacc agaggcgccg ggtgacaaag ctgttttagt tcttgacctc cttggactag   2160
gcggtgctgg gcgagcacga cctcagcgag cacgacgggg atgagcagag ccggcgggtg   2220
cgccacgacc cgctcgtgct ggagtcgctc gtgctgcccc tactcgtctc ggccgcccac   2280
gcgcaggtca tcatccccag cacgtacgtc ccgggcacca ccaaccacga catcgcgctg   2340
cgcgtccagt agtagggtc gtgcatgcag ggcccgtggt ggttggtgct gtagcgcgac   2400
ctccgcctgc accagcccgt ggtcctcact gaccatgtgg tgcccctctg cctgcccgaa   2460
gaggcggacg tggtcgggca ccaggagtga ctggtacacc acggggagac ggacgggctt   2520
cggacgttct ctgagaggac gctggccttc gtgcgcttct cattggtcag cggctggggc   2580
gcctgcaaga gactctcctg cgaccggaag cacgcgaaga gtaaccagtc gccgaccccg   2640
cagctgctgg accgtggcgc cacggccctg gagctcatgg tcctcaacgt gccccggctg   2700
gtcgacgacc tggcaccgcg gtgccgggac ctcgagtacc aggagttgca cggggccgac   2760
atgacccagg actgcctgca gcagtcacgg aaggtgggag actccccaaa tatcacggag   2820
tactgggtcc tgacgacgt cgtcagtgcc ttccaccctc tgaggggttt atagtgcctc   2880
tacatgttct gtgccggcta ctcggatggc agcaaggact cctgcaaggg ggacagtgga   2940
```

```
atgtacaaga cacggccgat gagcctaccg tcgttcctga ggacgttccc cctgtcacct   3000
ggcccacatg ccacccacta ccggggcacg tggtacctga cgggcatcgt cagctggggc   3060
ccgggtgtac ggtgggtgat ggccccgtgc accatggact gcccgtagca gtcgaccccg   3120
cagggctgcg caaccgtggg ccactttggg gtgtacacca gggtctccca gtacatcgag   3180
gtcccgacgc gttggcaccc ggtgaaaccc cacatgtggt cccagagggt catgtagctc   3240
tggctgcaaa agctcatgcg ctcagagcca cgcccaggag tcctcctgcg agccccattt   3300
accgacgttt tcgagtacgc gagtctcggt gcgggtcctc aggaggacgc tcggggtaaa   3360
cccgtggcg gtggctccgg cggaggtggg tccggtggcg gcggatcagg tggggggtgga   3420
gggccaccgc caccgaggcc gcctccaccc aggccaccgc cgcctagtcc accccacct   3480
tcaggcggtg gaggttccgg tggcggggga tccgacaaaa ctcacacatg cccaccgtgc   3540
agtccgccac ctccaaggcc accgcccct aggctgtttt gagtgtgtac gggtggcacg   3600
ccagctccgg aactcctggg cggaccgtca gtcttcctct tcccccaaa acccaaggac   3660
ggtcgaggcc ttgaggaccc gcctggcagt cagaaggaga aggggggttt tgggttcctg   3720
accctcatga tctcccggac ccctgaggtc acatgcgtgg tggtggacgt gagccacgaa   3780
tgggagtact agagggcctg gggactccag tgtacgcacc accacctgca ctcggtgctt   3840
gacccctgagg tcaagttcaa ctggtacgtg gacggcgtgg aggtgcataa tgccaagaca   3900
ctgggactcc agttcaagtt gaccatgcac ctgccgcacc tccacgtatt acggttctgt   3960
aagccgcggg aggagcagta caacagcacg taccgtgtgg tcagcgtcct caccgtcctg   4020
ttcggcgccc tcctcgtcat gttgtcgtgc atggcacacc agtcgcagga gtggcaggac   4080
caccaggact ggctgaatgg caaggagtac aagtgcaagg tctccaacaa agccctccca   4140
gtggtcctga ccgacttacc gttcctcatg ttcacgttcc agaggttgtt tcgggagggt   4200
gccccatcg agaaaaccat ctccaaagcc aagggcagc ccgagaacc acaggtgtac   4260
cgggggtagc tcttttggta gaggtttcgg tttccgtcg gggctcttgg tgtccacatg   4320
accctgcccc catcccggga tgagctgacc aagaaccagg tcagcctgac ctgcctggtc   4380
tgggacgggg gtagggccct actcgactgg ttcttggtcc agtcggactg gacggaccag   4440
aaaggcttct atcccagcga catcgccgtg gagtgggaga gcaatgggca gccggagaac   4500
tttccgaaga tagggtcgct gtagcggcac ctcaccctct cgttaccgt cggcctcttg   4560
aactacaaga ccacgcctcc cgtgttggac tccgacggct ccttcttcct ctacagcaag   4620
ttgatgttct ggtgcggagg gcacaacctg aggctgccga ggaagaagga gatgtcgttc   4680
ctcaccgtgg acaagagcag gtggcagcag gggaacgtct tctcatgctc cgtgatgcat   4740
gagtggcacc tgttctcgtc caccgtcgtc cccttgcaga agagtacgag gcactacgta   4800
gaggctctgc acaaccacta cacgcagaag agcctctccc tgtctccggg taaaggtggc   4860
ctccgagacg tgttggtgat gtgcgtcttc tcggagaggg acagaggccc atttccaccg   4920
ggcggatcag gtgggggtgg atcaggcggt ggaggttccg gtggcggggg atcagacaaa   4980
ccgcctagtc caccccacc tagtccgcca cctccaaggc caccgccccc tagtctgttt   5040
actcacacat gcccaccgtg cccagcacct gaactcctgg gaggaccgtc agtcttcctc   5100
tgagtgtgta cgggtggcac gggtcgtgga cttgaggacc ctcctggcag tcagaaggag   5160
ttccccccaa acccaaggac acccctcatg atctcccgga cccctgaggt cacatgcgtg   5220
aagggggggtt ttgggttcct gtgggagtac tagagggcct ggggactcca gtgtacgcac   5280
```

```
gtggtggacg tgagccacga agaccctgag gtcaagttca actggtacgt ggacggcgtg    5340
caccacctgc actcggtgct tctgggactc cagttcaagt tgaccatgca cctgccgcac    5400
gaggtgcata atgccaagac aaagccgcgg gaggagcagt acaacagcac gtaccgtgtg    5460
ctccacgtat tacggttctg tttcggcgcc ctcctcgtca tgttgtcgtg catggcacac    5520
gtcagcgtcc tcaccgtcct gcaccaggac tggctgaatg gcaaggagta caagtgcaag    5580
cagtcgcagg agtggcagga cgtggtcctg accgacttac cgttcctcat gttcacgttc    5640
gtctccaaca aagccctccc agcccccatc gagaaaacca tctccaaagc caagggcag    5700 cagaggttgt ttcgggaggg tcgggggtag ctcttttggt agaggtttcg gtttcccgtc    5760
ccccgagaac cacaggtgta caccctgccc ccatcccgcg atgagctgac caagaaccag    5820
ggggctcttg gtgtccacat gtgggacggg ggtagggcgc tactcgactg gttcttggtc    5880
gtcagcctga cctgcctggt caaaggcttc tatcccagcg acatcgccgt ggagtgggag    5940
cagtcggact ggacggacca gtttccgaag atagggtcgc tgtagcggca cctcacccctc    6000 agcaatgggc agccggagaa caactacaag accacgcctc ccgtgttgga ctccgacggc    6060
tcgttacccg tcggcctctt gttgatgttc tggtgcggag ggcacaacct gaggctgccg    6120
tccttcttcc tctacagcaa gctcaccgtg gacaagagca ggtggcagca ggggaacgtc    6180
aggaagaagg agatgtcgtt cgagtggcac ctgttctcgt ccaccgtcgt ccccttgcag    6240
ttctcatgct ccgtgatgca tgaggctctg cacaaccact acacgcagaa gagcctctcc    6300
aagagtacga ggcactacgt actccgagac gtgttggtga tgtgcgtctt ctcggagagg    6360
ctgtctccgg gtaaatgaga attcgacaga ggcccattta ctcttaag              6408
```

<210> SEQ ID NO 66
<211> LENGTH: 1060
<212> TYPE: PRT
<213> ORGANISM: Artificial Sequence
<220> FEATURE:
<223> OTHER INFORMATION: FVII-186

<400> SEQUENCE: 66

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
```

```
                165                 170                 175
Pro Ile Leu Glu Lys Arg Asn Ala Ser Lys Pro Gln Gly Arg Lys Arg
            180                 185                 190

Arg Lys Arg Gly Gly Gly Ser Gly Gly Gly Ser Gly Gly Gly
        195                 200                 205

Gly Ser Leu Gln Asp Ser Glu Val Asn Gln Glu Ala Lys Pro Glu Val
            210                 215                 220

Lys Pro Glu Val Lys Pro Glu Thr His Ile Asn Leu Lys Val Ser Asp
225                 230                 235                 240

Gly Ser Ser Glu Ile Phe Phe Lys Ile Lys Lys Thr Thr Pro Leu Arg
                245                 250                 255

Arg Leu Met Glu Ala Phe Ala Lys Arg Gln Gly Lys Glu Met Asp Ser
            260                 265                 270

Leu Arg Phe Leu Tyr Asp Gly Ile Arg Ile Gln Ala Asp Gln Ala Pro
        275                 280                 285

Glu Asp Leu Asp Met Glu Asp Asn Asp Ile Ile Glu Ala His Arg Glu
        290                 295                 300

Gln Ile Gly Gly Cys Pro Lys Gly Glu Cys Pro Trp Gln Val Leu Leu
305                 310                 315                 320

Leu Val Asn Gly Ala Gln Leu Cys Gly Gly Thr Leu Ile Asn Thr Ile
                325                 330                 335

Trp Val Val Ser Ala Ala His Cys Phe Asp Lys Ile Lys Asn Trp Arg
            340                 345                 350

Asn Leu Ile Ala Val Leu Gly Glu His Asp Leu Ser Glu His Asp Gly
        355                 360                 365

Asp Glu Gln Ser Arg Arg Val Ala Gln Val Ile Ile Pro Ser Thr Tyr
        370                 375                 380

Val Pro Gly Thr Thr Asn His Asp Ile Ala Leu Leu Arg Leu His Gln
385                 390                 395                 400

Pro Val Val Leu Thr Asp His Val Val Pro Leu Cys Leu Pro Glu Arg
                405                 410                 415

Thr Phe Ser Glu Arg Thr Leu Ala Phe Val Arg Phe Ser Leu Val Ser
            420                 425                 430

Gly Trp Gly Gln Leu Leu Asp Arg Gly Ala Thr Ala Leu Glu Leu Met
        435                 440                 445

Val Leu Asn Val Pro Arg Leu Met Thr Gln Asp Cys Leu Gln Gln Ser
        450                 455                 460

Arg Lys Val Gly Asp Ser Pro Asn Ile Thr Glu Tyr Met Phe Cys Ala
465                 470                 475                 480

Gly Tyr Ser Asp Gly Ser Lys Asp Ser Cys Lys Gly Asp Ser Gly Gly
                485                 490                 495

Pro His Ala Thr His Tyr Arg Gly Thr Trp Tyr Leu Thr Gly Ile Val
            500                 505                 510

Ser Trp Gly Gln Gly Cys Ala Thr Val Gly His Phe Gly Val Tyr Thr
        515                 520                 525

Arg Val Ser Gln Tyr Ile Glu Trp Leu Gln Lys Leu Met Arg Ser Glu
        530                 535                 540

Pro Arg Pro Gly Val Leu Leu Arg Ala Pro Phe Pro Gly Gly Gly Gly
545                 550                 555                 560

Ser Gly Gly Gly Ser Gly Gly Gly Ser Gly Gly Gly Ser
                565                 570                 575

Gly Gly Gly Gly Ser Gly Gly Gly Ser Asp Lys Thr His Thr Cys
            580                 585                 590
```

```
Pro Pro Cys Pro Ala Pro Glu Leu Leu Gly Gly Pro Ser Val Phe Leu
    595                 600                 605

Phe Pro Pro Lys Pro Lys Asp Thr Leu Met Ile Ser Arg Thr Pro Glu
610                 615                 620

Val Thr Cys Val Val Val Asp Val Ser His Glu Asp Pro Glu Val Lys
625                 630                 635                 640

Phe Asn Trp Tyr Val Asp Gly Val Glu Val His Asn Ala Lys Thr Lys
                645                 650                 655

Pro Arg Glu Glu Gln Tyr Asn Ser Thr Tyr Arg Val Val Ser Val Leu
                660                 665                 670

Thr Val Leu His Gln Asp Trp Leu Asn Gly Lys Glu Tyr Lys Cys Lys
            675                 680                 685

Val Ser Asn Lys Ala Leu Pro Ala Pro Ile Glu Lys Thr Ile Ser Lys
        690                 695                 700

Ala Lys Gly Gln Pro Arg Glu Pro Gln Val Tyr Thr Leu Pro Pro Ser
705                 710                 715                 720

Arg Asp Glu Leu Thr Lys Asn Gln Val Ser Leu Thr Cys Leu Val Lys
                725                 730                 735

Gly Phe Tyr Pro Ser Asp Ile Ala Val Glu Trp Glu Ser Asn Gly Gln
            740                 745                 750

Pro Glu Asn Asn Tyr Lys Thr Thr Pro Pro Val Leu Asp Ser Asp Gly
        755                 760                 765

Ser Phe Phe Leu Tyr Ser Lys Leu Thr Val Asp Lys Ser Arg Trp Gln
    770                 775                 780

Gln Gly Asn Val Phe Ser Cys Ser Val Met His Glu Ala Leu His Asn
785                 790                 795                 800

His Tyr Thr Gln Lys Ser Leu Ser Leu Ser Pro Gly Lys Gly Gly Gly
                805                 810                 815

Gly Ser Gly Gly Gly Gly Ser Gly Gly Gly Gly Ser Gly Gly Gly Gly
            820                 825                 830

Ser Asp Lys Thr His Thr Cys Pro Pro Cys Pro Ala Pro Glu Leu Leu
        835                 840                 845

Gly Gly Pro Ser Val Phe Leu Phe Pro Pro Lys Pro Lys Asp Thr Leu
    850                 855                 860

Met Ile Ser Arg Thr Pro Glu Val Thr Cys Val Val Val Asp Val Ser
865                 870                 875                 880

His Glu Asp Pro Glu Val Lys Phe Asn Trp Tyr Val Asp Gly Val Glu
                885                 890                 895

Val His Asn Ala Lys Thr Lys Pro Arg Glu Glu Gln Tyr Asn Ser Thr
            900                 905                 910

Tyr Arg Val Val Ser Val Leu Thr Val Leu His Gln Asp Trp Leu Asn
        915                 920                 925

Gly Lys Glu Tyr Lys Cys Lys Val Ser Asn Lys Ala Leu Pro Ala Pro
    930                 935                 940

Ile Glu Lys Thr Ile Ser Lys Ala Lys Gly Gln Pro Arg Glu Pro Gln
945                 950                 955                 960

Val Tyr Thr Leu Pro Pro Ser Arg Asp Glu Leu Thr Lys Asn Gln Val
                965                 970                 975

Ser Leu Thr Cys Leu Val Lys Gly Phe Tyr Pro Ser Asp Ile Ala Val
            980                 985                 990

Glu Trp Glu Ser Asn Gly Gln Pro  Glu Asn Asn Tyr Lys  Thr Thr Pro
        995                 1000                 1005
```

```
Pro  Val  Leu  Asp  Ser  Asp  Gly  Ser  Phe  Phe  Leu  Tyr  Ser  Lys  Leu
   1010                1015                         1020

Thr  Val  Asp  Lys  Ser  Arg  Trp  Gln  Gln  Gly  Asn  Val  Phe  Ser  Cys
   1025                1030                         1035

Ser  Val  Met  His  Glu  Ala  Leu  His  Asn  His  Tyr  Thr  Gln  Lys  Ser
   1040                1045                         1050

Leu  Ser  Leu  Ser  Pro  Gly  Lys
   1055                1060

<210> SEQ ID NO 67
<211> LENGTH: 6046
<212> TYPE: DNA
<213> ORGANISM: Artificial Sequence
<220> FEATURE:
<223> OTHER INFORMATION: FX-011

<400> SEQUENCE: 67
aagcttatgg gtcgtccact gcacctcgtc ctgctcagtg cctccctggc tggcctcctg      60
ttcgaatacc cagcaggtga cgtggagcag gacgagtcac ggagggaccg accggaggac     120
ctgctcgggg aaagtctgtt catccgcagg gagcaggcca caacatcct ggcgagggtc     180 gacgagcccc tttcagacaa gtaggcgtcc ctcgtccggt tgttgtagga ccgctcccag     240
aggagggcca attcctttct gaagagatg aagaaggac acctcgaaag agagtgcatg      300
tcctcccggt taaggaaaga acttctctac ttctttcctg tggagctttc tctcacgtac    360
gaagagacct gctcatacga agaggcccgc gaggtctttg aggacagcga caagacgaat    420
cttctctgga cgagtatgct tctccgggcg ctccagaaac tcctgtcgct gttctgctta    480
gaattctgga ataaatacaa agatggcgac cagtgtgaga ccagtccttg ccagaaccag    540
cttaagacct tatttatgtt tctaccgctg gtcacactct ggtcaggaac ggtcttggtc    600
ggcaaatgta agacggcct cggggaatac acctgcacct gtttagaagg attcgaaggc    660
ccgtttacat ttctgccgga gccccttatg tggacgtgga caaatcttcc taagcttccg    720
aaaaactgtg aattattcac acggaagctc tgcagcctgg acaacgggga ctgtgaccag    780 ttttttgacac ttaataagtg tgccttcgag acgtcggacc tgttgcccct gacactggtc    840
ttctgccacg aggaacagaa ctctgtggtg tgctcctgcg cccgcgggta caccctggct    900
aagacggtgc tccttgtctt gagacaccac acgaggacgc gggcgcccat gtgggaccga    960
gacaacggca aggcctgcat tcccacaggg ccctaccct gtgggaaaca gaccctggaa    1020
ctgttgccgt tccggacgta agggtgtccc gggatgggga cacccttgt ctgggacctt    1080 cgcaggaaga ggtcagtggc ccaggccacc agcagcagcg gggaggcccc tgacagcatc    1140
gcgtccttct ccagtcaccg ggtccggtgg tcgtcgtcgc cctccgggga ctgtcgtag    1200 acatggaagc catatgatgc agccgacctg gaccccaccg agaacccctt cgacctgctt    1260
tgtaccttcg gtatactacg tcggctggac ctggggtggc tcttggggaa gctgacgaa    1320 gacttcaacc agacgcagcc tgagagggc gacaacaacg gtggcggcgg atcaggtggg    1380
ctgaagttgg tctgcgtcgg actctccccg ctgttgttgc caccgccgcc tagtccaccc    1440
ggtggatcag gcggtggagg ttccggtggc ggggatcca ggaagaggag gaagaggtgc    1500
ccacctagtc cgccacctcc aaggccaccg cccctaggt ccttctcctc cttctccacg    1560
aaggacgggg agtgtccctg gcaggccctg ctcatcaatg aggaaaacga gggtttttgt    1620
ttcctgcccc tcacagggac cgtccggac gagtagttac tccttttgct cccaaaaaca    1680
ggaggtacca ttctgagcga gttctacatc ctaacggcag cccactgtct ctaccaagcc    1740
```

```
cctccatggt aagactcgct caagatgtag gattgccgtc gggtgacaga gatggttcgg    1800
aagagattca aggtgagggt aggggaccgg aacacggagc aggaggaggg cggtgaggcg    1860
ttctctaagt tccactccca tccgctggcc ttgtgcctcg tcctcctccc gccactccgc    1920
gtgcacgagg tggaggtggt catcaagcac aaccggttca caaaggagac ctatgacttc    1980
cacgtgctcc acctccacca gtagttcgtg ttggccaagt gtttcctctg gatactgaag    2040
gacatcgccg tgctccggct caagaccccc atcaccttcc gcatgaacgt ggcgcctgcc    2100
ctgtagcggc acgaggccga gttctggggg tagtggaagg cgtacttgca ccgcggacgg    2160
tgcctccccg agcgtgactg ggccgagtcc acgctgatga cgcagaagac ggggattgtg    2220
acggaggggc tcgcactgac ccggctcagg tgcgactact gcgtcttctg cccctaacac    2280
agcggcttcg ggcgcaccca cgagaagggc cggcagtcca ccaggctcaa gatgctggag    2340
tcgccgaagc ccgcgtgggt gctcttcccg gccgtcaggt ggtccgagtt ctacgacctc    2400
gtgccctacg tggaccgcaa cagctgcaag ctgtccagca gcttcatcat cacccagaac    2460
cacgggatgc acctggcgtt gtcgacgttc gacaggtcgt cgaagtagta gtgggtcttg    2520
atgttctgtg ccggctacga caccaagcag gaggatgcct gccaggggga cagcgggggc    2580
tacaagacac ggccgatgct gtggttcgtc ctcctacgga cggtccccct gtcgccccg    2640 ccgcacgtca cccgcttcaa ggacacctac ttcgtgacag gcatcgtcag ctggggagag    2700
ggcgtgcagt gggcgaagtt cctgtggatg aagcactgtc cgtagcagtc gacccctctc    2760
ggctgtgccc gtaagggaa gtacgggatc tacaccaagg tcaccgcctt cctcaagtgg    2820
ccgacacggg cattcccctt catgccctag atgtggttcc agtggcggaa ggagttcacc    2880
atcgacaggt ccatgaaaac caggggcttg cccaaggcca agagccatgc cccggaggtc    2940
tagctgtcca ggtacttttg gtccccgaac gggttccggt tctcggtacg gggcctccag    3000
ataacgtcct ctccattaaa agaagaccaa gtagatccgc ggctcattga tggtaaggac    3060
tattgcagga gaggtaattt tcttctggtt catctaggcg ccgagtaact accattcctg    3120
aaaactcaca catgcccacc gtgcccagct ccggaactcc tgggaggacc gtcagtcttc    3180

ttttgagtgt gtacgggtgg cacgggtcga ggccttgagg accctcctgg cagtcagaag    3240
ctcttccccc caaaacccaa ggacaccctc atgatctccc ggacccctga ggtcacatgc    3300
gagaaggggg gttttgggtt cctgtgggag tactagaggg cctggggact ccagtgtacg    3360
gtggtggtgg acgtgagcca cgaagaccct gaggtcaagt tcaactggta cgtggacggc    3420
caccaccacc tgcactcggt gcttctggga ctccagttca agttgaccat gcacctgccg    3480
gtggaggtgc ataatgccaa gacaaagccg cgggaggagc agtacaacag cacgtaccgt    3540
cacctccacg tattacggtt ctgtttcggc gccсcтccтcg tcatgttgtc gtgcatggca    3600
gtggtcagcg tcctcaccgt cctgcaccag gactggctga atggcaagga gtacaagtgc    3660
caccagtcgc aggagtggca ggacgtggtc ctgaccgact accgттcстcaтgттcacg    3720 aaggtctcca acaaagccct cccagccccc atcgagaaaa ccatctccaa agccaagggg    3780

ttccagaggt tgtttcggga gggtcggggg tagctctttt ggtagaggtt tcggtttccc    3840
cagccccgag aaccacaggt gtacaccctg cccccatccc gggatgagct gaccaagaac    3900
gtcggggctc ttggtgtcca catgtgggac gggggtaggg ccctactcga ctggttcttg    3960
caggtcagcc tgacctgcct ggtcaaaggc ttctatccca gcgacatcgc cgtggagtgg    4020
gtccagtcgg actggacgga ccagtttccg aagatagggt cgctgtagcg gcacctcacc    4080
```

```
gagagcaatg ggcagccgga gaacaactac aagaccacgc ctcccgtgtt ggactccgac    4140
ctctcgttac ccgtcggcct cttgttgatg ttctggtgcg gagggcacaa cctgaggctg    4200
ggctccttct tcctctacag caagctcacc gtcgacaaga gcaggtggca gcaggggaac    4260
ccgaggaaga aggagatgtc gttcgagtgg cagctgttct cgtccaccgt cgtcccttg     4320
gtcttctcat gctccgtgat gcatgaggct ctgcacaacc actacacgca aagagcctc     4380
cagaagagta cgaggcacta cgtactccga cgtgttgg tgatgtgcgt cttctcggag      4440
tccctgtctc cgggtaaacg cgccgccgg agcggtggcg gcggatcagg tgggggtgga     4500
agggacagag gcccatttgc cgcggcggcc tcgccaccgc cgcctagtcc accccacct     4560
tcaggcggtg gaggttccgg tggcggggga tccaggaaga ggaggaagag ggacaaaact    4620
agtccgccac ctccaaggcc accgcccct aggtccttct cctccttctc ctgttttga      4680
cacacatgcc caccgtgccc agcaccggaa ctcctgggcg gaccgtcagt cttcctcttc    4740
gtgtgtacgg gtggcacggg tcgtggcctt gaggacccgc ctggcagtca aaggagaag     4800
ccccaaaac caaggacac cctcatgatc tcccggaccc ctgaggtcac atgcgtggtg      4860
gggggttttg ggttcctgtg ggagtactag agggcctggg gactccagtg tacgcaccac    4920
gtggacgtga gccacgaaga ccctgaggtc aagttcaact ggtacgtgga cggcgtggag    4980
cacctgcact cggtgcttct gggactccag ttcaagttga ccatgcacct gccgcacctc    5040
gtgcataatg ccaagacaaa gccgcggag gagcagtaca acagcacgta ccgtgtggtc     5100
cacgtattac ggttctgttt cggcgccctc ctcgtcatgt tgtcgtgcat ggcacaccag    5160
agcgtcctca ccgtcctgca ccaggactgg ctgaatggca aggagtacaa gtgcaaggtc    5220
tcgcaggagt ggcaggacgt ggtcctgacc gacttaccgt tcctcatgtt cacgttccag    5280
tccaacaaag ccctcccagc ccccatcgag aaaaccatct ccaaagccaa agggcagccc    5340
aggttgtttc gggagggtcg ggggtagctc ttttggtaga ggtttcggtt tcccgtcggg    5400
cgagaaccac aggtgtacac cctgcccca tcccggatg agctgaccaa gaaccaggtc      5460
gctcttggtg tccacatgtg ggacgggggt agggccctac tcgactggtt cttggtccag   5520
agcctgacct gcctggtcaa aggcttctat cccagcgaca tcgccgtgga gtgggagagc    5580
tcggactgga cggaccagtt tccgaagata gggtcgctgt agcggcacct caccctctcg    5640
aatgggcagc cggagaacaa ctacaagacc acgcctcccg tgttggactc cgacggctcc    5700
ttacccgtcg gcctcttgtt gatgttctgg tgcggagggc acaacctgag gctgccgagg    5760
ttcttcctct acagcaagct caccgtggac aagagcaggt ggcagcaggg gaacgtcttc    5820
aagaaggaga tgtcgttcga gtggcacctg ttctcgtcca ccgtcgtccc cttgcagaag    5880
tcatgctccg tgatgcatga ggctctgcac aaccactaca cgcagaagag cctctccctg    5940
agtacgaggc actacgtact ccgagacgtg ttggtgatgt gcgtcttctc ggagagggac    6000
tctccgggta aatgagcggc cgcagaggcc catttactcg ccggcg                   6046
```

<210> SEQ ID NO 68
<211> LENGTH: 1002
<212> TYPE: PRT
<213> ORGANISM: Artificial Sequence
<220> FEATURE:
<223> OTHER INFORMATION: FX-011

<400> SEQUENCE: 68

```
Met Gly Arg Pro Leu His Leu Val Leu Leu Ser Ala Ser Leu Ala Gly
1               5                   10                  15
```

```
Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Thr Ser Pro Cys Gln
                85                  90                  95

Asn Gln Gly Lys Cys Lys Asp Gly Leu Gly Glu Tyr Thr Cys Thr Cys
        100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
        130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
        180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Asp Asn Asn Gly Gly Gly Ser Gly Gly Gly Gly
225                 230                 235                 240

Ser Gly Gly Gly Gly Ser Gly Gly Gly Ser Arg Lys Arg Lys
                245                 250                 255

Arg Cys Lys Asp Gly Glu Cys Pro Trp Gln Ala Leu Leu Ile Asn Glu
        260                 265                 270

Glu Asn Glu Gly Phe Cys Gly Gly Thr Ile Leu Ser Glu Phe Tyr Ile
        275                 280                 285

Leu Thr Ala Ala His Cys Leu Tyr Gln Ala Lys Arg Phe Lys Val Arg
        290                 295                 300

Val Gly Asp Arg Asn Thr Glu Gln Glu Glu Gly Gly Glu Ala Val His
305                 310                 315                 320

Glu Val Glu Val Val Ile Lys His Asn Arg Phe Thr Lys Glu Thr Tyr
                325                 330                 335

Asp Phe Asp Ile Ala Val Leu Arg Leu Lys Thr Pro Ile Thr Phe Arg
        340                 345                 350

Met Asn Val Ala Pro Ala Cys Leu Pro Glu Arg Asp Trp Ala Glu Ser
        355                 360                 365

Thr Leu Met Thr Gln Lys Thr Gly Ile Val Ser Gly Phe Gly Arg Thr
        370                 375                 380

His Glu Lys Gly Arg Gln Ser Thr Arg Leu Lys Met Leu Glu Val Pro
385                 390                 395                 400

Tyr Val Asp Arg Asn Ser Cys Lys Leu Ser Ser Phe Ile Ile Thr
                405                 410                 415

Gln Asn Met Phe Cys Ala Gly Tyr Asp Thr Lys Gln Glu Asp Ala Cys
        420                 425                 430

Gln Gly Asp Ser Gly Gly Pro His Val Thr Arg Phe Lys Asp Thr Tyr
```

```
            435                 440                 445
Phe Val Thr Gly Ile Val Ser Trp Gly Glu Gly Cys Ala Arg Lys Gly
450                 455                 460

Lys Tyr Gly Ile Tyr Thr Lys Val Thr Ala Phe Leu Lys Trp Ile Asp
465                 470                 475                 480

Arg Ser Met Lys Thr Arg Gly Leu Pro Lys Ala Lys Ser His Ala Pro
                    485                 490                 495

Glu Val Ile Thr Ser Ser Pro Leu Lys Glu Asp Gln Val Asp Pro Arg
                500                 505                 510

Leu Ile Asp Gly Lys Asp Lys Thr His Thr Cys Pro Pro Cys Pro Ala
            515                 520                 525

Pro Glu Leu Leu Gly Gly Pro Ser Val Phe Leu Phe Pro Pro Lys Pro
530                 535                 540

Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
                565                 570                 575

Asp Gly Val Glu Val His Asn Ala Lys Thr Lys Pro Arg Glu Glu Gln
                580                 585                 590

Tyr Asn Ser Thr Tyr Arg Val Val Ser Val Leu Thr Val Leu His Gln
            595                 600                 605

Asp Trp Leu Asn Gly Lys Glu Tyr Lys Cys Lys Val Ser Asn Lys Ala
610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Asp Glu Leu Thr
                645                 650                 655

Lys Asn Gln Val Ser Leu Thr Cys Leu Val Lys Gly Phe Tyr Pro Ser
                660                 665                 670

Asp Ile Ala Val Glu Trp Glu Ser Asn Gly Gln Pro Glu Asn Asn Tyr
            675                 680                 685

Lys Thr Thr Pro Pro Val Leu Asp Ser Asp Gly Ser Phe Phe Leu Tyr
            690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Lys Arg Arg Arg Arg Ser Gly Gly Gly
                740                 745                 750

Gly Ser Gly Gly Gly Ser Gly Gly Gly Ser Gly Gly Gly
            755                 760                 765

Ser Arg Lys Arg Arg Lys Arg Asp Lys Thr His Thr Cys Pro Pro Cys
            770                 775                 780

Pro Ala Pro Glu Leu Leu Gly Gly Pro Ser Val Phe Leu Phe Pro Pro
785                 790                 795                 800

Lys Pro Lys Asp Thr Leu Met Ile Ser Arg Thr Pro Glu Val Thr Cys
                805                 810                 815

Val Val Val Asp Val Ser His Glu Asp Pro Glu Val Lys Phe Asn Trp
                820                 825                 830

Tyr Val Asp Gly Val Glu Val His Asn Ala Lys Thr Lys Pro Arg Glu
            835                 840                 845

Glu Gln Tyr Asn Ser Thr Tyr Arg Val Val Ser Val Leu Thr Val Leu
850                 855                 860
```

```
His Gln Asp Trp Leu Asn Gly Lys Glu Tyr Lys Cys Lys Val Ser Asn
865                 870                 875                 880

Lys Ala Leu Pro Ala Pro Ile Glu Lys Thr Ile Ser Lys Ala Lys Gly
            885                 890                 895

Gln Pro Arg Glu Pro Gln Val Tyr Thr Leu Pro Pro Ser Arg Asp Glu
        900                 905                 910

Leu Thr Lys Asn Gln Val Ser Leu Thr Cys Leu Val Lys Gly Phe Tyr
    915                 920                 925

Pro Ser Asp Ile Ala Val Glu Trp Glu Ser Asn Gly Gln Pro Glu Asn
930                 935                 940

Asn Tyr Lys Thr Thr Pro Pro Val Leu Asp Ser Asp Gly Ser Phe Phe
945                 950                 955                 960

Leu Tyr Ser Lys Leu Thr Val Asp Lys Ser Arg Trp Gln Gln Gly Asn
            965                 970                 975

Val Phe Ser Cys Ser Val Met His Glu Ala Leu His Asn His Tyr Thr
        980                 985                 990

Gln Lys Ser Leu Ser Leu Ser Pro Gly Lys
    995                 1000
```

<210> SEQ ID NO 69
<211> LENGTH: 6280
<212> TYPE: DNA
<213> ORGANISM: Artificial Sequence
<220> FEATURE:
<223> OTHER INFORMATION: FX-012

<400> SEQUENCE: 69

```
aagcttatgg gtcgtccact gcacctcgtc ctgctcagtg cctccctggc tggcctcctg      60
ttcgaatacc cagcaggtga cgtggagcag gacgagtcac ggagggaccg accggaggac     120
ctgctcgggg aaagtctgtt catccgcagg gagcaggcca caacatcct ggcgagggtc     180
gacgagcccc tttcagacaa gtaggcgtcc ctcgtccggt tgttgtagga ccgctcccag     240
aggagggcca attcctttct tgaagagatg aagaaggac acctcgaaag agagtgcatg     300
tcctcccggt taaggaaaga acttctctac ttctttcctg tggagctttc tctcacgtac     360
gaagagacct gctcatacga gaggcccgc gaggtctttg aggacagcga caagacgaat     420
cttctctgga cgagtatgct ctccgggcg ctccagaaac tcctgtcgct gttctgctta     480
gaattctgga ataaatacaa agatggcgac cagtgtgaga ccagtccttg ccagaaccag     540
cttaagacct tatttatgtt tctaccgctg gtcacactct ggtcaggaac ggtcttggtc     600
ggcaaatgta agacggcct cggggaatac acctgcacct gtttagaagg attcgaaggc     660
ccgtttacat ttctgccgga gcccttatg tggacgtgga caaatcttcc taagcttccg     720
aaaaactgtg aattattcac acggaagctc tgcagcctgg acaacgggga ctgtgaccag     780
tttttgacac ttaataagtg tgccttcgag acgtcggacc tgttgcccct gacactggtc     840
ttctgccacg aggaacagaa ctctgtgtg tgctcctgcg cccgcgggta caccctggct     900
aagacggtgc tccttgtctt gagacaccac acgaggacgc gggcgcccat gtgggaccga     960
gacaacggca aggcctgcat tcccacaggg ccctaccct gtgggaaaca gaccctggaa    1020
ctgttgccgt tccggacgta agggtgtccc gggatgggga cacccttgt ctgggacctt    1080
cgcaggaaga ggggtggggg tggatcaggc ggtggaggtt ccggtggcgg ggatcctcc    1140
gcgtccttct ccccaccccc acctagtccg ccacctccaa ggccaccgcc cctaggagg    1200
ctgcaggact cagaagtcaa tcaagaagct aagccagagg tcaagccaga agtcaagcct    1260
```

```
gacgtcctga gtcttcagtt agttcttcga ttcggtctcc agttcggtct tcagttcgga   1320
gagactcaca tcaatttaaa ggtgtccgat ggatcttcag agatcttctt caagatcaaa   1380
ctctgagtgt agttaaattt ccacaggcta cctagaagtc tctagaagaa gttctagttt   1440
aagaccactc ctttaagaag gctgatggaa gcgttcgcta aaagacaggg taaggaaatg   1500
ttctggtgag gaaattcttc cgactacctt cgcaagcgat tttctgtccc attcctttac   1560
gactccttaa gattcttgta cgacggtatt agaattcaag ctgatcaggc ccctgaagat   1620
ctgaggaatt ctaagaacat gctgccataa tcttaagttc gactagtccg gggacttcta   1680
ttggacatgg aggataacga tattattgag gctcaccgcg aacagattgg aggttgcaag   1740
aacctgtacc tcctattgct ataataactc gagtggcgc ttgtctaacc tccaacgttc    1800
gacggggagt gtccctggca ggccctgctc atcaatgagg aaaacgaggg ttttgtgga    1860
ctgcccctca cagggaccgt ccgggacgag tagttactcc ttttgctccc aaaaacacct   1920
ggtaccattc tgagcgagtt ctacatccta acggcagccc actgtctcta ccaagccaag   1980
ccatggtaag actcgctcaa gatgtaggat tgccgtcggg tgacagagat ggttcggttc   2040
agattcaagg tgagggtagg ggaccggaac acggagcagg aggagggcgg tgaggcggtg   2100
tctaagttcc actcccatcc cctggccttg tgcctcgtcc tcctcccgcc actccgccac   2160
cacgaggtgg aggtggtcat caagcacaac cggttcacaa aggagaccta tgacttcgac   2220
gtgctccacc tccaccagta gttcgtgttg gccaagtgtt tcctctggat actgaagctg   2280
atcgccgtgc tccggctcaa gaccccatc accttccgca tgaacgtggc gcctgcctgc    2340
tagcggcacg aggccgagtt ctgggggtag tggaaggcgt acttgcaccg cggacggacg   2400
ctccccgagc gtgactgggc cgagtccacg ctgatgacgc agaagacggg gattgtgagc   2460
gaggggctcg cactgacccg gctcaggtgc gactactgcg tcttctgccc ctaacactcg   2520
ggcttcgggc gcacccacga gaagggccgg cagtccacca ggctcaagat gctggaggtg   2580
ccgaagcccg cgtgggtgct cttcccggcc gtcaggtggt ccgagttcta cgacctccac   2640
ccctacgtgg accgcaacag ctgcaagctg tccagcagct tcatcatcac ccagaacatg   2700
gggatgcacc tggcgttgtc gacgttcgac aggtcgtcga agtagtagtg ggtcttgtac   2760
ttctgtgccg gctacgacac caagcaggag gatgcctgcc aggggggacag cgggggcccg   2820
aagacacggc cgatgctgtg gttcgtcctc ctacggacgg tccccctgtc gccccggggc   2880
cacgtcaccc gcttcaagga cacctacttc gtgacaggca tcgtcagctg gggagagggc   2940
gtgcagtggg cgaagttcct gtggatgaag cactgtccgt agcagtcgac ccctctcccg   3000
tgtgcccgta aggggaagta cgggatctac accaaggtca ccgccttcct caagtggatc   3060
acacgggcat tccccttcat gcctagatg tggttccagt ggcggaagga gttcacctag    3120
gacaggtcca tgaaaaccag gggcttgccc aaggccaaga gccatgcccc ggaggtcata   3180
ctgtccaggt actttggtc cccgaacggg ttccggttct cggtacgggg cctccagtat    3240
acgtcctctc cattaaaaga agaccaagta gatccgcggc tcattgatgg taaggacaaa   3300
tgcaggagag gtaattttct tctggttcat ctaggcgccg agtaactacc attcctgttt   3360
actcacacat gcccaccgtg cccagctccg gaactcctgg gaggaccgtc agtcttcctc   3420
tgagtgtgta cgggtggcac gggtcgaggc cttgaggacc ctcctggcag tcagaaggag   3480
ttccccccaa aacccaagga caccctcatg atctcccgga cccctgaggt cacatgcgtg   3540
aagggggggtt ttgggttcct gtgggagtac tagagggcct ggggactcca gtgtacgcac   3600
```

```
gtggtggacg tgagccacga agaccctgag gtcaagttca actggtacgt ggacggcgtg    3660
caccacctgc actcggtgct tctgggactc cagttcaagt tgaccatgca cctgccgcac    3720
gaggtgcata atgccaagac aaagccgcgg gaggagcagt acaacagcac gtaccgtgtg    3780
ctccacgtat tacggttctg tttcggcgcc ctcctcgtca tgttgtcgtg catggcacac    3840
gtcagcgtcc tcaccgtcct gcaccaggac tggctgaatg gcaaggagta caagtgcaag    3900
cagtcgcagg agtggcagga cgtggtcctg accgacttac cgttcctcat gttcacgttc    3960
gtctccaaca aagccctccc agccccatc  gagaaaacca tctccaaagc caagggcag    4020
cagaggttgt ttcggagggt cgggggtag ctcttttggt agaggtttcg gtttcccgtc     4080
ccccgagaac acaggtgta caccctgccc ccatcccggg atgagctgac caagaaccag    4140
ggggctcttg tgtccacat gtgggacggg ggtagggccc tactcgactg gttcttggtc     4200
gtcagcctga cctgcctggt caaaggcttc tatcccagcg acatcgccgt ggagtgggag    4260
cagtcggact ggacggacca gtttccgaag atagggtcgc tgtagcggca cctcaccctc    4320
agcaatgggc agcggagaa caactacaag accacgcctc ccgtgttgga ctccgacggc     4380
tcgttacccg tcggcctctt gttgatgttc tggtgcggag ggcacaacct gaggctgccg    4440
tccttcttcc tctacagcaa gctcaccgtc gacaagagca ggtggcagca ggggaacgtc    4500
aggaagaagg agatgtcgtt cgagtggcag ctgttctcgt ccaccgtcgt cccctttgcag    4560
ttctcatgct ccgtgatgca tgaggctctg cacaaccact acacgcagaa gagcctctcc    4620
aagagtacga ggcactacgt actccgagac gtgttggtga tgtgcgtctt ctcggagagg    4680
ctgtctccgg gtaaacggcg ccgccggagc ggtggcggcg gatcaggtgg gggtggatca    4740
gacagaggcc catttgccgc ggcggcctcg ccaccgccgc ctagtccacc cccacctagt    4800
ggcggtggag gttccggtgg cggggggatcc aggaagagga ggaagaggga caaaactcac    4860
ccgccacctc caaggccacc gcccctagg tccttctcct cctctcccct gttttgagtg     4920
acatgcccac cgtgcccagc accggaactc ctgggcggac cgtcagtctt cctcttcccc    4980
tgtacgggtg gcacgggtcg tggccttgag gacccgcctg gcagtcagaa ggagaagggg    5040
ccaaaaccca aggacaccct catgatctcc cggacccctg aggtcacatg cgtggtggtg    5100
ggttttgggt tcctgtggga gtactagagg gcctgggac tccagtgtac gcaccaccac     5160
gacgtgagcc acgaagaccc tgaggtcaag ttcaactggt acgtggacgg cgtggaggtg    5220
ctgcactcgg tgcttctggg actccagttc aagttgacca tgcacctgcc gcacctccac    5280
cataatgcca agacaaagcc gcgggaggag cagtacaaca gcacgtaccg tgtggtcagc    5340
gtattacggt tctgtttcgg cgccctcctc gtcatgttgt cgtgcatggc acaccagtcg    5400
gtcctcaccg tcctgcacca ggactggctg aatggcaagg agtacaagtg caaggtctcc    5460
caggagtggc aggacgtggt cctgaccgac ttaccgttcc tcatgttcac gttccagagg    5520
aacaaagccc tccagccccc catcgagaaa accatctcca aagccaaagg cagccccga    5580
ttgtttcggg agggtcgggg gtagctcttt tggtagaggt tcggtttcc cgtcggggct     5640
gaaccacagg tgtacaccct gccccatcc cgggatgagc tgaccaagaa ccaggtcagc    5700
cttggtgtcc acatgtggga cggggtagg gccctactcg actggttctt ggtccagtcg     5760
ctgacctgcc tggtcaaagg cttctatccc agcgacatcg ccgtggagtg ggagagcaat    5820
gactggacgg accagtttcc gaagataggg tcgctgtagc ggcacctcac cctctcgtta    5880
gggcagccgg agaacaacta caagaccacg cctcccgtgt ggactccga cggctccttc     5940
cccgtcggcc tcttgttgat gttctggtgc ggagggcaca acctgaggct gccgaggaag    6000
```

-continued

```
ttcctctaca gcaagctcac cgtggacaag agcaggtggc agcagggaa cgtcttctca      6060 aaggagatgt cgttcgagtg gcacctgttc tcgtccaccg tcgtcccctt gcagaagagt      6120
tgctccgtga tgcatgaggc tctgcacaac cactacacgc agaagagcct ctccctgtct      6180
acgaggcact acgtactccg agacgtgttg gtgatgtgcg tcttctcgga gagggacaga      6240
ccgggtaaat gagcggccgc ggcccattta ctcgccggcg                            6280
```

<210> SEQ ID NO 70
<211> LENGTH: 1041
<212> TYPE: PRT
<213> ORGANISM: Artificial Sequence
<220> FEATURE:
<223> OTHER INFORMATION: FX-012

<400> SEQUENCE: 70

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Gly Gly Gly Ser Gly Gly Gly Ser
            180                 185                 190

Gly Gly Gly Gly Ser Ser Leu Gln Asp Ser Glu Val Asn Gln Glu Ala
        195                 200                 205

Lys Pro Glu Val Lys Pro Glu Val Lys Pro Glu Thr His Ile Asn Leu
    210                 215                 220

Lys Val Ser Asp Gly Ser Ser Glu Ile Phe Phe Lys Ile Lys Lys Thr
225                 230                 235                 240

Thr Pro Leu Arg Arg Leu Met Glu Ala Phe Ala Lys Arg Gln Gly Lys
                245                 250                 255

Glu Met Asp Ser Leu Arg Phe Leu Tyr Asp Gly Ile Arg Ile Gln Ala
            260                 265                 270

Asp Gln Ala Pro Glu Asp Leu Asp Met Glu Asp Asn Asp Ile Ile Glu
        275                 280                 285

Ala His Arg Glu Gln Ile Gly Gly Cys Lys Asp Gly Glu Cys Pro Trp
    290                 295                 300

Gln Ala Leu Leu Ile Asn Glu Glu Asn Glu Gly Phe Cys Gly Gly Thr
```

```
                305                 310                 315                 320
            Ile Leu Ser Glu Phe Tyr Ile Leu Thr Ala Ala His Cys Leu Tyr Gln
                            325                 330                 335

Ala Lys Arg Phe Lys Val Arg Val Gly Asp Arg Asn Thr Glu Gln Glu
                            340                 345                 350

Glu Gly Gly Glu Ala Val His Glu Val Glu Val Val Ile Lys His Asn
                            355                 360                 365

Arg Phe Thr Lys Glu Thr Tyr Asp Phe Asp Ile Ala Val Leu Arg Leu
                            370                 375                 380

Lys Thr Pro Ile Thr Phe Arg Met Asn Val Ala Pro Ala Cys Leu Pro
            385                 390                 395                 400

Glu Arg Asp Trp Ala Glu Ser Thr Leu Met Thr Gln Lys Thr Gly Ile
                            405                 410                 415

Val Ser Gly Phe Gly Arg Thr His Glu Lys Gly Arg Gln Ser Thr Arg
                            420                 425                 430

Leu Lys Met Leu Glu Val Pro Tyr Val Asp Arg Asn Ser Cys Lys Leu
                            435                 440                 445

Ser Ser Ser Phe Ile Ile Thr Gln Asn Met Phe Cys Ala Gly Tyr Asp
                            450                 455                 460

Thr Lys Gln Glu Asp Ala Cys Gln Gly Asp Ser Gly Gly Pro His Val
            465                 470                 475                 480

Thr Arg Phe Lys Asp Thr Tyr Phe Val Thr Gly Ile Val Ser Trp Gly
                            485                 490                 495

Glu Gly Cys Ala Arg Lys Gly Lys Tyr Gly Ile Tyr Thr Lys Val Thr
                            500                 505                 510

Ala Phe Leu Lys Trp Ile Asp Arg Ser Met Lys Thr Arg Gly Leu Pro
                            515                 520                 525

Lys Ala Lys Ser His Ala Pro Glu Val Ile Thr Ser Ser Pro Leu Lys
                            530                 535                 540

Glu Asp Gln Val Asp Pro Arg Leu Ile Asp Gly Lys Asp Lys Thr His
            545                 550                 555                 560

Thr Cys Pro Pro Cys Pro Ala Pro Glu Leu Leu Gly Gly Pro Ser Val
                            565                 570                 575

Phe Leu Phe Pro Pro Lys Pro Lys Asp Thr Leu Met Ile Ser Arg Thr
                            580                 585                 590

Pro Glu Val Thr Cys Val Val Asp Val Ser His Glu Asp Pro Glu
                            595                 600                 605

Val Lys Phe Asn Trp Tyr Val Asp Gly Val Glu Val His Asn Ala Lys
                            610                 615                 620

Thr Lys Pro Arg Glu Glu Gln Tyr Asn Ser Thr Tyr Arg Val Val Ser
            625                 630                 635                 640

Val Leu Thr Val Leu His Gln Asp Trp Leu Asn Gly Lys Glu Tyr Lys
                            645                 650                 655

Cys Lys Val Ser Asn Lys Ala Leu Pro Ala Pro Ile Glu Lys Thr Ile
                            660                 665                 670

Ser Lys Ala Lys Gly Gln Pro Arg Glu Pro Gln Val Tyr Thr Leu Pro
                            675                 680                 685

Pro Ser Arg Asp Glu Leu Thr Lys Asn Gln Val Ser Leu Thr Cys Leu
                            690                 695                 700

Val Lys Gly Phe Tyr Pro Ser Asp Ile Ala Val Glu Trp Glu Ser Asn
            705                 710                 715                 720

Gly Gln Pro Glu Asn Asn Tyr Lys Thr Thr Pro Pro Val Leu Asp Ser
                            725                 730                 735
```

```
Asp Gly Ser Phe Phe Leu Tyr Ser Lys Leu Thr Val Asp Lys Ser Arg
            740                 745                 750

Trp Gln Gln Gly Asn Val Phe Ser Cys Ser Val Met His Glu Ala Leu
        755                 760                 765

His Asn His Tyr Thr Gln Lys Ser Leu Ser Leu Ser Pro Gly Lys Arg
    770                 775                 780

Arg Arg Arg Ser Gly Gly Gly Ser Gly Gly Gly Ser Gly Gly Gly Gly
785                 790                 795                 800

Gly Gly Ser Gly Gly Gly Gly Ser Arg Lys Arg Arg Lys Arg Asp Lys
                805                 810                 815

Thr His Thr Cys Pro Pro Cys Pro Ala Pro Glu Leu Leu Gly Gly Pro
                820                 825                 830

Ser Val Phe Leu Phe Pro Pro Lys Pro Lys Asp Thr Leu Met Ile Ser
            835                 840                 845

Arg Thr Pro Glu Val Thr Cys Val Val Val Asp Val Ser His Glu Asp
850                 855                 860

Pro Glu Val Lys Phe Asn Trp Tyr Val Asp Gly Val Glu Val His Asn
865                 870                 875                 880

Ala Lys Thr Lys Pro Arg Glu Glu Gln Tyr Asn Ser Thr Tyr Arg Val
                885                 890                 895

Val Ser Val Leu Thr Val Leu His Gln Asp Trp Leu Asn Gly Lys Glu
            900                 905                 910

Tyr Lys Cys Lys Val Ser Asn Lys Ala Leu Pro Ala Pro Ile Glu Lys
        915                 920                 925

Thr Ile Ser Lys Ala Lys Gly Gln Pro Arg Glu Pro Gln Val Tyr Thr
    930                 935                 940

Leu Pro Pro Ser Arg Asp Glu Leu Thr Lys Asn Gln Val Ser Leu Thr
945                 950                 955                 960

Cys Leu Val Lys Gly Phe Tyr Pro Ser Asp Ile Ala Val Glu Trp Glu
                965                 970                 975

Ser Asn Gly Gln Pro Glu Asn Asn Tyr Lys Thr Thr Pro Pro Val Leu
            980                 985                 990

Asp Ser Asp Gly Ser Phe Phe Leu Tyr Ser Lys Leu Thr Val Asp Lys
        995                 1000                1005

Ser Arg Trp Gln Gln Gly Asn Val Phe Ser Cys Ser Val Met His
    1010                1015                1020

Glu Ala Leu His Asn His Tyr Thr Gln Lys Ser Leu Ser Leu Ser
    1025                1030                1035

Pro Gly Lys
    1040

<210> SEQ ID NO 71
<211> LENGTH: 264
<212> TYPE: PRT
<213> ORGANISM: Artificial Sequence
<220> FEATURE:
<223> OTHER INFORMATION: GFP protein

<400> SEQUENCE: 71

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45
```

```
Thr Thr Gly Lys Leu Pro Val Pro Trp Pro Thr Leu Val Thr Thr Phe
     50                  55                  60

Gly Tyr Gly Val Gln Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Ser Arg
225                 230                 235                 240

Thr Ser Gly Ser Pro Gly Leu Gln Glu Phe Asp Ile Lys Leu Ile Asp
                245                 250                 255

Thr Val Asp Leu Glu Ser Cys Asn
            260

<210> SEQ ID NO 72
<211> LENGTH: 474
<212> TYPE: PRT
<213> ORGANISM: Homo sapiens

<400> SEQUENCE: 72

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
         50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
```

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Trp Glu Ser Asn Gly Gln Pro Glu Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
210                 215                 220

Pro Gly Lys Gly Gly Gly Ser Gly Gly Gly Ser Gly Gly Gly
225                 230                 235                 240

Gly Ser Gly Gly Gly Ser Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
                290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Asp Glu
                370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
435                 440                 445

Val Phe Ser Cys Ser Val Met His Glu Ala Leu His Asn His Tyr Thr
                450                 455                 460

Gln Lys Ser Leu Ser Leu Ser Pro Gly Lys
465                 470

<210> SEQ ID NO 73
<211> LENGTH: 591
<212> TYPE: PRT
<213> ORGANISM: Homo sapiens

<400> SEQUENCE: 73

Arg Gly Val Phe Arg Arg Asp Ala His Lys Ser Glu Val Ala His Arg
1               5                   10                  15

Phe Lys Asp Leu Gly Glu Glu Asn Phe Lys Ala Leu Val Leu Ile Ala
                20                  25                  30

Phe Ala Gln Tyr Leu Gln Gln Cys Pro Phe Glu Asp His Val Lys Leu
                35                  40                  45

```
Val Asn Glu Val Thr Glu Phe Ala Lys Thr Cys Val Ala Asp Glu Ser
 50                  55                  60

Ala Glu Asn Cys Asp Lys Ser Leu His Thr Leu Phe Gly Asp Lys Leu
 65                  70                  75                  80

Cys Thr Val Ala Thr Leu Arg Glu Thr Tyr Gly Glu Met Ala Asp Cys
                 85                  90                  95

Cys Ala Lys Gln Glu Pro Glu Arg Asn Glu Cys Phe Leu Gln His Lys
                100                 105                 110

Asp Asp Asn Pro Asn Leu Pro Arg Leu Val Arg Pro Glu Val Asp Val
                115                 120                 125

Met Cys Thr Ala Phe His Asp Asn Glu Glu Thr Phe Leu Lys Lys Tyr
130                 135                 140

Leu Tyr Glu Ile Ala Arg Arg His Pro Tyr Phe Tyr Ala Pro Glu Leu
145                 150                 155                 160

Leu Phe Phe Ala Lys Arg Tyr Lys Ala Ala Phe Thr Glu Cys Cys Gln
                165                 170                 175

Ala Ala Asp Lys Ala Ala Cys Leu Leu Pro Lys Leu Asp Glu Leu Arg
                180                 185                 190

Asp Glu Gly Lys Ala Ser Ser Ala Lys Gln Arg Leu Lys Cys Ala Ser
                195                 200                 205

Leu Gln Lys Phe Gly Glu Arg Ala Phe Lys Ala Trp Ala Val Ala Arg
210                 215                 220

Leu Ser Gln Arg Phe Pro Lys Ala Glu Phe Ala Glu Val Ser Lys Leu
225                 230                 235                 240

Val Thr Asp Leu Thr Lys Val His Thr Glu Cys Cys His Gly Asp Leu
                245                 250                 255

Leu Glu Cys Ala Asp Asp Arg Ala Asp Leu Ala Lys Tyr Ile Cys Glu
                260                 265                 270

Asn Gln Asp Ser Ile Ser Ser Lys Leu Lys Glu Cys Cys Glu Lys Pro
                275                 280                 285

Leu Leu Glu Lys Ser His Cys Ile Ala Glu Val Glu Asn Asp Glu Met
290                 295                 300

Pro Ala Asp Leu Pro Ser Leu Ala Ala Asp Phe Val Glu Ser Lys Asp
305                 310                 315                 320

Val Cys Lys Asn Tyr Ala Glu Ala Lys Asp Val Phe Leu Gly Met Phe
                325                 330                 335

Leu Tyr Glu Tyr Ala Arg Arg His Pro Asp Tyr Ser Val Val Leu Leu
                340                 345                 350

Leu Arg Leu Ala Lys Thr Tyr Glu Thr Thr Leu Glu Lys Cys Cys Ala
                355                 360                 365

Ala Ala Asp Pro His Glu Cys Tyr Ala Lys Val Phe Asp Glu Phe Lys
370                 375                 380

Pro Leu Val Glu Glu Pro Gln Asn Leu Ile Lys Gln Asn Cys Glu Leu
385                 390                 395                 400

Phe Glu Gln Leu Gly Glu Tyr Lys Phe Gln Asn Ala Leu Leu Val Arg
                405                 410                 415

Tyr Thr Lys Lys Val Pro Gln Val Ser Thr Pro Thr Leu Val Glu Val
                420                 425                 430

Ser Arg Asn Leu Gly Lys Val Gly Ser Lys Cys Cys Lys His Pro Glu
                435                 440                 445

Ala Lys Arg Met Pro Cys Ala Glu Asp Tyr Leu Ser Val Val Leu Asn
450                 455                 460

Gln Leu Cys Val Leu His Glu Lys Thr Pro Val Ser Asp Arg Val Thr
```

```
                465               470               475               480
Lys Cys Cys Thr Glu Ser Leu Val Asn Arg Arg Pro Cys Phe Ser Ala
                    485               490               495
Leu Glu Val Asp Glu Thr Tyr Val Pro Lys Glu Phe Asn Ala Glu Thr
                500               505               510
Phe Thr Phe His Ala Asp Ile Cys Thr Leu Ser Glu Lys Glu Arg Gln
                515               520               525
Ile Lys Lys Gln Thr Ala Leu Val Glu Leu Val Lys His Lys Pro Lys
                530               535               540
Ala Thr Lys Glu Gln Leu Lys Ala Val Met Asp Asp Phe Ala Ala Phe
545                 550               555               560
Val Glu Lys Cys Cys Lys Ala Asp Asp Lys Glu Thr Cys Phe Ala Glu
                    565               570               575
Glu Gly Lys Lys Leu Val Ala Ala Ser Gln Ala Ala Leu Gly Leu
                580               585               590

<210> SEQ ID NO 74
<211> LENGTH: 10
<212> TYPE: PRT
<213> ORGANISM: Artificial Sequence
<220> FEATURE:
<223> OTHER INFORMATION: Cysteine-containing peptide

<400> SEQUENCE: 74

Gly Gly Gly Ser Gly Cys Gly Gly Gly Ser
1               5                   10

<210> SEQ ID NO 75
<211> LENGTH: 4544
<212> TYPE: PRT
<213> ORGANISM: Homo sapiens

<400> SEQUENCE: 75

Met Leu Thr Pro Pro Leu Leu Leu Leu Pro Leu Leu Ser Ala Leu
1               5                   10                  15

Val Ala Ala Ala Ile Asp Ala Pro Lys Thr Cys Ser Pro Lys Gln Phe
                20                  25                  30

Ala Cys Arg Asp Gln Ile Thr Cys Ile Ser Lys Gly Trp Arg Cys Asp
                35                  40                  45

Gly Glu Arg Asp Cys Pro Asp Gly Ser Asp Glu Ala Pro Glu Ile Cys
            50                  55                  60

Pro Gln Ser Lys Ala Gln Arg Cys Gln Pro Asn Glu His Asn Cys Leu
65              70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
                100                 105                 110

Gly Asn Cys Ser Arg Leu Gly Cys Gln His His Cys Val Pro Thr Leu
                115                 120                 125

Asp Gly Pro Thr Cys Tyr Cys Asn Ser Ser Phe Gln Leu Gln Ala Asp
            130                 135                 140

Gly Lys Thr Cys Lys Asp Phe Asp Glu Cys Ser Val Tyr Gly Thr Cys
145             150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
                180                 185                 190
```

```
Glu Pro Val Asp Arg Pro Val Leu Leu Ile Ala Asn Ser Gln Asn
        195                 200                 205

Ile Leu Ala Thr Tyr Leu Ser Gly Ala Gln Val Ser Thr Ile Thr Pro
210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
                260                 265                 270

Ile Asn Ile Ser Leu Ser Leu His His Val Glu Gln Met Ala Ile Asp
                275                 280                 285

Trp Leu Thr Gly Asn Phe Tyr Phe Val Asp Asp Ile Asp Asp Arg Ile
        290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
                340                 345                 350

Met Asp Gly Gln Asn Arg Thr Lys Leu Val Asp Ser Lys Ile Val Phe
                355                 360                 365

Pro His Gly Ile Thr Leu Asp Leu Val Ser Arg Leu Val Tyr Trp Ala
        370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
                420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
        450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
                500                 505                 510

Gly Ser Asp Gly Lys Ser Cys Lys Lys Pro Glu His Glu Leu Phe Leu
                515                 520                 525

Val Tyr Gly Lys Gly Arg Pro Gly Ile Ile Arg Gly Met Asp Met Gly
        530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
                580                 585                 590

Arg Glu Thr Ile Leu Lys Asp Gly Ile His Asn Val Glu Gly Val Ala
        595                 600                 605
```

Val Asp Trp Met Gly Asp Asn Leu Tyr Trp Thr Asp Gly Pro Lys
610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Asp Pro Lys
                660                 665                 670

Asp Ser Arg Arg Gly Arg Leu Glu Arg Ala Trp Met Asp Gly Ser His
                675                 680                 685

Arg Asp Ile Phe Val Thr Ser Lys Thr Val Leu Trp Pro Asn Gly Leu
690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735

Tyr Glu Gly Pro Glu Leu Asn His Ala Phe Gly Leu Cys His His Gly
                740                 745                 750

Asn Tyr Leu Phe Trp Thr Glu Tyr Arg Ser Gly Ser Val Tyr Arg Leu
                755                 760                 765

Glu Arg Gly Val Gly Gly Ala Pro Pro Thr Val Thr Leu Leu Arg Ser
770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
                820                 825                 830

Gln Val Leu Asp Ala Asp Gly Val Thr Cys Leu Ala Asn Pro Ser Tyr
                835                 840                 845

Val Pro Pro Pro Gln Cys Gln Pro Gly Glu Phe Ala Cys Ala Asn Ser
                850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                885                 890                 895

Ser Asp Arg Phe Lys Cys Glu Asn Asn Arg Cys Ile Pro Asn Arg Trp
                900                 905                 910

Leu Cys Asp Gly Asp Asn Asp Cys Gly Asn Ser Glu Asp Glu Ser Asn
                915                 920                 925

Ala Thr Cys Ser Ala Arg Thr Cys Pro Pro Asn Gln Phe Ser Cys Ala
930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                965                 970                 975

Phe Pro Leu Thr Gln Phe Thr Cys Asn Asn Gly Arg Cys Ile Asn Ile
                980                 985                 990

Asn Trp Arg Cys Asp Asn Asp Asn Asp Cys Gly Asp Asn Ser Asp Glu
                995                 1000                1005

Ala Gly Cys Ser His Ser Cys Ser Ser Thr Gln Phe Lys Cys Asn
        1010                1015                1020

Ser Gly Arg Cys Ile Pro Glu His Trp Thr Cys Asp Gly Asp Asn

-continued

```
            1025                1030                1035
Asp Cys Gly Asp Tyr Ser Asp Glu Thr His Ala Asn Cys Thr Asn
        1040                1045                1050
Gln Ala Thr Arg Pro Pro Gly Gly Cys His Thr Asp Glu Phe Gln
        1055                1060                1065
Cys Arg Leu Asp Gly Leu Cys Ile Pro Leu Arg Trp Arg Cys Asp
        1070                1075                1080
Gly Asp Thr Asp Cys Met Asp Ser Ser Asp Glu Lys Ser Cys Glu
        1085                1090                1095
Gly Val Thr His Val Cys Asp Pro Ser Val Lys Phe Gly Cys Lys
        1100                1105                1110
Asp Ser Ala Arg Cys Ile Ser Lys Ala Trp Val Cys Asp Gly Asp
        1115                1120                1125
Asn Asp Cys Glu Asp Asn Ser Asp Glu Glu Asn Cys Glu Ser Leu
        1130                1135                1140
Ala Cys Arg Pro Pro Ser His Pro Cys Ala Asn Asn Thr Ser Val
        1145                1150                1155
Cys Leu Pro Pro Asp Lys Leu Cys Asp Gly Asn Asp Asp Cys Gly
        1160                1165                1170
Asp Gly Ser Asp Glu Gly Glu Leu Cys Asp Gln Cys Ser Leu Asn
        1175                1180                1185
Asn Gly Gly Cys Ser His Asn Cys Ser Val Ala Pro Gly Glu Gly
        1190                1195                1200
Ile Val Cys Ser Cys Pro Leu Gly Met Glu Leu Gly Pro Asp Asn
        1205                1210                1215
His Thr Cys Gln Ile Gln Ser Tyr Cys Ala Lys His Leu Lys Cys
        1220                1225                1230
Ser Gln Lys Cys Asp Gln Asn Lys Phe Ser Val Lys Cys Ser Cys
        1235                1240                1245
Tyr Glu Gly Trp Val Leu Glu Pro Asp Gly Glu Ser Cys Arg Ser
        1250                1255                1260
Leu Asp Pro Phe Lys Pro Phe Ile Ile Phe Ser Asn Arg His Glu
        1265                1270                1275
Ile Arg Arg Ile Asp Leu His Lys Gly Asp Tyr Ser Val Leu Val
        1280                1285                1290
Pro Gly Leu Arg Asn Thr Ile Ala Leu Asp Phe His Leu Ser Gln
        1295                1300                1305
Ser Ala Leu Tyr Trp Thr Asp Val Val Glu Asp Lys Ile Tyr Arg
        1310                1315                1320
Gly Lys Leu Leu Asp Asn Gly Ala Leu Thr Ser Phe Glu Val Val
        1325                1330                1335
Ile Gln Tyr Gly Leu Ala Thr Pro Glu Gly Leu Ala Val Asp Trp
        1340                1345                1350
Ile Ala Gly Asn Ile Tyr Trp Val Glu Ser Asn Leu Asp Gln Ile
        1355                1360                1365
Glu Val Ala Lys Leu Asp Gly Thr Leu Arg Thr Thr Leu Leu Ala
        1370                1375                1380
Gly Asp Ile Glu His Pro Arg Ala Ile Ala Leu Asp Pro Arg Asp
        1385                1390                1395
Gly Ile Leu Phe Trp Thr Asp Trp Asp Ala Ser Leu Pro Arg Ile
        1400                1405                1410
Glu Ala Ala Ser Met Ser Gly Ala Gly Arg Arg Thr Val His Arg
        1415                1420                1425
```

-continued

Glu Thr Gly Ser Gly Gly Trp Pro Asn Gly Leu Thr Val Asp Tyr
1430                1435                1440

Leu Glu Lys Arg Ile Leu Trp Ile Asp Ala Arg Ser Asp Ala Ile
1445                1450                1455

Tyr Ser Ala Arg Tyr Asp Gly Ser Gly His Met Glu Val Leu Arg
1460                1465                1470

Gly His Glu Phe Leu Ser His Pro Phe Ala Val Thr Leu Tyr Gly
1475                1480                1485

Gly Glu Val Tyr Trp Thr Asp Trp Arg Thr Asn Thr Leu Ala Lys
1490                1495                1500

Ala Asn Lys Trp Thr Gly His Asn Val Thr Val Val Gln Arg Thr
1505                1510                1515

Asn Thr Gln Pro Phe Asp Leu Gln Val Tyr His Pro Ser Arg Gln
1520                1525                1530

Pro Met Ala Pro Asn Pro Cys Glu Ala Asn Gly Gly Gln Gly Pro
1535                1540                1545

Cys Ser His Leu Cys Leu Ile Asn Tyr Asn Arg Thr Val Ser Cys
1550                1555                1560

Ala Cys Pro His Leu Met Lys Leu His Lys Asp Asn Thr Thr Cys
1565                1570                1575

Tyr Glu Phe Lys Lys Phe Leu Leu Tyr Ala Arg Gln Met Glu Ile
1580                1585                1590

Arg Gly Val Asp Leu Asp Ala Pro Tyr Tyr Asn Tyr Ile Ile Ser
1595                1600                1605

Phe Thr Val Pro Asp Ile Asp Asn Val Thr Val Leu Asp Tyr Asp
1610                1615                1620

Ala Arg Glu Gln Arg Val Tyr Trp Ser Asp Val Arg Thr Gln Ala
1625                1630                1635

Ile Lys Arg Ala Phe Ile Asn Gly Thr Gly Val Glu Thr Val Val
1640                1645                1650

Ser Ala Asp Leu Pro Asn Ala His Gly Leu Ala Val Asp Trp Val
1655                1660                1665

Ser Arg Asn Leu Phe Trp Thr Ser Tyr Asp Thr Asn Lys Lys Gln
1670                1675                1680

Ile Asn Val Ala Arg Leu Asp Gly Ser Phe Lys Asn Ala Val Val
1685                1690                1695

Gln Gly Leu Glu Gln Pro His Gly Leu Val Val His Pro Leu Arg
1700                1705                1710

Gly Lys Leu Tyr Trp Thr Asp Gly Asp Asn Ile Ser Met Ala Asn
1715                1720                1725

Met Asp Gly Ser Asn Arg Thr Leu Leu Phe Ser Gly Gln Lys Gly
1730                1735                1740

Pro Val Gly Leu Ala Ile Asp Phe Pro Glu Ser Lys Leu Tyr Trp
1745                1750                1755

Ile Ser Ser Gly Asn His Thr Ile Asn Arg Cys Asn Leu Asp Gly
1760                1765                1770

Ser Gly Leu Glu Val Ile Asp Ala Met Arg Ser Gln Leu Gly Lys
1775                1780                1785

Ala Thr Ala Leu Ala Ile Met Gly Asp Lys Leu Trp Trp Ala Asp
1790                1795                1800

Gln Val Ser Glu Lys Met Gly Thr Cys Ser Lys Ala Asp Gly Ser
1805                1810                1815

```
Gly Ser Val Val Leu Arg Asn Ser Thr Thr Leu Val Met His Met
    1820                1825            1830

Lys Val Tyr Asp Glu Ser Ile Gln Leu Asp His Lys Gly Thr Asn
    1835                1840            1845

Pro Cys Ser Val Asn Asn Gly Asp Cys Ser Gln Leu Cys Leu Pro
    1850                1855            1860

Thr Ser Glu Thr Thr Arg Ser Cys Met Cys Thr Ala Gly Tyr Ser
    1865                1870            1875

Leu Arg Ser Gly Gln Gln Ala Cys Glu Gly Val Gly Ser Phe Leu
    1880                1885            1890

Leu Tyr Ser Val His Glu Gly Ile Arg Gly Ile Pro Leu Asp Pro
    1895                1900            1905

Asn Asp Lys Ser Asp Ala Leu Val Pro Val Ser Gly Thr Ser Leu
    1910                1915            1920

Ala Val Gly Ile Asp Phe His Ala Glu Asn Asp Thr Ile Tyr Trp
    1925                1930            1935

Val Asp Met Gly Leu Ser Thr Ile Ser Arg Ala Lys Arg Asp Gln
    1940                1945            1950

Thr Trp Arg Glu Asp Val Val Thr Asn Gly Ile Gly Arg Val Glu
    1955                1960            1965

Gly Ile Ala Val Asp Trp Ile Ala Gly Asn Ile Tyr Trp Thr Asp
    1970                1975            1980

Gln Gly Phe Asp Val Ile Glu Val Ala Arg Leu Asn Gly Ser Phe
    1985                1990            1995

Arg Tyr Val Val Ile Ser Gln Gly Leu Asp Lys Pro Arg Ala Ile
    2000                2005            2010

Thr Val His Pro Glu Lys Gly Tyr Leu Phe Trp Thr Glu Trp Gly
    2015                2020            2025

Gln Tyr Pro Arg Ile Glu Arg Ser Arg Leu Asp Gly Thr Glu Arg
    2030                2035            2040

Val Val Leu Val Asn Val Ser Ile Ser Trp Pro Asn Gly Ile Ser
    2045                2050            2055

Val Asp Tyr Gln Asp Gly Lys Leu Tyr Trp Cys Asp Ala Arg Thr
    2060                2065            2070

Asp Lys Ile Glu Arg Ile Asp Leu Glu Thr Gly Glu Asn Arg Glu
    2075                2080            2085

Val Val Leu Ser Ser Asn Asn Met Asp Met Phe Ser Val Ser Val
    2090                2095            2100

Phe Glu Asp Phe Ile Tyr Trp Ser Asp Arg Thr His Ala Asn Gly
    2105                2110            2115

Ser Ile Lys Arg Gly Ser Lys Asp Asn Ala Thr Asp Ser Val Pro
    2120                2125            2130

Leu Arg Thr Gly Ile Gly Val Gln Leu Lys Asp Ile Lys Val Phe
    2135                2140            2145

Asn Arg Asp Arg Gln Lys Gly Thr Asn Val Cys Ala Val Ala Asn
    2150                2155            2160

Gly Gly Cys Gln Gln Leu Cys Leu Tyr Arg Gly Arg Gly Gln Arg
    2165                2170            2175

Ala Cys Ala Cys Ala His Gly Met Leu Ala Glu Asp Gly Ala Ser
    2180                2185            2190

Cys Arg Glu Tyr Ala Gly Tyr Leu Leu Tyr Ser Glu Arg Thr Ile
    2195                2200            2205

Leu Lys Ser Ile His Leu Ser Asp Glu Arg Asn Leu Asn Ala Pro
```

```
                2210                2215                2220
Val Gln Pro Phe Glu Asp Pro Glu His Met Lys Asn Val Ile Ala
    2225                2230                2235

Leu Ala Phe Asp Tyr Arg Ala Gly Thr Ser Pro Gly Thr Pro Asn
    2240                2245                2250

Arg Ile Phe Phe Ser Asp Ile His Phe Gly Asn Ile Gln Gln Ile
    2255                2260                2265

Asn Asp Asp Gly Ser Arg Arg Ile Thr Ile Val Glu Asn Val Gly
    2270                2275                2280

Ser Val Glu Gly Leu Ala Tyr His Arg Gly Trp Asp Thr Leu Tyr
    2285                2290                2295

Trp Thr Ser Tyr Thr Thr Ser Thr Ile Thr Arg His Thr Val Asp
    2300                2305                2310

Gln Thr Arg Pro Gly Ala Phe Glu Arg Glu Thr Val Ile Thr Met
    2315                2320                2325

Ser Gly Asp Asp His Pro Arg Ala Phe Val Leu Asp Glu Cys Gln
    2330                2335                2340

Asn Leu Met Phe Trp Thr Asn Trp Asn Glu Gln His Pro Ser Ile
    2345                2350                2355

Met Arg Ala Ala Leu Ser Gly Ala Asn Val Leu Thr Leu Ile Glu
    2360                2365                2370

Lys Asp Ile Arg Thr Pro Asn Gly Leu Ala Ile Asp His Arg Ala
    2375                2380                2385

Glu Lys Leu Tyr Phe Ser Asp Ala Thr Leu Asp Lys Ile Glu Arg
    2390                2395                2400

Cys Glu Tyr Asp Gly Ser His Arg Tyr Val Ile Leu Lys Ser Glu
    2405                2410                2415

Pro Val His Pro Phe Gly Leu Ala Val Tyr Gly Glu His Ile Phe
    2420                2425                2430

Trp Thr Asp Trp Val Arg Arg Ala Val Gln Arg Ala Asn Lys His
    2435                2440                2445

Val Gly Ser Asn Met Lys Leu Leu Arg Val Asp Ile Pro Gln Gln
    2450                2455                2460

Pro Met Gly Ile Ile Ala Val Ala Asn Asp Thr Asn Ser Cys Glu
    2465                2470                2475

Leu Ser Pro Cys Arg Ile Asn Asn Gly Gly Cys Gln Asp Leu Cys
    2480                2485                2490

Leu Leu Thr His Gln Gly His Val Asn Cys Ser Cys Arg Gly Gly
    2495                2500                2505

Arg Ile Leu Gln Asp Asp Leu Thr Cys Arg Ala Val Asn Ser Ser
    2510                2515                2520

Cys Arg Ala Gln Asp Glu Phe Glu Cys Ala Asn Gly Glu Cys Ile
    2525                2530                2535

Asn Phe Ser Leu Thr Cys Asp Gly Val Pro His Cys Lys Asp Lys
    2540                2545                2550

Ser Asp Glu Lys Pro Ser Tyr Cys Asn Ser Arg Arg Cys Lys Lys
    2555                2560                2565

Thr Phe Arg Gln Cys Ser Asn Gly Arg Cys Val Ser Asn Met Leu
    2570                2575                2580

Trp Cys Asn Gly Ala Asp Asp Cys Gly Asp Gly Ser Asp Glu Ile
    2585                2590                2595

Pro Cys Asn Lys Thr Ala Cys Gly Val Gly Glu Phe Arg Cys Arg
    2600                2605                2610
```

-continued

```
Asp Gly Thr Cys Ile Gly Asn Ser Ser Arg Cys Asn Gln Phe Val
2615                2620                2625

Asp Cys Glu Asp Ala Ser Asp Glu Met Asn Cys Ser Ala Thr Asp
2630                2635                2640

Cys Ser Ser Tyr Phe Arg Leu Gly Val Lys Gly Val Leu Phe Gln
2645                2650                2655

Pro Cys Glu Arg Thr Ser Leu Cys Tyr Ala Pro Ser Trp Val Cys
2660                2665                2670

Asp Gly Ala Asn Asp Cys Gly Asp Tyr Ser Asp Glu Arg Asp Cys
2675                2680                2685

Pro Gly Val Lys Arg Pro Arg Cys Pro Leu Asn Tyr Phe Ala Cys
2690                2695                2700

Pro Ser Gly Arg Cys Ile Pro Met Ser Trp Thr Cys Asp Lys Glu
2705                2710                2715

Asp Asp Cys Glu His Gly Glu Asp Glu Thr His Cys Asn Lys Phe
2720                2725                2730

Cys Ser Glu Ala Gln Phe Glu Cys Gln Asn His Arg Cys Ile Ser
2735                2740                2745

Lys Gln Trp Leu Cys Asp Gly Ser Asp Asp Cys Gly Asp Gly Ser
2750                2755                2760

Asp Glu Ala Ala His Cys Glu Gly Lys Thr Cys Gly Pro Ser Ser
2765                2770                2775

Phe Ser Cys Pro Gly Thr His Val Cys Val Pro Glu Arg Trp Leu
2780                2785                2790

Cys Asp Gly Asp Lys Asp Cys Ala Asp Gly Ala Asp Glu Ser Ile
2795                2800                2805

Ala Ala Gly Cys Leu Tyr Asn Ser Thr Cys Asp Asp Arg Glu Phe
2810                2815                2820

Met Cys Gln Asn Arg Gln Cys Ile Pro Lys His Phe Val Cys Asp
2825                2830                2835

His Asp Arg Asp Cys Ala Asp Gly Ser Asp Glu Ser Pro Glu Cys
2840                2845                2850

Glu Tyr Pro Thr Cys Gly Pro Ser Glu Phe Arg Cys Ala Asn Gly
2855                2860                2865

Arg Cys Leu Ser Ser Arg Gln Trp Glu Cys Asp Gly Glu Asn Asp
2870                2875                2880

Cys His Asp Gln Ser Asp Glu Ala Pro Lys Asn Pro His Cys Thr
2885                2890                2895

Ser Pro Glu His Lys Cys Asn Ala Ser Ser Gln Phe Leu Cys Ser
2900                2905                2910

Ser Gly Arg Cys Val Ala Glu Ala Leu Leu Cys Asn Gly Gln Asp
2915                2920                2925

Asp Cys Gly Asp Ser Ser Asp Glu Arg Gly Cys His Ile Asn Glu
2930                2935                2940

Cys Leu Ser Arg Lys Leu Ser Gly Cys Ser Gln Asp Cys Glu Asp
2945                2950                2955

Leu Lys Ile Gly Phe Lys Cys Arg Cys Arg Pro Gly Phe Arg Leu
2960                2965                2970

Lys Asp Asp Gly Arg Thr Cys Ala Asp Val Asp Glu Cys Ser Thr
2975                2980                2985

Thr Phe Pro Cys Ser Gln Arg Cys Ile Asn Thr His Gly Ser Tyr
2990                2995                3000
```

```
Lys Cys Leu Cys Val Glu Gly Tyr Ala Pro Arg Gly Gly Asp Pro
    3005                3010                3015

His Ser Cys Lys Ala Val Thr Asp Glu Glu Pro Phe Leu Ile Phe
    3020                3025                3030

Ala Asn Arg Tyr Tyr Leu Arg Lys Leu Asn Leu Asp Gly Ser Asn
    3035                3040                3045

Tyr Thr Leu Leu Lys Gln Gly Leu Asn Asn Ala Val Ala Leu Asp
    3050                3055                3060

Phe Asp Tyr Arg Glu Gln Met Ile Tyr Trp Thr Asp Val Thr Thr
    3065                3070                3075

Gln Gly Ser Met Ile Arg Arg Met His Leu Asn Gly Ser Asn Val
    3080                3085                3090

Gln Val Leu His Arg Thr Gly Leu Ser Asn Pro Asp Gly Leu Ala
    3095                3100                3105

Val Asp Trp Val Gly Gly Asn Leu Tyr Trp Cys Asp Lys Gly Arg
    3110                3115                3120

Asp Thr Ile Glu Val Ser Lys Leu Asn Gly Ala Tyr Arg Thr Val
    3125                3130                3135

Leu Val Ser Ser Gly Leu Arg Glu Pro Arg Ala Leu Val Val Asp
    3140                3145                3150

Val Gln Asn Gly Tyr Leu Tyr Trp Thr Asp Trp Gly Asp His Ser
    3155                3160                3165

Leu Ile Gly Arg Ile Gly Met Asp Gly Ser Ser Arg Ser Val Ile
    3170                3175                3180

Val Asp Thr Lys Ile Thr Trp Pro Asn Gly Leu Thr Leu Asp Tyr
    3185                3190                3195

Val Thr Glu Arg Ile Tyr Trp Ala Asp Ala Arg Glu Asp Tyr Ile
    3200                3205                3210

Glu Phe Ala Ser Leu Asp Gly Ser Asn Arg His Val Val Leu Ser
    3215                3220                3225

Gln Asp Ile Pro His Ile Phe Ala Leu Thr Leu Phe Glu Asp Tyr
    3230                3235                3240

Val Tyr Trp Thr Asp Trp Glu Thr Lys Ser Ile Asn Arg Ala His
    3245                3250                3255

Lys Thr Thr Gly Thr Asn Lys Thr Leu Leu Ile Ser Thr Leu His
    3260                3265                3270

Arg Pro Met Asp Leu His Val Phe His Ala Leu Arg Gln Pro Asp
    3275                3280                3285

Val Pro Asn His Pro Cys Lys Val Asn Asn Gly Gly Cys Ser Asn
    3290                3295                3300

Leu Cys Leu Leu Ser Pro Gly Gly Gly His Lys Cys Ala Cys Pro
    3305                3310                3315

Thr Asn Phe Tyr Leu Gly Ser Asp Gly Arg Thr Cys Val Ser Asn
    3320                3325                3330

Cys Thr Ala Ser Gln Phe Val Cys Lys Asn Asp Lys Cys Ile Pro
    3335                3340                3345

Phe Trp Trp Lys Cys Asp Thr Glu Asp Asp Cys Gly Asp His Ser
    3350                3355                3360

Asp Glu Pro Pro Asp Cys Pro Glu Phe Lys Cys Arg Pro Gly Gln
    3365                3370                3375

Phe Gln Cys Ser Thr Gly Ile Cys Thr Asn Pro Ala Phe Ile Cys
    3380                3385                3390

Asp Gly Asp Asn Asp Cys Gln Asp Asn Ser Asp Glu Ala Asn Cys
```

-continued

```
          3395                3400                3405

Asp Ile His Val Cys Leu Pro Ser Gln Phe Lys Cys Thr Asn Thr
    3410                3415                3420

Asn Arg Cys Ile Pro Gly Ile Phe Arg Cys Asn Gly Gln Asp Asn
    3425                3430                3435

Cys Gly Asp Gly Glu Asp Glu Arg Asp Cys Pro Glu Val Thr Cys
    3440                3445                3450

Ala Pro Asn Gln Phe Gln Cys Ser Ile Thr Lys Arg Cys Ile Pro
    3455                3460                3465

Arg Val Trp Val Cys Asp Arg Asp Asn Asp Cys Val Asp Gly Ser
    3470                3475                3480

Asp Glu Pro Ala Asn Cys Thr Gln Met Thr Cys Gly Val Asp Glu
    3485                3490                3495

Phe Arg Cys Lys Asp Ser Gly Arg Cys Ile Pro Ala Arg Trp Lys
    3500                3505                3510

Cys Asp Gly Glu Asp Cys Gly Asp Gly Ser Asp Glu Pro Lys
    3515                3520                3525

Glu Glu Cys Asp Glu Arg Thr Cys Glu Pro Tyr Gln Phe Arg Cys
    3530                3535                3540

Lys Asn Asn Arg Cys Val Pro Gly Arg Trp Gln Cys Asp Tyr Asp
    3545                3550                3555

Asn Asp Cys Gly Asp Asn Ser Asp Glu Glu Ser Cys Thr Pro Arg
    3560                3565                3570

Pro Cys Ser Glu Ser Glu Phe Ser Cys Ala Asn Gly Arg Cys Ile
    3575                3580                3585

Ala Gly Arg Trp Lys Cys Asp Gly Asp His Asp Cys Ala Asp Gly
    3590                3595                3600

Ser Asp Glu Lys Asp Cys Thr Pro Arg Cys Asp Met Asp Gln Phe
    3605                3610                3615

Gln Cys Lys Ser Gly His Cys Ile Pro Leu Arg Trp Arg Cys Asp
    3620                3625                3630

Ala Asp Ala Asp Cys Met Asp Gly Ser Asp Glu Glu Ala Cys Gly
    3635                3640                3645

Thr Gly Val Arg Thr Cys Pro Leu Asp Glu Phe Gln Cys Asn Asn
    3650                3655                3660

Thr Leu Cys Lys Pro Leu Ala Trp Lys Cys Asp Gly Glu Asp Asp
    3665                3670                3675

Cys Gly Asp Asn Ser Asp Glu Asn Pro Glu Glu Cys Ala Arg Phe
    3680                3685                3690

Val Cys Pro Pro Asn Arg Pro Phe Arg Cys Lys Asn Asp Arg Val
    3695                3700                3705

Cys Leu Trp Ile Gly Arg Gln Cys Asp Gly Thr Asp Asn Cys Gly
    3710                3715                3720

Asp Gly Thr Asp Glu Asp Cys Glu Pro Pro Thr Ala His Thr
    3725                3730                3735

Thr His Cys Lys Asp Lys Lys Glu Phe Leu Cys Arg Asn Gln Arg
    3740                3745                3750

Cys Leu Ser Ser Ser Leu Arg Cys Asn Met Phe Asp Asp Cys Gly
    3755                3760                3765

Asp Gly Ser Asp Glu Glu Cys Ser Ile Asp Pro Lys Leu Thr
    3770                3775                3780

Ser Cys Ala Thr Asn Ala Ser Ile Cys Gly Asp Glu Ala Arg Cys
    3785                3790                3795
```

```
Val Arg Thr Glu Lys Ala Ala Tyr Cys Ala Cys Arg Ser Gly Phe
3800                3805                3810

His Thr Val Pro Gly Gln Pro Gly Cys Gln Asp Ile Asn Glu Cys
3815                3820                3825

Leu Arg Phe Gly Thr Cys Ser Gln Leu Cys Asn Asn Thr Lys Gly
3830                3835                3840

Gly His Leu Cys Ser Cys Ala Arg Asn Phe Met Lys Thr His Asn
3845                3850                3855

Thr Cys Lys Ala Glu Gly Ser Glu Tyr Gln Val Leu Tyr Ile Ala
3860                3865                3870

Asp Asp Asn Glu Ile Arg Ser Leu Phe Pro Gly His Pro His Ser
3875                3880                3885

Ala Tyr Glu Gln Ala Phe Gln Gly Asp Glu Ser Val Arg Ile Asp
3890                3895                3900

Ala Met Asp Val His Val Lys Ala Gly Arg Val Tyr Trp Thr Asn
3905                3910                3915

Trp His Thr Gly Thr Ile Ser Tyr Arg Ser Leu Pro Pro Ala Ala
3920                3925                3930

Pro Pro Thr Thr Ser Asn Arg His Arg Arg Gln Ile Asp Arg Gly
3935                3940                3945

Val Thr His Leu Asn Ile Ser Gly Leu Lys Met Pro Arg Gly Ile
3950                3955                3960

Ala Ile Asp Trp Val Ala Gly Asn Val Tyr Trp Thr Asp Ser Gly
3965                3970                3975

Arg Asp Val Ile Glu Val Ala Gln Met Lys Gly Glu Asn Arg Lys
3980                3985                3990

Thr Leu Ile Ser Gly Met Ile Asp Glu Pro His Ala Ile Val Val
3995                4000                4005

Asp Pro Leu Arg Gly Thr Met Tyr Trp Ser Asp Trp Gly Asn His
4010                4015                4020

Pro Lys Ile Glu Thr Ala Ala Met Asp Gly Thr Leu Arg Glu Thr
4025                4030                4035

Leu Val Gln Asp Asn Ile Gln Trp Pro Thr Gly Leu Ala Val Asp
4040                4045                4050

Tyr His Asn Glu Arg Leu Tyr Trp Ala Asp Ala Lys Leu Ser Val
4055                4060                4065

Ile Gly Ser Ile Arg Leu Asn Gly Thr Asp Pro Ile Val Ala Ala
4070                4075                4080

Asp Ser Lys Arg Gly Leu Ser His Pro Phe Ser Ile Asp Val Phe
4085                4090                4095

Glu Asp Tyr Ile Tyr Gly Val Thr Tyr Ile Asn Asn Arg Val Phe
4100                4105                4110

Lys Ile His Lys Phe Gly His Ser Pro Leu Val Asn Leu Thr Gly
4115                4120                4125

Gly Leu Ser His Ala Ser Asp Val Val Leu Tyr His Gln His Lys
4130                4135                4140

Gln Pro Glu Val Thr Asn Pro Cys Asp Arg Lys Lys Cys Glu Trp
4145                4150                4155

Leu Cys Leu Leu Ser Pro Ser Gly Pro Val Cys Thr Cys Pro Asn
4160                4165                4170

Gly Lys Arg Leu Asp Asn Gly Thr Cys Val Pro Val Pro Ser Pro
4175                4180                4185
```

-continued

```
Thr Pro Pro Pro Asp Ala Pro Arg Pro Gly Thr Cys Asn Leu Gln
    4190                4195                4200

Cys Phe Asn Gly Gly Ser Cys Phe Leu Asn Ala Arg Arg Gln Pro
    4205                4210                4215

Lys Cys Arg Cys Gln Pro Arg Tyr Thr Gly Asp Lys Cys Glu Leu
    4220                4225                4230

Asp Gln Cys Trp Glu His Cys Arg Asn Gly Gly Thr Cys Ala Ala
    4235                4240                4245

Ser Pro Ser Gly Met Pro Thr Cys Arg Cys Pro Thr Gly Phe Thr
    4250                4255                4260

Gly Pro Lys Cys Thr Gln Gln Val Cys Ala Gly Tyr Cys Ala Asn
    4265                4270                4275

Asn Ser Thr Cys Thr Val Asn Gln Gly Asn Gln Pro Gln Cys Arg
    4280                4285                4290

Cys Leu Pro Gly Phe Leu Gly Asp Arg Cys Gln Tyr Arg Gln Cys
    4295                4300                4305

Ser Gly Tyr Cys Glu Asn Phe Gly Thr Cys Gln Met Ala Ala Asp
    4310                4315                4320

Gly Ser Arg Gln Cys Arg Cys Thr Ala Tyr Phe Glu Gly Ser Arg
    4325                4330                4335

Cys Glu Val Asn Lys Cys Ser Arg Cys Leu Glu Gly Ala Cys Val
    4340                4345                4350

Val Asn Lys Gln Ser Gly Asp Val Thr Cys Asn Cys Thr Asp Gly
    4355                4360                4365

Arg Val Ala Pro Ser Cys Leu Thr Cys Val Gly His Cys Ser Asn
    4370                4375                4380

Gly Gly Ser Cys Thr Met Asn Ser Lys Met Met Pro Glu Cys Gln
    4385                4390                4395

Cys Pro Pro His Met Thr Gly Pro Arg Cys Glu Glu His Val Phe
    4400                4405                4410

Ser Gln Gln Gln Pro Gly His Ile Ala Ser Ile Leu Ile Pro Leu
    4415                4420                4425

Leu Leu Leu Leu Leu Leu Val Leu Val Ala Gly Val Val Phe Trp
    4430                4435                4440

Tyr Lys Arg Arg Val Gln Gly Ala Lys Gly Phe Gln His Gln Arg
    4445                4450                4455

Met Thr Asn Gly Ala Met Asn Val Glu Ile Gly Asn Pro Thr Tyr
    4460                4465                4470

Lys Met Tyr Glu Gly Gly Glu Pro Asp Asp Val Gly Gly Leu Leu
    4475                4480                4485

Asp Ala Asp Phe Ala Leu Asp Pro Asp Lys Pro Thr Asn Phe Thr
    4490                4495                4500

Asn Pro Val Tyr Ala Thr Leu Tyr Met Gly Gly His Gly Ser Arg
    4505                4510                4515

His Ser Leu Ala Ser Thr Asp Glu Lys Arg Glu Leu Leu Gly Arg
    4520                4525                4530

Gly Pro Glu Asp Glu Ile Gly Asp Pro Leu Ala
    4535                4540
```

<210> SEQ ID NO 76
<211> LENGTH: 13
<212> TYPE: PRT
<213> ORGANISM: Artificial Sequence
<220> FEATURE:
<223> OTHER INFORMATION: Biotin Acceptor Peptide

```
<400> SEQUENCE: 76

Leu Asn Asp Ile Phe Glu Ala Gln Lys Ile Glu Trp His
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Lipoate Acceptor Peptide 2 (LAP2)

<400> SEQUENCE: 77

Gly Phe Glu Ile Asp Lys Val Trp Tyr Asp Leu Asp Ala
1               5                   10

<210> SEQ ID NO 78
<211> LENGTH: 5
<212> TYPE: PRT
<213> ORGANISM: Artificial Sequence
<220> FEATURE:
<223> OTHER INFORMATION: HAPylation motif
<220> FEATURE:
<221> NAME/KEY: REPEAT
<222> LOCATION: (1)..(5)
<223> OTHER INFORMATION: Repeat from 1- 400

<400> SEQUENCE: 78

Gly Gly Gly Gly Ser
1               5

<210> SEQ ID NO 79

<400> SEQUENCE: 79

000

<210> SEQ ID NO 80

<400> SEQUENCE: 80

000

<210> SEQ ID NO 81
<211> LENGTH: 35
<212> TYPE: PRT
<213> ORGANISM: Artificial Sequence
<220> FEATURE:
<223> OTHER INFORMATION: SYN470
<220> FEATURE:
<221> NAME/KEY: MISC_FEATURE
<222> LOCATION: (34)..(35)
<223> OTHER INFORMATION: PEG4

<400> SEQUENCE: 81

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr Gly
        35

<210> SEQ ID NO 82
<211> LENGTH: 29
<212> TYPE: PRT
<213> ORGANISM: Artificial Sequence
<220> FEATURE:
```

<223> OTHER INFORMATION: CTP Peptide

<400> SEQUENCE: 82

Asp Ser Ser Ser Ser Lys Ala Pro Pro Pro Ser Leu Pro Ser Pro Ser
1               5                   10                  15

Arg Leu Pro Gly Pro Ser Asp Thr Pro Ile Leu Pro Gln
            20                  25

<210> SEQ ID NO 83
<211> LENGTH: 6
<212> TYPE: PRT
<213> ORGANISM: Artificial Sequence
<220> FEATURE:
<223> OTHER INFORMATION: FVII

<400> SEQUENCE: 83

Ile Val Gly Gly Lys Val
1               5

<210> SEQ ID NO 84
<211> LENGTH: 11
<212> TYPE: PRT
<213> ORGANISM: Artificial Sequence
<220> FEATURE:
<223> OTHER INFORMATION: FVII

<400> SEQUENCE: 84

Ile Val Gly Gly Lys Val Cys Pro Lys Gly Glu
1               5                   10

<210> SEQ ID NO 85
<211> LENGTH: 6
<212> TYPE: PRT
<213> ORGANISM: Artificial Sequence
<220> FEATURE:
<223> OTHER INFORMATION: Factor X

<400> SEQUENCE: 85

Ile Val Gly Gly Gln Glu
1               5

<210> SEQ ID NO 86
<211> LENGTH: 11
<212> TYPE: PRT
<213> ORGANISM: Artificial Sequence
<220> FEATURE:
<223> OTHER INFORMATION: Factor X

<400> SEQUENCE: 86

Ile Val Gly Gly Gln Glu Cys Lys Asp Gly Glu
1               5                   10

<210> SEQ ID NO 87
<211> LENGTH: 99
<212> TYPE: PRT
<213> ORGANISM: Artificial Sequence
<220> FEATURE:
<223> OTHER INFORMATION: SUMO Protein

<400> SEQUENCE: 87

Ser Leu Gln Asp Ser Glu Val Asn Gln Glu Ala Lys Pro Glu Val Lys
1               5                   10                  15

Pro Glu Val Lys Pro Glu Thr His Ile Asn Leu Lys Val Ser Asp Gly
            20                  25                  30

Ser Ser Glu Ile Phe Phe Lys Ile Lys Lys Thr Thr Pro Leu Arg Arg

```
                35                  40                  45
Leu Met Glu Ala Phe Ala Lys Arg Gln Gly Lys Glu Met Asp Ser Leu
        50                  55                  60

Arg Phe Leu Tyr Asp Gly Ile Arg Ile Gln Ala Asp Gln Ala Pro Glu
65                  70                  75                  80

Asp Leu Asp Met Glu Asp Asn Asp Ile Ile Glu Ala His Arg Glu Gln
                85                  90                  95

Ile Gly Gly

<210> SEQ ID NO 88
<211> LENGTH: 6
<212> TYPE: PRT
<213> ORGANISM: Artificial Sequence
<220> FEATURE:
<223> OTHER INFORMATION: intracellular processing site

<400> SEQUENCE: 88

Arg Lys Arg Arg Lys Arg
1               5

<210> SEQ ID NO 89
<211> LENGTH: 4
<212> TYPE: PRT
<213> ORGANISM: Artificial Sequence
<220> FEATURE:
<223> OTHER INFORMATION: intracellular processing site

<400> SEQUENCE: 89

Arg Arg Arg Arg
1

<210> SEQ ID NO 90
<211> LENGTH: 10
<212> TYPE: PRT
<213> ORGANISM: Artificial Sequence
<220> FEATURE:
<223> OTHER INFORMATION: FX-PABC peptide
<220> FEATURE:
<221> NAME/KEY: MOD_RES
<222> LOCATION: (1)..(1)
<223> OTHER INFORMATION: Xaa is DPhe
<220> FEATURE:
<221> NAME/KEY: MOD_RES
<222> LOCATION: (2)..(2)
<223> OTHER INFORMATION: Xaa is Pip
    220>
<221> NAME/KEY: MOD_RES
<222> LOCATION: (4)..(4)
<223> OTHER INFORMATION: Xaa is P-amino benzyl carbamate

<400> SEQUENCE: 90

Xaa Xaa Arg Xaa Ile Val Gly Gly Gln Glu
1               5                   10
```